(12) United States Patent
Kettle et al.

(10) Patent No.: US 11,407,765 B2
(45) Date of Patent: Aug. 9, 2022

(54) TETRACYCLIC HETEROARYL COMPOUNDS

(71) Applicant: AstraZeneca AB, Södertälje (SE)

(72) Inventors: Jason Grant Kettle, Cambridge (GB); Sharanjeet Kaur Bagal, Cambridge (GB); Andrew John Eatherton, Cambridge (GB); Shaun Michael Fillery, Cambridge (GB); Graeme Richard Robb, Cambridge (GB); Scott Gibson Lamont, Cambridge (GB); Paul David Kemmitt, Cambridge (GB); Frederick Woolf Goldberg, Cambridge (GB)

(73) Assignee: AstraZeneca, AB, Södertälje (SE)

( * ) Notice: Subject to any disclaimer, the term of this patent is extended or adjusted under 35 U.S.C. 154(b) by 0 days.

(21) Appl. No.: 17/053,400

(22) PCT Filed: May 7, 2019

(86) PCT No.: PCT/EP2019/061754
§ 371 (c)(1),
(2) Date: Nov. 6, 2020

(87) PCT Pub. No.: WO2019/215203
PCT Pub. Date: Nov. 14, 2019

(65) Prior Publication Data
US 2021/0221823 A1  Jul. 22, 2021

Related U.S. Application Data

(60) Provisional application No. 62/754,814, filed on Nov. 2, 2018, provisional application No. 62/668,321, filed on May 8, 2018.

(51) Int. Cl.
*C07D 498/14* (2006.01)

(52) U.S. Cl.
CPC .................. *C07D 498/14* (2013.01)

(58) Field of Classification Search
CPC ................................... C07D 498/14
USPC ................................... 514/211.15
See application file for complete search history.

(56) References Cited

FOREIGN PATENT DOCUMENTS

| | | |
|---|---|---|
| WO | 2013155223 A1 | 10/2013 |
| WO | 2014143659 A1 | 9/2014 |
| WO | 2014152588 A1 | 9/2014 |
| WO | 2015054572 A1 | 4/2015 |
| WO | 2016049524 A1 | 3/2016 |
| WO | 2016164675 A1 | 10/2016 |
| WO | 2016168540 A1 | 10/2016 |
| WO | 2017015562 A1 | 1/2017 |
| WO | 2017058728 A1 | 4/2017 |
| WO | 2017058768 A1 | 4/2017 |
| WO | 2017058792 A1 | 4/2017 |
| WO | 2017058805 A1 | 4/2017 |
| WO | 2017058807 A1 | 4/2017 |
| WO | 2017058902 A1 | 4/2017 |
| WO | 2017058915 A1 | 4/2017 |
| WO | 2017087528 A1 | 5/2017 |
| WO | 2017201161 A1 | 11/2017 |
| WO | 2018064510 A1 | 4/2018 |
| WO | 2018068017 A1 | 4/2018 |
| WO | 2018119183 A2 | 6/2018 |
| WO | 2018140512 A1 | 8/2018 |
| WO | 2018140513 A1 | 8/2018 |
| WO | 2018140514 A1 | 8/2018 |
| WO | 2018140598 A1 | 8/2018 |
| WO | 2018140599 A1 | 8/2018 |
| WO | 2018140600 A1 | 8/2018 |
| WO | 2018143315 A1 | 8/2018 |
| WO | 2018206539 A1 | 11/2018 |
| WO | 2018217651 A1 | 11/2018 |
| WO | 2018218069 A1 | 11/2018 |
| WO | 2018218070 A2 | 11/2018 |
| WO | 2018218071 A1 | 11/2018 |
| WO | 2019051291 A1 | 3/2019 |

(Continued)

OTHER PUBLICATIONS

Anonymous, "MRTX849 in Patients With Cancer Having a KRAS G12C Mutation KRYSTAL-1", ClinicalTrials.Gov, 2018, Available at: https://clinicaitrials.gov/ct2/show/NCT03785249 (retrieved Apr. 6, 2021).

(Continued)

*Primary Examiner* — Kahsay Habte

(57) ABSTRACT

The specification relates to compounds of Formula (I)

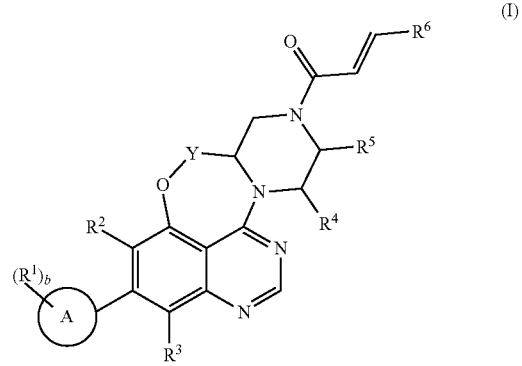

and pharmaceutically acceptable salts thereof. The specification also relates to processes and intermediates used for their preparation, pharmaceutical compositions containing them and their use in the treatment of cell proliferative disorders.

19 Claims, No Drawings

(56) References Cited

FOREIGN PATENT DOCUMENTS

| WO | 2019099524 A1 | 5/2019 |
|---|---|---|
| WO | 2019110751 A1 | 6/2019 |
| WO | 2019150305 A1 | 8/2019 |
| WO | 2019155399 A1 | 8/2019 |

OTHER PUBLICATIONS

Fell et al. "Discovery of Tetrahydropyridopyrimidines as Irreversible Covalent Inhibitors of KRAS-G12C with In Vivo Activity" ACS Medicinal Chemistry Letters, 2018, vol. 9, pp. 1230-1234.

Fell et al., "Identification of the Clinical Development Candidate MRTX849, a Covalent $KRAS^{G12C}$ Inhibitor for the Treatment of Cancer" Journal of Medicinal Chemistry, 2020, vol. 63, pp. 6679-6693.

Hansen, et al. "The reactivity-driven biochemical mechanism of covalent $KRAS^{G12C}$ inhibitors." Nature Structural Molecular Biology, 2018, vol. 25, pp. 454-462.

Janes et al. "Targeting KRAS Mutant Cancers with a Covalent G12C-Specific Inhibitor." Cell, 2018, vol. 172, pp. 578-589.

Kettle et al. "Structure-Based Design and Pharmacokinetic Optimization of Covalent Allosteric Inhibitors of the Mutant GTPase $KRAS^{G12C}$" Journal of Medicinal Chemistry, 2020, vol. 63, pp. 4468-4483.

Lanman et al. "Discovery of a Covalent Inhibitor of KRASG12C (AMG 510) for the Treatment of Solid Tumors" Journal of Medicinal Chemistry, 2020, vol. 63, pp. 52-65.

Marx et al, "Structure-based Drug Discovery of MRTX1257: A Selective, Covalent Kras G12C Inhibitor with Oral Activity in Animal Models of Cancer" 2019, Abstracts of Papers, 257th ACS National Meeting & Exposition, Orlando, FL, United States. Available at: https://www.morressier.com/article/structurebased-drug-discovery-mrtx1257-selective-covalent-kras-g12c-inhibitor-oral-activity-animal-models-cancer/5fc643a32d78d1fec4668986.

Marx et al. "Structure-Based Drug Discovery of MRTX1257, a Selective, Covalent KRAS G12C Inhibitor with Oral Activity in Animal Models of Cancer." Mirati.com, 2018, Available at: https://www.mirati.com/wp-content/uploads/KRAS-Poster-AACR-RAS.pdf.

Ostrem, et al. "K-Ras(G12C) inhibitors allosterically control GIP affinity and effector interactions" Nature, 2013, vol. 503, pp. 548-551.

Patricelli, et al. "Selective Inhibition of Oncogenic KRAS Output with Small Molecules Targeting the Inactive State" Cancer Discovery, 2016, vol. 6, pp. 316-329.

Shin et al. "Discovery of N-(1-Acryloylazetidin-3-yl)-2-(1H-indol-1-yl)acetamides as Covalent Inhibitors of $KRAS^{G12C}$" ACS Medicinal Chemistry Letters, 2019, vol. 10, pp. 1302-1308.

TETRACYCLIC HETEROARYL COMPOUNDS

CROSS-REFERENCE TO RELATED APPLICATION

This application is a U.S. National Phase Application of International Application No. PCT/EP2019/061754, filed on May 7, 2019, which claims the benefit under 35 U.S.C. § 119(e) of U.S. Provisional Application No. 62/668,321, filed on May 8, 2018, and U.S. Provisional Application No. 62/754,814, filed on Nov. 2, 2018. Each of the above-listed applications is incorporated by reference herein in their entirety.

The specification relates to certain tetracyclic heteroaryl compounds and pharmaceutically acceptable salts thereof that inhibit G12C mutant RAS proteins and consequently exhibit anti-cancer activity. The specification also relates to use of said tetracyclic heteroaryl compounds and pharmaceutically acceptable salts thereof in methods of treatment of the human or animal body, for example in prevention or treatment of cancer. The specification also relates to processes and intermediate compounds involved in the preparation of said tetracyclic heteroaryl compounds and to pharmaceutical compositions containing them.

The KRAS, NRAS and HRAS genes encode a set of closely related small GTPase proteins KRas, NRas and HRas, collectively referred to herein as the Ras proteins or Ras, that share 82-90% overall sequence identity. The Ras proteins are critical components of signalling pathways transmitting signals from cell-surface receptors to regulate cellular proliferation, survival and differentiation. Ras functions as a molecular switch cycling between an inactive GDP-bound state and an active GTP-bound state. The GDP/GTP cycle of Ras is tightly regulated in cells by guanine nucleotide exchange factors (GEFs) such as Sos1 and Sos2, which promote the exchange of GDP for GTP, and GTPase activating proteins (GAPs) such as NF-1 and p120RasGAP which stimulate the intrinsic GTPase activity of Ras hydrolysing GTP to GDP.

The Ras proteins are 188-189 amino acids in length and have a highly conserved N-terminal G-domain containing the p-loop region, which binds nucleotide, and the switch I and switch II regions which are important for regulatory and effector protein interactions. The C-terminal region of the Ras proteins are more divergent and contain elements which regulate the association of Ras with the membrane including the conserved carboxyl terminal CAXX box motif which is necessary for post-translational prenylation modifications. On binding to GTP the switch I and switch II regions of Ras undergo a conformational change which enables its interaction and activation of effector proteins to regulate down-stream signalling pathways. The best characterised effector of Ras is the serine/threonine kinase Raf which regulates the activity of the mitogen-activate protein kinase (MAPK) pathway. The PI3K pathway is another important effector pathway down-stream of Ras with the p110 catalytic subunit of the class I phosphoinositide 3-kinases interacting with Ras. Other effectors of Ras including RalGDS, Tiam1, PLC-ε and Rassf1 have been have also been described (Cox, et al. Nature Reviews Drug Discovery, 2014, 13:828-851).

RAS mutations are frequently found in cancer and approximately 30% of all human cancers have a mutation in KRAS, NRAS or HRAS genes. Oncogenic Ras is typically, but not exclusively, associated with mutations at glycine 12, glycine 13 or glutamine 61 of Ras. These residues are located at the active site of Ras and mutations impair intrinsic and/or GAP-catalysed GTPase activity favouring the formation of GTP bound Ras and aberrant activation of down-stream effector pathways. KRAS is the most frequently mutated RAS gene in cancer followed by NRAS and then HRAS. There are several tumour types that exhibit a high frequency of activating mutations in KRAS including pancreatic (~90% prevalence), colorectal (~40% prevalence) and non-small cell lung cancer (~30% prevalence). KRAS mutations are also found in other cancer types including multiple myeloma, uterine cancer, bile duct cancer, stomach cancer, bladder cancer, diffuse large B cell lymphoma, rhabdomyosarcoma, cutaneous squamous cell carcinoma, cervical cancer, testicular germ cell cancer and others.

Glycine to cysteine mutations at residue 12 of Ras (the G12C mutation) is generated from a G.C to T.A base transversion at codon 12, a mutation commonly found in RAS genes that accounts for 14% of all KRAS, 2% of all NRAS and 2% of all HRAS mutations across cancer types. The G12C mutation is particularly enriched in KRAS mutant non-small cell lung cancer with approximately half carrying this mutation, which has been associated with the DNA adducts formed by tobacco smoke. The G12C mutation is not exclusively associated with lung cancer and is found in other RAS mutant cancer types including 8% of all KRAS mutant colorectal cancer.

To date there have been no inhibitors of G12C mutant Ras proteins which have been approved for therapeutic use. Hence there is a need for new inhibitors of G12C mutant Ras proteins that possess the required pharmaceutical properties to be suitable for clinical use. The compounds of the specification have been found to possess anti-tumour activity, being useful in inhibiting the uncontrolled cellular proliferation which arises from malignant disease. The compounds of the specification provide an anti-tumour effect by, as a minimum, acting as inhibitors of G12C mutant Ras proteins.

According to a first aspect of the specification there is provided a compound of the Formula (I):

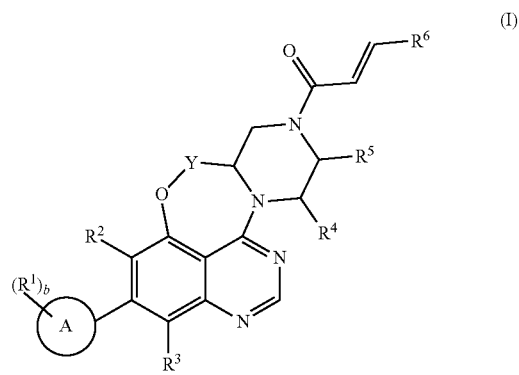

wherein:
Ring A is selected from phenyl and bicyclic heteroaryl;
$R^1$ in each occurrence is independently selected from $C_{1-4}$alkyl, halo, hydroxy, $C_{1-4}$alkoxy, $C_{1-3}$fluoroalkyl, $C_{1-3}$fluoroalkoxy, cyano and acetylenyl;
b is 0, 1, 2 or 3;
Y is $CH_2$ or $CH_2CH_2$;
$R^2$ is cyano, halo, $C_{1-4}$alkyl, $C_{1-4}$alkoxy or $C_{1-3}$fluoroalkyl;
$R^3$ is F, Me, Et, MeO or $C_{1-2}$fluoroalkyl;
$R^4$ is H or Me;
$R^5$ is H or Me;
$R^6$ is H or $CH_2NMe_2$;

or a pharmaceutically acceptable salt thereof, provided that when Y is $CH_2$, $R^2$ is Cl, $R^3$ is F, A is phenyl, b is 2, the groups $R^1$ are F and OH and are each ortho to the biaryl bond, and when both $R^4$ and $R^6$ are H, then $R^5$ is Me.

In a further aspect there is provided a pharmaceutical composition comprising a compound of Formula (I).

In a further aspect there is provided a method of treating cancer by administering to a subject suffering from cancer an effective amount of a compound of Formula (I).

In a further aspect there is provided a compound of Formula (I) for use as a medicament.

In a further aspect there is provided a compound of Formula (I) for use in the treatment of cancer.

In a further aspect there is provided a compound of Formula (I) for use in the manufacture of a medicament, for example a medicament for the treatment of cancer.

In a further aspect there is provided a kit comprising a pharmaceutical composition comprising a compound of Formula (I) and instructions for its use, for example for use in the treatment of cancer.

In a further aspect there is provided a method for the manufacture of a compound of Formula (I).

It has been found that the compounds of the present specification possess potent anti-tumour activity that, it is believed, derives from inhibition of the G12C mutant Ras proteins that are key mediators of proliferation and survival in certain tumour cells.

Due to their ability to bind to and inhibit the normal function of Ras G12C mutant proteins the compounds of the present specification may be of value as anti-tumour agents, in particular as selective inhibitors of the proliferation, survival, motility, dissemination and invasiveness of mammalian cancer cells leading to inhibition of tumour growth and survival and to inhibition of metastatic tumour growth. Particularly, the compounds of the present specification may be of value as anti-proliferative and anti-invasive agents in the containment and/or treatment of solid tumour disease. Particularly, the compounds of the present specification may be useful in the prevention or treatment of those tumours which are sensitive to inhibition of G12C mutant Ras and that are involved in the cell-signalling leading to the proliferation and survival of tumour cells.

It is believed that the compounds of the present specification interact with, and then covalently bind to, G12C mutant Ras through the acrylamide motif located on the upper piperazine ring of Formula (I). In binding to G12C mutant Ras, the compounds of the specification (as described herein) impair or substantially eliminate the ability of the G12C Ras proteins to access their active, pro-proliferative/pro-survival confirmation.

It has been discovered that the stereochemistry of the carbon atom of the piperazine ring that is bonded to the group Y (as marked with an asterisk in the figure below) is a key determinant of Ras G12C inhibitory activity, with the Ras G12C inhibitory activity between each enantiomer varying significantly. For the discussion of the properties of the compounds according to the specification herein the numbering shown in the figure below will be used throughout, albeit the names of the compounds as generated by the chemical naming software does not always adhere to this naming convention. The group O—Y is thus attached to C-5 of the quinazoline and may thus be referred to as a C-5 tether group. The groups $R^2$, A and $R^3$ are attached to C-6, C-7 and C-8 of the quinazoline motif, respectively. As the group A is an aromatic group the bond between C-7 of the quinazoline and A is a biaryl bond.

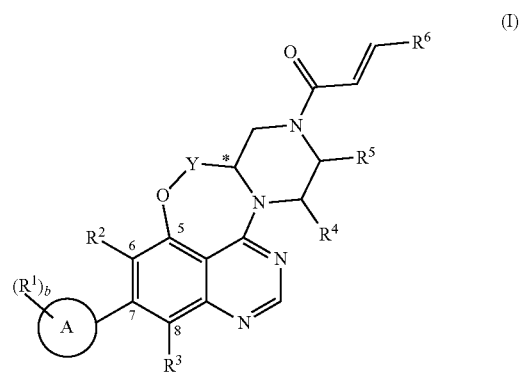

In addition to the importance of the stereochemical configuration of the carbon to which Y is bound, the compounds according to the specification are atropisomeric due to the restricted rotation around the biaryl bond that links C-7 of the quinazoline ring to the aromatic ring A. It has been discovered that incorporation of a substituent $R^2$ at C-6 of the quinazoline ring and a substituent $R^3$ at C-8 of the quinazoline ring, in conjunction with substituents $R^1$ can deliver stable atropisomeric forms of the compounds of Formula (I) that can be separated and that are stable to storage. Furthermore, it has been discovered that the activity of each individual atropisomer of the compounds of the Formula (I) as inhibitors of Ras G12C mutant protein can vary to a large degree. In the examples reported herein activity differences of 10-fold or greater and sometimes 100-fold or more are observed between atropisomeric pairs of compounds of Formula (I). The activity difference between atropisomers may derive from the advantageous ability of the substituents $R^2$ and $R^3$ to hold the group A and the substituent(s) $R^1$ on A, in a conformation close to, or in, their optimal conformation for binding to G12C Ras mutant protein thus lowering the energy required for binding of the inhibitor to the target protein.

It has been established that the compounds of Formula (I), and in particular those compounds of Formula (I) with the preferred enantiomeric and atropisomeric form, can be very potent inhibitors of Ras G12C mutant protein. Where enantioselective syntheses have been performed wherein stereochemical configuration of a chiral starting material is retained through the synthesis, the preferred enantiomer has been identified to be that illustrated in the figure below. It has thus been found that optimum activity is delivered when the stereochemical configuration of the bond from the piperazine to Y differs for systems in which Y=$CH_2$ and those in which Y=$CH_2CH_2$. It has been assumed that where the syntheses are performed in a racemic manner and then the products are separated by chiral chromatography then the most active compounds have the same stereochemistry at the asymmetric piperazine carbon as presented below. Nonetheless, for the avoidance of doubt, the present disclosure encompasses all isomers and atropisomers of the compounds of Formula (I). It will be understood that the compounds having the stereochemical arrangement that gives optimal Ras G12C inhibitory activity are preferred embodiments of the specification.

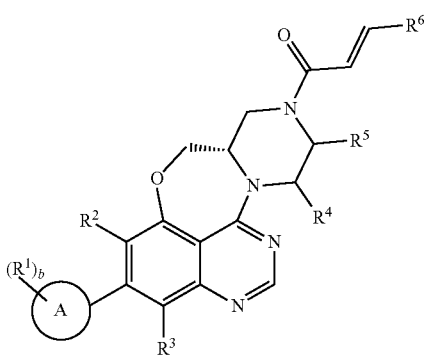

(I)

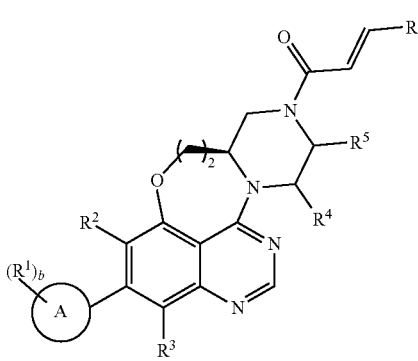

(I)

It has been found that the compounds of Formula (I) having the stereochemistry shown above exhibit higher activity as inhibitors of G12C Ras mutant protein than compounds having the opposite stereochemistry or compounds lacking the group O—Y, that in compounds of Formula (I) tethers C-5 of the quinazoline ring to the piperazine ring.

In addition to the above, it has further been determined that incorporation of a substituent on the piperazine ring (i.e. $R^4$ or $R^5$) can improve the metabolic profile of the compounds according to Formula (I). Compounds of Formula (I) in which $R^5$ is methyl have proven particularly advantageous in this respect. Incorporation of a methyl group at $R^5$ has advantageously been observed to greatly improve oral bioavailability in in vivo studies, this is believed to be due to a reduction in off-target reactivity with glutathione in rodents. For example, in the otherwise identical compounds, incorporation of a $R^5$ methyl group caused an improvement in oral bioavailability from 0 to 30% and a 30-fold reduction in clearance. This difference in oral bioavailability is seen for Example 4 (a compound in which $R^5$ is Me, see below) that has oral bioavailability in rats of 31% and the corresponding compound in which $R^5$ is H (not claimed herein, reported in WO2018/206539) that has an oral bioavailability of 0% in rat (a significant effect on clearance between the two compounds is also observed Example 4 has Cl of 29 ml/min/kg cf $R^5$ desmethyl compound 962 ml/min/kg—a figure reflecting the short, 12 minute, half life of this compound in rat blood). Incorporation of a methyl group at $R^5$ has also been observed to improve cell permeability (Example 4, Caco AB of 58 $P_{app}$ 1E$^{-6}$ cm/s, the corresponding compound where $R^5$ is H that has 5.8 $P_{app}$ 1 E$^{-6}$ cm/s). In instances wherein Y=CH$_2$CH$_2$, incorporation of a $R^5$ methyl group likewise delivers good cell permeability, good oral bioavailability and low clearance (see e.g. Example 39 below, 72 $P_{app}$ 1 E$^{-6}$ cm/s, F(rat) 75%, Cl(rat) 22 ml/min/kg). $R^5$ methylation therefore delivers compounds with enhanced pharmacokinetic properties. In instances wherein Y=CH$_2$CH$_2$, the stereochemistry of the $R^5$ group has also proven to have a significant effect on the selective inhibitory effect on G12C mutant Ras.

Described herein are compounds that can bind to G12C mutant Ras. In biochemical and cell based assays the compounds of the present specification are shown to be potent G12C mutant Ras protein binders and may therefore be useful in the treatment of disorders mediated by KRas, NRas or HRas G12C mutations, in particular in the treatment of cancers expressing G12C mutated KRas, NRas or HRas proteins, such as pancreatic, colorectal, uterine, bile duct, stomach, bladder, cervical, testicular germ cell and non-small cell lung cancer and multiple myeloma, diffuse large B cell lymphoma, rhabdomyosarcoma and cutaneous squamous cell carcinoma. In binding to G12C mutant Ras protein that are critical components of signalling pathways transmitting signals from cell-surface receptors to regulate cellular proliferation, survival and differentiation, the compounds according to the specification can inhibit or abrogate cellular proliferation, survival and differentiation of cells such as tumour cells that express G12C mutant Ras protein.

Accordingly, the present specification provides a method for providing a selective inhibitory effect on G12C mutant Ras which comprises administering an effective amount of a compound of the Formula (I), or a pharmaceutically acceptable salt thereof, as defined hereinbefore.

The present specification also relates to processes for the manufacture of compounds of Formula (I), to pharmaceutical compositions containing them, to methods of treatment comprising administering the said compounds to patients, for example humans, in need thereof, to the use of compounds of Formula (I) for the manufacture of medicaments, for example for use in the treatment of a patient suffering from a hyperproliferative disease such as cancer.

Unless defined otherwise, all technical and scientific terms used herein have the same meaning as commonly understood by one of ordinary skill in the art to which this disclosure is related. For example, the *Concise Dictionary of Biomedicine and Molecular Biology*, Juo, Pei-Show, 2nd ed., 2002, CRC Press; *The Dictionary of Cell and Molecular Biology*, 3rd ed., 1999, Academic Press; and the *Oxford Dictionary of Biochemistry and Molecular Biology*, Revised, 2000, Oxford University Press, provide one of skill with a general dictionary of many of the terms used in this disclosure.

So that the present specification may be more readily understood, certain terms are explicitly defined below. In addition, definitions are set forth as appropriate throughout the detailed description.

Units, prefixes, and symbols are denoted in their Système International de Unites (SI) accepted form. Numeric ranges are inclusive of the numbers defining the range.

The term "pharmaceutical composition" refers to a preparation which is in such form as to permit the biological activity of the active ingredient, and which contains no additional components which are unacceptably toxic to a subject to which the composition would be administered. Such compositions can be sterile. A pharmaceutical composition according to the present specification will comprise a compound of Formula (I) and a pharmaceutically acceptable excipient.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present disclosure if the patient shows, e.g., total, partial, or transient remission of a certain type of cancer.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The ring A in the compounds of Formula (I) is selected from phenyl and bicyclic heteroaryl. Bicyclic heteroaryl as used herein refers to an aromatic group comprising two fused rings and containing 1, 2, 3 or 4 N atoms, or one O atom, or one S atom, or 1 N atom and one S atom, or 1 N atom and one O atom, or 2 N atoms and one S atom, or 2 N atoms and one O atom. Bicyclic heteroaryl groups include those groups where both fused rings are aromatic, or where one fused ring is aromatic and the other fused ring is partially or fully saturated. The said partially or fully saturated fused ring may also comprise a carbonyl group. The at least one heteroatom in the bicyclic heteroaryl group may be present in an aromatic ring or a saturated ring. The bicyclic heteroaryl groups A of the compounds of Formula (I) are [6,6] or [6,5] ring systems, examples of suitable bicyclic heteroaryl groups include indolyl, benzofuranyl, benzothienyl, benzoxazolyl, benzimidazolyl, benzotriazolyl, indazolyl, azaindolyl, azaindazolyl, pyrrolo[1,2-b]pyridazinyl and pyrrolo[2,3-b]pyridinyl, quinolinyl, isoquinolinyl, quinazolinyl, cinnolinyl, phthalazinyl, quinoxalinyl and naphthyridinyl and partially saturated derivatives thereof.

$R^1$ in each occurrence is independently selected from $C_{1-4}$alkyl, halo, hydroxy, $C_{1-4}$ alkoxy, $C_{1-3}$fluoroalkyl, $C_{1-3}$fluoroalkoxy, cyano and acetylenyl. For the avoidance of doubt, $C_{1-4}$alkyl refers to a straight or branched alkyl group containing from 1 to 4 carbon atoms, use of numerical subscripts throughout the specification, for example for alkoxy, fluoroalkyl and fluoroalkoxy groups is consistent with this usage.

The term halo as used herein refers to an atom selected from F, Cl, Br or I. In embodiments of the specification the halo groups in the compounds of Formula (I), and in particular for the groups $R^2$ and $R^1$, F and Cl are preferred halo groups.

The group $R^2$ is selected from is cyano, halo, $C_{1-4}$alkyl, $C_{1-4}$alkoxy or $C_{1-3}$fluoroalkyl. Examples of preferred $R^2$ groups include Cl, methyl and cyano, for example Cl. The group $R^3$ is selected from F, Me, Et, MeO or $C_{1-2}$fluoroalkyl, for example F, Me or MeO.

In the instance where the compound of Formula (I) is such that Y is $CH_2$, $R^2$ is Cl, $R^3$ is F, A is phenyl, b is 2, the groups $R^1$ are F and OH and are each ortho to the biaryl bond, and, furthermore, when both $R^4$ and $R^6$ are H, then the group $R^5$ is Me (and is not H). It will thus be understood that the compound 1-((8aS)-6-chloro-4-fluoro-5-(2-fluoro-6-hydroxyphenyl)-8a,9,11,12-tetrahydropyrazino[2',1':3,4] [1,4]oxazepino[5,6,7-de]quinazolin-10(8H)-yl)prop-2-en-1-one, as shown below, is not a compound according to Formula (I) and is not claimed herein.

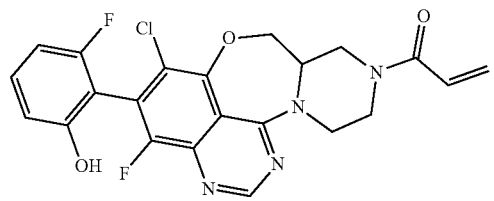 [SMILES: C=CC(=O)N1CCN2c3ncnc4c(F)c(-c5c(O)cccc5F)c(Cl)c(c34)OCC2C1]

For the avoidance of doubt, where multiple substituents are independently selected from a given group, the selected substituents may comprise the same substituents or different substituents from within the given group. By way of example only, where ring A is phenyl substituted with $(R^1)_b$, and where b is 2, the two $R^1$ substituents could be the same, for instance both fluoro, or could be different, for instance one fluoro and one hydroxy.

For the further avoidance of doubt, the use of "〜" in formulas of this specification denotes the point of attachment between different groups.

As noted above, the specification provides a compound of the Formula (I):

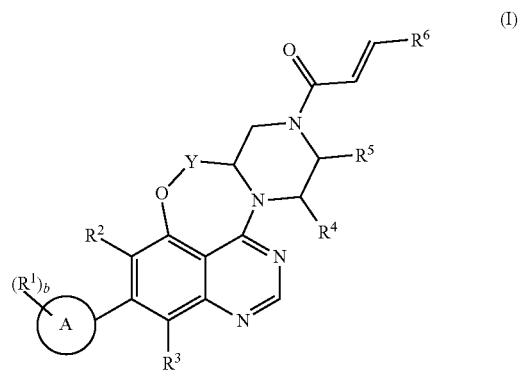

wherein:
Ring A is selected from phenyl and bicyclic heteroaryl;
$R^1$ in each occurrence is independently selected from $C_{1-4}$alkyl, halo, hydroxy, $C_{1-4}$ alkoxy, $C_{1-3}$fluoroalkyl, $C_{1-3}$fluoroalkoxy, cyano and acetylenyl;
b is 0, 1, 2 or 3;
Y is $CH_2$ or $CH_2CH_2$;
$R^2$ is cyano, halo, $C_{1-4}$alkyl, $C_{1-4}$alkoxy or $C_{1-3}$fluoroalkyl;
$R^3$ is F, Me, Et, MeO or $C_{1-2}$fluoroalkyl;
$R^4$ is H or Me;
$R^5$ is H or Me;
$R^6$ is H or $CH_2NMe_2$;
or a pharmaceutically acceptable salt thereof, provided that when Y is $CH_2$, $R^2$ is Cl, $R^3$ is F, A is phenyl, b is 2, the groups $R^1$ are F and OH and are each ortho to the biaryl bond, and when both $R^4$ and $R^6$ are H, then $R^5$ is Me.

In one embodiment there is provided a compound of Formula (I) as defined above.

In one embodiment there is provided a pharmaceutically acceptable salt of a compound of Formula (I).

In embodiments, the compound of Formula (I) is a compound of Formula (Ia) wherein Y is $CH_2$.

In embodiments, the compound of Formula (I) is a compound of Formula (Ib) wherein Y is $CH_2CH_2$.

In embodiments, the compound of Formula (I), (Ia) or (Ib) is a compound of Formula (Ic) in which the group $R^2$ is selected from Cl, Me, or CN (cyano). In embodiments, the compound of Formula (Ic) is a compound of Formula (Id) in which the group $R^2$ is Cl.

In embodiments, the compound of Formula (I), (Ia), (Ib), (Ic) or (Id) is a compound of Formula (Ie) in which the group $R^3$ is selected from F, Me or MeO. In embodiments, the compound of Formula (Ie) is a compound of Formula (If) in which the group $R^3$ is F.

In embodiments, the compound of Formula (I), (Ia), (Ib), (Ic), (Id), (Ie) or (If) is a compound of Formula (Ig) in which the group $R^4$ is H.

In embodiments, the compound of Formula (I), (Ia), (Ib), (Ic), (Id), (Ie), (If) or (Ig) is a compound of Formula (Ih) in which the group $R^5$ is H. In embodiments the compound of Formula (I), (Ia), (Ib), (Ic), (Id), (Ie), (If) or (Ig) is a compound of Formula (Ii) in which the group $R^5$ is Me.

In embodiments, the compound of Formula (I), (Ia), (Ib), (Ic), (Id), (Ie), (If), (Ig), (Ih) or (Ii) is a compound of Formula (Ij) in which the group $R^6$ is H.

In embodiments, the compound of Formula (I), (Ia), (Ib), (Ic), (Id), (Ie), (If), (Ig), (Ih), (Ii) or (Ij) is a compound of Formula (Ik) in which the group A is phenyl.

In embodiments, the compound of Formula (Ik) is a compound of Formula (Il) in which the integer b is 2 or 3 and at least one $R^1$ group is OH. In embodiments, the compound of Formula (Ik) or (Il) is a compound of Formula (Im) in which at least two substituents $R^1$ are ortho to the biaryl bond.

In embodiments, the compound of Formula (Ik) is a compound of Formula (In) in which the group $A(R^1)_b$ is

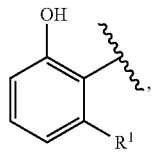

optionally wherein $R^1$ is selected from Me, F, Cl and CN (cyano). In embodiments, the $R^1$ group in the compound of Formula (In) is selected from Me, Cl and CN.

In embodiments, the compound of Formula (Ik) is a compound of Formula (Io) in which the group $A(R^1)_b$ is

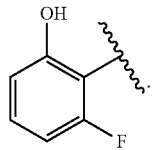 [SMILES: *c1c(O)cccc1F]

In embodiments the compound of Formula (I), (Ia), (Ib), (Ic), (Id), (Ie), (If), (Ig), (Ih), (Ii) or (Ij) is a compound of Formula (Ip) in which the group A is bicyclic heteroaryl.

In embodiments, the compound of Formula (Ip) is a compound of Formula (Iq) in which the bicyclic heteroaryl group is selected from the group consisting of:

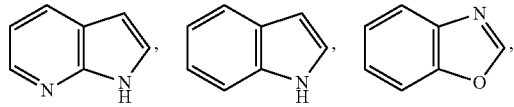

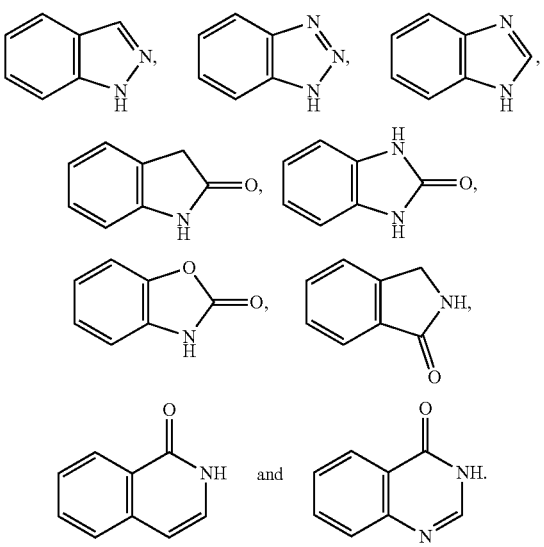

In embodiments, the compound of Formula (Ip) is a compound of Formula (Ir) in which the bicyclic heteroaryl group is selected from the group consisting of:

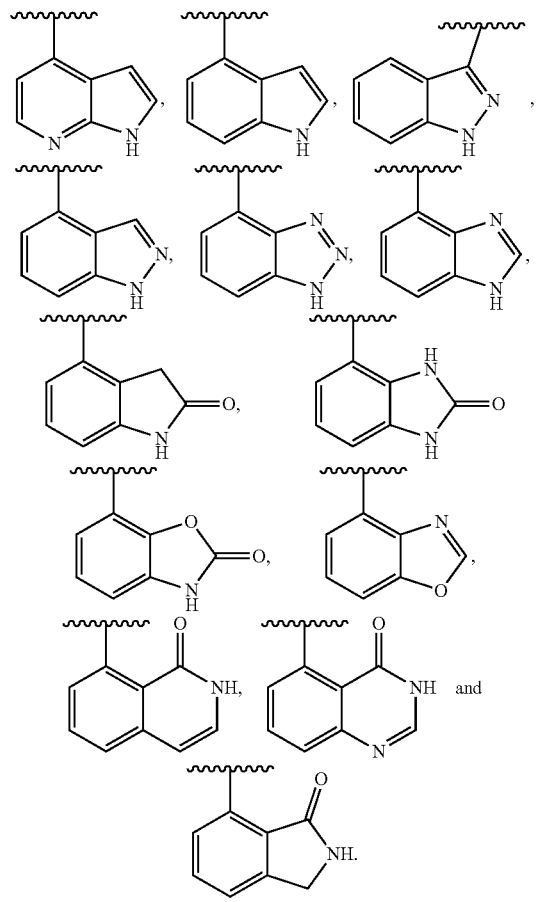

In embodiments, the compound of Formula (Ip) is a compound of Formula (Is) in which the bicyclic heteroaryl group is selected from the group consisting of:

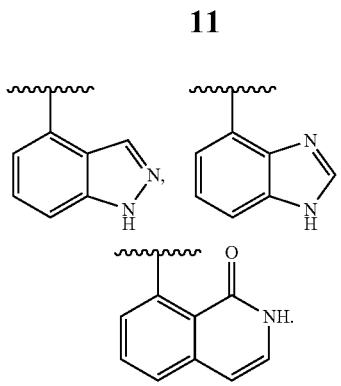

In embodiments, the compound of Formula (Ip) is a compound of Formula (It) in which the bicyclic heteroaryl group is selected from the group consisting of:

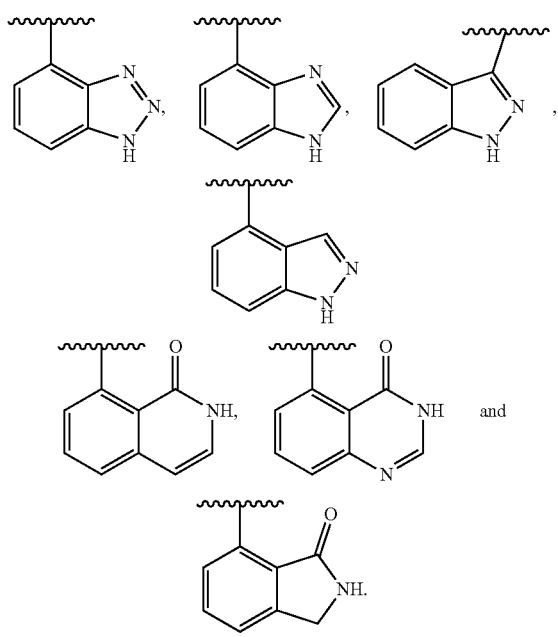

In embodiments, the compounds of Formula (I), i.e. any of compounds of Formula (I), (Ia), (Ib) . . . to (It), is a compound of Formula (Iu) or (Iv) in which the stereochemistry is as shown below:

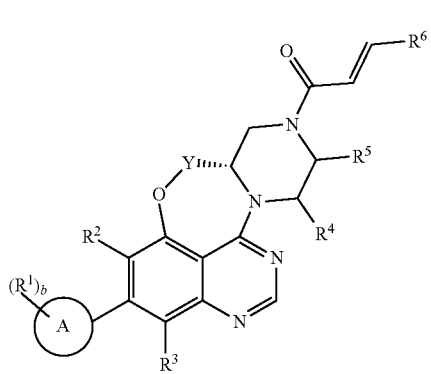

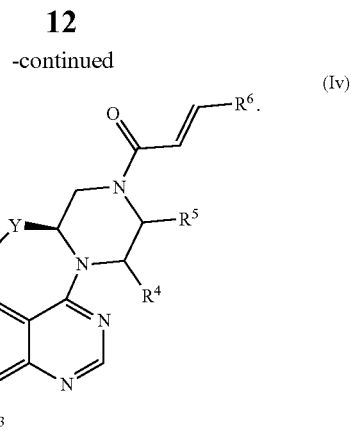

In embodiments, the compound of Formula (Iu) is a compound of Formula (Iui) in which Y=CH$_2$. In embodiments, the compound of Formula (Iv) is a compound of Formula (Ivi) in which Y=CH$_2$CH$_2$.

In embodiments, the compounds of Formula (I), i.e. any of compounds of Formula (I), (Ia), (Ib) . . . to (Ivi), is a compound of Formula (Iw) in which R$^4$ is H and R$^5$ is Me.

In embodiments the compound of Formula (I) is selected from each enantiomeric and atropisomeric form of:

7-[(8aS)-10-Acryloyl-6-chloro-4-fluoro-8,8a,9,10,11,12-hexahydropyrazino[2',1':3,4][1,4]oxazepino [5,6,7-de]quinazolin-5-yl]-6-methyl-2,3-dihydro-1H-isoindol-1-one;

1-[(8aS,11S)-6-Chloro-4-fluoro-5-(2-fluoro-6-hydroxyphenyl)-11-methyl-8a,9,11,12-tetrahydropyrazino[2',1':3,4][1,4]oxazepino[5,6,7-de]quinazolin-10(8H)-yl]prop-2-en-1-one;

1-[(8aS,11R)-6-Chloro-4-fluoro-5-(2-fluoro-6-hydroxyphenyl)-11-methyl-8a,9,11,12-tetrahydropyrazino[2',1':3,4][1,4]oxazepino[5,6,7-de]quinazolin-10(8H)-yl]prop-2-en-1-one;

5-[(8aS)-10-Acryloyl-6-chloro-4-fluoro-8,8a,9,10,11,12-hexahydropyrazino[2',1':3,4][1,4]oxazepino[5,6,7-de]quinazolin-5-yl]-6-methylquinazolin-4(3H)-one;

1-[(8aS)-6-Chloro-4-fluoro-5-(5-methyl-1H-benzimidazol-4-yl)-8a,9,11,12-tetrahydropyrazino [2',1':3,4][1,4]oxazepino[5,6,7-de]quinazolin-10(8H)-yl]prop-2-en-1-one;

8-[(8aS)-6-Chloro-4-fluoro-10-(prop-2-enoyl)-8,8a,9,10,11,12-hexahydropyrazino[2',1':3,4][1,4] oxazepino[5,6,7-de]quinazolin-5-yl]isoquinolin-1(2H)-one;

1-[(8aS)-6-Chloro-4-fluoro-5-(1H-indazol-3-yl)-8a,9,11,12-tetrahydropyrazino[2',1':3,4][1,4] oxazepino[5,6,7-de]quinazolin-10(8H)-yl]prop-2-en-1-one;

1-[(8aS)-6-Chloro-4-fluoro-5-(2-hydroxy-6-methylphenyl)-8a,9,11,12-tetrahydropyrazino [2',1':3,4][1,4]oxazepino [5,6,7-de]quinazolin-10(8H)-yl]prop-2-en-1-one;

(2E)-1-[(8aS)-6-Chloro-4-fluoro-5-(2-fluoro-6-hydroxyphenyl)-8a,9,11,12-tetrahydropyrazino [2',1':3,4][1,4] oxazepino[5,6,7-de]quinazolin-10(8H)-yl]-4-(dimethylamino)but-2-en-1-one;

8-[(8aS)-6-Chloro-4-fluoro-10-(prop-2-enoyl)-8,8a,9,10,11,12-hexahydropyrazino[2',1':3,4][1,4] oxazepino[5,6,7-de]quinazolin-5-yl]-7-methylisoquinolin-1(2H)-one;

1-[(8aS)-6-Chloro-4-fluoro-5-(5-methyl-1H-benzotriazol-4-yl)-8a,9,11,12-tetrahydropyrazino [2',1':3,4][1,4]oxazepino[5,6,7-de]quinazolin-10(8H)-yl]prop-2-en-1-one;

1-((8aS)-6-chloro-4-fluoro-5-(5-fluoro-1H-benzo[d]imidazol-4-yl)-8a,9,11,12-tetrahydropyrazino [2',1':3,4][1,4] oxazepino[5,6,7-de]quinazolin-10(8H)-yl)prop-2-en-1-one;

1-[(8aS)-6-Chloro-4-fluoro-5-(5-fluoro-1H-indazol-4-yl)-8a,9,11,12-tetrahydropyrazino[2',1':3,4] [1,4]oxazepino[5,6,7-de]quinazolin-10(8H)-yl]prop-2-en-1-one;

1-((8aS)-6-Chloro-4-fluoro-5-(5-fluoro-1-methyl-1H-benzo[d]imidazol-4-yl)-8a,9,11,12-tetrahydropyrazino[2',1':3,4][1,4]oxazepino[5,6,7-de]quinazolin-10(8H)-yl)prop-2-en-1-one;

1-[(8aS)-6-Chloro-4-fluoro-5-(5-fluoro-1H-benzotriazol-4-yl)-8a,9,11,12-tetrahydropyrazino[2',1':3,4] [1,4]oxazepino[5,6,7-de]quinazolin-10(8H)-yl]prop-2-en-1-one;

8-[(8aS)-6-Chloro-4-fluoro-10-(prop-2-enoyl)-8,8a,9,10,11,12-hexahydropyrazino[2',1':3,4][1,4] oxazepino[5,6,7-de]quinazolin-5-yl]-7-fluoroisoquinolin-1(2H)-one;

(2E)-1-[(8aS)-6-chloro-4-fluoro-5-(5-methyl-1H-indazol-4-yl)-8a,9,11,12-tetrahydropyrazino[2',1':3,4] [1,4]oxazepino[5,6,7-de]quinazolin-10(8H)-yl]-4-(dimethylamino)but-2-en-1-one;

1-[(6aR,9S)-3-Chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl]prop-2-en-1-one;

1-[(6aR,9S)-3-Chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl]prop-2-en-1-one;

8-[3-Chloro-1-fluoro-8-(prop-2-enoyl)-6,6a,7,8,9,10-hexahydro-5H-pyrazino[1',2':5,6][1,5]oxazocino [4,3,2-de]quinazolin-2-yl]-7-methylisoquinolin-1(2H)-one;

1-[(6aS,9R)-3-Chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl]prop-2-en-1-one;

1-[(6aR,9R)-3-Chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl]prop-2-en-1-one;

1-[(6aS,9S)-3-Chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl]prop-2-en-1-one;

1-[(8aS)-4-Chloro-6-fluoro-5-(2-fluoro-6-hydroxyphenyl)-8a,9,11,12-tetrahydropyrazino[2',1':3,4] [1,4]oxazepino[5,6,7-de]quinazolin-10(8H)-yl]prop-2-en-1-one;

1-[(8aS,11R)-6-Chloro-4-fluoro-11-methyl-5-(5-methyl-1H-benzimidazol-4-yl)-8a,9,11,12-tetrahydropyrazino[2',1':3,4][1,4]oxazepino[5,6,7-de]quinazolin-10(8H)-yl] prop-2-en-1-one;

8-[(8aS,11R)-6-Chloro-4-fluoro-11-methyl-10-(prop-2-enoyl)-8,8a,9,10,11,12-hexahydropyrazino [2',1':3,4][1,4]oxazepino[5,6,7-de]quinazolin-5-yl]-7-methylisoquinolin-1(2H)-one;

(2E)-1-[(8aS,11R)-6-Chloro-4-fluoro-11-methyl-5-(5-methyl-1H-benzimidazol-4-yl)-8a,9,11,12-tetrahydropyrazino[2',1':3,4] [1,4]oxazepino[5,6,7-de]quinazolin-10 (8H)-yl]-4-(dimethylamino)but-2-en-1-one; and (2E)-1-[(8aS,11R)-6-Chloro-4-fluoro-11-methyl-5-(5-methyl-1H-indazol-4-yl)-8a,9,11,12-tetrahydropyrazino [2',1':3,4][1,4]oxazepino[5,6,7-de]quinazolin-10(8H)-yl]-4-(dimethylamino)but-2-en-1-one;

or a pharmaceutically acceptable salt thereof.

In embodiments of the present specification there is provided a pharmaceutical composition which comprises a compound of the Formula (I) or a pharmaceutically acceptable salt thereof, in association with a pharmaceutically acceptable excipient, optionally further comprising one or more of the other stereoisomeric forms of the compound of Formula (I) or pharmaceutically acceptable salt thereof, wherein the compound of Formula (I) or pharmaceutically acceptable salt thereof is present within the composition with a diastereomeric excess (% d.e.) of ≥90%.

In embodiments of the present specification there is provided a pharmaceutical composition which comprises a compound of the Formula (I) or a pharmaceutically acceptable salt thereof, in association with a pharmaceutically acceptable excipient, optionally further comprising one or more of the other stereoisomeric forms of the compound of Formula (I) or pharmaceutically acceptable salt thereof, wherein the compound of Formula (I) or pharmaceutically acceptable salt thereof is present within the composition with an enantiomeric excess (% ee) of 90% and a diastereomeric excess (% de) of ≥90%.

The compounds of Formula (I) and pharmaceutically acceptable salts thereof may be prepared, used or supplied in amorphous form, crystalline form, or semi-crystalline form and any given compound of Formula (I) or pharmaceutically acceptable salt thereof may be capable of being formed into more than one crystalline/polymorphic form, including hydrated (e.g. hemi-hydrate, a mono-hydrate, a di-hydrate, a tri-hydrate or other stoichiometry of hydrate) and/or solvated forms. It is to be understood that the present specification encompasses any and all such solid forms of the compound of Formula (I) and pharmaceutically acceptable salts thereof.

In further embodiments of the present specification there is provided a compound of Formula (I), which is obtainable by the methods described in the 'Examples' section hereinafter.

The present specification is intended to include all isotopes of atoms occurring in the present compounds. Isotopes will be understood to include those atoms having the same atomic number but different mass numbers. For example, isotopes of hydrogen include tritium and deuterium. Isotopes of carbon include $^{13}C$ and $^{14}C$. Isotopically labelled compounds of Formula (I) can generally be prepared by conventional techniques known to those skilled in the art or by processes analogous to those described in the accompanying Examples using appropriate isotopically labelled reagents in place of the non-labelled reagents previously employed.

A suitable pharmaceutically acceptable salt of a compound of the Formula (I) is, for example, an acid addition salt. A suitable pharmaceutically acceptable salt of a compound of the Formula (I) may be, for example, an acid-addition salt of a compound of the Formula (I), for example an acid-addition salt with an inorganic or organic acid.

A further suitable pharmaceutically acceptable salt of a compound of the Formula (I) is, for example, a salt formed within the human or animal body after administration of a compound of the Formula (I) to said human or animal body.

The compound of Formula (I) or pharmaceutically acceptable salt thereof may be prepared as a co-crystal solid form. It is to be understood that a pharmaceutically acceptable co-crystal of a compound of the Formula (I) or pharmaceutically acceptable salts thereof, form an aspect of the present specification.

For use in a pharmaceutical context it may be preferable to provide a compound of Formula (I) or a pharmaceutically acceptable salt thereof without large amounts of the other stereoisomeric forms being present.

Accordingly, in an embodiment of the present specification there is provided a composition comprising a compound of Formula (I) or a pharmaceutically acceptable salt thereof, optionally together with one or more of the other stereoisomeric forms of the compound of Formula (I) or pharmaceutically acceptable salt thereof, wherein the compound of Formula (I) or pharmaceutically acceptable salt thereof is present within the composition with a diastereomeric excess (% de) of 90%.

The compound of Formula (I), or a pharmaceutically acceptable salt thereof, will normally be administered via the oral or intravenous route, in the form of pharmaceutical preparations comprising the active ingredient or a pharmaceutically acceptable salt or solvate thereof, or a solvate of such a salt, in a pharmaceutically acceptable dosage form. Depending upon the disorder and patient to be treated and the route of administration, the compositions may be administered at varying doses, for example at a dose of from 1 mg to 1000 mg.

The pharmaceutical formulations of the compound of Formula (I) described above may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). In one form the pharmaceutical might be in the form of a capsule, for example a two-piece hard shell capsule or a soft elastic gelatin (SEG) capsule comprising a compound of Formula (I) and, optionally, a pharmaceutically acceptable excipient. The pharmaceutical composition may contain an amount of from 1 mg to 1000 mg of the compound of Formula (I) or a pharmaceutically acceptable salt thereof.

According to a further embodiment there is provided a compound of Formula (I), or a pharmaceutically acceptable salt thereof, as defined hereinbefore, for use as a medicament in a warm-blooded animal such as man.

According to a further embodiment, there is provided a compound of Formula (I), or a pharmaceutically acceptable salt thereof, as defined hereinbefore for use in the production of an anti-proliferative effect in a warm-blooded animal such as man.

According to a further embodiment, there is provided a compound of Formula (I), or a pharmaceutically acceptable salt thereof, as defined hereinbefore for use in a warm-blooded animal such as man as an anti-invasive agent in the containment and/or treatment of solid tumour disease.

According to a further embodiment, there is provided the use of a compound of Formula (I), or a pharmaceutically acceptable salt thereof, as defined hereinbefore, for the production of an anti-proliferative effect in a warm-blooded animal such as man.

According to a further embodiment, there is provided the use of a compound of Formula (I), or a pharmaceutically acceptable salt thereof, as defined hereinbefore, in the manufacture of a medicament for use in the production of an anti-proliferative effect in a warm-blooded animal such as man.

According to a further embodiment, there is provided the use of a compound of Formula (I), or a pharmaceutically acceptable salt thereof, as defined hereinbefore, in the manufacture of a medicament for use in a warm-blooded animal such as man as an anti-invasive agent in the containment and/or treatment of solid tumour disease.

According to a further embodiment, there is provided a method for producing an anti-proliferative effect in a warm-blooded animal, such as man, in need of such treatment which comprises administering to said animal an effective amount of a compound of Formula (I), or a pharmaceutically acceptable salt thereof, as defined hereinbefore.

In this specification, unless otherwise stated, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

According to a further embodiment, there is provided a method for producing an anti-invasive effect by the containment and/or treatment of solid tumour disease in a warm-blooded animal, such as man, in need of such treatment which comprises administering to said animal an effective amount of a compound of Formula (I), or a pharmaceutically acceptable salt thereof, as defined hereinbefore.

According to a further embodiment, there is provided a compound of Formula (I), or a pharmaceutically acceptable salt thereof, as defined hereinbefore, for use in the prevention or treatment of cancer in a warm-blooded animal such as man.

According to a further embodiment, there is provided the use of a compound of Formula (I), or a pharmaceutically acceptable salt thereof, as defined hereinbefore in the manufacture of a medicament for use in the prevention or treatment of cancer in a warm-blooded animal such as man.

According to a further embodiment, there is provided a method for the prevention or treatment of cancer in a warm-blooded animal, such as man, in need of such treatment which comprises administering to said animal an effective amount of a compound of Formula (I), or a pharmaceutically acceptable salt thereof, as defined hereinbefore.

According to a further embodiment, there is provided a compound of Formula (I), or a pharmaceutically acceptable salt thereof, as defined hereinbefore for use in the prevention or treatment of solid tumour disease in a warm-blooded animal such as man.

According to a further embodiment, there is provided the use of a compound of Formula (I), or a pharmaceutically acceptable salt thereof, as defined hereinbefore, in the manufacture of a medicament for use in the prevention or treatment of solid tumour disease in a warm-blooded animal such as man.

According to a further embodiment, there is provided a method for the prevention or treatment of solid tumour disease in a warm-blooded animal, such as man, in need of such treatment which comprises administering to said animal an effective amount of a compound of Formula (I), or a pharmaceutically acceptable salt thereof, as defined hereinbefore.

According to a further embodiment, there is provided a compound of Formula (I), or a pharmaceutically acceptable salt thereof, as defined hereinbefore, for use in the prevention or treatment of tumours which are sensitive to inhibition of G12C mutant Ras.

According to a further embodiment, there is provided the use of a compound of Formula (I), or a pharmaceutically acceptable salt thereof, as defined hereinbefore, in the manufacture of a medicament for use in the prevention or treatment of those tumours which are sensitive to inhibition of G12C mutant Ras.

According to a further embodiment, there is provided a method for the prevention or treatment of those tumours which are sensitive to inhibition of G12C mutant RAS, which comprises administering to said animal an effective amount of a compound of Formula (I), or a pharmaceutically acceptable salt thereof, as defined hereinbefore, to a patient in need thereof.

According to a further embodiment, there is provided a compound of Formula (I), or a pharmaceutically acceptable salt thereof, as defined hereinbefore for use in providing an inhibitory effect on G12C mutant Ras.

According to a further embodiment, there is provided the use of a compound of Formula (I), or a pharmaceutically acceptable salt thereof, as defined hereinbefore in the manufacture of a medicament for use in providing an inhibitory effect on G12C mutant Ras.

According to a further embodiment, there is also provided a method for providing an inhibitory effect on G12C mutant RAS which comprises administering an effective amount of a compound of Formula (I), or a pharmaceutically acceptable salt thereof, as defined hereinbefore, to a patient in need thereof.

According to a further embodiment, there is provided a compound of Formula (I), or a pharmaceutically acceptable salt thereof, as defined hereinbefore, for use in providing a selective inhibitory effect on G12C mutant Ras.

According to a further embodiment, there is provided the use of a compound of Formula (I), or a pharmaceutically acceptable salt thereof, as defined hereinbefore, in the manufacture of a medicament for use in providing a selective inhibitory effect on G12C mutant Ras.

According to a further embodiment, there is also provided a method for providing a selective inhibitory effect on G12C mutant Ras which comprises administering an effective amount of a compound of Formula (I), or a pharmaceutically acceptable salt thereof, as defined hereinbefore, to a patient in need thereof.

Described herein are compounds that can bind to G12C mutant Ras. In biochemical and cell based assays the compounds of the present specification are shown to be potent G12C mutant Ras protein binders and may therefore be useful in the treatment of disorders mediated by KRas, NRas or HRas G12C mutations, in particular in the treatment of cancers expressing G12C mutated KRas, NRas or HRas proteins, such as pancreatic, colorectal, uterine, bile duct, stomach, bladder, cervical, testicular germ cell and non-small cell lung cancer and multiple myeloma, diffuse large B cell lymphoma, rhabdomyosarcoma and cutaneous squamous cell carcinoma.

According to a further embodiment, there is provided a compound of Formula (I), or a pharmaceutically acceptable salt thereof, as defined hereinbefore, for use in the treatment of disorders mediated by KRas, NRas or HRas G12C mutations.

According to a further embodiment, there is provided a method for treating disorders mediated by KRas, NRas or HRas G12C mutations, which comprises administering an effective amount of a compound of Formula (I), or a pharmaceutically acceptable salt thereof, as defined hereinbefore, to a patient in need thereof.

According to a further embodiment, there is provided the use of a compound of Formula (I), or a pharmaceutically acceptable salt thereof, as defined hereinbefore, in the manufacture of a medicament for use in the treatment of disorders mediated by KRas, NRas or HRas G12C mutations.

According to a further embodiment, there is provided a compound of Formula (I), or a pharmaceutically acceptable salt thereof, as defined hereinbefore, for use in the treatment of non-small cell lung cancer or colorectal cancer.

According to a further embodiment, there is provided a compound of Formula (I), or a pharmaceutically acceptable salt thereof, as defined hereinbefore, for use in the treatment of non-small cell lung cancer.

According to a further embodiment, there is provided a method for treating non-small cell lung cancer or colorectal cancer, which comprises administering an effective amount of a compound of Formula (I), or a pharmaceutically acceptable salt thereof, as defined hereinbefore, to a patient in need thereof.

According to a further embodiment, there is provided a method for treating non-small cell lung cancer, which comprises administering an effective amount of a compound of Formula (I), or a pharmaceutically acceptable salt thereof, as defined hereinbefore.

According to a further embodiment, there is provided the use of a compound of Formula (I), or a pharmaceutically acceptable salt thereof, as defined hereinbefore, in the manufacture of a medicament for use in the treatment of breast or gynaecological cancers.

According to a further embodiment, there is provided the use of a compound of Formula (I), or a pharmaceutically acceptable salt thereof, as defined hereinbefore, in the manufacture of a medicament for use in the treatment of non-small cell lung cancer or colorectal cancer.

According to a further aspect of the specification, there is provided the use of a compound of Formula (I), or a pharmaceutically acceptable salt thereof, as defined hereinbefore, in the manufacture of a medicament for use in the treatment of non-small cell lung cancer.

The anti-cancer treatment defined herein may be applied as a sole therapy or may involve, in addition to the compounds of the specification, conventional surgery or radiotherapy or chemotherapy.

Accordingly, in one embodiment, there is provided a compound of Formula (I), or a pharmaceutically acceptable salt thereof, and an additional anti-tumour substance for the conjoint treatment of cancer.

According to an embodiment of the specification there is provided a combination suitable for use in the treatment of cancer comprising a compound of Formula (I) or a pharmaceutically acceptable salt thereof and another anti-tumour agent.

In a further embodiment of the specification there is provided a compound of Formula (I), or a pharmaceutically acceptable salt thereof, in combination with another anti-tumour agent.

Although the compounds of Formula (I) are primarily of value as therapeutic agents for use in warm-blooded animals (including man), they are also useful whenever it is required to inhibit G12C mutant Ras. Thus, they are useful as pharmacological standards for use in the development of new biological tests and in the search for new pharmacological agents.

Another embodiment is based on identifying a link between the G12C KRas, HRas or NRas mutation status of a patient and potential susceptibility to treatment with a compound of Formula (I). A Ras inhibitor, such as a compound of Formula (I), may then advantageously be used to treat patients with G12C KRas, HRas or NRas mutations who may be resistant to other therapies. This therefore provides opportunities, methods and tools for selecting patients for treatment with a compound of Formula (I), particularly cancer patients. The selection is based on whether the tumour cells to be treated possess wild-type or G12C mutant KRAS, HRAS or NRAS gene. The G12C KRAS, HRAS or NRAS gene status could therefore be used as a biomarker to indicate that selecting treatment with a compound of Formula (I) may be advantageous. A patient identified as susceptible for successful treatment with a compound of Formula (I) can then be treated with such a compound. A method of treatment may thus encompass a first patient selection step and treatment of a patient in need thereof with an effective amount of a compound of Formula (I).

According to embodiments, there is provided a method for selecting a patient for treatment with a compound of Formula (I), the method comprising providing a tumour cell-containing sample from a patient; determining whether the RAS gene in the patient's tumour cell-containing sample encodes for wild-type (glycine at position 12) or mutant (cysteine at position 12) KRas, HRas or NRas protein; and selecting a patient for treatment with a compound of Formula (I) based thereon. A method of treatment may encompass such a method of patient selection.

The method may include or exclude the actual patient sample isolation step. Thus, according to one embodiment there is provided a method for selecting a patient for treatment with a compound of Formula (I), the method comprising determining whether the RAS gene in a tumour cell-containing sample previously isolated from the patient encodes for wild-type (glycine at position 12) or mutant (cysteine at position 12) KRas, HRas or NRas protein; and selecting a patient for treatment with a compound of Formula (I) based thereon.

In embodiments, the patient is selected for treatment with a compound of Formula (I) if the tumour cell DNA has a G12C mutant KRAS gene.

In embodiments, the patient is selected for treatment with a compound of Formula (I) if the tumour cell DNA has a G12C mutant HRAS gene.

In embodiments, the patient is selected for treatment with a compound of Formula (I) if the tumour cell DNA has a G12C mutant NRAS gene.

According to another embodiment, there is provided a compound of Formula (I), or a pharmaceutically acceptable salt thereof, for use in treating cancers with tumour cells identified as harbouring a G12C mutant KRAS gene.

According to another embodiment, there is provided a compound of Formula (I), or a pharmaceutically acceptable salt thereof, for use in treating cancers with tumour cells identified as harbouring a G12C mutant HRAS gene.

According to another aspect of the specification there is provided a compound of Formula (I), or a pharmaceutically acceptable salt thereof, for use in treating cancers with tumour cells identified as harbouring a G12C mutant NRAS gene.

According to another embodiment, there is provided a method of treating cancers with tumour cells identified as harbouring a G12C mutant KRAS, HRAS or NRAS gene comprising administering an effective amount of a compound of Formula (I) or a pharmaceutically acceptable salt thereof.

According to another embodiment, there is provided a pharmaceutical composition comprising a compound of Formula (I) for use in the prevention and treatment of cancer with tumour cells identified as harbouring a G12C mutant KRAS, HRAS or NRAS gene.

It will be appreciated that the following examples are provided so that the nature of the invention may be fully understood. It will also be appreciated that the following examples are not intended to limit the scope of the description in any way.

Biological Assays

The following assays were used to measure the effects of the compounds of the present specification.

KRasG12C Functional Assay

The inactive GDP loaded biotinylated KRas$^{G12C}$ protein was expressed, purified and GDP loaded in house. All enzyme and substrate solutions were prepared in assay buffer containing 20 mM HEPES (pH 7.5), 5 mM MgCl2, 150 mM NaCl, and 0.01% Tween 20. 10 nM GDP loaded biotinylated KRas$^{G12C}$ and 37.5 ng/ml Streptavidin Europium Cryptate (Cisbio) were prepared in assay buffer, 50 was dispensed into each well of a 384 polystyrene, Hibase, medium binding white assay plate (Greiner, #784075) containing test and reference samples prepared in DMSO and the samples incubated for 4 hrs. In a separate mix 20 nM GST-Raf Ras binding domain (GST-Raf RBD, purified in house) and 4 µg/ml anti-GST XL665 antibody (Cisbio) was prepared in assay buffer containing 50 mM Potassium Fluoride and 0.05 mg/ml BSA and equilibrated for 4 hours before adding 0.6 µM Guanosine 5'-[γ-thio]triphosphate (GTPγS, Sigma) and 0.08 µM SOS (purified in house). 5 µl of the GST-RAF RBD mix was then dispensed into each well of the assay plate. This addition initiates the nucleotide exchange reaction and transition of inactive GDP loaded KRas$^{G12C}$ to active GTPγS KRas$^{G12C}$. This is detected simultaneously via the specific binding interaction between active GTPγS KRas$^{G12C}$ with GST-Raf RBD which brings the europium and XL665 into close proximity enabling an increased FRET signal to be detected on a Pherastar (BMG) plate reader equipped with the HTRF filter module. Any compound which prevents the activation of KRas via inhibiting the nucleotide exchange process, or inhibits the active KRas:Raf RBD binding interaction, will result in a reduced FRET signal. IC$_{50}$ values were calculated from normalised dose-response response FRET data curve fitted in Genedata screener (Basel, Switzerland).

KRasG12C Mass Spectrometry Adducting Assay

The inactive GDP loaded biotinylated KRas$^{G12C}$ protein was expressed, purified and GDP loaded in house. Enzyme solutions were prepared in assay buffer containing 20 mM HEPES (pH 7.5), 5 mM MgCl2, and 150 mM NaCl. 4 µM GDP loaded biotinylated KRas$^{G12C}$ was prepared in assay buffer and 50 µl added into each well of a 96 well polypropylene assay plate (Greiner, #651201) containing 500 nl of 1 mM test compounds (final concentration 10 µM), this was allowed to react for 4 hours before the addition of 501111% Formic acid to quench the reaction. The plate was sealed before reading on a Xevo G2 QTOF (Waters) and Acquity LC system (Waters). 10 µl of sample was injected onto a Xbridge BEH300; C4; 3.5 um; 2.1×50 mm column (Waters) running a 3 minute gradient. Blank samples were run in between each test sample.

Data was analysed in Mass Lynx software (Waters), the Total ion count (TIC) trace was used and the eluted protein peak data combined. Using the combined spectrum the data was deconvoluted using MaxEnt1 method. The peak area for apo-protein KRas$^{G12C}$ (APO) and KRAS+relative cmpd mass (adduct) were measured, and a percentage adduct was calculated using the following calculation:

Percent adduct=100*(area of adduct peak/(sum of APO+adduct peaks)

The data shown in Table A were generated for the Examples (the data below may be a result from a single experiment or an average of two or more experiments).

TABLE A

| Example No. | KRasG12C functional assay IC50 value (μM) | KRasG12C M. S. Binding Mean adduct % |
|---|---|---|
| 1 | 0.019 | 98 |
| 2 | 0.29 | 25 |
| 3 | 0.113 | 54 |
| 4 | 0.05 | 96 |
| 5 | 6.349 | 14 |
| 6 | 0.098 | 95 |
| 7 | 7.628 | |
| 8 | 0.012 | 96 |
| 9 | 0.23 | 22 |
| 10 | 0.068 | 94 |
| 11 | 0.201 | 96 |
| 12 | 0.031 | 95 |
| 13 | 9.698 | |
| 14 | 0.059 | 94 |
| 15 | 19.66 | |
| 16 | 0.01 | 91 |
| 17 | 0.373 | 30 |
| 18 | 0.239 | 25 |
| 19 | 0.024 | 94 |
| 20 | 0.029 | 100 |
| 21 | 1.306 | |
| 22 | 0.03 | 95 |
| 23 | 8.959 | |
| 24 | 0.097 | 99 |
| 25 | 13.852 | |
| 26 | 0.051 | 100 |
| 27 | 12.037 | |
| 28 | 0.005 | 92 |
| 29 | 2.856 | |
| 30 | 0.17 | 94 |
| 31 | 6.833 | |
| 32 | 3.13 | |
| 33 | 0.229 | |
| 34 | 1.213 | |
| 35 | 8.507 | |
| 36 | 0.002 | |
| 37 | 0.180 | |
| 38 | 3.65 | |
| 39 | 0.003 | |
| 40 | 2.54 | |
| 41 | 0.674 | |
| 42 | 0.111 | 95.528 |
| 43 | 2.900 | |
| 44 | 0.062 | |
| 45 | 0.089 | |
| 46 | 0.059 | |
| 47 | 11.2 | |
| 48 | 0.046 | |
| 49 | 30 | |
| 50 | 0.14 | |
| 51 | 1.75 | |
| 52 | 2.14 | |
| 53 | 0.186 | |

EXAMPLES

The specification will now be illustrated in the following Examples in which, unless stated otherwise:

(i) all syntheses were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment or Biotage v10 evaporator in vacuo and work up procedures were carried out after removal of residual solids by filtration;

(iii) flash column chromatography was performed on Merck Kieselgel silica (Art. 9385) or on reversed phase silica (Fluka silica gel 90 C18) or on Silicycle cartridges (40-63 μm silica, 4 to 330 g weight) or on Grace resolv cartridges (4-120 g) or on RediSep Rf 1.5 Flash columns or on RediSep Rf high performance Gold Flash columns (150-415 g weight) or on RediSep Rf Gold C18 Reversed-phase columns (20-40 μm silica) or on Interchim puriFlash cartridges (50 μm silica, 4-800 g) either manually or automated using an Isco CombiFlash Companion system or similar system;

(iv) preparative reverse phase HPLC was performed on a Waters instrument (600/2700 or 2525) fitted with a ZMD or ZQ ESCi mass spectrometers and a Waters X-Terra or a Waters X-Bridge or a Waters SunFire reverse-phase column (C-18, 5 microns silica, 19 mm or 50 mm diameter, 100 mm length, flow rate of 40 mL/minute) using decreasingly polar mixtures of water (containing 1% ammonia) and acetonitrile or decreasingly polar mixtures of water (containing 0.1% formic acid) and acetonitrile as eluents;

(vi) yields, where present, are not necessarily the maximum attainable;

(vii) in general, the structures of end products of the Formula I were confirmed by nuclear magnetic resonance (NMR) spectroscopy; NMR chemical shift values were measured on the delta scale [proton magnetic resonance spectra were determined using a Bruker Avance 500 (500 MHz), Bruker Avance 400 (400 MHz), Bruker Avance 300 (300 MHz) or Bruker DRX (300 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublets; dt, doublet of triplets; bs, broad signal;

(viii) in general, end products of the Formula I were also characterized by mass spectroscopy following liquid chromatography (LCMS or UPLC); in general, reverse-phase C18 silica was used with a flow rate of 1 mL/minute and detection was by Electrospray Mass Spectrometry and by UV absorbance recording a wavelength range of 220-320 nm. Analytical UPLC was performed on CSH C18 reverse-phase silica, using a Waters XSelect CSH C18 column with dimensions 2.1×50 mm and particle size 1.7 micron). Gradient analysis was employed using decreasingly polar mixtures as eluent, for example decreasingly polar mixtures of water (containing 0.1% formic acid or 0.1% ammonia) as solvent A and acetonitrile as solvent B. A typical 2 minute analytical UPLC method would employ a solvent gradient over 1.3 minutes, at approximately 1 mL per minute, from a 97:3 mixture of solvents A and B respectively to a 3:97 mixture of solvents A and B. The reported molecular ion corresponds to the [M+H]+ unless otherwise specified; for molecules with multiple isotopic patterns (Br, Cl, etc.) the reported value is the one obtained for the lowest isotope mass unless otherwise specified;

(ix) ion exchange purification was generally performed using an SCX-2 (Biotage) cartridge;

(x) where reactions refer to the use of a microwave, one of the following microwave reactors were used: Biotage Initiator, Personal Chemistry Emrys Optimizer, Personal Chemistry Smithcreator or CEM Explorer;

(xi) intermediate purity was assessed by thin layer chromatographic, mass spectroscopy, LCMS, UPLC/MS, HPLC and/or NMR analysis;

(xii) the following abbreviations have been used:
DCM dichloromethane
DCE 1,2-dichloroethane
DEA diethylamine
DIPEA diisopropylethylamine
DMA N,N-dimethylacetamide
DMF N,N-dimethylformamide
DMSO dimethylsulfoxide
d.e. diastereomeric excess
dppf 1,1'-bis(diphenylphosphino)ferrocene EtOAc ethyl acetate EtOH ethanol HATU (1-[bis(dimethylamino)methylene]-1H-1,2,3-triazolo[4,5-b]pyridinium 3-oxid hexafluorophosphate)

HCl hydrochloric acid

HCOOH Formic acid

HPLC high performance liquid chromatography mCPBA meta-chloroperoxybenzoic acid

MeCN acetonitrile

MeOH methanol

NMR nuclear magnetic resonance

IPA/i-PrOH isopropanol

Pd—C Palladium on activated carbon

Pd118 Dichloro [1,1'-bis(di-tertbutylphosphino)ferrocene] palladium(II)

PyBOP (Benzotriazol-1-yloxy)tripyrrolidinophosphonium hexafluorophosphate

RuPhos Pd G3 (2-Dicyclohexylphosphino-2',6'-diisopropoxy-1,1'-biphenyl)[2-(2'-amino-1,1'-biphenyl)]palladium(II) methanesulfonate scCO$_2$ supercritical CO$_2$ SFC supercritical fluid chromatography TBME tert-butyl methyl ether TEA triethylamine TFA trifluoroacetic acid THF tetrahydrofuran tR retention time Compounds are otherwise referred to by their IUPAC names or were named using ACD/ChemSketch 2017 commercially available from ACD Labs.

Tert-Butyl (S)-3-(((tert-butyldimethylsilyl)oxy)methyl)piperazine-1-carboxylate

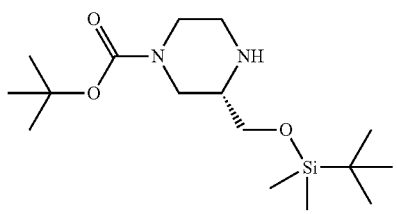 [SMILES: CC(C)(C)OC(=O)N1CCN[C@H](CO[Si](C)(C)C(C)(C)C)C1]

A solution of tert-butyldimethylsilyl chloride (1.53 g, 10.17 mmol) in DCM (10 ml) was added dropwise to (S)-4-N-Boc-2-hydroxymethyl-piperazine (2 g, 9.25 mmol) and triethylamine (2.58 ml, 18.49 mmol) in DCM (50 ml) at 20° C. over a period of 5 minutes under air. The resulting solution was stirred at 20° C. for 16 hours then evaporated to dryness. The residue was purified by flash silica chromatography, elution gradient 0 to 5% EtOH in EtOAc. Pure fractions were evaporated to dryness to afford tert-butyl (S)-3-(((tert-butyldimethylsilyl)oxy)methyl)piperazine-1-carboxylate (2.84 g, 93%) as a colourless oil. 1H NMR (500 MHz, CDCl$_3$) 0.00 (s, 6H), 0.84 (s, 9H), 1.40 (s, 9H), 2.48 (s, 1H), 2.6-2.87 (m, 3H), 2.92 (d, 1H), 3.41 (dd, 1H), 3.52 (s, 1H), 3.85 (s, 2H).

(E)-N-(3-Bromo-2,5-difluorophenyl)-2-(hydroxyimino)acetamide

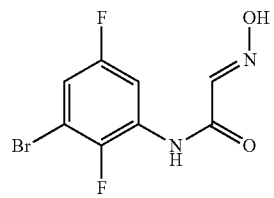 [SMILES: O=C(/C=N/O)Nc1cc(F)cc(Br)c1F]

Sodium sulfate (23.24 g, 163.62 mmol), hydroxylamine hydrochloride (4.97 g, 71.59 mmol) and 2,2,2-trichloroethane-1,1-diol (5.07 g, 30.68 mmol) were dissolved in water (103 ml). A solution of 3-bromo-2,5-difluoroaniline hydrochloride (5 g, 20.45 mmol) in water (8.21 ml), EtOH (14.36 ml) and conc. HCl (3.49 ml) was added and the reaction was stirred overnight at 60° C., forming a precipitate. The precipitate was collected by filtration and washed with water, then dried under vacuum to afford (E)-N-(3-bromo-2,5-difluorophenyl)-2-(hydroxyimino)acetamide (5.3 g, 93%) as a beige solid. This was used without further purification. 1H NMR (500 MHz, DMSO) 7.51 (ddd, 1H), 7.78 (s, 1H), 7.85 (ddd, 1H), 10.08 (s, 1H), 12.43 (s, 1H). m/z: ES− [M−H]− 277.

6-Bromo-4,7-difluoroindoline-2,3-dione

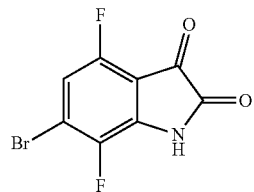

(E)-N-(3-Bromo-2,5-difluorophenyl)-2-(hydroxyimino)acetamide (7.62 g, 27.31 mmol) was added portionwise to sulfuric acid (68.3 ml) heated at 60° C. The reaction was stirred at 90° C. for 1 hour. The reaction mixture was cooled to room temperature and slowly added to ice water. The resulting precipitate was collected by filtration, washing with water and dried under vacuum to afford 6-bromo-4,7-difluoroindoline-2,3-dione (5.1 g, 71%) as a dark red solid. This was used without further purification. 1H NMR (500 MHz, DMSO) 7.38 (dd, 1H), 11.91 (s, 1H). m/z: ES− [M−H]− 260/262.

2-Amino-4-bromo-3,6-difluorobenzoic acid

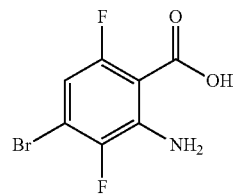 [SMILES: Nc1c(F)c(Br)cc(F)c1C(=O)O]

Hydrogen peroxide (30% in H₂O) (9.70 ml, 95 mmol) was added dropwise to 6-bromo-4,7-difluoroindoline-2,3-dione (4.98 g, 19 mmol) in sodium hydroxide (2M in H₂O) (86 ml, 171 mmol). The reaction was stirred at room temperature for 16 hours. Excess hydrogen peroxide was quenched with excess sodium sulfite, and the mixture was neutralised to pH7. The resulting brown precipitate filtered off and the remaining solution was acidified to pH2 with conc. HCl. The resulting cream precipitate was collected by filtration, washed with water and dried under vacuum to afford 2-amino-4-bromo-3,6-difluorobenzoic acid (3.10 g, 65%) as a brown solid. This was used without further purification. 1H NMR (500 MHz, DMSO) 6.71 (1H, dd), 6.84 (2H, s), 13.37 (1H, s). m/z: ES− [M−H]− 250 & 252.

7-Bromo-5,8-difluoroquinazolin-4(3H)-one

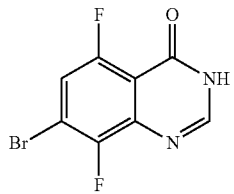 [SMILES: O=c1[nH]cnc2c(F)c(Br)cc(F)c12]

Formimidamide acetate (15.35 g, 147.47 mmol) and 2-amino-4-bromo-3,6-difluorobenzoic acid (3.1 g, 12.29 mmol) in ethanol (49 ml) were stirred at reflux for 16 hours. The reaction mixture was evaporated to dryness and re-dissolved in EtOAc (100 ml), and washed sequentially with saturated brine (2×150 ml). The organic layer was dried with MgSO₄, filtered and evaporated to afford 7-bromo-5,8-difluoroquinazolin-4(3H)-one (2.9 g, 90%) as a yellow solid. This was used without further purification. 1H NMR (500 MHz, DMSO) 7.73 (dd, 1H), 8.17 (s, 1H), 12.62 (s, 1H). m/z: ES− [M−H]− 258 & 260.

Tert-butyl (S)-4-(7-bromo-5,8-difluoroquinazolin-4-yl)-3-(((tert-butyldimethylsilyl)oxy)methyl)piperazine-1-carboxylate

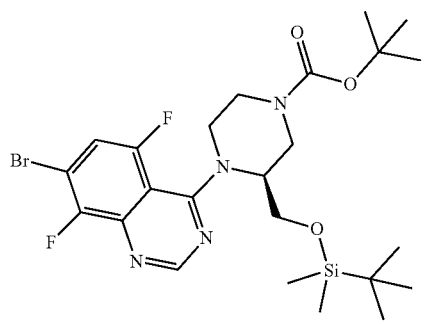 [SMILES: CC(C)(C)OC(=O)N1CCN(c2ncnc3c(F)c(Br)cc(F)c23)[C@H](CO[Si](C)(C)C(C)(C)C)C1]

((1H-Benzo[d][1,2,3]triazol-1-yl)oxy)tri(pyrrolidin-1-yl)phosphonium hexafluorophosphate(V) (2.59 g, 4.98 mmol) was added to 7-bromo-5,8-difluoroquinazolin-4(3H)-one (1 g, 3.83 mmol) and DIPEA (1.61 ml, 9.19 mmol) in DMA (13.72 ml). The resulting solution was stirred at room temperature overnight and the reaction mixture poured into water, extracted with EtOAc (100 ml), washed with saturated brine (100 ml), dried over MgSO₄, filtered and evaporated to afford crude product. The crude product was purified by flash silica chromatography, elution gradient 0 to 100% EtOAc in heptane. Pure fractions were evaporated to dryness to afford tert-butyl (S)-4-(7-bromo-5,8-difluoroquinazolin-4-yl)-3-(((tert-butyldimethylsilyl)oxy)methyl)piperazine-1-carboxylate (0.66 g, 30%) as a pale yellow oil. 1H NMR (500 MHz, CDCl₃) −0.10 (s, 6H), 0.72 (s, 9H), 1.49 (s, 9H), 3.02 (s, 1H), 3.27 (d, 1H), 3.35-3.47 (m, 1H), 3.66 (s, 1H), 3.77-3.85 (m, 1H), 3.91 (d, 1H), 4.17 (d, 2H), 4.32 (s, 1H), 7.22-7.31 (m, 1H), 8.65 (s, 1H). m/z: ES+ [M+H]+ 573 & 575.

Tert-butyl (S)-10-bromo-9-fluoro-3,4,13,13a-tetrahydropyrazino[2',1':3,4][1,4]oxazepino[5,6,7-de]quinazoline-2(1H)-carboxylate

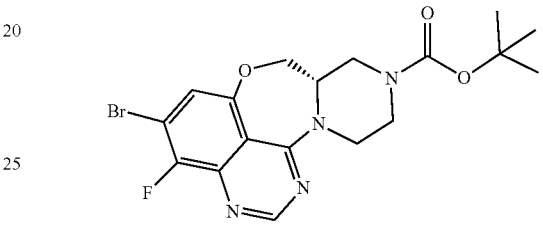

Tetra-butylammonium fluoride (1M in THF) (1.37 ml, 1.37 mmol) was added to tert-butyl (S)-4-(7-bromo-5,8-difluoroquinazolin-4-yl)-3-(((tert-butyldimethylsilyl)oxy)methyl)piperazine-1-carboxylate (0.66 g, 1.14 mmol) in THF (3.2 ml). The resulting solution was stirred at room temperature for 1 hour. The reaction was heated at 65° C. for 1 hour then cooled to room temperature, diluted with EtOAc (100 ml), washed with water (100 ml), saturated brine (100 ml), the organic layer dried over MgSO₄, filtered and evaporated to afford tert-butyl (S)-10-bromo-9-fluoro-3,4,13,13a-tetrahydropyrazino[2',1':3,4][1,4]oxazepino[5,6,7-de]quinazoline-2(1H)-carboxylate (0.54 g, >100%) as a beige foam. This was used without further purification. 1H NMR (500 MHz, CDCl₃) 1.49 (s, 9H), 3.07 (s, 2H), 3.1-3.2 (m, 1H), 3.84 (ddt, 1H), 3.98-4.24 (m, 2H), 4.30 (dd, 1H), 4.38 (dd, 1H), 5.06 (d, 1H), 7.14 (d, 1H), 8.65 (s, 1H). m/z: ES+ [M+H]+ 439/441.

7-Bromo-6-iodo-2,3-dihydro-1H-isoindol-1-one

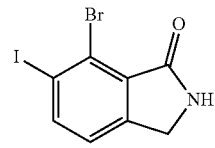

7-bromo-2,3-dihydro-1H-isoindol-1-one (5.7 g, 26.88 mmol) was added to sulfuric acid (60 ml) at 0° C. The resulting mixture was stirred at 0° C. for 30 minutes. Then N-iodosuccinimide (9.07 g, 40.32 mmol) was added in one portion and the resulting suspension stirred at 0° C. for 2 hours. The reaction mixture was poured into ice water, causing a precipitate to form. The precipitate was extracted with ethyl acetate (3×200 ml). Both organic and aqueous phases contained precipitates. The organic phase was washed with 10% Na₂S₂O₃ (200 ml) to remove excess iodine. The organic layer was dried with sodium sulphate, filtered and evaporated to afford 7-bromo-6-iodo-2,3-dihydro-1H-isoindol-1-one (7.2 g, 79%) as a white solid. 1H NMR (400 MHz, DMSO, 30° C.) 4.11 (2H, s), 7.43 (1H, d), 7.83 (1H, d), 8.90 (1H, s). m/z: ES+ [M+H]+=338.

7-Bromo-6-methyl-2,3-dihydro-1H-isoindol-1-one

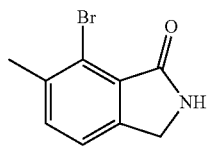

Triphenylphosphine palladium chloride (0.706 g, 1.01 mmol) was added to potassium carbonate (2.78 g, 20.12 mmol), 2,4,6-trimethyl-1,3,5,2,4,6-trioxatriborinane (0.631 g, 5.03 mmol) and 7-bromo-6-iodo-2,3-dihydro-1H-isoindol-1-one (3.4 g, 10.06 mmol) in toluene/H$_2$O (50 ml) (3:1 ratio) under nitrogen. The resulting mixture was stirred at 100° C. overnight. The solvent was removed under reduced pressure. The crude product was purified by preparative chiral-HPLC (Column: Enantiocel-C1, 5*25 cm, 5 um; Mobile Phase A: CO$_2$:70, Mobile Phase B: MeOH-Preparative: 30; Flow rate: 160 ml/min; 220 nm; rT 1:7.38; rT 2:8.53). The fractions containing the desired compound were evaporated to dryness to afford 7-bromo-6-methyl-2, 3-dihydro-1H-isoindol-1-one (420 mg, 45.7%) as a white solid. 1H NMR (400 MHz, DMSO, 30° C.) 2.42 (3H, s), 4.27 (2H, s), 7.46 (1H, d), 7.55 (1H, d), 8.63 (1H, s). m/z: ES+[M+H]$^+$=226.

[(8aS)-10-(Tert-butoxycarbonyl)-4-fluoro-8,8a,9,10, 11,12-hexahydropyrazino[2',1':3,4][1,4]oxazepino[5, 6,7-de]quinazolin-5-yl]boronic acid

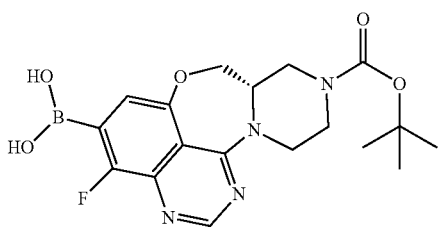 [SMILES: CC(C)(C)OC(=O)N1CCN2c3ncnc4c(F)c(B(O)O)cc(c34)OC[C@@H]2C1]

Pd(dppf)Cl$_2$CH$_2$Cl$_2$ (335 mg, 0.41 mmol) was added to tert-butyl (8aS)-5-bromo-4-fluoro-8a,9,11,12-tetrahydropyrazino[2',1':3,4][1,4]oxazepino[5,6,7-de]quinazoline-10 (8H)-carboxylate (900 mg, 2.05 mmol), 4,4,4',4',5,5,5',5'-octamethyl-2,2'-bi(1,3,2-dioxaborolane) (1041 mg, 4.10 mmol) and potassium acetate (503 mg, 5.12 mmol) in 1,4-dioxane (20 ml) under nitrogen. The resulting mixture was stirred at 100° C. for 2 hours. The solvent was removed under reduced pressure. The crude product was purified by flash C18-flash chromatography, elution gradient 0 to 40% MeCN in water (0.1% TFA). Pure fractions were evaporated to dryness to afford [(8aS)-10-(tert-butoxycarbonyl)-4-fluoro-8,8a,9,10,11,12-hexahydropyrazino[2',1':3,4][1,4] oxazepino[5,6,7-de]quinazolin-5-yl]boronic acid (700 mg, 85%) as a pale yellow solid. 1H NMR (400 MHz, CDCl$_3$, 30° C.) 1.52 (9H, s), 2.85-4.68 (8H, m), 5.37 (1H, s), 7.49 (1H, d), 8.64 (1H, s). Two exchangeable protons not observed. m/z: ES+ [M+H]+=405.

Tert-butyl (8aS)-4-fluoro-5-(5-methyl-3-oxo-2,3-dihydro-1H-isoindol-4-yl)-8a,9,11,12-tetrahydropyrazino[2',1':3,4][1,4]oxazepino[5,6,7-de]quinazoline-10(8H)-carboxylate

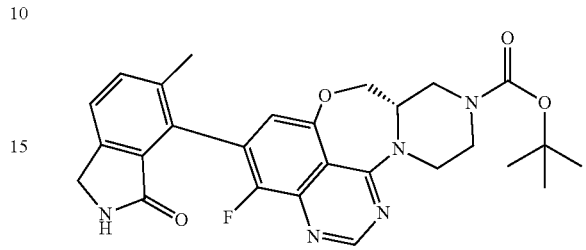

Methanesulfonato(2-dicyclohexylphosphino-2',6'-di-i-propoxy-1,1'-biphenyl)(2-amino-1,1'-biphenyl-2-yl)palladium(II) (129 mg, 0.15 mmol) was added to 2-dicyclohexylphosphino-2',6'-di-i-propoxy-1,1'-biphenyl (72.2 mg, 0.15 mmol), potassium carbonate (428 mg, 3.10 mmol), [(8aS)-10-(tert-butoxycarbonyl)-4-fluoro-8,8a,9,10,11,12-hexahydropyrazino[2',1':3,4][1,4]oxazepino[5,6,7-de]quinazolin-5-yl]boronic acid (626 mg, 1.55 mmol) and 7-bromo-6-methyl-2,3-dihydro-1H-isoindol-1-one (350 mg, 1.55 mmol) in 1,4-dioxane/H$_2$O (0.5 ml) (3:1 ratio) at room temperature under nitrogen. The resulting mixture was stirred at 100° C. for 2 hours. The solvent was removed under reduced pressure. The crude product was purified by flash silica chromatography, elution gradient 6% MeOH in DCM. Pure fractions were evaporated to dryness to afford tert-butyl (8aS)-4-fluoro-5-(5-methyl-3-oxo-2,3-dihydro-1H-isoindol-4-yl)-8a,9,11,12-tetrahydropyrazino[2',1':3,4] [1,4]oxazepino [5,6,7-de]quinazoline-10(8H)-carboxylate (470 mg, 60%) as a pale yellow solid. 1H NMR (400 MHz, CDCl$_3$, 30° C.) 1.52 (9H, s), 2.24 (3H, d), 2.99-3.35 (3H, m), 3.48-3.97 (1H, m), 4.02-4.29 (2H, m), 4.35-4.58 (4H, m), 5.08-5.27 (1H, m), 6.06 (1H, s), 6.92 (1H, d), 7.46 (1H, d), 7.53 (1H, d), 8.72 (1H, s). m/z: ES+ [M+H]+=506.

Tert-butyl (8aS)-6-chloro-4-fluoro-5-(5-methyl-3-oxo-2,3-dihydro-1H-isoindol-4-yl)-8a,9,11,12-tetrahydropyrazino[2',1':3,4][1,4]oxazepino[5,6,7-de] quinazoline-10(8H)-carboxylate

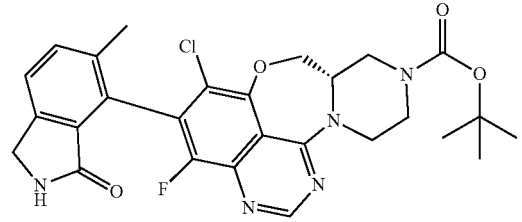 [SMILES: Cc1ccc2c(c1-c1c(Cl)c3c4c(ncnc4c1F)N1CCN(C(=O)OC(C)(C)C)C[C@H]1CO3)C(=O)NC2]

A mixture of N-chlorosuccinimide (186 mg, 1.39 mmol) and tert-butyl (8aS)-4-fluoro-5-(5-methyl-3-oxo-2,3-dihydro-1H-isoindol-4-yl)-8a,9,11,12-tetrahydropyrazino[2', 1':3,4][1,4]oxazepino[5,6,7-de]quinazoline-10(8H)-carboxylate (470 mg, 0.93 in DMF (0.5 ml)) were sealed into a microwave tube.

The reaction was heated at 120° C. for 30 minutes in the microwave reactor and cooled to room temperature. The crude product was purified by flash C18-flash chromatography, elution gradient 0 to 35% MeCN in water (0.1% HCOOH). Pure fractions were evaporated to dryness to afford tert-butyl (8aS)-6-chloro-4-fluoro-5-(5-methyl-3-oxo-2,3-dihydro-1H-isoindol-4-yl)-8a,9,11,12-tetrahydropyrazino[2',1':3,4][1,4]oxazepino[5,6,7-de]quinazoline-10(8H)-carboxylate (260 mg, 52%) as a pale yellow solid. 1H NMR (400 MHz, DMSO, 30° C.) 1.45 (9H, s), 2.09 (3H, d), 2.98-3.47 (3H, m), 3.81-4.17 (3H, m), 4.37 (2H, s), 4.61-4.68 (2H, m), 4.83-4.94 (1H, m), 7.61 (1H, d), 8.51 (1H, d), 8.64 (1H, s). 1 exchangeable proton not observed. m/z: ES+ [M+H]+=540.

7-[(8aS)-6-Chloro-4-fluoro-8,8a,9,10,11,12-hexahydropyrazino[2',1':3,4][1,4]oxazepino[5,6,7-de]quinazolin-5-yl]-6-methyl-2,3-dihydro-1H-isoindol-1-one—Atropisomer 1 and Atropisomer 2

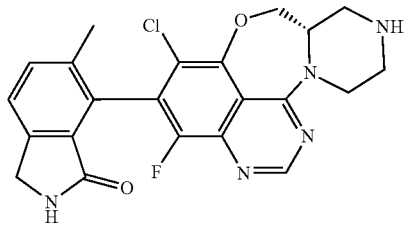 [SMILES: Cc1ccc2c(c1-c1c(Cl)c3c4c(ncnc4c1F)N1CCNC[C@H]1CO3)C(=O)NC2]

HCl in 1,4-dioxane (5 ml, 20 mmol) was added to tert-butyl (8aS)-6-chloro-4-fluoro-5-(5-methyl-3-oxo-2,3-dihydro-1H-isoindol-4-yl)-8a,9,11,12-tetrahydropyrazino[2',1':3,4][1,4]oxazepino[5,6,7-de]quinazoline-10(8H)-carboxylate (260 mg, 0.48 mmol) in MeOH (3 ml) at room temperature. The resulting solution was stirred at room temperature for 2 hours. The solvent was removed under reduced pressure. The crude product was purified by preparative HPLC (Column: Xselect CSH OBD Column 30*150 mm 5 um n; Mobile Phase A: Water (0.1% HCOOH), Mobile Phase B: ACN; Flow rate: 60 ml/min; Gradient: 10% B to 20% B in 8 min; 254/220 nm; rT: 7.03, 7.97 min) and MeCN as eluents. Fractions containing the desired compound were evaporated to dryness to afford a first eluting atropisomer of 7-[(8aS)-6-chloro-4-fluoro-8,8a,9,10,11,12-hexahydropyrazino[2',1':3,4][1,4] oxazepino[5,6,7-de]quinazolin-5-yl]-6-methyl-2,3-dihydro-1H-isoindol-1-one (Atropisomer 1) (80 mg, 38%) as a white solid. 1H NMR (400 MHz, DMSO, 30° C.) 2.08 (3H, s), 2.77 (2H, d), 2.99-3.14 (3H, m), 4.01 (1H, s), 4.36 (2H, s), 4.42-4.59 (2H, m), 4.96 (1H, d), 7.55-7.65 (1H, m), 8.15 (1H, s), 8.48 (1H, s), 8.57 (1H, s). One exchangeable proton not seen. m/z: ES+ [M+H]+=440.

A 2$^{nd}$ eluting atropisomer (Atropisomer 2) (70 mg, 33%) was obtained as a white solid. 1H NMR (400 MHz, DMSO, 30° C.) 2.09 (3H, s), 2.74-2.92 (2H, m), 3.08 (3H, m), 3.93 (1H, d), 4.36 (2H, s), 4.46-4.59 (2H, m), 4.93 (1H, d), 7.55-7.68 (1H, m), 8.17 (1H, s), 8.49 (1H, s), 8.57 (1H, s). One exchangeable proton not seen. m/z: ES+ [M+H]+=440.

7-[(8aS)-10-Acryloyl-6-chloro-4-fluoro-8,8a,9,10,11,12-hexahydropyrazino[2',1':3,4][1,4]oxazepino[5,6,7-de]quinazolin-5-yl]-6-methyl-2,3-dihydro-1H-isoindol-1-one—Atropisomer 1 (Example 1)

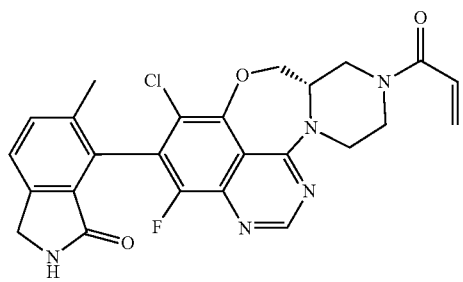 [SMILES: C=CC(=O)N1CCN2c3ncnc4c(F)c(-c5c(C)ccc6c5C(=O)NC6)c(Cl)c(c34)OC[C@@H]2C1]

A solution of acryloyl chloride (16.46 mg, 0.18 mmol) in DMF (0.2 ml) was added to a stirred solution of DIPEA (0.064 ml, 0.36 mmol) and 7-[(8aS)-6-chloro-4-fluoro-8,8a,9,10,11,12-hexahydropyrazino[2',1':3,4][1,4]oxazepino[5,6,7-de]quinazolin-5-yl]-6-methyl-2,3-dihydro-1H-isoindol-1-one (Atropisomer 1) (80 mg, 0.18 mmol) in DMF (0.3 ml) at 0° C. The resulting solution was stirred at 0° C. for 1 hour. The crude product was purified by flash C18-flash chromatography, elution gradient 0 to 35% MeCN in water (NH$_4$OH). Pure fractions were evaporated to dryness to afford 7-[(8aS)-10-acryloyl-6-chloro-4-fluoro-8,8a,9,10,11,12-hexahydropyrazino[2',1':3,4][1,4]oxazepino [5,6,7-de]quinazolin-5-yl]-6-methyl-2,3-dihydro-1H-isoindol-1-one (Atropisomer 1, Example 1) (19 mg, 21%) as a white solid. 1H NMR (400 MHz, DMSO, 30° C.) 2.08 (3H, s), 3.01-3.13 (1H, m), 3.32-3.53 (2H, m), 4.09-4.53 (5H, m), 4.54-4.72 (2H, m), 4.76-5.04 (1H, m), 5.77 (1H, d), 6.19 (1H, d), 6.77-6.98 (1H, m), 7.56-7.66 (2H, m), 8.48 (1H, s), 8.62 (1H, s). m/z: ES+ [M+H]+=494.

7-[(8aS)-10-Acryloyl-6-chloro-4-fluoro-8,8a,9,10,11,12-hexahydropyrazino[2',1':3,4][1,4]oxazepino[5,6,7-de]quinazolin-5-yl]-6-methyl-2,3-dihydro-1H-isoindol-1-one—Atropisomer 2 (Example 2)

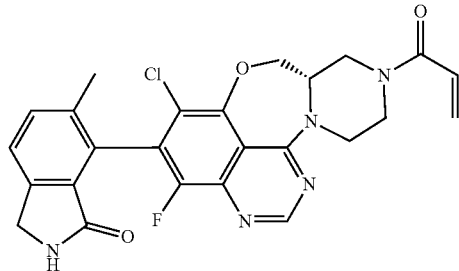 [SMILES: C=CC(=O)N1CCN2c3ncnc4c(F)c(-c5c(C)ccc6c5C(=O)NC6)c(Cl)c(c34)OC[C@@H]2C1]

A solution of acryloyl chloride (14.40 mg, 0.16 mmol) in DMF (0.2 ml) was added to a stirred solution of DIPEA (0.056 ml, 0.32 mmol) and 7-[(8aS)-6-chloro-4-fluoro-8,8a,9,10,11,12-hexahydropyrazino[2',1':3,4][1,4]oxazepino[5,6,7-de]quinazolin-5-yl]-6-methyl-2,3-dihydro-1H-isoindol-1-one—Atropisomer 2 (70 mg, 0.16 mmol) in DMF (0.3 ml) at 0° C. The resulting solution was stirred at 0° C. for 1 hour. The crude product was purified by flash C18-flash chromatography, elution gradient 0 to 30% MeCN in water (NH₄OH). Pure fractions were evaporated to dryness to afford 7-[(8aS)-10-acryloyl-6-chloro-4-fluoro-8,8a,9,10,11,12-hexahydropyrazino[2',1':3,4][1,4]oxazepino [5,6,7-de]quinazolin-5-yl]-6-methyl-2,3-dihydro-1H-isoindol-1-one (Atropisomer 2, Example 2) (27.0 mg, 34.4%) as a white solid. 1H NMR (400 MHz, DMSO, 30° C.) 2.10 (3H, s), 2.97-3.30 (2H, m), 3.36-3.57 (1H, m), 3.98-4.56 (5H, m), 4.58-4.72 (2H, m), 4.76-5.00 (1H, m), 5.76 (1H, d), 6.19 (1H, d), 6.78-6.98 (1H, m), 7.56-7.68 (2H, m), 8.50 (1H, s), 8.62 (1H, s). m/z: ES+ [M+H]+=494.

Methyl N-benzyl-D-serinate

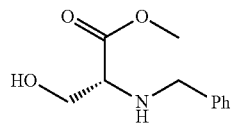

TEA (44.8 ml, 321.38 mmol) was added to a solution of methyl D-serinate hydrochloride (50 g, 321.38 mmol) and benzaldehyde (33 ml, 321.38 mmol) in methanol (250 ml) at 0° C. The resulting suspension was stirred at room temperature for 2 hours. Then sodium borohydride (24 g, 634.39 mmol) was added slowly and the mixture stirred at room temperature for another 2 hours. The reaction mixture was quenched with water (200 ml), extracted with DCM (3×100 ml), the organic layer was dried over sodium sulphate, filtered and evaporated. The crude product was purified by flash silica chromatography, elution gradient 0 to 60% EtOAc in petroleum ether. Pure fractions were evaporated to dryness to afford methyl N-benzyl-D-serinate (40 g, 60%) as a colourless oil. 1H NMR (400 MHz, CDCl₃, 30° C.) 2.51 (2H, s), 3.48 (1H, dd), 3.65 (1H, dd), 3.76-3.84 (5H, m), 3.92 (1H, d), 7.36 (5H, m). m/z: ES+ [M+H]+=210.

Methyl N-(tert-butoxycarbonyl)-L-alanyl-N-benzyl-D-serinate

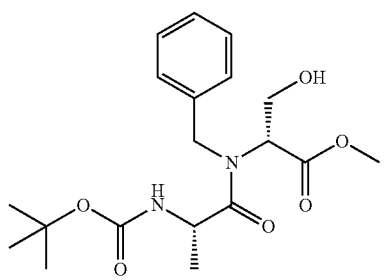 [SMILES: COC(=O)[C@@H](CO)N(Cc1ccccc1)C(=O)[C@H](C)NC(=O)OC(C)(C)C]

Isobutyl chloroformate (15.66 g, 114.70 mmol) was added to a solution of methyl N-(tert-butoxycarbonyl)-L-alaninate (27.1 g, 143.37 mmol) and N-Methylmorpholine (11.6 g, 114.70 mmol) in THF (100 ml) at 0° C. and the reaction temperature was allowed to rise to 25° C. and stirred for 1 hour. N-benzyl-D-serinate (20 g, 95.58 mmol) in THF (100 ml) was then added and the mixture was stirred overnight. The reaction mixture was filtered and washed with EtOAc. After removing the solvents under reduced pressure, the crude product was purified by flash silica chromatography, elution gradient 0 to 50% EtOAc in petroleum ether. Pure fractions were evaporated to dryness to afford methyl N-(tert-butoxycarbonyl)-L-alanyl-N-benzyl-D-serinate (16 g, 44%) as a colourless oil. 1H NMR (400 MHz, CDCl₃, 30° C.) 1.22 (3H, d), 1.44 (9H, s), 3.74 (3H, s), 3.91 (2H, d), 4.06 (1H, m), 4.53-4.63 (1H, m), 4.72 (1H, m), 4.84 (1H, m), 5.28 (1H, m), 7.31-7.45 (5H, m). One exchangeable proton not seen. m/z: ES+ [M+H]+=381.

(3R,6S)-1-Benzyl-3-(hydroxymethyl)-6-methylpiperazine-2,5-dione

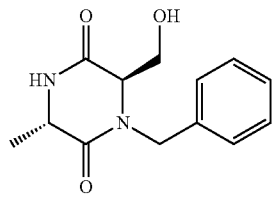 [SMILES: C[C@@H]1NC(=O)[C@@H](CO)N(Cc2ccccc2)C1=O]

TFA (20 ml, 259.60 mmol) was added to a solution of methyl N-(tert-butoxycarbonyl)-L-alanyl-N-benzyl-D-serinate (10 g, 26.29 mmol) in DCM (200 ml) at 25° C. The mixture was stirred at 25° C. for 2 hours. The reaction mixture was basified with saturated aqueous sodium carbonate and stirred at 25° C. for 1 hour, extracted and the organic solvent evaporated. The crude product was purified by flash silica chromatography, elution gradient 0 to 60% EtOAc in petroleum ether. Pure fractions were evaporated to dryness to afford (3R,6S)-1-benzyl-3-(hydroxymethyl)-6-methylpiperazine-2,5-dione (4.8 g, 74%) as a yellow oil. 1H NMR (400 MHz, CDCl₃, 30° C.). 1.50 (3H, d), 3.49 (1H, s), 3.80 (1H, d), 3.91 (1H, dd), 3.98-4.08 (2H, m), 4.37 (1H, d), 5.34 (1H, d), 7.23-7.41 (5H, m). One exchangeable proton not seen. m/z: ES+ [M+H]+=249.

[(2S,5S)-1-Benzyl-5-methylpiperazin-2-yl]methanol

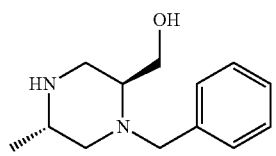 [SMILES: C[C@H]1CN(Cc2ccccc2)[C@H](CO)CN1]

Lithium aluminum hydride (5.26 g, 138.55 mmol) was added slowly to a solution of (3R,6S)-1-benzyl-3-(hydroxymethyl)-6-methylpiperazine-2,5-dione (4.3 g, 17.32 mmol) in THF (75 ml) at 0° C. The resulting mixture was then stirred at 65° C. for 5 hours. The reaction mixture was quenched with water (2.9 ml), 15% NaOH aqueous (8.7 ml) and water (2.9 ml) separately. The reaction mixture was filtered through celite, washed with EtOAc (100 ml). After removing the solvent under reduced pressure [(2S,5S)-1-benzyl-5-methylpiperazin-2-yl]methanol (3.8 g, 100%) was obtained as colorless oil. 1H NMR (400 MHz, CDCl₃, 30° C.) 0.98 (3H, d), 2.06 (3H, m), 2.35-2.43 (1H, m), 2.72-2.82 (2H, m), 3.03-3.08 (2H, m), 3.14 (1H, m), 3.48 (1H, dd), 4.03 (1H, dd), 4.18 (1H, d), 7.30-7.40 (5H, m). m/z: ES+ [M+H]+= 221.

Tert-butyl (2S,5S)-4-benzyl-5-(hydroxymethyl)-2-methylpiperazine-1-carboxylate

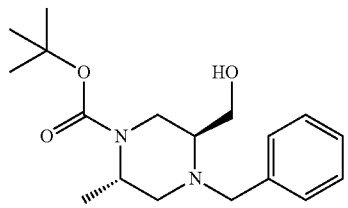 [SMILES: C[C@H]1CN(Cc2ccccc2)[C@H](CO)CN1C(=O)OC(C)(C)C]

Di-tert-butyl dicarbonate (9.06 ml, 39.03 mmol) was added to a solution of [(2S,5S)-1-benzyl-5-methylpiperazin-2-yl]methanol (4.3 g, 19.52 mmol) and TEA (4.08 ml, 29.28 mmol) in DCM (200 ml) at 25° C. The resulting solution was stirred at 25° C. overnight. After removing the solvent by evaporation, the crude product was purified by flash silica chromatography, elution gradient 0 to 100% EtOAc in petroleum ether. Pure fractions were evaporated to dryness to afford tert-butyl (2S,5S)-4-benzyl-5-(hydroxymethyl)-2-methylpiperazine-1-carboxylate (3.3 g, 53%) as a colourless oil. 1H NMR (400 MHz, CDCl$_3$, 30° C.) 1.22 (3H, d), 1.49 (9H, s), 1.68 (1H, s), 2.35 (1H, s), 2.81 (2H, m), 3.28 (1H, dd), 3.61-3.83 (4H, m), 4.02 (1H, d), 4.09 (1H, s), 7.34 (5H, d). m/z: ES+ [M+H]+=321.

Tert-butyl (2S,5S)-5-(hydroxymethyl)-2-methylpiperazine-1-carboxylate

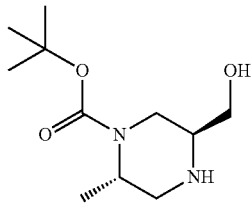 [SMILES: C[C@H]1CN[C@H](CO)CN1C(=O)OC(C)(C)C]

10% Pd—C (0.11 g, 1.03 mmol) was added to a solution of tert-butyl (2S,5S)-4-benzyl-5-(hydroxymethyl)-2-methylpiperazine-1-carboxylate (3.3 g, 10.30 mmol) in EtOH (5 ml) at room temperature under nitrogen. The resulting solution was purged with hydrogen and stirred under 1 atmosphere of hydrogen at 25° C. for 24 hours. The mixture was filtered through a Celite pad and washed with DCM (20 ml). After removing the solvents under reduced pressure, the product tert-butyl (2S,5S)-5-(hydroxymethyl)-2-methylpiperazine-1-carboxylate (2.2 g, 93%) was obtained as a white solid. 1H NMR (400 MHz, CDCl$_3$, 30° C.) 1.20-1.27 (3H, m), 1.48 (9H, s), 2.40 (2H, s), 2.51-2.56 (1H, m), 3.07 (2H, m), 3.23 (1H, m), 3.52 (1H, m), 3.66-3.76 (2H, m), 4.07-4.22 (1H, m). m/z: ES+ [M+H]+=231.

Tert-butyl (2S,5S)-5-{[(7-bromo-8-fluoro-4-hydroxyquinazolin-5-yl)oxy]methyl}-2-methylpiperazine-1-carboxylate

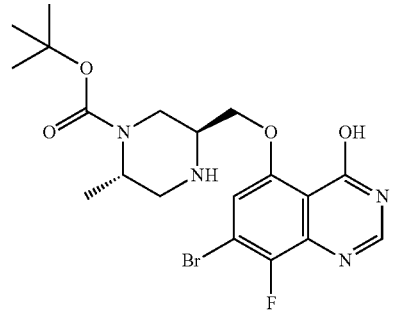 [SMILES: C[C@H]1CN[C@H](COc2cc(Br)c(F)c3ncnc(O)c23)CN1C(=O)OC(C)(C)C]

Sodium hydride (0.575 g, 14.37 mmol) was added to a solution of tert-butyl (2S,5S)-5-(hydroxymethyl)-2-methylpiperazine-1-carboxylate (0.882 g, 3.83 mmol) and 7-bromo-5,8-difluoroquinazolin-4(3H)-one (1 g, 3.83 mmol) in THF (40 ml) at room temperature. The resulting mixture was stirred at 60° C. for 4 hours. The reaction mixture was quenched with saturated NH$_4$Cl (20 ml), extracted with EtOAc (3×30 ml), the organic layer was dried over sodium sulphate, filtered and evaporated. The crude product was purified by flash silica chromatography, elution gradient 0 to 80% EtOAc in petroleum ether. Pure fractions were evaporated to dryness to afford tert-butyl (2S,5S)-5-{[(7-bromo-8-fluoro-4-hydroxyquinazolin-5-yl)oxy]methyl}-2-methylpiperazine-1-carboxylate (1 g, 55%) as a tan solid. 1H NMR (400 MHz, CDCl$_3$, 30° C.) 1.27 (3H, d), 1.49 (9H, s), 3.56 (1H, dd), 3.66 (1H, dd), 3.85 (1H, dd), 4.11 (1H, m), 4.24-4.32 (2H, m), 4.46 (1H, dd), 4.64 (1H, dd), 7.17 (1H, d), 8.62 (1H, s). Two exchangeable protons not observed. m/z: ES+ [M+H]+=471.

Tert-butyl (8aS,11S)-5-bromo-4-fluoro-11-methyl-8a,9,11,12-tetrahydropyrazino[2',1':3,4][1,4]oxazepino[5,6,7-de]quinazoline-10(8H)-carboxylate

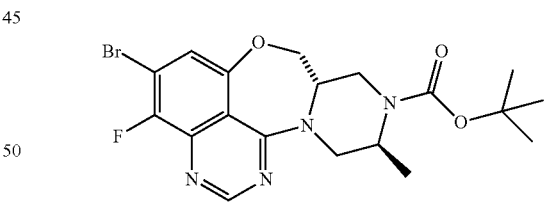

2,3,4,6,7,8,9,10-Octahydropyrimido[1,2-a]azepine (291 mg, 1.91 mmol) was added to a solution of tert-butyl (2S,5S)-5-{[(7-bromo-8-fluoro-4-hydroxyquinazolin-5-yl)oxy]methyl}-2-methylpiperazine-1-carboxylate (900 mg, 1.91 mmol) and ((1H-benzo[d][1,2,3]triazol-1-yl)oxy)tri(pyrrolidin-1-yl)phosphonium hexafluorophosphate(V) (994 mg, 1.91 mmol) at 0° C. The resulting solution was stirred at 25° C. for 4 hours. The crude product was purified by flash C18-flash chromatography, elution gradient 0 to 100% MeOH in water (0.1% HCOOH). Pure fractions were evaporated to dryness to afford tert-butyl (8aS,11S)-5-bromo-4-fluoro-11-methyl-8a,9,11,12-tetrahydropyrazino[2',1':3,4][1,4] oxazepino[5,6,7-de]quinazoline-10(8H)-carboxylate (388 mg, 45%) as a tan solid. 1H NMR (400 MHz, CDCl₃, 30° C.) 1.27 (3H, d), 1.49 (9H, s), 3.56 (1H, dd), 3.66 (1H, dd), 3.85 (1H, dd), 4.11 (1H, m), 4.24-4.32 (2H, m), 4.46 (1H, dd), 4.64 (1H, dd), 7.17 (1H, d), 8.62 (1H, s). m/z: ES+ [M+H]+=453.

Tert-butyl (8aS,11S)-5-bromo-6-chloro-4-fluoro-11-methyl-8a,9,11,12-tetrahydropyrazino[2',1':3,4][1,4]oxazepino[5,6,7-de]quinazoline-10(8H)-carboxylate

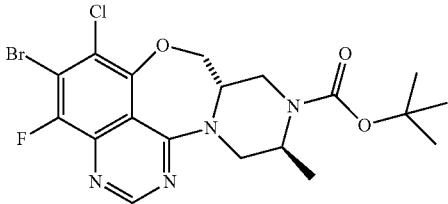 [SMILES: C[C@H]1CN2c3ncnc4c(F)c(Br)c(Cl)c(c34)OC[C@@H]2CN1C(=O)OC(C)(C)C]

N-Chlorosuccinimide (110 mg, 0.83 mmol) was added to a solution of tert-butyl (8aS,11S)-5-bromo-4-fluoro-11-methyl-8a,9,11,12-tetrahydropyrazino[2',1':3,4][1,4]oxazepino[5,6,7-de]quinazoline-10(8H)-carboxylate (340 mg, 0.75 mmol) in DMF (7.5 ml) at room temperature. The resulting solution was stirred at 60° C. for 4 hours. The crude product was purified by flash C18-flash chromatography, elution gradient 50 to 100% MeOH in water (0.1% HCOOH). Pure fractions were evaporated to dryness to afford tert-butyl (8aS,11S)-5-bromo-6-chloro-4-fluoro-11-methyl-8a,9,11,12-tetrahydropyrazino[2',1':3,4][1,4]oxazepino[5,6,7-de]quinazoline-10(8H)-carboxylate (310 mg, 85%) as a tan solid. 1H NMR (400 MHz, CDCl₃, 30° C.) 1.29 (3H, d), 1.49 (9H, s), 3.49-3.57 (1H, m), 3.67 (1H, dd), 3.91 (1H, dd), 4.14 (1H, dd), 4.25-4.35 (1H, m), 4.38 (1H, dd), 4.62-4.76 (2H, m), 8.68 (1H, s). m/z: ES+ [M+H]+=487.

Tert-butyl (3S,13aS)-11-chloro-9-fluoro-10-(2-fluoro-6-hydroxyphenyl)-3-methyl-3,4,13,13a-tetrahydropyrazino[2',1':3,4][1,4]oxazepino[5,6,7-de]quinazoline-2(1H)-carboxylate

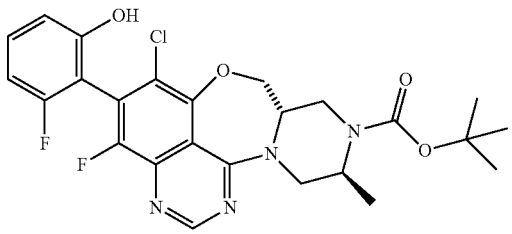 [SMILES: C[C@H]1CN2c3ncnc4c(F)c(-c5c(O)cccc5F)c(Cl)c(c34)OC[C@@H]2CN1C(=O)OC(C)(C)C]

Potassium carbonate (54.4 mg, 0.39 mmol) was added to a mixture of tert-butyl (8aS,11S)-5-bromo-6-chloro-4-fluoro-11-methyl-8a,9,11,12-tetrahydropyrazino[2',1':3,4][1,4]oxazepino[5,6,7-de]quinazoline-10(8H)-carboxylate (96 mg, 0.20 mmol), (2-fluoro-6-hydroxyphenyl)boronic acid (77 mg, 0.49 mmol), dicyclohexyl(2',6'-diisopropoxy-[1,1'-biphenyl]-2-yl)phosphane (18.37 mg, 0.04 mmol) and RuPhos-Pd-G3 (32.9 mg, 0.04 mmol) in water (2 ml) and 1,4-dioxane (8 ml) (1:4 ratio) at room temperature under nitrogen. The resulting mixture was stirred at 100° C. for 2 hours. After evaporating the solvents, the crude product was purified by flash C18-flash chromatography, elution gradient 0 to 70% MeCN in water (0.1% TFA). Pure fractions were evaporated to dryness to afford tert-butyl (8aS,11S)-6-chloro-4-fluoro-5-(2-fluoro-6-hydroxyphenyl)-11-methyl-8a,9,11,12-tetrahydropyrazino[2',1':3,4][1,4]oxazepino[5,6,7-de]quinazoline-10(8H)-carboxylate (28 mg, 27%) as a yellow solid. 1H NMR (400 MHz, CDCl₃, 30° C.) 1.26 (3H, d), 1.53 (9H, s), 3.61-3.74 (2H, m), 3.83 (1H, m), 4.00 (1H, m), 4.32 (2H, m), 4.46 (1H, m), 4.57 (1H, m), 6.73 (1H, d), 6.93 (1H, d), 7.29-7.36 (1H, m), 8.25 (1H, s). One exchangeable proton not seen. m/z: ES+ [M+H]+=519.

2-[(8aS,11S)-6-Chloro-4-fluoro-11-methyl-8,8a,9,10,11,12-hexahydropyrazino[2',1':3,4][1,4]oxazepino[5,6,7-de]quinazolin-5-yl]-3-fluorophenol

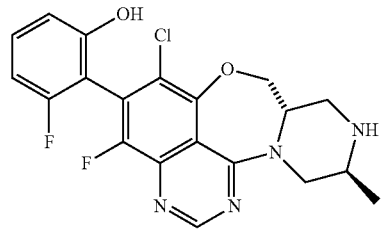 [SMILES: C[C@H]1CN2c3ncnc4c(F)c(-c5c(O)cccc5F)c(Cl)c(c34)OC[C@@H]2CN1]

HCl (2 ml, 65.83 mmol) was added to a solution of tert-butyl (3S,13aS)-11-chloro-9-fluoro-10-(2-fluoro-6-hydroxyphenyl)-3-methyl-3,4,13,13a-tetrahydropyrazino[2',1':3,4][1,4]oxazepino[5,6,7-de]quinazoline-2(1H)-carboxylate (40 mg, 0.08 mmol) in MeOH (2 ml) at 25° C. The solution was stirred at 25° C. for 1 hour. The crude product was purified by ion exchange chromatography, using an SCX column. The desired product was eluted from the column using 7M NH₃/MeOH and pure fractions were evaporated to dryness to afford 2-[(8aS,11S)-6-chloro-4-fluoro-11-methyl-8,8a,9,10,11,12-hexahydropyrazino[2',1':3,4][1,4]oxazepino[5,6,7-de]quinazolin-5-yl]-3-fluorophenol (25 mg, 77%) as a pale yellow solid. 1H NMR (400 MHz, CD₃OD, 30° C.) 1.26 (3H, d), 2.88 (1H, dd), 2.97-3.04 (1H, m), 3.04-3.15 (2H, m), 3.28 (1H, dd), 4.07 (1H, m), 4.47-4.57 (1H, m), 4.57-4.65 (1H, m), 5.20 (1H, dd), 6.69-6.77 (1H, m), 6.79 (1H, m), 7.33 (1H, m), 8.55 (1H, s). One exchangeable proton not seen. m/z: ES+[M+H]+=419.

1-[(8aS,11S)-6-Chloro-4-fluoro-5-(2-fluoro-6-hydroxyphenyl)-11-methyl-8a,9,11,12-tetrahydropyrazino[2',1':3,4][1,4]oxazepino[5,6,7-de]quinazolin-10(8H)-yl]prop-2-en-1-one (Example 3)

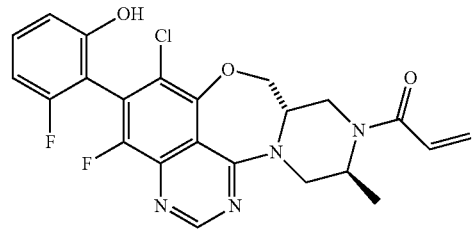 [SMILES: C=CC(=O)N1C[C@H]2COc3c(Cl)c(-c4c(O)cccc4F)c(F)c4ncnc(c34)N2C[C@@H]1C]

DIPEA (0.021 ml, 0.12 mmol) was added to a solution of 2-[(8aS,11S)-6-chloro-4-fluoro-11-methyl-8,8a,9,10,11,12-hexahydropyrazino[2',1':3,4][1,4]oxazepino[5,6,7-de]quinazolin-5-yl]-3-fluorophenol (25 mg, 0.06 mmol) and acryloyl chloride (5.4 mg, 0.06 mmol) in THF (2 ml) at 0° C. The resulting solution was stirred at 0° C. for 1 hour. After removing the solvent by evaporation, the crude product was purified by flash C18-flash chromatography, elution gradient 0 to 60% MeCN in water (0.1% NH₄HCO₃). Pure fractions were evaporated to dryness to afford 1-[(8aS,11S)-6-chloro-4-fluoro-5-(2-fluoro-6-hydroxyphenyl)-11-methyl-8a,9,11,12-tetrahydropyrazino[2',1':3,4][1,4]oxazepino[5,6,7-de]quinazolin-10(8H)-yl]prop-2-en-1-one (Example 3) (16 mg, 57%) as a pale yellow solid. 1H NMR (400 MHz, DMSO, 30° C.) 1.23 (3H, d), 3.89 (3H, m), 4.24-4.58 (4H, m), 4.71 (1H, d), 5.75 (1H, dd), 6.20 (1H, dd), 6.68-6.98 (3H, m), 7.35 (1H, m), 8.57 (1H, s), 10.28 (1H, s). m/z: ES+ [M+H]+= 473.

Methyl N-benzyl-D-serinate

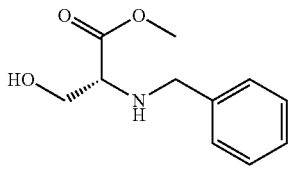

TEA (44.8 ml, 321.38 mmol) was added to a solution of methyl D-serinate hydrochloride (50 g, 321.38 mmol) and benzaldehyde (33 ml, 321.38 mmol) in methanol (250 ml) at 0° C. The resulting suspension was stirred at room temperature for 2 hours. Then sodium borohydride (24 g, 634.39 mmol) was added slowly and the mixture was stirred at room temperature for another 2 hours. The reaction mixture was quenched with water (200 ml), extracted with DCM (3×100 ml), the organic layer was dried over sodium sulphate, filtered and evaporated. The crude product was purified by flash silica chromatography, elution gradient 0 to 60% EtOAc in petroleum ether. Pure fractions were evaporated to dryness to afford methyl N-benzyl-D-serinate (40 g, 60%) as a colourless oil. 1H NMR (400 MHz, CDCl₃, 30° C.) 2.51 (2H, s), 3.48 (1H, dd), 3.65 (1H, dd), 3.76-3.84 (5H, m), 3.92 (1H, d), 7.36 (5H, m). m/z: ES+ [M+H]+=210.

Methyl N-(tert-butoxycarbonyl)-D-alanyl-N-benzyl-D-serinate

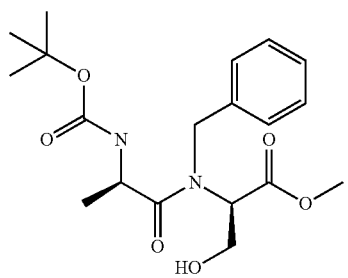 [SMILES: COC(=O)[C@@H](CO)N(Cc1ccccc1)C(=O)[C@@H](C)NC(=O)OC(C)(C)C]

N-Methylmorpholine (14.5 g, 143.37 mmol) was added to a solution of methyl N-(tert-butoxycarbonyl)-D-alaninate (27.1 g, 143.37 mmol) and Isobutyl chloroformate (19.58 g, 143.37 mmol) in THF (100 ml) at 0° C. The resulting solution was stirred at 0° C. for 1 hour. Then methyl N-benzyl-D-serinate (20 g, 95.58 mmol) in THF (100 ml) was added. The mixture was stirred at 25° C. overnight. After removing the solvents, the crude product was purified by flash silica chromatography, elution gradient 20 to 80% EtOAc in petroleum ether. Pure fractions were evaporated to dryness to afford methyl N-(tert-butoxycarbonyl)-D-alanyl-N-benzyl-D-serinate (18 g, 50%) as a colourless liquid. 1H NMR (300 MHz, CDCl₃, 30° C.) 1.30 (3H, d), 1.44 (9H, s), 3.73 (3H, s), 3.82 (1H, m), 4.06-4.20 (1H, m), 4.32 (1H, m), 4.66 (1H, m), 4.73 (2H, d), 5.31 (1H, d), 7.30-7.44 (5H, m). One exchangeable proton not seen. m/z: ES+ [M+H]+=381.

(3R,6R)-1-Benzyl-6-(hydroxymethyl)-3-methylpiperazine-2,5-dione

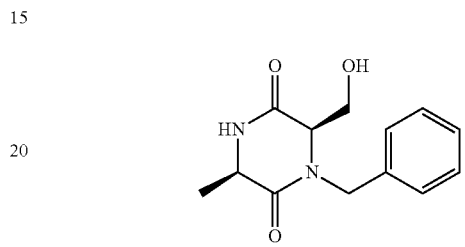

TFA (40 ml, 519.19 mmol) was added to a solution of methyl N-(tert-butoxycarbonyl)-D-alanyl-N-benzyl-D-serinate (18 g, 47.31 mmol) in DCM (400 ml). The resulting solution was stirred at 25° C. for 2 hours. The reaction mixture was basified with saturated sodium carbonate and stirred for 1 hour, extracted and the organic solvent evaporated. The crude product was purified by C18-flash chromatography, elution gradient 0 to 60% MeOH in water (0.1% HCOOH). Pure fractions were evaporated to dryness to afford (3R,6R)-1-benzyl-6-(hydroxymethyl)-3-methylpiperazine-2,5-dione (5.6 g, 46%) as a colourless foam. 1H NMR (300 MHz, CDCl₃, 30° C.) 1.61 (3H, d), 3.26 (1H, s), 3.80-4.27 (5H, m), 5.33 (1H, d), 7.25-7.53 (6H, m). m/z: ES+ [M+H]+=249.

[(2S,5R)-1-Benzyl-5-methylpiperazin-2-yl]methanol

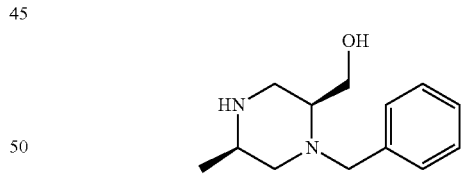

Lithium aluminium hydride (3.42 g, 90.22 mmol) was added portionwise to (3R,6R)-1-benzyl-6-(hydroxymethyl)-3-methylpiperazine-2,5-dione (2.8 g, 11.28 mmol) in THF (50 ml) at 0° C. under nitrogen. The resulting solution was stirred at 65° C. for 4 hours. The reaction mixture was quenched with water (3.3 ml), 15% NaOH aqueous (9.9 ml) and water (9.9 ml) separately. The mixture was filtered and evaporated to afford [(2S,5R)-1-benzyl-5-methylpiperazin-2-yl]methanol (2.4 g, 97%) as colourless oil. 1H NMR (400 MHz, CDCl₃, 30° C.) 1.03 (3H, d), 2.59 (1H, dd), 2.69 (1H, d), 3.03 (2H, m), 3.15-3.20 (1H, m), 3.24 (1H, m), 3.82-3.91 (3H, m), 4.10 (1H, m), 7.33-7.39 (5H, m). Two exchangeable protons not observed. m/z: ES+ [M+H]+=221.

tert-Butyl (2R,5S)-4-benzyl-5-(hydroxymethyl)-2-methylpiperazine-1-carboxylate

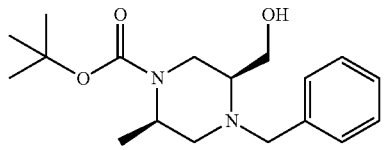 [SMILES: C[C@@H]1CN(Cc2ccccc2)[C@H](CO)CN1C(=O)OC(C)(C)C]

Triethylamine (3.51 g, 34.72 mmol) was added to a solution of [(2S,5R)-1-benzyl-5-methylpiperazin-2-yl]methanol (5.1 g, 23.15 mmol) and di-tert-butyl dicarbonate (10.1 g, 46.3 mmol) in DCM (230 ml) at 25° C. The solution was stirred at 25° C. overnight. After evaporating the solvent, the crude product was purified by flash silica chromatography, elution gradient 0 to 50% EtOAc in petroleum ether. Pure fractions were evaporated to dryness to afford tert-butyl (2R,5S)-4-benzyl-5-(hydroxymethyl)-2-methylpiperazine-1-carboxylate (3.1 g, 42%) as a yellow solid. 1H NMR (400 MHz, CDCl$_3$, 30° C.) 1.19 (3H, d), 1.48 (9H, s), 2.32 (2H, m), 2.42 (1H, d), 2.62-2.71 (1H, m), 3.15 (1H, d), 3.24 (1H, t), 3.50 (1H, d), 3.87 (1H, d), 3.99 (1H, m), 4.18 (2H, d), 7.34 (5H, m). m/z: ES+ [M+H]+=321.

Tert-butyl (2R,5S)-5-(hydroxymethyl)-2-methylpiperazine-1-carboxylate

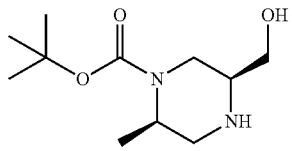 [SMILES: C[C@@H]1CN[C@H](CO)CN1C(=O)OC(C)(C)C]

10% Pd—C (1.030 g, 9.67 mmol) was added in one portion to tert-butyl (2R,5S)-4-benzyl-5-(hydroxymethyl)-2-methylpiperazine-1-carboxylate (3.1 g, 9.67 mmol) in ethanol (20 ml) at 25° C. under nitrogen. The resulting solution was stirred under an atmosphere of hydrogen at 25° C. for 24 hours. The reaction mixture was filtered through celite and washed with DCM (100 ml). After removing the solvent by evaporation, tert-butyl (2R,5S)-5-(hydroxymethyl)-2-methylpiperazine-1-carboxylate (2.2 g, 99%) was obtained as colorless oil. 1H NMR (400 MHz, CDCl$_3$, 30° C.) 1.22 (3H, d), 1.48 (9H, s), 2.32 (2H, s), 2.69-2.83 (2H, m), 2.86 (1H, dd), 2.97 (1H, dd), 3.49-3.59 (1H, m), 3.62-3.74 (1H, m), 3.80 (1H, s), 4.20 (1H, s). m/z: ES+ [M+H]+=231.

Tert-butyl (2R,5S)-5-{[(7-bromo-8-fluoro-4-hydroxyquinazolin-5-yl)oxy]methyl}-2-methylpiperazine-1-carboxylate

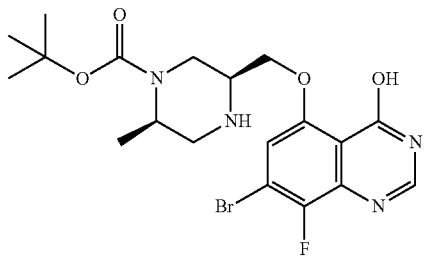 [SMILES: C[C@@H]1CN[C@H](COc2cc(Br)c(F)c3ncnc(O)c23)CN1C(=O)OC(C)(C)C]

Sodium hydride (326 mg, 8.14 mmol) was added to a solution of tert-butyl (2R,5S)-5-(hydroxymethyl)-2-methylpiperazine-1-carboxylate (500 mg, 2.17 mmol) and 7-bromo-5,8-difluoroquinazolin-4-ol (567 mg, 2.17 mmol) in THF (50 ml) at room temperature. The resulting mixture was stirred at 45° C. for 12 hours. The reaction mixture was quenched with water and evaporated to dryness. The crude product was purified by C18-flash chromatography, elution gradient 0 to 60% MeCN in water (0.1% TFA). Pure fractions were evaporated to dryness to afford tert-butyl (2R,5S)-5-{[(7-bromo-8-fluoro-4-hydroxyquinazolin-5-yl)oxy]methyl}-2-methylpiperazine-1-carboxylate (395 mg, 39%) as a tan solid. 1H NMR (400 MHz, CDCl$_3$, 30° C.) 1.23 (3H, d), 1.50 (9H, s), 3.10 (2H, m), 3.25 (1H, m), 4.06 (3H, m), 4.29 (2H, m), 7.05 (1H, d), 8.10 (1H, s). Two exchangeable protons not observed. m/z: ES+ [M+H]+=471.

Tert-butyl (8aS,11R)-5-bromo-4-fluoro-11-methyl-8a,9,11,12-tetrahydropyrazino[2',1':3,4][1,4]oxazepino[5,6,7-de]quinazoline-10(8H)-carboxylate

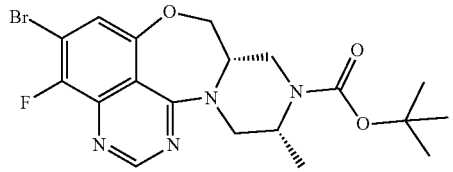 [SMILES: C[C@@H]1CN2c3ncnc4c(F)c(Br)cc(c34)OC[C@@H]2CN1C(=O)OC(C)(C)C]

2,3,4,6,7,8,9,10-Octahydropyrimido[1,2-a]azepine (111 mg, 0.73 mmol) was added to a solution of tert-butyl (2R,5S)-5-{[(7-bromo-8-fluoro-4-hydroxyquinazolin-5-yl)oxy]methyl}-2-methylpiperazine-1-carboxylate (345 mg, 0.73 mmol) and ((1H-benzo[d][1,2,3]triazol-1-yl)oxy)tri(pyrrolidin-1-yl)phosphonium hexafluorophosphate(V) (381 mg, 0.73 mmol) in acetonitrile (35 ml) at 0° C. The resulting solution was stirred at 25° C. for 24 hours. The crude product was purified by flash C18-flash chromatography, elution gradient 0 to 60% MeCN in water (0.1% TFA). Pure fractions were evaporated to dryness to afford tert-butyl (8aS,11R)-5-bromo-4-fluoro-11-methyl-8a,9,11,12-tetrahydropyrazino[2',1':3,4][1,4]oxazepino[5,6,7-de]quinazoline-10(8H)-carboxylate (192 mg, 58%) as a yellow solid. 1H NMR (400 MHz, CDCl$_3$, 30° C.) 8.67 (s, 1H), 7.21 (d, 1H), 5.26-5.03 (m, 1H), 4.41 (s, 2H), 4.14 (d, 1H), 3.97 (d, 1H), 3.82 (s, 1H), 3.45-3.19 (m, 2H), 1.52 (s, 9H), 1.13 (d, 3H). m/z: ES+ [M+H]+=453.

Tert-butyl (8aS,11R)-5-bromo-6-chloro-4-fluoro-11-methyl-8a,9,11,12-tetrahydropyrazino[2',1':3,4][1,4]oxazepino[5,6,7-de]quinazoline-10(8H)-carboxylate

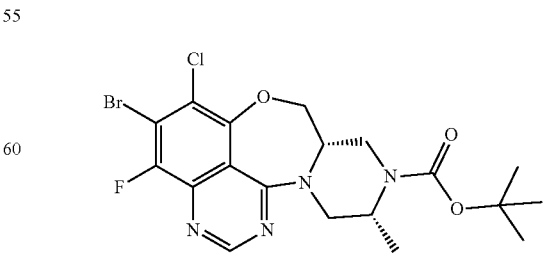

N-Chlorosuccinimide (56.6 mg, 0.42 mmol) was added to a solution of tert-butyl (8aS,11R)-5-bromo-4-fluoro-11- methyl-8a,9,11,12-tetrahydropyrazino[2',1':3,4][1,4]oxazepino[5,6,7-de]quinazoline-10(8H)-carboxylate (192 mg, 0.42 mmol) in DMF (4 ml) at room temperature. The resulting solution was stirred at 60° C. for 4 hours. The crude product was purified by C18 flash chromatography, elution gradient 0% to 90% CH3CN in water (0.1% TFA). Pure fractions were evaporated to dryness to afford tert-butyl (8aS,11R)-5-bromo-6-chloro-4-fluoro-11-methyl-8a,9,11,12-tetrahydropyrazino[2',1':3,4] [1,4]oxazepino[5,6,7-de]quinazoline-10(8H)-carboxylate (184 mg, 89%) as a tan solid. 1H NMR (400 MHz, CDCl$_3$, 30° C.) 1.14 (3H, d), 1.50 (9H, s), 3.26-3.74 (2H, m), 4.02-4.73 (5H, m), 5.16-5.44 (1H, m), 8.77 (1H, s). m/z: ES+ [M+H]+=487.

Tert-butyl (8aS,11R)-6-chloro-4-fluoro-5-(2-fluoro-6-hydroxyphenyl)-11-methyl-8a,9,11,12-tetrahydropyrazino[2',1':3,4][1,4]oxazepino[5,6,7-de]quinazoline-10(8H)-carboxylate (Atropisomer 1 and 2)

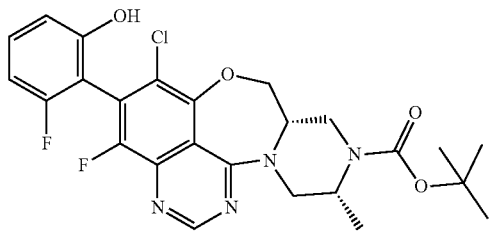 [SMILES: C[C@@H]1CN2c3ncnc4c(F)c(-c5c(O)cccc5F)c(Cl)c(c34)OC[C@@H]2CN1C(=O)OC(C)(C)C]

RuPhos-Pd-G3 (240 mg, 0.29 mmol) was added to a solution of tert-butyl (8aS,11R)-5-bromo-6-chloro-4-fluoro-11-methyl-8a,9,11,12-tetrahydropyrazino[2',1':3,4][1,4]oxazepino[5,6,7-de]quinazoline-10(8H)-carboxylate (700 mg, 1.44 mmol), (2-fluoro-6-hydroxyphenyl)boronic acid (559 mg, 3.58 mmol), potassium carbonate (595 mg, 4.31 mmol) and dicyclohexyl(2',6'-diisopropoxy-[1,1'-biphenyl]-2-yl)phosphane (134 mg, 0.29 mmol) in 1,4-dioxane/H$_2$O (10 ml)(4:1 ratio) under nitrogen. The resulting mixture was stirred at 100° C. for 30 minutes. The solvent was removed under reduced pressure. The crude product was purified by flash silica chromatography, elution gradient 0 to 40% EtOAc in petroleum ether. Pure fractions were evaporated to dryness to afford:

Atropisomer 1 of tert-butyl (8aS,11R)-6-chloro-4-fluoro-5-(2-fluoro-6-hydroxyphenyl)-11-methyl-8a,9,11,12-tetrahydropyrazino[2',1':3,4][1,4]oxazepino[5,6,7-de]quinazoline-10(8H)-carboxylate (250 mg, 34%) as a pale yellow solid 1H NMR (400 MHz, CDCl$_3$, 30° C.) 1.12 (3H, s), 1.49 (9H, s), 3.19-3.63 (3H, m), 3.75-3.87 (1H, m), 3.93-4.18 (1H, m), 4.22-4.63 (2H, m), 4.67-5.06 (1H, m), 6.73 (1H, t), 6.89 (1H, d), 7.24-7.36 (1H, m), 8.50 (1H, s). One exchangeable proton not seen. m/z: ES+ [M+H]+=519.

Atropisomer 2 of tert-butyl (8aS,11R)-6-chloro-4-fluoro-5-(2-fluoro-6-hydroxyphenyl)-11-methyl-8a,9,11,12-tetrahydropyrazino[2',1':3,4][1,4]oxazepino[5,6,7-de]quinazoline-10(8H)-carboxylate (270 mg, 36%) as a pale yellow solid. 1H NMR (400 MHz, CDCl$_3$, 30° C.) 1.07-1.20 (3H, m), 1.52 (9H, s), 3.14-3.53 (3H, m), 3.77-3.91 (1H, m), 3.95-4.18 (1H, m), 4.29-4.57 (2H, m), 5.03-5.24 (1H, m), 6.76 (1H, t), 6.90 (1H, d), 7.27-7.37 (1H, m), 8.50 (1H, s). One exchangeable proton not seen. m/z: ES+ [M+H]+=519.

2-[(8aS,11R)-6-chloro-4-fluoro-11-methyl-8,8a,9,10,11,12-hexahydropyrazino[2',1':3,4] [1,4]oxazepino [5,6,7-de]quinazolin-5-yl]-3-fluorophenol (Atropisomer 1)

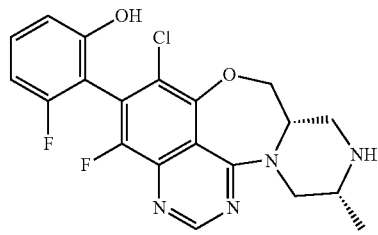 [SMILES: C[C@@H]1CN2c3ncnc4c(F)c(-c5c(O)cccc5F)c(Cl)c(c34)OC[C@@H]2CN1]

A solution of 4M HCl in 1,4-dioxane (5 ml, 20 mmol) was added slowly to a stirred solution of Atropisomer 1 of tert-butyl (8aS,11R)-6-chloro-4-fluoro-5-(2-fluoro-6-hydroxyphenyl)-11-methyl-8a,9,11,12-tetrahydropyrazino[2',1':3,4][1,4]oxazepino[5,6,7-de]quinazoline-10(8H)-carboxylate (250 mg, 0.48 mmol) obtained above in MeOH (2 ml). The resulting solution was stirred at room temperature for 1 hour and the solvent then removed under reduced pressure to afford Atropisomer of 2-[(8aS,11R)-6-chloro-4-fluoro-11-methyl-8,8a,9,10,11,12-hexahydropyrazino[2',1': 3,4][1,4] oxazepino[5,6,7-de]quinazolin-5-yl]-3-fluorophenol.1HCl (400 mg, 183%) as yellow solid which was used in the next step directly without further purification. 1H NMR (400 MHz, CD$_3$OD, 30° C.) 1.43 (3H, d), 3.53-3.64 (1H, m), 3.66 (1H, d), 3.74 (4H, d), 3.93-4.04 (1H, m), 4.13 (1H, s), 6.73-6.86 (2H, m), 7.32-7.43 (1H, m), 8.83 (1H, s). Two exchangeable protons not seen m/z: ES+ [M+H]+=419.

1-[(8aS,11R)-6-Chloro-4-fluoro-5-(2-fluoro-6-hydroxyphenyl)-11-methyl-8a,9,11,12-tetrahydropyrazino[2',1':3,4][1,4]oxazepino[5,6,7-de]quinazolin-10(8H)-yl]prop-2-en-1-one—Atropisomer 1, Example 4

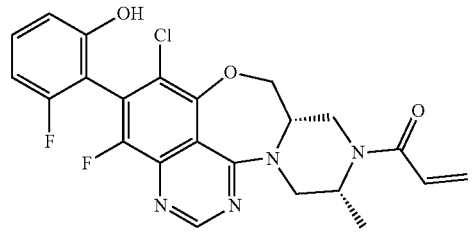 [SMILES: C=CC(=O)N1C[C@H]2COc3c(Cl)c(-c4c(O)cccc4F)c(F)c4ncnc(c34)N2C[C@H]1C]

Acryloyl chloride (46.1 mg, 0.51 mmol) was added to 2-[(8aS,11R)-6-chloro-4-fluoro-11-methyl-8,8a,9,10,11,12-hexahydropyrazino[2',1':3,4][1,4]oxazepino[5,6,7-de]quinazolin-5-yl]-3-fluorophenol.1HCl (400 mg, 0.88 mmol) and DIPEA (227 mg, 1.76 mmol) in THF (5 ml) at 0° C. The resulting solution was stirred at 0° C. for 40 minutes. The crude product was purified by flash C18-flash chromatography, elution gradient 0 to 30% MeCN in water (0.1% NH$_4$HCO$_3$). Pure fractions were evaporated to dryness to afford 1-[(8aS,11R)-6-chloro-4-fluoro-5-(2-fluoro-6-hydroxyphenyl)-11-methyl-8a,9,11,12-tetrahydropyrazino[2',1':3,4][1,4]oxazepino [5,6,7-de]quinazolin-10(8H)-yl]prop-2-en-1-one (130 mg, 31%) as a white solid. 1H NMR (400

MHz, DMSO, 30° C.) 1.12 (3H, dd), 3.10-3.21 (0.5H, m), 3.50-3.60 (1.5H, m), 3.98-4.14 (1H, m), 4.21-4.77 (4H, m), 4.89-5.06 (1H, m), 5.70-5.80 (1H, m), 6.04-6.23 (1H, m), 6.77-6.92 (3H, m), 7.32-7.42 (1H, m), 8.63 (1H, s). One exchangeable proton not seen. m/z: ES+ [M+H]+=473.

2-[(8aS,11R)-6-Chloro-4-fluoro-11-methyl-8,8a,9,10,11,12-hexahydropyrazino[2',1':3,4] [1,4]oxazepino[5,6,7-de]quinazolin-5-yl]-3-fluorophenol, Atropisomer 2

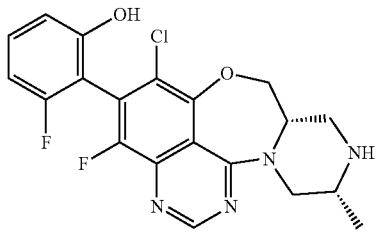 [SMILES: C[C@@H]1CN2c3ncnc4c(F)c(-c5c(O)cccc5F)c(Cl)c(c34)OC[C@@H]2CN1]

A solution of 4M HCl in 1,4-dioxane (5 ml, 20 mmol) was added slowly to a stirred solution of Atropisomer 2 of tert-butyl (8aS,11R)-6-chloro-4-fluoro-5-(2-fluoro-6-hydroxyphenyl)-11-methyl-8a,9,11,12-tetrahydropyrazino[2',1':3,4][1,4]oxazepino[5,6,7-de]quinazoline-10(8H)-carboxylate (270 mg, 0.52 mmol) obtained above in MeOH (3 ml). The resulting solution was stirred at room temperature for 1 hour and the solvent then removed under reduced pressure to afford 2-[(8aS,11R)-6-chloro-4-fluoro-11-methyl-8,8a,9,10,11,12-hexahydropyrazino [2',1':3,4][1,4] oxazepino[5,6,7-de]quinazolin-5-yl]-3-fluorophenol.1HCl (400 mg, 169%) as yellow solid. Product used in the next step directly without further purification. 1H NMR (400 MHz, CD₃OD, 30° C.) 1.43 (3H, d), 3.55-3.60 (1H, m), 3.63-3.68 (1H, m), 3.71-3.80 (4H, m), 3.90-4.00 (1H, m), 4.10 (1H, s), 6.73-6.86 (2H, m), 7.32-7.46 (1H, m), 8.83 (1H, s). Two exchangeable protons not seen. m/z: ES+ [M+H]+=419.

1-[(8aS,11R)-6-Chloro-4-fluoro-5-(2-fluoro-6-hydroxyphenyl)-11-methyl-8a,9,11,12-tetrahydropyrazino[2',1':3,4][1,4]oxazepino[5,6,7-de]quinazolin-10(8H)-yl]prop-2-en-1-one Atropisomer 2, Example 5

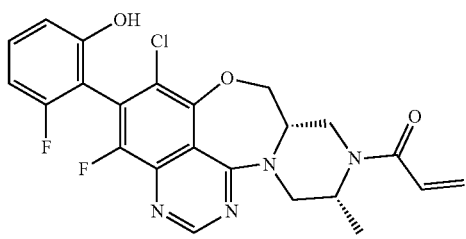

Acryloyl chloride (43.7 mg, 0.48 mmol) was added to Atropisomer 2 of 2-[(8aS,11R)-6-chloro-4-fluoro-11-methyl-8,8a,9,10,11,12-hexahydropyrazino[2',1':3,4][1,4] oxazepino[5,6,7-de]quinazolin-5-yl]-3-fluorophenol.1HCl (400 mg, 0.88 mmol), and DIPEA (227 mg, 1.76 mmol) in THF (5 ml) at 0° C. The resulting solution was stirred at 0°

C. for 40 minutes. The crude product was purified by flash C18-flash chromatography, elution gradient 0 to 30% MeCN in water (0.1% NH₄HCO₃). Pure fractions were evaporated to dryness to afford 1-[(8aS,11R)-6-chloro-4-fluoro-5-(2-fluoro-6-hydroxyphenyl)-11-methyl-8a,9,11,12-tetrahydropyrazino [2',1':3,4][1,4]oxazepino[5,6,7-de]quinazolin-10 (8H)-yl]prop-2-en-1-one (160 mg, 38%) as a white solid. 1H NMR (400 MHz, DMSO, 30° C.) 1.11 (3H, dd), 3.16 (0.5H, t), 3.41-3.61 (1.5H, m), 3.93-4.07 (1H, m), 4.20-4.83 (4H, m), 4.88-5.05 (1H, m), 5.70-5.80 (1H, m), 6.13-6.24 (1H, m), 6.76-6.93 (3H, m), 7.36 (1H, q), 8.59 (1H, s), 10.27 (1H, s). m/z: ES+ [M+H]+=473.

6-Amino-2-bromo-3-methylbenzoic acid

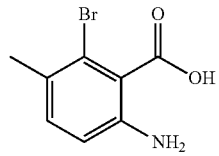

A mixture of 3N NaOH (80 ml, 79.15 mmol) and 4-bromo-5-methyl-1H-indole-2,3-dione (19 g, 79.15 mmol) was heated at 80° C. To the solution was added hydrogen peroxide (18 ml, 176.22 mmol) slowly and the mixture was stirred for 1 hour and the mixture cooled to 5° C. then acidified to pH5 with concentrated HCl. The solution was evaporated to dryness and methanol (100 ml) then added. The mixture was filtered and the filtrate was evaporated to yield 6-amino-2-bromo-3-methylbenzoic acid (18 g, 99%) as brown solid. 1H NMR (400 MHz, DMSO, 30° C.) 2.21 (3H, s), 6.71 (1H, d), 7.07 (1H, d). Three exchangeable protons not observed. m/z: ES+ [M+H]+=230.

5-Bromo-6-methylquinazolin-4(3H)-one

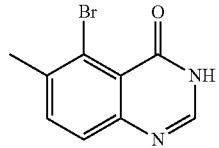

6-Amino-2-bromo-3-methylbenzoic acid (15 g, 65.2 mmol) was dissolved in formamide (45 ml) and sealed into a microwave tube. The reaction was heated to 200° C. for 1 hour in the microwave reactor then cooled to room temperature. The reaction mixture was diluted with EtOH (200 ml). The precipitate was collected by filtration, washed with EtOH (20 ml) and dried under vacuum to afford 5-bromo-6-methylquinazolin-4(3H)-one (9 g, 58%) as a brown solid. 1H NMR (400 MHz, DMSO, 30° C.) 2.47 (3H, s), 7.56 (1H, d), 7.74 (1H, d), 8.04 (1H, s), 12.24 (1H, s). m/z: ES+ [M+H]+=239.

5-Bromo-4-methoxy-6-methylquinazoline

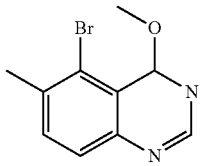

PyBOP (6.53 g, 12.55 mmol) was added in one portion to 5-bromo-6-methylquinazolin-4(3H)-one (2 g, 8.37 mmol) and DIPEA (2.92 ml, 16.73 mmol) in DMF (20 ml) at 25° C. The resulting solution was stirred at 40° C. for 16 hours. Sodium methoxide in methanol (1.506 g, 8.37 mmol) was then added and the resulting solution was stirred at 40° C. for 16 hours. The reaction mixture was poured into water (100 ml), extracted with EtOAc (2×100 ml), the organic layer was dried over MgSO$_4$, filtered and evaporated. The crude product was purified by flash C18-flash chromatography, elution gradient 5 to 80% MeCN in water. Pure fractions were evaporated to dryness to afford 5-bromo-4-methoxy-6-methylquinazoline (1.5 g, 71%) as a white solid. 1H NMR (400 MHz, DMSO, 30° C.) 2.55 (3H, s), 4.11 (3H, s), 7.83 (1H, d), 7.90 (1H, d), 8.75 (1H, s). m/z: ES+ [M+H]+=254.

Tert-Butyl (8aS)-4-fluoro-5-(4-methoxy-6-methylquinazolin-5-yl)-8a,9,11,12-tetrahydropyrazino[2',1':3,4][1,4]oxazepino[5,6,7-de]quinazoline-10(8H)-carboxylate

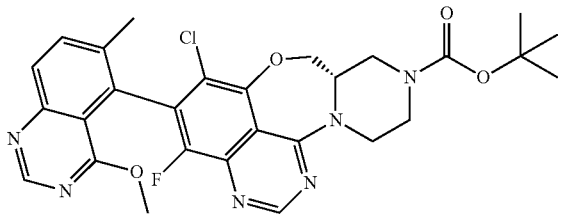 [SMILES: COc1ncnc2ccc(C)c(-c3c(Cl)c4c5c(ncnc5c3F)N3CCN(C(=O)OC(C)(C)C)C[C@H]3CO4)c12]

RuPhos-Pd-G3. (51.7 mg, 0.06 mmol) was added to ([(8aS)-10-(tert-butoxycarbonyl)-4-fluoro-8,8a,9,10,11,12-hexahydropyrazino[2',1':3,4][1,4]oxazepino[5,6,7-de]quinazolin-5-yl]boronic acid (250 mg, 0.62 mmol), 5-bromo-4-methoxy-6-methylquinazoline (188 mg, 0.74 mmol), 2-dicyclohexylphosphino-2',6'-di-i-propoxy-1,1'-biphenyl (28.9 mg, 0.06 mmol) and potassium carbonate (214 mg, 1.55 mmol) in 1,4-dioxane (0.4 ml) and water (0.1 ml) (4:1 ratio) under nitrogen. The resulting mixture was stirred at 100° C. for 40 minutes. The solvent was removed under reduced pressure. The crude product was purified by flash silica chromatography, elution gradient 0 to 5% MeOH in DCM. Pure fractions were evaporated to dryness to afford crude product. The crude product was purified by flash C18-flash chromatography, elution gradient 0 to 55% MeOH in water (0.1% TFA). Pure fractions were evaporated to dryness to afford tert-butyl (8aS)-4-fluoro-5-(4-methoxy-6-methylquinazolin-5-yl)-8a,9,11,12-tetrahydropyrazino[2',1':3,4][1,4]oxazepino[5,6,7-de]quinazoline-10(8H)-carboxylate (150 mg, 46%) as a yellow solid. 1H NMR (400 MHz, DMSO, 30° C.) 1.46 (9H, s), 2.11 (3H, d), 2.16-2.37 (2H, m), 2.52-3.56 (6H, m), 3.86-5.05 (4H, m), 7.74 (1H, d), 7.84 (1H, d), 7.99 (1H, s), 8.11 (1H, s), 8.71 (1H, s). m/z: ES+ [M+H]+=533.

Tert-butyl (8aS)-6-chloro-4-fluoro-5-(4-methoxy-6-methylquinazolin-5-yl)-8a,9,11,12-tetrahydropyrazino[2',1':3,4][1,4]oxazepino[5,6,7-de]quinazoline-10(8H)-carboxylate

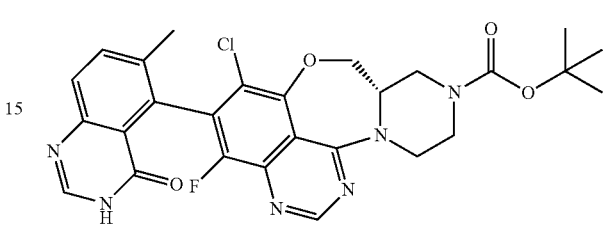

N-Chlorosuccinimide (36.1 mg, 0.27 mmol) was added to tert-butyl (8aS)-4-fluoro-5-(4-methoxy-6-methylquinazolin-5-yl)-8a,9,11,12-tetrahydropyrazino[2',1':3,4][1,4]oxazepino[5,6,7-de]quinazoline-10(8H)-carboxylate (120 mg, 0.23 mmol) in acetonitrile (0.5 ml). The resulting mixture was stirred at 40° C. for 4 hours. The solvent was removed under reduced pressure to afford the crude product tert-butyl (8aS)-6-chloro-4-fluoro-5-(4-methoxy-6-methylquinazolin-5-yl)-8a,9,11,12-tetrahydropyrazino [2',1':3,4][1,4]oxazepino[5,6,7-de]quinazoline-10(8H)-carboxylate (200 mg, >100%) which was used directly in the next step without further purification. m/z: ES+ [M+H]+=567.

5-[(8aS)-6-Chloro-4-fluoro-8,8a,9,10,11,12-hexahydropyrazino[2',1':3,4][1,4]oxazepino[5,6,7-de]quinazolin-5-yl]-6-methylquinazolin-4(3H)-one

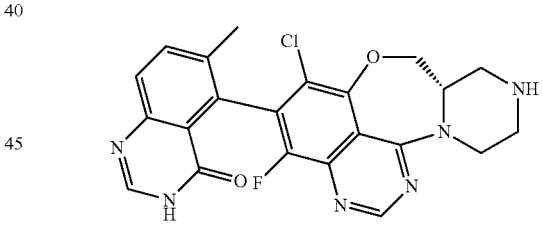

Boron tribromide in DCM (2 ml, 2 mmol) was added to tert-butyl (8aS)-6-chloro-4-fluoro-5-(4-methoxy-6-methylquinazolin-5-yl)-8a,9,11,12-tetrahydropyrazino[2',1':3,4][1,4]oxazepino[5,6,7-de]quinazoline-10(8H)-carboxylate (190 mg, 0.34 mmol). The resulting suspension was stirred at room temperature for 2 hours. The solvent was removed under reduced pressure. The crude product was purified by flash C18-flash chromatography, elution gradient 0 to 50% MeOH in water (NH$_4$HCO$_3$). Pure fractions were evaporated to dryness to afford 5-[(8aS)-6-chloro-4-fluoro-8,8a,9,10,11,12-hexahydropyrazino[2',1':3,4][1,4]oxazepino[5,6,7-de]quinazolin-5-yl]-6-methylquinazolin-4(3H)-one (50 mg, 33%) as a white solid. 1H NMR (400 MHz, DMSO, 30° C.) 2.06 (3H, d), 2.60-2.83 (2H, m), 2.94-3.12 (3H, m), 3.17 (1H, d), 3.83-4.16 (1H, m), 4.37-4.60 (2H, m), 4.88-5.00 (1H, m), 7.72 (1H, d), 7.84 (1H, d), 8.04 (1H, s), 8.54 (1H, s). One exchangeable proton not seen. m/z: ES+ [M+H]+= 453.

5-[(8aS)-10-Acryloyl-6-chloro-4-fluoro-8,8a,9,10,11,12-hexahydropyrazino[2',1':3,4][1,4]oxazepino[5,6,7-de]quinazolin-5-yl]-6-methylquinazolin-4(3H)-one—Atropisomer 1 (Example 6) and Atropisomer 2 (Example 7)

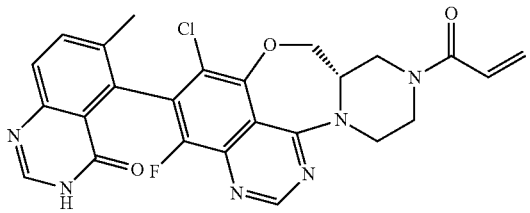 [SMILES: C=CC(=O)N1CCN2c3ncnc4c(F)c(-c5c(C)ccc6nc[nH]c(=O)c56)c(Cl)c(c34)OC[C@@H]2C1]

A solution of acryloyl chloride (9 mg, 0.10 mmol) in DMF (2 ml) was added to a stirred solution of 5-[(8aS)-6-chloro-4-fluoro-8,8a,9,10,11,12-hexahydropyrazino[2',1':3,4][1,4]oxazepino[5,6,7-de]quinazolin-5-yl]-6-methylquinazolin-4(3H)-one (45 mg, 0.10 mmol) and DIPEA (0.035 ml, 0.20 mmol) in DMF (3 ml) at 0° C. The resulting solution was stirred at 0° C. for 1 hour. The crude product was purified by flash C18-flash chromatography, elution gradient 0 to 48% MeOH in water (NH₄OH). Pure fractions were evaporated to dryness to afford crude product. The crude product was purified by preparative chiral-HPLC (Column: CHIRALPAK IA 2*25 cm, 5 um; Mobile Phase A:Hex:DCM=3:1 (10 mM NH₃-MeOH)-HPLC, Mobile Phase B: EtOH-HPLC; Flow rate: 14 ml/min; Gradient: 50 B to 50 B in 15 min; 220/254 nm; tR 1:9.761; tR 2:12.395). The fractions containing the desired compound were evaporated to dryness to afford the 1$^{st}$ eluting atropisomer of 5-[(8aS)-10-acryloyl-6-chloro-4-fluoro-8,8a,9,10,11,12-hexahydropyrazino[2',1':3,4][1,4]oxazepino[5,6,7-de]quinazolin-5-yl]-6-methylquinazolin-4(3H)-one (Atropisomer 1, Example 6) (7 mg, 14%) as a white solid. 1H NMR (400 MHz, DMSO, 30° C.) 2.05 (3H, s), 2.98-3.14 (1H, m), 3.33-3.57 (2H, m), 4.00-4.52 (3H, m), 4.52-4.72 (2H, m), 4.73-4.97 (1H, m), 5.72-5.80 (1H, m), 6.15-6.24 (1H, m), 6.75-7.03 (1H, m), 7.74 (1H, d), 7.85 (1H, d), 8.05 (1H, s), 8.61 (1H, s), 12.01 (1H, s). m/z: ES+ [M+H]+=407.

A 2$^{nd}$ eluting atropisomer of the same compound, Atropsiomer 2, (Example 7) was obtained as a white solid (7 mg, 14%). 1H NMR (400 MHz, DMSO, 30° C.) 2.07 (3H, s), 3.00-3.26 (1H, m), 3.33-3.59 (2H, m), 4.00-4.57 (3H, m), 4.57-4.74 (2H, m), 4.78-4.96 (1H, m), 5.72-5.80 (1H, m), 6.15-6.24 (1H, m), 6.84-6.89 (1H, m), 7.74 (1H, d), 7.86 (1H, d), 8.05 (1H, s), 8.61 (1H, s). One exchangeable proton not seen. m/z: ES+ [M+H]+=407.

(+/−)-4-Bromo-5-methyl-1-(oxan-2-yl)-1H-benzimidazole

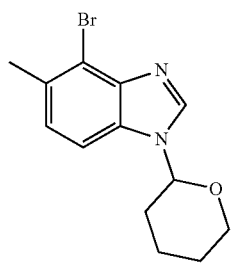 [SMILES: Cc1ccc2c(ncn2C2CCCCO2)c1Br]

A mixture of 4-bromo-5-methyl-1H-benzimidazole (CAS No: 952511-48-7; 1.06 g, 5.02 mmol), 3,4-dihydro-2H-pyran (2.3 ml, 25.11 mmol) and 4-methylbenzenesulfonic acid hydrate (0.143 g, 0.75 mmol) in THF (45 ml) was stirred at 65° C. under nitrogen for 20 hours. The reaction mixture was allowed to cool, concentrated and diluted with EtOAc (150 ml), and washed sequentially with saturated NaHCO₃ (75 ml), and saturated brine (50 ml). The organic layer was dried with MgSO₄, filtered and evaporated to afford crude product. The crude product was purified by flash silica chromatography, elution gradient 0 to 80% EtOAc in heptane. Pure fractions were evaporated to dryness to afford (+/−)-4-bromo-5-methyl-1-(oxan-2-yl)-1H-benzimidazole (1.08 g, 72.9%) as a tan solid. $^{1}$H NMR (400 MHz, CDCl₃, 30° C.) 1.66-1.8 (3H, m), 2.06-2.18 (3H, m), 2.53 (3H, s), 3.68-3.78 (1H, m), 4.05-4.14 (1H, m), 5.45 (1H, dd), 7.17 (1H, d), 7.35 (1H, d), 8.06 (1H, s). [M+H]+ 295, 297.

Tert-butyl (8aS)-4-fluoro-5-(4,4,5,5-tetramethyl-1,3,2-dioxaborolan-2-yl)-8a,9,11,12-tetrahydropyrazino[2',1':3,4][1,4]oxazepino[5,6,7-de]quinazoline-10(8H)-carboxylate and [(8aS)-10-(tert-butoxycarbonyl)-4-fluoro-8,8a,9,10,11,12-hexahydropyrazino[2',1':3,4][1,4]oxazepino[5,6,7-de]quinazolin-5-yl]boronic acid

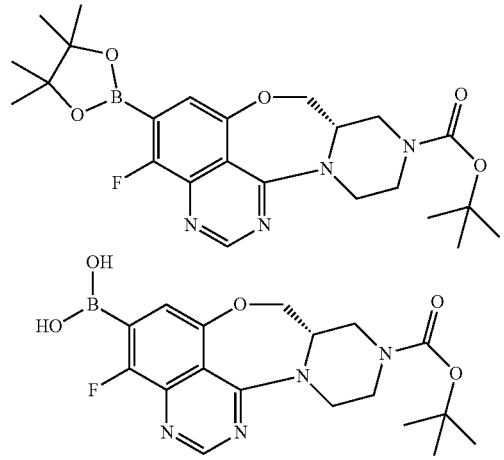

[1,1'-Bis(diphenylphosphino)ferrocene]dichloropalladium(II) complex with dichloromethane (0.335 g, 0.41 mmol), bis(pinacolato)diboron (3.12 g, 12.29 mmol) and potassium acetate (0.804 g, 8.20 mmol) were added to a stirred and degassed solution of tert-butyl (8aS)-5-bromo-4-fluoro-8a,9,11,12-tetrahydropyrazino[2',1':3,4][1,4]oxazepino[5,6,7-de]quinazoline-10(8H)-carboxylate (1.8 g, 4.10 mmol) in dioxane (65 ml) under nitrogen. The resulting mixture was stirred at 90° C. for 17 hours. The reaction mixture was allowed to cool, evaporated and partitioned between EtOAc (150 ml), and water (75 ml)/saturated brine (50 ml), the mixture was filtered through celite. The organic layer was separated, dried with MgSO₄, filtered and evaporated to afford the crude product, as a mixture of pinacol ester and boronic acid (assumed 4.10 mmol) as a brown oil which solidified on standing and which was used without further purification. m/z (ES+), [M+H]+ 405 (boronic acid) and 487 (pinacol ester).

Tert-butyl (8aS)-4-fluoro-5-[5-methyl-1-(oxan-2-yl)-1H-benzimidazol-4-yl]-8a,9,11,12-tetrahydropyrazino[2',1':3,4][1,4]oxazepino[5,6,7-de]quinazoline-10(8H)-carboxylate

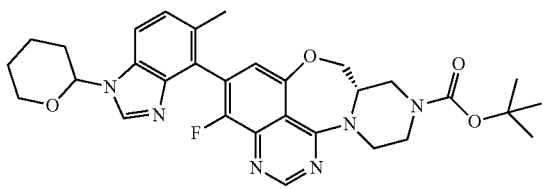 [SMILES: Cc1ccc2c(ncn2C2CCCCO2)c1-c1cc2c3c(ncnc3c1F)N1CCN(C(=O)OC(C)(C)C)C[C@H]1CO2]

RuPhos Pd G3 (0.306 g, 0.37 mmol), dicyclohexyl(2',6'-diisopropoxy-[1,1'-biphenyl]-2-yl)phosphane (0.171 g, 0.37 mmol) and potassium carbonate (1.011 g, 7.32 mmol) were added to a stirred and degassed solution of tert-butyl (8aS)-4-fluoro-5-(4,4,5,5-tetramethyl-1,3,2-dioxaborolan-2-yl)-8a,9,11,12-tetrahydropyrazino[2',1':3,4][1,4]oxazepino[5,6,7-de]quinazoline-10(8H)-carboxylate and [(8aS)-10-(tert-butoxycarbonyl)-4-fluoro-8,8a,9,10,11,12-hexahydropyrazino[2',1':3,4][1,4]oxazepino [5,6,7-de]quinazolin-5-yl]boronic acid (1.95 g, 4.02 mmol) and (+/−)-4-bromo-5-methyl-1-(oxan-2-yl)-1H-benzimidazole (1.08 g, 3.66 mmol) in dioxane (100 ml) and water (25 ml), the mixture was evacuated with nitrogen (5 cycles), and stirred at 80° C. for 90 minutes. The reaction mixture was allowed to cool, diluted with EtOAc (150 ml), and washed with water (75 ml)/saturated brine (75 ml) separated and the aqueous layer was re extracted with EtOAc (100 ml). The organic extracts were combined, dried with MgSO$_4$, filtered and evaporated to afford crude product. The crude product was purified by flash silica chromatography, elution gradient 0 to 5% MeOH in DCM. Pure fractions were evaporated to dryness to afford tert-butyl (8aS)-4-fluoro-5-[5-methyl-1-(oxan-2-yl)-1H-benzimidazol-4-yl]-8a,9,11,12-tetrahydropyrazino[2',1':3,4][1,4]oxazepino[5,6,7-de]quinazoline-10(8H)-carboxylate (2.09 g, 99%) as a brown foam. $^1$H NMR (400 MHz, CDCl$_3$, 30° C.) 1.51 (9H, s), 1.69-1.8 (3H, m), 2.08-2.21 (3H, m), 2.33 (3H, d), 3.01-3.31 (3H, m), 3.71-3.9 (2H, m), 4.13 (3H, d), 4.34-4.54 (2H, m), 5.08 (1H, d), 5.44-5.55 (1H, m), 7.05 (1H, dt), 7.26-7.29 (1H, m), 7.46-7.54 (1H, m), 7.99 (1H, dd), 8.68 (1H, d). m/z (ES+), [M+H]+ 575.

Tert-butyl (8aS)-6-Chloro-4-fluoro-5-[5-methyl-1-(oxan-2-yl)-1H-benzimidazol-4-yl]-8a,9,11,12-tetrahydropyrazino[2',1':3,4][1,4]oxazepino[5,6,7-de]quinazoline-10(8H)-carboxylate—Atropisomer 1 and Atropisomer 2

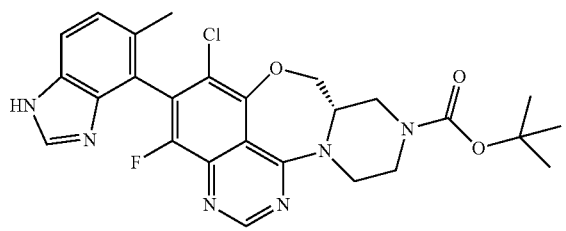 [SMILES: Cc1ccc2[nH]cnc2c1-c1c(Cl)c2c3c(ncnc3c1F)N1CCN(C(=O)OC(C)(C)C)C[C@H]1CO2]

1-Chloropyrrolidine-2,5-dione (0.534 g, 4.00 mmol) was added to a stirred solution of tert-butyl (8aS)-4-fluoro-5-[5-methyl-1-(oxan-2-yl)-1H-benzimidazol-4-yl]-8a,9,11,12-tetrahydropyrazino[2',1':3,4] [1,4]oxazepino[5,6,7-de]quinazoline-10(8H)-carboxylate (2.09 g, 3.64 mmol) in DMF (20 ml) at rt. The resulting solution was stirred at 120° C. for 17 h. The reaction mixture was allowed to cool, diluted with water (25 ml), EtOAc (125 ml) was added and the emulsion was filtered through celite. The organic layer separated further washed with saturated brine (2×100 ml), dried with a phase separating cartridge, filtered and evaporated to afford crude product. The crude product was purified by flash silica chromatography, elution gradient 0 to 8% MeOH in DCM. Pure fractions were evaporated to dryness and the atropisomers were separated by preparative HPLC (Waters XSelect CSH C18 column, 30×100 mm id, 5 micron particle size), using decreasingly polar mixtures of water (containing 1% by volume of NH$_4$OH (28-30% in H$_2$O)) and MeCN as eluents. Fractions containing the desired compounds were evaporated to dryness to afford tert-butyl (8aS)-6-chloro-4-fluoro-5-[5-methyl-1-(oxan-2-yl)-1H-benzimidazol-4-yl]-8a,9,11,12-tetrahydropyrazino[2',1':3,4][1,4]oxazepino[5,6,7-de]quinazoline-10(8H)-carboxylate—Atropisomer 1 (0.342 g, 17.9%) $^1$H NMR (400 MHz, CDCl$_3$) 1.58 (s, 9H), 2.23 and 2.29 (s, 3H*), 2.98-3.33 (m, 3H), 3.48 (brs, 0.6H), 3.84-4.05 (m, 1H), 4.05-4.23 (m, 1H), 4.37-4.59 (m, 2H), 4.59-4.93 (br s, 1H), 5.01 (d, J=12.9 Hz, 0.4H), 7.23 and 7.29 (d, 1H*), 7.49 and 7.78 (d, J=8.3 Hz, 1H), 7.93 and 7.94 (s, 1H*), 8.25 and 8.67 (s, 1H*), 9.71 and 11.73 (br s, 1H*) *tautomers at the benzimidazole NH were observed in a 2:1 ratio. $^{19}$F NMR (376 MHz, CDCl$_3$, 30° C.) −126.93, −124.43. m/z (ES+), [M+H]+ 525,527.

A 2$^{nd}$ eluting atropisomer of the same compound—Atropisomer 2 (0.185 g, 9.69%) was also obtained. $^1$H NMR (400 MHz, CDCl$_3$) 1.57 (s, 9H), 2.23 and 2.24 (s, 3H*), 2.93-3.4 (m, 3H), 3.76-3.88 (m, 1H), 4.03-4.30 (m, 2H), 4.36-4.51 (m, 1.5H), 4.57 (d, J=13.2 Hz, 0.5H), 4.93-5.06 (m, 0.5H), 5.09-5.25 (m, 0.5H), 7.22 and 7.30 (d, J=8.3 Hz, 1H*), 7.49 and 7.79 (d, J=8.3 Hz, 1H*), 7.94 (s, 1H), 8.24 and 8.68 (s, 1H*), 9.82 and 11.94 (br s, 1H*). *tautomers at the benzimidazole NH were observed in a 2:1 ratio. $^{19}$F NMR (376 MHz, CDCl$_3$, 30° C.) −127.08, −123.84, m/z (ES+), [M+H]+ 525, 527.

(8aS)-6-Chloro-4-fluoro-5-[5-methyl-1-(oxan-2-yl)-1H-benzimidazol-4-yl]-8,8a,9,10,11,12-hexahydropyrazino[2',1':3,4][1,4]oxazepino[5,6,7-de]quinazoline—Atropisomer 2

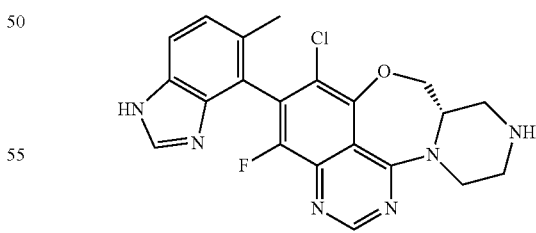

4M HCl in dioxane (1.4 ml, 5.64 mmol) in MeOH (1 ml) was added to a stirred solution of tert-butyl (8aS)-6-chloro-4-fluoro-5-[5-methyl-1-(oxan-2-yl)-1H-benzimidazol-4-yl]-8a,9,11,12-tetrahydropyrazino[2',1':3,4][1,4]oxazepino[5,6,7-de]quinazoline-10(8H)-carboxylate—Atropsiomer 2 (185 mg, 0.35 mmol) in MeOH (1 ml). The resulting solution was stirred at room temperature for 6 h. The reaction mixture was purified by ion exchange chromatography, using an SCX column. The desired product was eluted from the column using 1M NH₃/MeOH and pure fractions were evaporated to dryness to afford (8aS)-6-chloro-4-fluoro-5-[5-methyl-1-(oxan-2-yl)-1H-benzimidazol-4-yl]-8,8a,9,10,11,12-hexahydropyrazino[2',1':3,4][1,4]oxazepino[5,6,7-de]quinazoline—Atropisomer 2 (147 mg, 98%) as a brown solid. $^1$H NMR (400 MHz, DMSO) 2.15 (s, 3H), 2.75-2.97 (m, 2H), 3.04-3.23 (m 3H), 4.06 (br s, 1H), 4.57 (m, 2H), 4.99 (d, J=12.8 Hz, 1H), 7.21 (d, J=8.3 Hz, 1H), 7.51-7.57 and 7.62-7.67 (m, 1H*), 8.09 (s, 1H), 8.60 (s, 1H), 12.18 and 12.48 (s, 1H*), *tautomers at the benzimidazole NH were observed in a 1:1 ratio. $^{19}$F NMR (376 MHz, DMSO) −127.77, 128.21 ppm (tautomer ratio 1:1). m/z (ES+), [M+H]+ 425,427.

(8aS)-6-Chloro-4-fluoro-5-[5-methyl-1-(oxan-2-yl)-1H-benzimidazol-4-yl]-8,8a,9,10,11,12-hexahydropyrazino[2',1':3,4][1,4]oxazepino[5,6,7-de]quinazoline—Atropisomer 1

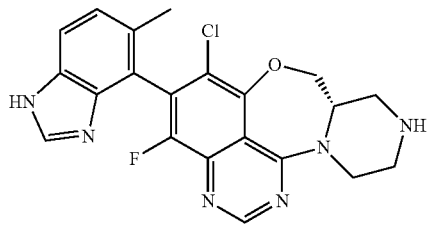 [SMILES: Cc1ccc2[nH]cnc2c1-c1c(Cl)c2c3c(ncnc3c1F)N1CCNC[C@H]1CO2]

(8aS)-6-Chloro-4-fluoro-5-[5-methyl-1-(oxan-2-yl)-1H-benzimidazol-4-yl]-8,8a,9,10,11,12-hexahydropyrazino[2',1':3,4][1,4]oxazepino[5,6,7-de]quinazoline—Atropisomer 1 was prepared in an analogous manner to the corresponding Atropisomer 2 described above, starting from tert-butyl (8aS)-6-chloro-4-fluoro-5-[5-methyl-1-(oxan-2-yl)-1H-benzimidazol-4-yl]-8a,9,11,12-tetrahydropyrazino[2',1':3,4][1,4]oxazepino[5,6,7-de]quinazoline-10(8H)-carboxylate—Atropisomer 1. The product Atropisomer 1 exhibited: $^1$H NMR (400 MHz, DMSO) 2.17 and 2.18 (3H, s*), 2.7-2.88 (2H, m), 2.97-3.18 (3H, m), 3.96 (1H, br s), 4.49 (1H, dd), 4.57-4.66 (1H, m), 4.9-5.0 (1H, m), 7.16-7.29 (1H, m), 7.54 and 7.65 (1H, d*), 8.08 (1H, d), 8.58 (1H, d), 12.15 and 12.47 (1H, s), *tautomers at the benzimidazole NH were observed in a 1:1 ratio, NH piperazine not observed. $^{19}$F NMR (376 MHz, DMSO) −128.38, −128.10 ppm (tautomer ratio 1:1), m/z (ES+), [M+H]+ 425,427.

1-[(8aS)-6-Chloro-4-fluoro-5-(5-methyl-1H-benzimidazol-4-yl)-8a,9,11,12-tetrahydropyrazino[2',1':3,4][1,4]oxazepino[5,6,7-de]quinazolin-10(8H)-yl] prop-2-en-1-one—Atropisomer 2 (Example 8)

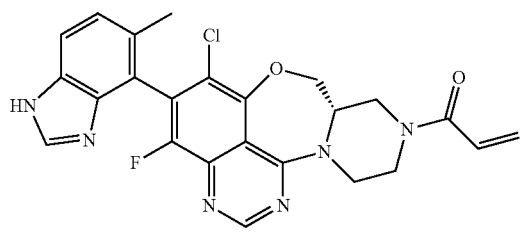 [SMILES: C=CC(=O)N1CCN2c3ncnc4c(F)c(-c5c(C)ccc6[nH]cnc56)c(Cl)c(c34)OC[C@@H]2C1]

A solution of acryloyl chloride (0.026 ml, 0.32 mmol) in DCM (0.5 ml) was added slowly to a stirred solution of (8aS)-6-chloro-4-fluoro-5-[5-methyl-1-(oxan-2-yl)-1H-benzimidazol-4-yl]-8,8a,9,10,11,12-hexahydropyrazino[2',1':3,4][1,4]oxazepino[5,6,7-de]quinazoline—Atropisomer 2 (137 mg, 0.32 mmol) and triethylamine (0.090 ml, 0.64 mmol) in DCM (5 ml) cooled to −70° C. The resulting solution was stirred at −70° C. for 30 minutes. The DCM was evaporated and the residue diluted with DMSO and purified by preparative HPLC (Waters CSH C18 OBD column, 30×100 mm id, 5 micron particle size), using decreasingly polar mixtures of water (containing 1% by volume of NH₄OH (28-30% in H₂O)) and MeCN as eluents. Shallow gradient: 25 to 50% MeCN). Fractions containing the desired compound were evaporated to dryness afford 1-[(8aS)-6-chloro-4-fluoro-5-(5-methyl-1H-benzimidazol-4-yl)-8a,9,11,12-tetrahydropyrazino [2',1':3,4][1,4]oxazepino [5,6,7-de]quinazolin-10(8H)-yl]prop-2-en-1-one—Atropisomer 2, Example 8, as a white solid (17.8 mg, 11.5%). $^1$H NMR (400 MHz, DMSO, 30° C.) 2.16 (3H, s), 3.01-3.17 (1H, m), 3.42-3.54 (1H, m), 4.04-4.24 (2H, m), 4.28-4.57 (2H, m), 4.66 (2H, s), 4.81-4.99 (1H, m), 5.77 (1H, dd), 6.20 (1H, dd), 6.79-6.97 (1H, m), 7.22 (1H, d), 7.60 (1H, d), 8.09 (1H, s), 8.64 (1H, s), 12.25 (1H brs), m/z (ES+), [M+H]+ 479, 481.

1-[(8aS)-6-Chloro-4-fluoro-5-(5-methyl-1H-benzimidazol-4-yl)-8a,9,11,12-tetrahydropyrazino[2',1':3,4][1,4]oxazepino[5,6,7-de]quinazolin-10(8H)-yl] prop-2-en-1-one—Atropisomer 1 (Example 9)

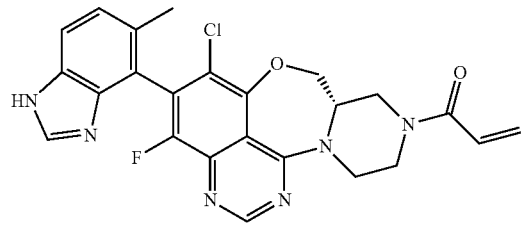 [SMILES: C=CC(=O)N1CCN2c3ncnc4c(F)c(-c5c(C)ccc6[nH]cnc56)c(Cl)c(c34)OC[C@@H]2C1]

1-[(8aS)-6-Chloro-4-fluoro-5-(5-methyl-1H-benzimidazol-4-yl)-8a,9,11,12-tetrahydropyrazino [2',1':3,4][1,4] oxazepino[5,6,7-de]quinazolin-10(8H)-yl]prop-2-en-1-one—Atropisomer 1 (Example 9) was prepared in an analogous manner to Example 8 starting from (8aS)-6-chloro-4-fluoro-5-[5-methyl-1-(oxan-2-yl)-1H-benzimidazol-4-yl]-8,8a,9,10,11,12-hexahydropyrazino[2',1':3,4][1,4] oxazepino [5,6,7-de]quinazoline—Atropisomer 1. Example 9, exhibited: $^1$H NMR (400 MHz, DMSO) 2.18 (3H, s), 2.98-3.2 (1H, m), 3.4-3.56 (2H, m), 4.06-4.56 (3H, m), 4.56-4.97 (3H, m), 5.77 (1H, d), 6.20 (1H, d), 6.87 (1H, s), 7.14-7.29 (1H, m), 7.54 and 7.66 (1H, d*), 8.09 (1H, d), 8.64 (1H, d), 12.16 and 12.49 (1H, s*), *tautomers at the benzimidazole NH were observed in a 1:1 ratio. $^{19}$F NMR (376 MHz, DMSO, 30° C.) −128.18, −127.94 ppm (tautomer ratio 1:1), m/z (ES+), [M+H]+ 479,481.

8-Bromo-2-{[2-(trimethylsilyl)ethoxy]methyl}isoquinolin-1(2H)-one

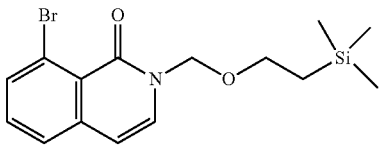 [SMILES: C[Si](C)(C)CCOCn1ccc2cccc(Br)c2c1=O]

To a stirred solution of 8-bromoisoquinolin-1(2H)-one (2.5 g, 11.16 mmol) in anhydrous DMF (50 ml) under a nitrogen atmosphere was added sodium hydride (60% dispersion in mineral oil) (0.669 g, 16.74 mmol). The resultant suspension was stirred at room temperature for 5 minutes before (2-(chloromethoxy)ethyl)trimethylsilane (2.96 ml, 16.74 mmol) was added drop-wise. The reaction mixture was allowed to stir at room temperature for 16 hours. Additional sodium hydride (60% dispersion in mineral oil) (260 mg, 6.54 mmol) was added at room temperature and the reaction was allowed to stir for five minutes. (2-(chloromethoxy)ethyl)trimethylsilane (2.96 ml, 16.74 mmol) was added (1.2 ml, 7.12 ml) and the reaction was allowed to stir for 1 hour. The reaction was quenched by addition of water (150 ml) and the mixture was extracted with EtOAc (2×100 ml). The organic layers were passed through a phase separator cartridge and concentrated under reduced pressure to give an orange gum. The crude product was purified by flash silica chromatography, elution gradient 0 to 20% EtOAc in heptane. Pure fractions were evaporated to dryness to afford 8-bromo-2-{[2-(trimethylsilyl)ethoxy]methyl}isoquinolin-1(2H)-one (2.76 g, 69.8%) as a yellow oil which solidified on standing. 1H NMR (400 MHz, DMSO, 30° C.) −0.00 (9H, s), 0.86-0.97 (2H, m), 3.63 (2H, dd), 5.33 (2H, s), 6.66 (1H, d), 7.56 (2H, dd), 7.68 (1H, dd), 7.78 (1H, dd).

8-(4,4,5,5-Tetramethyl-1,3,2-dioxaborolan-2-yl)-2-{[2-(trimethylsilyl)ethoxy]methyl}isoquinolin-1(2H)-one

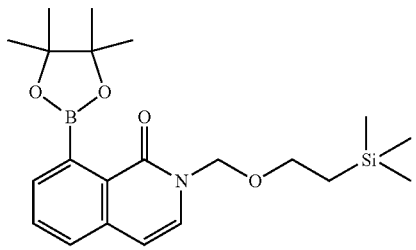

PdCl$_2$(dppf).DCM (0.403 g, 0.49 mmol) was added to a degassed solution of 8-bromo-2-((2-(trimethylsilyl)ethoxy)methyl)isoquinolin-1(2H)-one (1.4 g, 3.95 mmol), 4,4,4',4',5,5,5',5'-octamethyl-2,2'-bi(1,3,2-dioxaborolane) (2.308 g, 9.09 mmol) and potassium acetate (1.94 g, 19.76 mmol) in 1,4-dioxane (35 ml). The mixture was degassed for an additional 5 minutes then heated at 100° C. for 16 hours. The cooled reaction mixture was diluted with EtOAc (50 ml), washed with sequentially with water (25 ml), 2M aqueous Na$_2$CO$_3$ (2×25 ml) and brine (25 ml). The organic portion was dried (MgSO$_4$), filtered and the filtrate concentrated. The crude product was purified by flash silica chromatography, elution gradient 0 to 25% EtOAc in heptane. Pure fractions were evaporated to dryness to afford 8-(4,4,5,5-tetra methyl-1,3,2-dioxaborolan-2-yl)-2-{[2-(trimethylsilyl) ethoxy] methyl}isoquinolin-1(2H)-one (0.938 g, 59.1%) as a yellow gum. 1H NMR (400 MHz, CDCl$_3$, 30° C.) 0.00 (9H, d), 0.98 (2H, d), 1.47 (12H, s), 3.6-3.69 (2H, m), 5.41 (2H, s), 6.51 (1H, d), 7.16 (1H, d), 7.50 (2H, ddd), 7.59-7.65 (1H, m). m/z: ES+ [M+H]+ 402.

Tert-butyl (8aS)-6-chloro-4-fluoro-5-(1-oxo-2-{[2-(trimethylsilyl)ethoxy]methyl}-1,2-dihydroisoquinolin-8-yl)-8a,9,11,12-tetrahydropyrazino[2',1':3,4][1,4]oxazepino[5,6,7-de]quinazoline-10(8H)-carboxylate

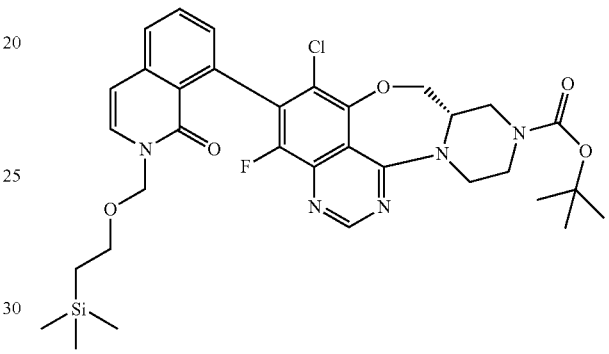

8-(4,4,5,5-tetramethyl-1,3,2-dioxaborolan-2-yl)-2-{[2-(trimethylsilyl)ethoxy]methyl}isoquinolin-1(2H)-one (0.928 g, 2.31 mmol), {2',6'-bis[(propan-2-yl)oxy][1,1'-biphenyl]-2-yl}(dicyclohexyl)phosphane (0.108 g, 0.23 mmol), RuPhos-Pd-G3 (0.193 g, 0.23 mmol), potassium carbonate (0.959 g, 6.94 mmol) and tert-butyl (8aS)-5-bromo-6-chloro-4-fluoro-8a,9,11,12-tetrahydropyrazino[2',1':3,4][1,4]oxazepino[5,6,7-de]quinazoline-10(8H)-carboxylate (1.095 g, 2.31 mmol) were combined. A degassed mixture of dioxane (16 ml) and water (4 ml) was added and the reaction was degassed for a further 1 minute then heated at 80° C. for 30 minutes. The reaction was allowed to stir at 80° C. for a further 16 hours. The reaction allowed to cool then degassed for 5 minutes with nitrogen. Additional dicyclohexyl(2',6'-diisopropoxy-[1,1'-biphenyl]-2-yl)phosphane (0.108 g, 0.23 mmol) and RuPhos Pd G3 (0.193 g, 0.23 mmol) were added and the reaction was allowed to stir at 80° C. for a further 24 hours. The cooled reaction mixture was diluted with EtOAc (100 ml), washed with water (50 ml) and brine (50 ml) passed through a phase separation cartridge and concentrated under reduced pressure. The crude product was purified by flash silica chromatography, elution gradient 0 to 50% EtOAc. Pure fractions were evaporated to dryness to afford tert-butyl (8aS)-6-chloro-4-fluoro-5-(1-oxo-2-{[2-(trimethylsilyl)ethoxy]methyl}-1,2-dihydroisoquinolin-8-yl)-8a,9,11,12-tetrahydropyrazino[2',1':3,4][1,4]oxazepino[5,6,7-de]quinazoline-10(8H)-carboxylate (0.500 g, 32.4%) as a beige gum. 1H NMR (400 MHz, CDCl$_3$, 30° C.) 0.00 (9H, s), 1.63 (9H, s), 3.02-3.35 (3H, m), 3.56-3.63 (2H, m), 3.78-4.34 (4H, m), 4.4-4.71 (3H, m), 5.04 (1H, d), 5.26 (1H, dd), 5.39 (1H, dd), 6.64 (1H, dd), 7.23-7.37 (2H, m), 7.70 (1H, d), 7.78 (1H, td), 8.71 (1H, s). m/z: ES+ [M+H]+ 668, 670.

8-[(8aS)-6-Chloro-4-fluoro-8,8a,9,10,11,12-hexahydropyrazino[2',1':3,4][1,4]oxazepino[5,6,7-de]quinazolin-5-yl]isoquinolin-1(2H)-one

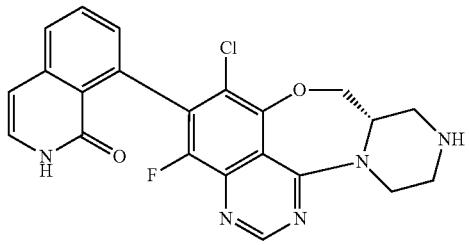 [SMILES: O=c1[nH]ccc2cccc(-c3c(Cl)c4c5c(ncnc5c3F)N3CCNC[C@H]3CO4)c12]

2,2,2-trifluoroacetic acid (2.8 ml, 36.34 mmol) was added to a solution of tert-butyl (13aS)-11-chloro-9-fluoro-10-(1-oxo-2-((2-(trimethylsilyl)ethoxy)methyl)-1,2-dihydroisoquinolin-8-yl)-3,4,13,13a-tetrahydropyrazino[2',1':3,4][1,4]oxazepino[5,6,7-de]quinazoline-2(1H)-carboxylate (0.50 g, 0.75 mmol) in THF (2 ml) and water (0.2 ml) in a microwave vial. The resulting mixture was stirred at 105° C. in the microwave for 40 minutes. The volatiles were removed under reduced pressure and the resulting residue azeotroped with toluene (3×5 ml). The crude product was purified by ion exchange chromatography, using an SCX column loading with MeOH and washing with methanol. The desired product was eluted from the column using 7M NH₃/MeOH and pure fractions were evaporated to dryness to afford 8-[(8aS)-6-chloro-4-fluoro-8,8a,9,10,11,12-hexahydropyrazino[2',1':3,4][1,4] oxazepino[5,6,7-de]quinazolin-5-yl]isoquinolin-1(2H)-one (0.287 g, 88%) as a beige foam. 1H NMR (400 MHz, DMSO, 30° C.) 2.71-2.97 (2H, m), 3.05-3.22 (3H, m), 3.84-4.2 (2H, m), 4.43-4.67 (2H, m), 5.02 (1H, t), 6.72 (1H, d), 7.22-7.39 (2H, m), 7.84-7.91 (2H, m), 8.64 (1H, dd), 11.11 (1H, d). m/z: ES+[M+H]+ 438, 440.

8-[(8aS)-6-Chloro-4-fluoro-10-(prop-2-enoyl)-8,8a,9,10,11,12-hexahydropyrazino[2',1':3,4][1,4]oxazepino[5,6,7-de]quinazolin-5-yl]isoquinolin-1(2H)-one (Example 10)

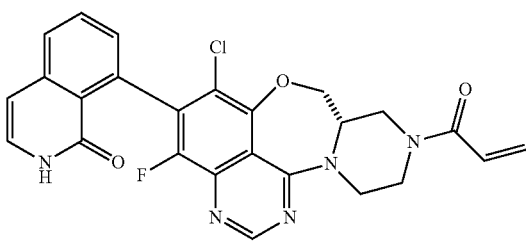 [SMILES: C=CC(=O)N1CCN2c3ncnc4c(F)c(-c5cccc6cc[nH]c(=O)c56)c(Cl)c(c34)OC[C@@H]2C1]

To a solution of 8-[(8aS)-6-chloro-4-fluoro-8,8a,9,10,11,12-hexahydropyrazino[2',1':3,4][1,4] oxazepino[5,6,7-de]quinazolin-5-yl]isoquinolin-1(2H)-one (287 mg, 0.66 mmol) in DCM (16.4 ml), IPA (4.1 ml) and pyridine (0.106 ml, 1.31 mmol) at −78° C. was added a solution of acryloyl chloride (0.056 ml, 0.69 mmol) in dichloromethane (3.85 ml) slowly drop-wise over 5 minutes. The reaction mixture was stirred at −78° C. for ten minutes. Additional acryloyl chloride (7.9 μL, 0.1 mmol) in DCM (0.55 ml) was added and the reaction was allowed to stir at −78° C. for an additional 10 minutes. The reaction mixture was warmed to room temperature and the volatiles were removed under reduced pressure. 1M Methanolic ammonia (2 ml) was added followed by DMSO (4 ml) and the crude product was purified by preparative HPLC (3× injections, Waters CSH C18 OBD column, 30×100 mm id, 5 micron particle size), using decreasingly polar mixtures of water (containing 1% by volume of NH₄OH (28-30% in H₂O)) and MeCN (25-50% gradient) as eluents. Pure fractions were evaporated to afford 8-[(8aS)-6-chloro-4-fluoro-10-(prop-2-enoyl)-8,8a,9,10,11,12-hexahydropyrazino[2',1':3,4][1,4]oxazepino[5,6,7-de]quinazolin-5-yl]isoquinolin-1(2H)-one (45.0 mg, 13.96%) as a white solid. 1H NMR (400 MHz, CDCl₃, 30° C.) 3.03-3.36 (2H, m), 3.38-3.68 (1H, m), 3.83-4.13 (2H, m), 4.42-4.61 (2H, m), 4.61-4.81 (1H, m), 4.98-5.13 (1H, m), 5.80 (1H, d), 6.38 (1H, d), 6.59 (2H, dd), 7.01 (1H, dd), 7.21-7.33 (1H, m), 7.67 (1H, dt), 7.75 (1H, td), 8.55-9.04 (2H, m). m/z: ES+ [M+H]+ 492, 494.

3-Bromo-1-{[2-(trimethylsilyl)ethoxy]methyl}-1H-indazole

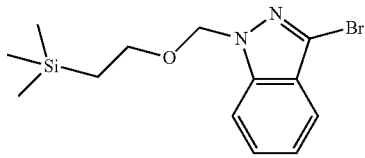 [SMILES: C[Si](C)(C)CCOCn1nc(Br)c2ccccc21]

3-Bromo-1H-indazole (5 g, 25.38 mmol) was stirred as a suspension in DMF (100 ml) under nitrogen then cooled to 0° C. Sodium hydride (60% dispersion in mineral oil) (1.218 g, 30.45 mmol) was added portion-wise and the reaction was stirred at 0° C. for 15 minutes. (2-(chloromethoxy)ethyl)trimethylsilane (5.39 ml, 30.45 mmol) was added drop-wise then the reaction was allowed to reach room temperature over 16 hours. The reaction was quenched with NH₄Cl (50 ml) and diluted with water (300 ml) and ethyl acetate (300 ml). The layers were separated and the organic phase was washed with water (2×200 ml), passed through a phase separator cartridge and concentrated under reduced pressure to afford a brown oil. The oil was purified by flash silica chromatography, elution gradient of 0-10% EtOAc in heptanes to afford 3-bromo-1-{[2-(trimethylsilyl)ethoxy]methyl}-1H-indazole (4.33 g, 52.1%) as a white solid. 1H NMR (400 MHz, CDCl₃, 30° C.) −0.00 (9H, s), 0.9-0.99 (2H, m), 3.57-3.69 (2H, m), 5.75 (2H, s), 7.26-7.37 (1H, m), 7.53 (1H, ddd), 7.62 (1H, d), 7.67-7.76 (1H, m).

3-(4,4,5,5-Tetramethyl-1,3,2-dioxaborolan-2-yl)-1-{[2-(trimethylsilyl)ethoxy]methyl}-1H-indazole

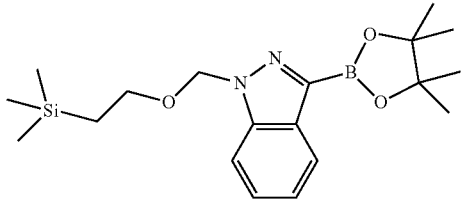

3-Bromo-1-{[2-(trimethylsilyl)ethoxy]methyl}-1H-indazole (3.80 g, 11.61 mmol) was dissolved in degassed 1,4-dioxane (50 ml) and potassium acetate (4.56 g, 46.44 mmol), 4,4,4',4',5,5,5',5'-octamethyl-2,2'-bi(1,3,2-dioxaborolane) (3.83 g, 15.09 mmol) and Pd(dppf)Cl$_2$.DCM complex (1.7 g, 2.32 mmol) were added under nitrogen with stirring. The reaction was then heated at 80° C. for 16 hours and then heated to 90° C. and stirred for an additional 8 hours. The volatiles were removed under reduced pressure and the resulting residue was partitioned between water (60 ml) and DCM (60 ml). The layers were separated and the aqueous extracted with DCM (2×60 ml). The organic phases were combined, passed through a phase separator cartridge and concentrated under reduced pressure to afford a dark residue. The residue was dissolved in DCM and purified by flash silica chromatography, elution gradient to 0-40% EtOAc in heptane. Product containing fractions concentrated under reduced pressure to afford 3-(4,4,5,5-tetra methyl-1,3,2-dioxaborolan-2-yl)-1-((2-(trimethylsilyl)ethoxy) methyl)-1H-indazole (2.44 g, 56.1%), which was used with no further purification. 1H NMR (400 MHz, CDCl$_3$, 30° C.) 0.00 (9H, s), 0.93 (2H, d), 1.50 (12H, s), 3.63 (2H, dd), 5.92 (2H, s), 7.32 (1H, s), 7.48 (1H, ddd), 7.70 (1H, d), 8.14-8.23 (1H, m).

Tert-butyl (8aS)-6-chloro-4-fluoro-5-(1-{[2-(trimethylsilyl)ethoxy]methyl}-1H-indazol-3-yl)-8a,9,11,12-tetrahydropyrazino[2',1':3,4][1,4]oxazepino[5,6,7-de]quinazoline-10(8H)-carboxylate

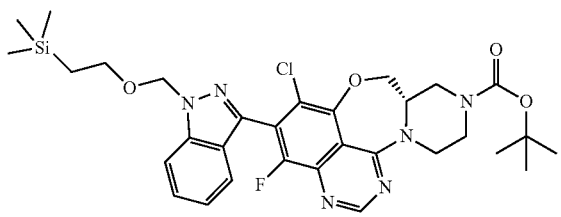 [SMILES: CC(C)(C)OC(=O)N1CCN2c3ncnc4c(F)c(-c5nn(COCC[Si](C)(C)C)c6ccccc56)c(Cl)c(c34)OC[C@@H]2C1]

3-(4,4,5,5-tetra methyl-1,3,2-dioxaborolan-2-yl)-1-{[2-(trimethylsilyl)ethoxy]methyl}-1H-indazole (0.553 g, 1.48 mmol), {2',6'-bis[(propan-2-yl)oxy][1,1'-biphenyl]-2-yl}(dicyclohexyl)phosphane (0.049 g, 0.11 mmol), RuPhos-Pd-G3 (0.088 g, 0.11 mmol), potassium carbonate (0.292 g, 2.11 mmol) and tert-butyl (8aS)-5-bromo-6-chloro-4-fluoro-8a,9,11,12-tetrahydropyrazino[2',1':3,4][1,4]oxazepino [5,6,7-de]quinazoline-10(8H)-carboxylate (0.50 g, 1.06 mmol) were combined. A degassed mixture of dioxane (10 ml) and water (2.5 ml) was added and the reaction was degassed for a further 1 minute then heated at 80° C. for 30 minutes. The cooled reaction mixture was diluted with EtOAc (100 ml), washed sequentially with water (35 ml) and brine (35 ml), then passed through a phase separator cartridge and the organic phase concentrated under reduced pressure. The crude material was purified by flash silica chromatography, elution gradient 0-60% EtOAc in heptane. Product containing fractions were combined and concentrated to afford tert-butyl (8aS)-6-chloro-4-fluoro-5-(1-{[2-(trimethylsilyl)ethoxy]methyl}-1H-indazol-3-yl)-8a,9,11,12-tetrahydropyrazino[2',1':3,4][1,4] oxazepino[5,6,7-de]quinazoline-10(8H)-carboxylate (0.450 g, 66.5%) as a yellow gum. 1H NMR (400 MHz, CDCl$_3$, 30° C.) 0.00 (9H, s), 0.94-0.99 (2H, m), 1.59 (9H, s), 3.13-3.35 (3H, m), 3.66-3.76 (2H, m), 3.99 (1H, s), 4.1-4.32 (2H, m), 4.59 (2H, qd), 5.12 (1H, d), 5.94 (2H, s), 7.31 (1H, d), 7.56 (1H, ddd), 7.63 (1H, d), 7.76 (1H, d), 8.80 (1H, s). m/z: ES+ [M+H]+ 641, 643.

(8aS)-6-Chloro-4-fluoro-5-(1H-indazol-3-yl)-8,8a,9,10,11,12-hexahydropyrazino[2',1':3,4][1,4]oxazepino[5,6,7-de]quinazoline

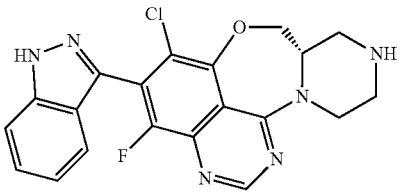 [SMILES: Fc1c(-c2n[nH]c3ccccc23)c(Cl)c2c3c(ncnc13)N1CCNC[C@H]1CO2]

2,2,2-trifluoroacetic acid (2 ml, 25.96 mmol) was added to a solution of tert-butyl (8aS)-6-chloro-4-fluoro-5-(1-{[2-(trimethylsilyl)ethoxy]methyl}-1H-indazol-3-yl)-8a,9,11, 12-tetrahydropyrazino [2',1':3,4][1,4]oxazepino[5,6,7-de] quinazoline-10(8H)-carboxylate (360 mg, 0.56 mmol) in THF (1.4 ml) and water (0.14 ml) in a microwave vial. The resulting mixture was stirred at 105° C. for 20 minutes. The volatiles were removed under reduced pressure and the resulting residue azeotroped with toluene (3×5 ml). The crude product was purified by ion exchange chromatography, using an SCX column loading with MeOH and washing with methanol. The desired product was eluted from the column using 7M methanolic ammonia and pure fractions were evaporated to dryness to afford (8aS)-6-chloro-4-fluoro-5-(1H-indazol-3-yl)-8,8a,9,10,11,12-hexahydropyrazino[2',1':3,4]oxazepino [5,6,7-de]quinazoline (220 mg, 95%) as a beige foam. 1H NMR (400 MHz, DMSO, 30° C.) 2.7-2.93 (2H, m), 3.06-3.24 (3H, m), 3.86-4.25 (1H, m), 4.53-4.78 (2H, m), 5.08 (1H, d), 7.19-7.34 (1H, m), 7.54 (1H, ddd), 7.61 (1H, d), 7.76 (1H, d), 8.70 (1H, s), 13.65 (1H, s). 1 exchangeable NH signal not observed. m/z: ES+ [M+H]+ 411, 413.

1-[(8aS)-6-Chloro-4-fluoro-5-(1H-indazol-3-yl)-8a,9,11,12-tetrahydropyrazino[2',1':3,4][1,4]oxazepino [5,6,7-de]quinazolin-10(8H)-yl]prop-2-en-1-one (Example 11)

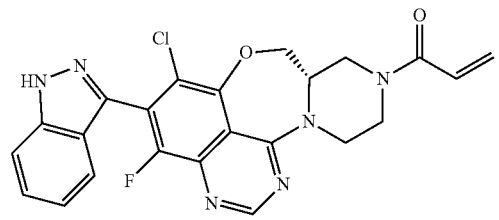 [SMILES: C=CC(=O)N1CCN2c3ncnc4c(F)c(-c5n[nH]c6ccccc56)c(Cl)c(c34)OC[C@@H]2C1]

To a solution of (8aS)-6-chloro-4-fluoro-5-(1H-indazol-3-yl)-8,8a,9,10,11,12-hexahydropyrazino[2',1':3,4][1,4] oxazepino[5,6,7-de]quinazoline (205 mg, 0.50 mmol) in DCM (11.7 ml), IPA (4.1 ml) and pyridine (0.08 ml, 1.00 mmol) at −78° C. was added a solution of acryloyl chloride (0.042 ml, 0.52 mmol) in dichloromethane (2.85 ml) slowly drop-wise over 5 minutes. The reaction mixture was stirred at −78° C. for 10 minutes. Additional acryloyl chloride (7.9 μL, 0.1 mmol) in DCM (0.55 ml) was added and the reaction was stirred at −78° C. for an additional 10 minutes. The reaction mixture was warmed to room temperature and the DCM was removed under reduced pressure. 1M methanolic ammonia (2 ml) was added and the crude product was purified by preparative HPLC (2× injections, Waters CSH C18 OBD column, 30×100 mm id, 5 micron particle size), using decreasingly polar mixtures of water (containing 1% by volume of NH$_4$OH (28-30% in H$_2$O)) and MeCN (25-50% gradient) as eluents. Pure fractions were evaporated to afford 1-[(8aS)-6-chloro-4-fluoro-5-(1H-indazol-3-yl)-8a,9,11,12-tetrahydropyrazino[2',1':3,4][1,4]oxazepino[5,6,7-de]quinazolin-10(8H)-yl]prop-2-en-1-one (27.0 mg, 11.64%) as a white solid. 1H NMR (400 MHz, DMSO, 30° C.) 3.16 (1H, d), 3.48 (2H, d), 4.14-4.23 (1H, m), 4.29-4.58 (2H, m), 4.66-4.81 (2H, m), 4.87-5.02 (1H, m), 5.82 (1H, dd), 6.26 (1H, dd), 6.92 (1H, s), 7.2-7.29 (1H, m), 7.47-7.52 (1H, m), 7.56 (1H, d), 7.72 (1H, d), 8.71 (1H, s), 13.62 (1H, s). m/z: ES+ [M+H]+ 465,467.

(2-Hydroxy-6-methylphenyl)boronic acid

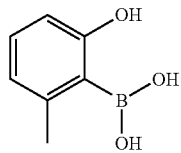

A solution of n-butyl lithium (1.6 M in hexanes, 18.38 ml, 29.41 mmol) was slowly added to a stirred solution of 2-bromo-3-methylphenol (2.5 g, 13.37 mmol) at −78° C. in THF (100 ml). The reaction was allowed to warm to room temperature and stirred at this temperature for 2 hours. The reaction mixture was cooled to −78° C. and trimethyl borate (2.474 ml, 22.19 mmol) was added and the reaction was allowed to stir at −78° C. for 30 minutes. The reaction was allowed to warm to room temperature and stirred at this temperature for 16 hours. 2M HCl aqueous solution (100 ml) was added and the reaction was stirred at room temperature for 1 hour. DCM (150 ml) was added and the layers were separated. The aqueous portion was extracted with DCM (150 ml) and the combined organic portions were passed through a phase separator cartridge and concentrated under reduced pressure to afford a yellow oil. Heptane (20 ml) was added and the resulting precipitate was collected by filtration, washed with DCM (10 ml) and dried under vacuum to afford (2-hydroxy-6-methylphenyl)boronic acid (0.811 g, 39.9%) as a white solid. 1H NMR (400 MHz, D$_2$O, 30° C.) 2.30 (3H, s), 6.69 (1H, t), 6.81 (1H, d), 7.18 (1H, t). 3 exchangeable OH signals not observed. m/z: ES−, [M−H]− 151.

Tert-butyl (8aS)-6-Chloro-4-fluoro-5-(2-hydroxy-6-methylphenyl)-8,8a,9,10,11,12-hexahydropyrido[2',1':3,4][1,4]oxazepino[5,6,7-de]quinazoline-10-carboxylate—Atropisomer 1 and Atropisomer 2

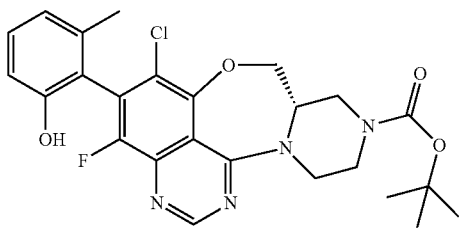 [SMILES: Cc1cccc(O)c1-c1c(Cl)c2c3c(ncnc3c1F)N1CCN(C(=O)OC(C)(C)C)C[C@H]1CO2]

(2-hydroxy-6-methylphenyl)boronic acid (0.305 g, 2.01 mmol), {2',6'-bis[(propan-2-yl)oxy][1,1'-biphenyl]-2-yl}(dicyclohexyl)phosphane (0.049 g, 0.11 mmol), RuPhos-Pd-G3 (0.088 g, 0.11 mmol), potassium carbonate (0.438 g, 3.17 mmol) and tert-butyl (8aS)-5-bromo-6-chloro-4-fluoro-8a,9,11,12-tetrahydropyrazino[2',1':3,4][1,4]oxazepino[5,6,7-de]quinazoline-10(8H)-carboxylate (0.5 g, 1.06 mmol) were combined in a reaction tube. A degassed mixture of dioxane (12 ml) and water (3 ml) was added and the reaction was degassed for a further 1 minute then heated at 80° C. for 90 minutes. The cooled reaction mixture was diluted with EtOAc (100 ml), washed sequentially with water (35 ml) and brine (35 ml), passed through a phase separator cartridge and concentrated under reduced pressure. The crude material was purified by flash silica chromatography, elution gradient 0-80% EtOAc in heptane. Product containing fractions were evaporated to afford a solid which was purified by chiral SFC (Phenomenex A1, 30×250 mm, 5 micron, Mobile phase: 30% 2-propanol+0.1% DEA/70% scCO$_2$, Flow rate: 90 ml/min, BPR:120 bar, Column temperature: 40° C.) to afford the 1$^{st}$ eluting atropisomer tert-butyl (8aS)-6-chloro-4-fluoro-5-(2-hydroxy-6-methylphenyl)-8,8a,9,10,11,12-hexahydropyrido [2',1':3,4][1,4]oxazepino[5,6,7-de]quinazoline-10-carboxylate—Atropisomer 1 (165 mg, 62%, d.e. 100%). 1H NMR (400 MHz, DMSO, 30° C.) 1.45 (9H, s), 1.97 (3H, s), 3.05-3.2 (2H, m), 3.22-3.27 (1H, m), 3.94 (1H, d), 4-4.14 (2H, m), 4.61 (2H, qd), 4.85 (1H, d), 6.81 (2H, dd), 7.18 (1H, t), 8.59 (1H, s), 9.44 (1H, s). m/z: ES+ [M+H]+ 501, 503. A 2nd eluting atropisomer of the same compound, Atropisomer 2 (151 mg, 57%, d.e. 100%) was also obtained. 1H NMR (400 MHz, DMSO, 30° C.) 1.51 (9H, s), 2.00 (3H, s), 3.12-3.26 (2H, m), 3.25-3.32 (1H, m), 4.00 (1H, d), 4.10 (2H, ddd), 4.67 (2H, d), 4.91 (1H, d), 6.87 (2H, d), 7.17-7.31 (1H, m), 8.65 (1H, s), 9.50 (1H, s). m/z: ES+ [M+H]+ 501, 503.

2-[(8aS)-6-Chloro-4-fluoro-8,8a,9,10,11,12-hexahydropyrazino[2',1':3,4][1,4]oxazepino[5,6,7-de]quinazolin-5-yl]-3-methylphenol—Atropisomer 2

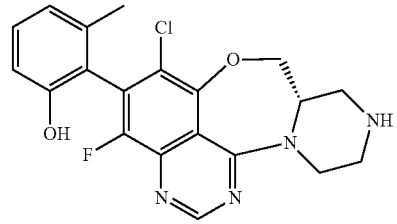 [SMILES: Cc1cccc(O)c1-c1c(Cl)c2c3c(ncnc3c1F)N1CCNC[C@H]1CO2]

Tert-butyl (8aS)-6-chloro-4-fluoro-5-(2-hydroxy-6-methylphenyl)-8,8a,9,10,11,12-hexahydropyrido [2',1':3,4][1,4]oxazepino[5,6,7-de]quinazoline-10-carboxylate—Atropisomer 2 (150 mg, 0.30 mmol) was stirred in MeOH (1.6 ml) then hydrogen chloride (4N in 1,4-dioxane) (1.6 ml, 6.40 mmol) was added at room temperature. The reaction was then stirred at room temperature for 1 hour. The reaction was purified by ion exchange chromatography, using a SCX column. The desired product was eluted from the column using 1M NH$_3$/MeOH and pure fractions were evaporated to dryness to afford 2-[(8aS)-6-chloro-4-fluoro-8,8a,9,10,11,12-hexahydropyrazino[2',1':3,4][1,4]oxazepino[5,6,7-de]quinazolin-5-yl]-3-methylphenol—Atropisomer 2 (91 mg, 76%) as a beige solid. 1H NMR (400 MHz, DMSO, 30° C.) 1.95 (3H, s), 2.66-2.8 (2H, m), 2.86-3.13 (4H, m), 3.82-3.98

(1H, m), 4.47 (1H, dd), 4.55 (1H, dd), 4.93 (1H, d), 6.80 (2H, d), 7.17 (1H, t), 8.55 (1H, s), 9.43 (1H, s). m/z: ES+ [M+H]+ 401, 403.

2-[(8aS)-6-Chloro-4-fluoro-8,8a,9,10,11,12-hexahydropyrazino[2',1':3,4][1,4]oxazepino[5,6,7-de]quinazolin-5-yl]-3-methylphenol—Atropisomer 1

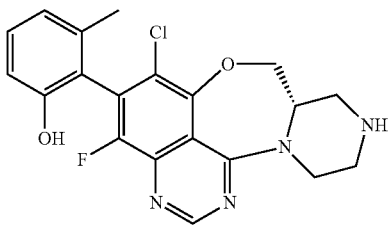 [SMILES: Cc1cccc(O)c1-c1c(Cl)c2c3c(ncnc3c1F)N1CCNC[C@H]1CO2]

2-[(8aS)-6-Chloro-4-fluoro-8,8a,9,10,11,12-hexahydropyrazino[2',1':3,4][1,4]oxazepino[5,6,7-de]quinazolin-5-yl]-3-methylphenol—Atropisomer 1 was prepared in an analogous fashion to the foregoing Atropisomer 2, by deprotecting tert-butyl (8aS)-6-chloro-4-fluoro-5-(2-hydroxy-6-methylphenyl)-8,8a,9,10,11,12-hexahydropyrido[2',1':3,4][1,4]oxazepino[5,6,7-de]quinazoline-10-carboxylate—Atropisomer 1. Atropisomer 1 (120 mg, 91%) was isolated as a beige solid. 1H NMR (400 MHz, DMSO, 30° C.) 2.01 (3H, s), 2.71-2.88 (2H, m), 3.08 (4H, dt), 3.98 (1H, dd), 4.52 (1H, dd), 4.62 (1H, dd), 4.99 (1H, d), 6.81. m/z: ES+ [M+H]+ 401, 403.

1-[(8aS)-6-Chloro-4-fluoro-5-(2-hydroxy-6-methylphenyl)-8a,9,11,12-tetrahydropyrazino[2',1':3,4][1,4]oxazepino[5,6,7-de]quinazolin-10(8H)-yl]prop-2-en-1-one—Atropisomer 2 (Example 12)

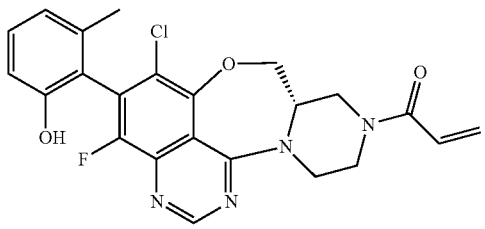 [SMILES: C=CC(=O)N1CCN2c3ncnc4c(F)c(-c5c(C)cccc5O)c(Cl)c(c34)OC[C@@H]2C1]

To a solution of 2-[(8aS)-6-chloro-4-fluoro-8,8a,9,10,11,12-hexahydropyrazino[2',1':3,4] [1,4]oxazepino[5,6,7-de]quinazolin-5-yl]-3-methylphenol Atropisomer 2 (91 mg, 0.23 mmol) in DCM (5.3 ml), IPA (1.9 ml) and pyridine (0.037 ml, 0.45 mmol) at −78° C. was added a solution of acryloyl chloride (22 μL, 0.27 mmol) in dichloromethane (1.52 ml) (slowly drop-wise over 5 minutes) and the reaction mixture stirred at −78° C. for ten minutes. Additional stock solution of acryloyl chloride (7.9 μL, 0.1 mmol) in DCM (0.55 ml) was added and the reaction was allowed to stir at −78° C. for an additional 10 minutes. The reaction mixture was brought up to room temperature and the DCM was removed under reduced pressure. 1M methanolic ammonia (2 ml) and DMSO (1 ml) was added and the crude product was purified by preparative HPLC (2× injections, Waters CSH C18 OBD column, 30×100 mm id, 5 micron particle size), using decreasingly polar mixtures of water (containing 1% by volume of NH4OH (28-30% in H2O)) and MeCN (25-50% gradient) as eluents. Pure fractions were evaporated to afford 1-[(8aS)-6-chloro-4-fluoro-5-(2-hydroxy-6-methylphenyl)-8a,9,11,12-tetrahydropyrazino[2',1':3,4][1,4]oxazepino[5,6,7-de]quinazolin-10(8H)-yl]prop-2-en-1-one—Atropisomer 2, Example 11, (29.9 mg, 29%, d.e. 100%) as a white solid. 1H NMR (400 MHz, DMSO, 30° C.) 2.00 (3H, s), 3.08-3.23 (1H, m), 3.44-3.55 (1H, m), 4.09-4.17 (1H, m), 4.18-4.62 (3H, m), 4.67-4.74 (2H, m), 4.85-4.99 (1H, m), 5.82 (1H, dd), 6.25 (1H, dd), 6.86 (2H, d), 6.89-6.99 (1H, m), 7.19-7.29 (1H, m), 8.66 (1H, s), 9.52 (1H, s). m/z: ES+ [M+H]+ 455, 457.

1-[(8aS)-6-Chloro-4-fluoro-5-(2-hydroxy-6-methylphenyl)-8a,9,11,12-tetrahydropyrazino[2',1':3,4][1,4]oxazepino[5,6,7-de]quinazolin-10(8H)-yl]prop-2-en-1-one—Atropisomer 1 (Example 13)

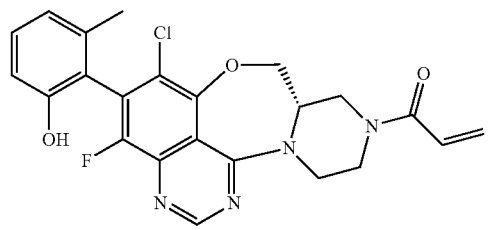 [SMILES: C=CC(=O)N1CCN2c3ncnc4c(F)c(-c5c(C)cccc5O)c(Cl)c(c34)OC[C@@H]2C1]

1-[(8aS)-6-Chloro-4-fluoro-5-(2-hydroxy-6-methylphenyl)-8a,9,11,12-tetrahydropyrazino[2',1':3,4] [1,4]oxazepino[5,6,7-de]quinazolin-10(8H)-yl]prop-2-en-1-one—Atropisomer 1 (Example 13) was prepared in an analogous manner to Example 12, starting from 2-[(8aS)-6-chloro-4-fluoro-8,8a,9,10,11,12-hexahydropyrazino[2',1':3,4][1,4]oxazepino[5,6,7-de]quinazolin-5-yl]-3-methylphenol—Atropisomer 1. Example 13 was isolated as a white solid (45 mg, 32%, d.e. 99%). 1H NMR (400 MHz, DMSO, 30° C.) 2.02 (3H, s), 3.07-3.22 (1H, m), 3.41-3.53 (1H, m), 4.05-4.29 (2H, m), 4.29-4.61 (2H, m), 4.65-4.76 (2H, m), 4.84-4.98 (1H, m), 5.82 (1H, dd), 6.25 (1H, dd), 6.85 (2H, d), 6.89-7.03 (1H, m), 7.23 (1H, t), 8.66 (1H, s), 9.52 (1H, s). m/z: ES+ [M+H]+ 455, 457.

(2E)-1-[(8aS)-6-Chloro-4-fluoro-5-(2-fluoro-6-hydroxyphenyl)-8a,9,11,12-tetrahydropyrazino[2',1':3,4][1,4]oxazepino[5,6,7-de]quinazolin-10(8H)-yl]-4-(dimethylamino)but-2-en-1-one—Atropisomer 2 (Example 14)

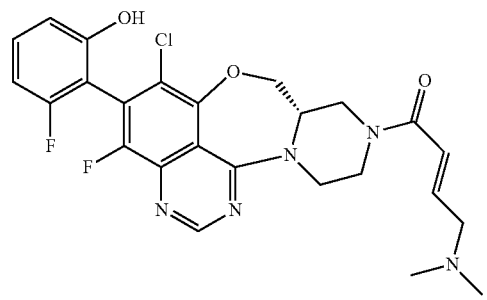 [SMILES: CN(C)C/C=C/C(=O)N1CCN2c3ncnc4c(F)c(-c5c(O)cccc5F)c(Cl)c(c34)OC[C@@H]2C1]

DIPEA (287 μl, 1.65 mmol) was added in one portion to 2-[(8aS)-6-chloro-4-fluoro-8,8a,9,10,11,12-hexahydropyrazino[2',1':3,4][1,4]oxazepino[5,6,7-de]quinazolin-5-yl]-3-fluorophenol—Atropisomer 2 (222 mg, 0.55 mmol), HATU (250 mg, 0.66 mmol) and (E)-4-(dimethylamino)but-2-enoic acid. HCl salt (100 mg, 0.60 mmol) in DMA (24.5 ml) at room temperature under nitrogen. The resulting solution was stirred at room temperature for 1 hour. The reaction mixture was poured into water (80 ml), extracted with EtOAc (3×80 ml) and washed with brine (80 ml). The organic portion was dried over MgSO$_4$, filtered and evaporated to afford a crude product. The crude product was purified by preparative HPLC (Waters XSelect CSH C18 column, 5μ silica, 50 mm diameter, 100 mm length), using decreasingly polar mixtures of water (containing 1% by volume of NH$_4$OH (28-30% in H$_2$O)) and MeCN as eluents. Fractions containing the desired compound were evaporated to dryness to afford (2E)-1-[(8aS)-6-chloro-4-fluoro-5-(2-fluoro-6-hydroxyphenyl)-8a,9,11,12-tetrahydropyrazino[2',1':3,4][1,4] oxazepino[5,6,7-de]quinazolin-10(8H)-yl]-4-(dimethylamino) but-2-en-1-one—Atropisomer 2, Example 14, (72.0 mg, 25.4%, d.e. 100%) as a solid. 1H NMR (400 MHz, DMSO, 30° C.) 2.17 (6H, s), 2.99-3.16 (3H, m), 3.41 (1H, s), 4.02-4.2 (2H, m), 4.23-4.54 (2H, m), 4.55-4.75 (2H, m), 4.75-4.95 (1H, m), 6.63-6.72 (2H, m), 6.76 (1H, t), 6.83 (1H, d), 7.33 (1H, q), 8.61 (1H, s). 1 exchangeable OH signal not observed. m/z: ES+ [M+H]+ 516, 518.

(2E)-1-[(8aS)-6-Chloro-4-fluoro-5-(2-fluoro-6-hydroxyphenyl)-8a,9,11,12-tetrahydropyrazino[2',1':3,4][1,4]oxazepino[5,6,7-de]quinazolin-10(8H)-yl]-4-(dimethylamino)but-2-en-1-one—Atropisomer 1 (Example 15)

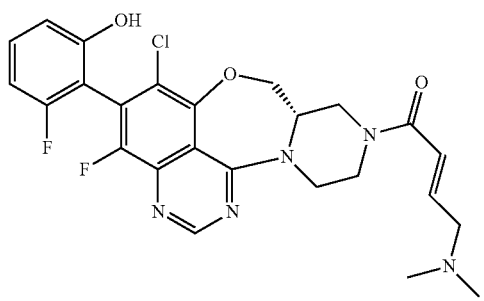 [SMILES: CN(C)C/C=C/C(=O)N1CCN2c3ncnc4c(F)c(-c5c(O)cccc5F)c(Cl)c(c34)OC[C@@H]2C1]

(2E)-1-[(8aS)-6-Chloro-4-fluoro-5-(2-fluoro-6-hydroxyphenyl)-8a,9,11,12-tetrahydropyrazino [2',1':3,4][1,4]oxazepino[5,6,7-de]quinazolin-10(8H)-yl]-4-(dimethylamino)but-2-en-1-one—Atropisomer 1, Example 15, was prepared in an analogous fashion Example 14, starting from 2-[(8aS)-6-chloro-4-fluoro-8,8a,9,10,11,12-hexahydropyrazino[2',1':3,4][1,4]oxazepino[5,6,7-de]quinazolin-5-yl]-3-fluorophenol—Atropisomer 1. Example 15 was isolated as a solid (85 mg, 37%, d.e. 99%). 1H NMR (400 MHz, DMSO, 30° C.) 2.23 (6H, s), 3.02-3.25 (3H, m), 3.42-3.62 (1H, m), 4.05-4.3 (2H, m), 4.3-4.59 (2H, m), 4.63-4.79 (2H, m), 4.85-5.02 (1H, m), 6.68-6.8 (2H, m), 6.8-6.95 (2H, m), 7.40 (1H, q), 8.67 (1H, s), 10.25 (1H, s). m/z: ES+ [M+H]+ 516, 518.

8-Bromo-7-methylisoquinoline

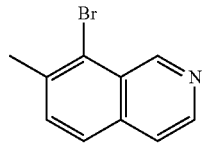

2,2-Diethoxyethan-1-amine (3.77 ml, 25.95 mmol) was added to a stirred solution of 2-bromo-3-methylbenzaldehyde (4.92 g, 24.72 mmol) in anhydrous toluene (14 ml) and was heated to 100° C. for 4 hours. The reaction mixture was allowed to cool to room temperature then was concentrated under reduced pressure. The resulting residue was azeotroped with toluene (3×15 ml) to remove residual water from the condensation. The yellow crude oil residue was dissolved in DCM (21 ml) and cooled to 0° C. Aluminium trichloride (10.88 g, 81.57 mmol) was added portion-wise and the resulting dark red suspension was left to stir at 0° C. for 30 minutes and was then allowed to slowly warm to room temperature over 18 hours. The reaction mixture was added into ice water drop-wise (150 g, caution, very effervescent) and was diluted with DCM (100 ml). The reaction mixture was carefully basified with 2M aqueous NaOH solution (~120 ml). The resulting emulsion was further diluted with water (500 ml) and DCM (700 ml), shaken in a separator funnel then the layers were allowed to separate over a period of 1 hour. Water (400 ml) and brine were added (400 ml) and the layers were separated then the aqueous layer was extracted with DCM-MeOH (5:2; 2×500 ml). The combined organic extracts which were passed through a phase separator cartridge and the filtrate was concentrated under reduced pressure to afford the crude product. The crude product was purified by flash silica chromatography, elution gradient 0 to 40% EtOAc in heptane. Fractions containing the desired product were evaporated to dryness to afford 8-bromo-7-methylisoquinoline (3.30 g, 60.1%) as an orange solid. 1H NMR (400 MHz, CDCl$_3$, 30° C.) 2.64 (3H, s), 7.49-7.63 (2H, m), 7.69 (1H, d), 8.55 (1H, d), 9.67 (1H, s). m/z: ES+ [M+H]+ 222.

8-Bromo-7-methylisoquinoline 2-oxide

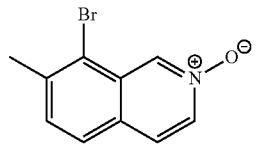

meta-Chloroperoxybenzoic acid (4.00 g, 17.83 mmol) was added to a stirred solution of 8-bromo-7-methylisoquinoline (3.3 g, 14.86 mmol) in DCM (150 ml) at 0° C. After 30 minutes the ice bath was removed and stirring was continued at room temperature for 2 hours. The reaction mixture was quenched with a saturated solution of sodium bicarbonate (50 ml) and the layers were separated. The aqueous portion was extracted with DCM (3×30 ml) and the combined organic layers were dried over MgSO$_4$, filtered and concentrated under reduced pressure to afford 8-bromo-7-methylisoquinoline 2-oxide (3.54 g, 100%) as a white solid which was used without further purification. 1H NMR (400 MHz, DMSO, 30° C.) 2.57 (3H, s), 7.61 (1H, d), 7.92 (1H, d), 7.98 (1H, d), 8.17-8.26 (1H, m), 8.85 (1H, s). m/z: ES+[M+H]+ 240.

8-Bromo-1-methoxy-7-methylisoquinoline

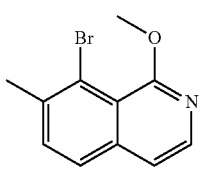

Triethylamine (2.072 ml, 14.87 mmol) was added to a stirred suspension of 8-bromo-7-methylisoquinoline 2-oxide (1.77 g, 7.43 mmol) and methyl chloroformate (0.574 ml, 7.43 mmol) at 0° C. The reaction was allowed to stir for 16 hours in a melting ice bath. The reaction was cooled to 0° C. and additional methyl chloroformate (0.86 ml, 1.5 equiv) and triethylamine (3.1 ml, 3 equiv) were added then the reaction was stirred for a further 1.5 hours at room temperature. The volatiles were removed under reduced pressure. The residue was dissolved in EtOAc (100 ml) and washed sequentially with water (50 ml) and brine (50 ml). The organic portion was passed through a phase separating cartridge and concentrated under reduced pressure. The crude product was purified by flash silica chromatography, elution gradient 0 to 20% EtOAc in heptane. Pure fractions were evaporated to dryness to afford 8-bromo-1-methoxy-7-methylisoquinoline (1.1 g, 58%) as a white solid. 1H NMR (400 MHz, CDCl$_3$, 30° C.) 2.60 (3H, s), 4.10 (3H, s), 7.17 (1H, d), 7.47 (1H, d), 7.56 (1H, d), 7.94 (1H, d). m/z: ES+ [M+H]+ 254.

Tert-butyl (8aS)-4-fluoro-5-(1-methoxy-7-methyl-isoquinolin-8-yl)-8a,9,11,12-tetrahydropyrazino [2',1':3,4][1,4]oxazepino[5,6,7-de]quinazoline-10(8H)-carboxylate

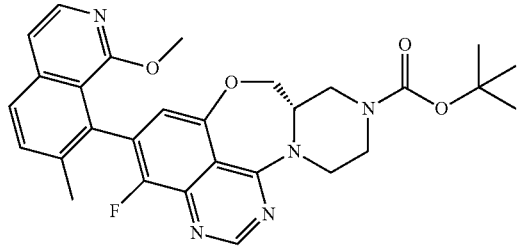 [SMILES: COc1nccc2ccc(C)c(-c3cc4c5c(ncnc5c3F)N3CCN(C(=O)OC(C)(C)C)C[C@H]3CO4)c12]

RuPhos-Pd-G3 (152 mg, 0.18 mmol), {2',6'-bis[(propan-2-yl)oxy][1,1'-biphenyl]-2-yl}(dicyclohexyl)phosphane, potassium carbonate (504 mg, 3.64 mmol), 8-bromo-1-methoxy-7-methylisoquinoline (459 mg, 1.82 mmol) and [(8aS)-10-(tert-butoxycarbonyl)-4-fluoro-8,8a,9,10,11,12-hexahydropyrazino[2',1':3,4][1,4]oxazepino[5,6,7-de]quinazolin-5-yl]boronic acid (735 mg, 1.82 mmol) were combined under nitrogen and degassed dioxane (40 ml) and degassed water (10 ml) was then added. The resulting mixture was degassed for a further 1 minute and then stirred under nitrogen at 80° C. for 60 minutes. The reaction mixture was allowed to cool, diluted with EtOAc (125 ml) and washed sequentially with water (50 ml) and saturated brine (25 ml). The aqueous portion was further extracted with EtOAc (75 ml). The organic extracts were combined, dried with MgSO$_4$, filtered and evaporated to afford crude product. The crude product was purified by flash silica chromatography (40 gram silica cartridge), elution gradient 0 to 70% EtOAc in heptane. Pure fractions were evaporated to dryness to afford tert-butyl (8aS)-4-fluoro-5-(1-methoxy-7-methylisoquinolin-8-yl)-8a,9,11,12-tetrahydropyrazino[2',1':3,4][1,4]oxazepino[5,6,7-de]quinazoline-10(8H)-carboxylate (793 mg, 82%) as a brown foam. 1H NMR (400 MHz, CDCl$_3$, 30° C.) 1.51 (9H, s), 2.20 (3H, s), 3.08-3.24 (3H, m), 3.55 (3H, d), 3.90 (1H, d), 4.09-4.19 (2H, m), 4.31-4.39 (1H, m), 4.43-4.55 (1H, m), 5.14 (1H, s), 6.81 (1H, d), 7.24 (1H, d), 7.59 (1H, d), 7.74 (1H, d), 7.95 (1H, d), 8.71 (1H, s). m/z ES+ [M+H]+ 532.

Tert-butyl (8aS)-6-chloro-4-fluoro-5-(1-methoxy-7-methylisoquinolin-8-yl)-8a,9,11,12-tetrahydropyrazino[2',1':3,4][1,4]oxazepino[5,6,7-de]quinazoline-10(8H)-carboxylate—Atropisomer 1 and Atropisomer 2

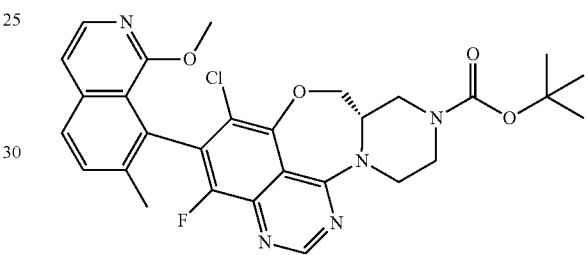

N-Chlorosuccinimide (173 mg, 1.30 mmol) was added to a stirred solution of tert-butyl (8aS)-4-fluoro-5-(1-methoxy-7-methylisoquinolin-8-yl)-8a,9,11,12-tetrahydropyrazino [2',1':3,4][1,4]oxazepino [5,6,7-de]quinazoline-10(8H)-carboxylate (690 mg, 1.30 mmol) in DMF (7 ml) at room temperature. The resulting solution was stirred at 120° C. for 30 minutes. Further N-chlorosuccinimide (30 mg, 0.22 mmol) was added and the reaction was allowed to stir at 120° C. for a further 15 minutes. The reaction mixture was allowed to cool then purified by reverse phase chromatography by loading the reaction mixture onto a RP column (150 gram C18 RF gold) then eluting with a gradient of 40-80% MeCN in water with formic acid 0.1% as a modifier. Fractions containing the desired compound were evaporated to dryness to afford tert-butyl (8aS)-6-chloro-4-fluoro-5-(1-methoxy-7-methylisoquinolin-8-yl)-8a,9,11,12-tetrahydropyrazino[2',1':3,4][1,4]oxazepino[5,6,7-de]quinazoline-10(8H)-carboxylate as a beige foam. The solid was dissolved in MeOH (2 ml) and purified using chiral SFC (Phenomenex C2, 30×250 mm, 5 micron, Mobile phase: 30% MeOH+ 0.1% NH$_3$/70% scCO$_2$, Flow rate: 100 ml/min, BPR:120 bar, Column temperature: 40° C., UV @ 220 nm) to afford tert-butyl (8aS)-6-chloro-4-fluoro-5-(1-methoxy-7-methyl-isoquinolin-8-yl)-8a,9,11,12-tetrahydropyrazino[2',1':3,4] [1,4]oxazepino[5,6,7-de]quinazoline-10(8H)-carboxylate—Atropisomer 1 (125 mg, 34%, d.e. 98%) as the first eluting peak. 1H NMR (400 MHz, CDCl$_3$, 30° C.) 1.52 (9H, s), 2.17 (3H, s), 3.03-3.24 (3H, m), 3.56 (3H, s), 3.82-4.02 (1H, m), 4.02-4.31 (2H, m), 4.39-4.6 (2H, m), 4.82-5.23 (1H, m), 7.27 (1H, s), 7.63 (1H, d), 7.78 (1H, d), 7.96 (1H, d), 8.71 (1H, s). m/z ES+ [M+H]+ 566. A 2$^{nd}$ eluting peak proved to be Atropisomer 2 (120 mg, 33%, d.e. 97%) of the same compound. 1H NMR (400 MHz, CDCl₃, 30° C.) 1.52 (9H, s), 2.17 (3H, s), 3.11-3.3 (3H, m), 3.56 (3H, s), 3.97 (1H, s), 4.06-4.25 (2H, m), 4.39-4.48 (1H, m), 4.51-4.65 (1H, m), 4.98-5.14 (1H, m), 7.27 (1H, s), 7.63 (1H, d), 7.78 (1H, d), 7.96 (1H, d), 8.71 (1H, s). m/z: ES+ [M+H]+ 566.

8-[(8aS)-6-Chloro-4-fluoro-8,8a,9,10,11,12-hexahydropyrazino[2',1':3,4][1,4]oxazepino[5,6,7-de]quinazolin-5-yl]-7-methylisoquinolin-1(2H)-one—Atropisomer 1

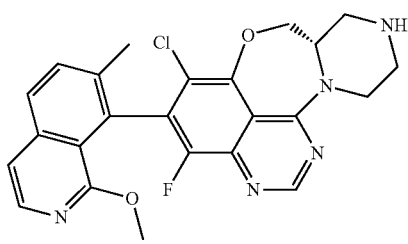 [SMILES: COc1nccc2ccc(C)c(-c3c(Cl)c4c5c(ncnc5c3F)N3CCNC[C@H]3CO4)c12]

A microwave vial was charged with tert-butyl (8aS)-6-chloro-4-fluoro-5-(1-methoxy-7-methylisoquinolin-8-yl)-8a,9,11,12-tetrahydropyrazino[2',1':3,4][1,4]oxazepino[5,6,7-de]quinazoline-10(8H)-carboxylate—Atropisomer 1 (125 mg, 0.22 mmol), lithium chloride (46.8 mg, 1.10 mmol), 4-methylbenzenesulfonic acid hydrate (210 mg, 1.10 mmol) and anhydrous DMF (4 ml). The microwave vial was sealed and irradiated in the microwave at 120° C. for 30 minutes. The crude product was purified by ion exchange chromatography, using an SCX column. The column was washed with MeOH, then the desired product was eluted from the column using 1M methanolic ammonia and the pure fractions were evaporated to dryness to afford 8-[(8aS)-6-chloro-4-fluoro-8,8a,9,10,11,12-hexahydropyrazino[2',1':3,4][1,4]oxazepino[5,6,7-de]quinazolin-5-yl]-7-methylisoquinolin-1(2H)-one—Atropisomer 1 (100 mg, 100%) as an off white solid. 1H NMR (400 MHz, CDCl₃, 30° C.) 2.14 (3H, s), 2.95 (1H, s), 3.07-3.19 (4H, m), 3.89 (1H, d), 4.41 (1H, dd), 4.52 (1H, dd), 5.06 (1H, d), 6.50 (1H, d), 6.93 (1H, d), 7.57 (1H, d), 7.63 (1H, d), 8.57 (1H, s), 8.65 (1H, s). 1 exchangeable NH signal not observed. m/z: ES+ [M+H]+ 452, 454.

8-[(8aS)-6-Chloro-4-fluoro-8,8a,9,10,11,12-hexahydropyrazino[2',1':3,4][1,4]oxazepino[5,6,7-de]quinazolin-5-yl]-7-methylisoquinolin-1(2H)-one—Atropisomer 2

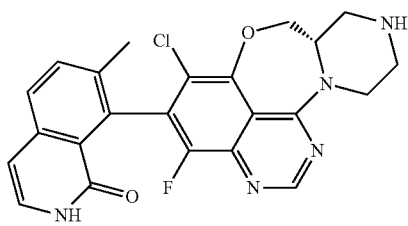 [SMILES: Cc1ccc2cc[nH]c(=O)c2c1-c1c(Cl)c2c3c(ncnc3c1F)N1CCNC[C@H]1CO2]

8-[(8aS)-6-Chloro-4-fluoro-8,8a,9,10,11,12-hexahydropyrazino[2',1':3,4][1,4]oxazepino[5,6,7-de]quinazolin-5-yl]-7-methylisoquinolin-1(2H)-one—Atropisomer 2 was prepared in an analogous fashion to the foregoing Atropisomer 1, starting from tert-butyl (8aS)-6-chloro-4-fluoro-5-(1-methoxy-7-methylisoquinolin-8-yl)-8a,9,11,12-tetrahydropyrazino[2',1':3,4][1,4]oxazepino[5,6,7-de]quinazoline-10(8H)-carboxylate—Atropisomer 2. The desired atropisomer 2 (95 mg, 99%) was isolated as an off white solid. 1H NMR (400 MHz, CDCl₃, 30° C.) 2.14 (3H, s), 2.88-2.95 (1H, m), 3-3.2 (4H, m), 3.84-3.96 (1H, m), 4.40 (1H, dd), 4.48 (1H, dd), 5.07 (1H, dd), 6.49 (1H, d), 6.89 (1H, d), 7.56 (1H, d), 7.58-7.67 (1H, m), 8.65 (1H, s), 9.09 (1H, s). 1 exchangeable NH signal not observed. m/z: ES+[M+H]+ 452, 454.

8-[(8aS)-6-Chloro-4-fluoro-10-(prop-2-enoyl)-8,8a,9,10,11,12-hexahydropyrazino[2',1':3,4][1,4] oxazepino[5,6,7-de]quinazolin-5-yl]-7-methylisoquinolin-1(2H)-one—Atropisomer 1 (Example 16)

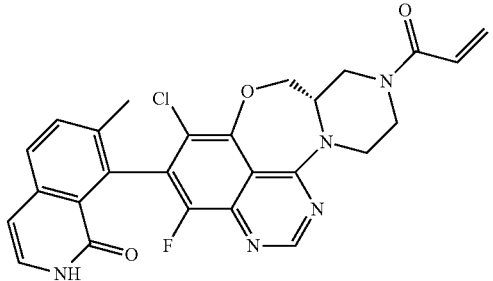 [SMILES: C=CC(=O)N1CCN2c3ncnc4c(F)c(-c5c(C)ccc6cc[nH]c(=O)c56)c(Cl)c(c34)OC[C@@H]2C1]

To a solution of 8-[(8aS)-6-chloro-4-fluoro-8,8a,9,10,11,12-hexahydropyrazino[2',1':3,4][1,4] oxazepino[5,6,7-de]quinazolin-5-yl]-7-methylisoquinolin-1(2H)-one—Atropisomer 1 (0.1 g, 0.22 mmol) in dichloromethane (3 ml), 2-propanol (1 ml) and triethylamine (0.031 ml, 0.22 mmol) at −78° C. was added a solution of acryloyl chloride (0.019 ml, 0.23 mmol) in dichloromethane (1 ml) (added slowly drop-wise over 5 minutes) and the reaction mixture stirred at −78° C. for ten minutes. The reaction mixture was warmed to room temperature, diluted with DCM (20 ml) and washed with water (20 ml). The organic layer was passed through phase separating cartridge and concentrated under reduced pressure to afford a crude product. The crude product was purified by preparative HPLC (Waters XSelect CSH C18 column, 5μ silica, 30 mm diameter, 100 mm length), using decreasingly polar mixtures of water (containing 1% by volume of NH₄OH (28-30% in H₂O)) and MeCN (gradient of 25 to 50%) as eluents. Fractions containing the desired compound were evaporated to dryness to afford 8-[(8aS)-6-chloro-4-fluoro-10-(prop-2-enoyl)-8,8a,9,10,11,12-hexahydropyrazino[2',1':3,4][1,4] oxazepino[5,6,7-de]quinazolin-5-yl]-7-methylisoquinolin-1(2H)-one—Atropisomer 1 (0.055 g, 49.1%, d.e. 96%) as a white solid. 1H NMR (400 MHz, DMSO, 30° C.) 2.03 (3H, s), 3.01-3.13 (1H, m), 3.36-3.56 (1H, m), 4.07-4.26 (2H, m), 4.26-4.53 (2H, m), 4.53-4.69 (2H, m), 4.77-4.97 (1H, m), 5.76 (1H, dd), 6.20 (1H, dd), 6.59 (1H, dd), 6.81-6.98 (1H, m), 7.09-7.15 (1H, m), 7.72 (2H, s), 8.60 (1H, s), 10.89 (1H, d). m/z: ES+ [M+H]+ 506, 508.

8-[(8aS)-6-Chloro-4-fluoro-10-(prop-2-enoyl)-8,8a,9,10,11,12-hexahydropyrazino[2',1':3,4][1,4] oxazepino[5,6,7-de]quinazolin-5-yl]-7-methylisoquinolin-1(2H)-one—Atropisomer 2 (Example 17)

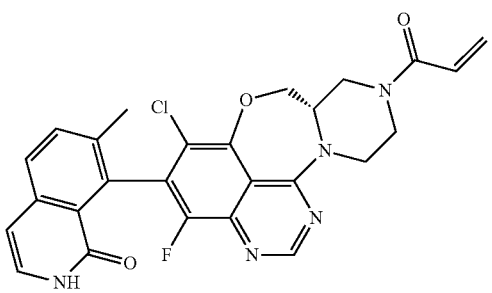 [SMILES: C=CC(=O)N1CCN2c3ncnc4c(F)c(-c5c(C)ccc6cc[nH]c(=O)c56)c(Cl)c(c34)OC[C@@H]2C1]

8-[(8aS)-6-Chloro-4-fluoro-10-(prop-2-enoyl)-8,8a,9,10,11,12-hexahydropyrazino[2',1':3,4][1,4] oxazepino[5,6,7-de]quinazolin-5-yl]-7-methylisoquinolin-1(2H)-one—Atropisomer 2 (Example 17) was prepared in an analogous fashion to Example 16, starting from 8-[(8aS)-6-chloro-4-fluoro-8,8a,9,10,11,12-hexahydropyrazino[2',1':3,4][1,4] oxazepino[5,6,7-de]quinazolin-5-yl]-7-methylisoquinolin-1 (2H)-one—Atropisomer 2 (95 mg, 0.21 mmol). Example 17 (52 mg, 49%, d.e. 95.8%) was isolated as a white solid. 1H NMR (400 MHz, DMSO, 30° C.) 2.05 (3H, s), 3.02-3.23 (1H, m), 3.50 (1H, d), 4-4.23 (2H, m), 4.29-4.57 (2H, m), 4.57-4.73 (2H, m), 4.75-4.96 (1H, m), 5.76 (1H, dd), 6.20 (1H, dd), 6.59 (1H, d), 6.8-6.98 (1H, m), 7.09-7.17 (1H, m), 7.72 (2H, s), 8.60 (1H, s), 10.89 (1H, d). m/z: ES+ [M+H]+ 506, 508.

4-Bromo-5-methyl-1H-benzotriazole

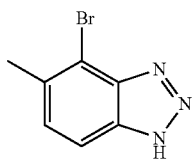

A solution of sodium nitrite (1.132 g, 16.41 mmol) in water (6 ml) was added drop-wise to a stirred solution of 3-bromo-4-methylbenzene-1,2-diamine (2.0 g, 9.95 mmol) in acetic acid (20 ml) and water (8 ml) at 0° C. The resulting mixture was stirred at room temperature for 1 hour. The precipitate was collected by filtration, washed with water (3×15 ml) and dried in the vacuum oven at 50° C. to afford 4-bromo-5-methyl-1H-benzotriazole (1.51 g, 72%) as a brown solid, which was used without further purification. 1H NMR (400 MHz, DMSO, 30° C.) 2.51 (3H, s), 7.43 (1H, d), 7.80 (1H, s), 15.99 (1H, s). m/z: ES+[M+H]+ 212, 214.

4-Bromo-5-methyl-1-(oxan-2-yl)-1H-benzotriazole

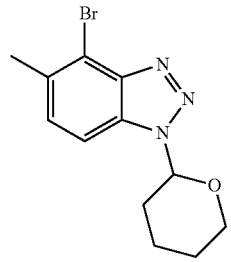 [SMILES: Cc1ccc2c(nnn2C2CCCCO2)c1Br]

3,4-Dihydro-2H-pyran (0.774 ml, 8.49 mmol) was added to 4-bromo-5-methyl-1H-benzotriazole (1.5 g, 7.07 mmol) and 4-methylbenzenesulfonic acid hydrate (0.269 g, 1.41 mmol) in DCM (16 ml) at 20° C. The resulting mixture was stirred at reflux for 1 hour. The reaction mixture was allowed to cool and the solvent was removed under reduced pressure. The crude product was purified by flash silica chromatography, elution gradient 0 to 100% EtOAc in heptane. Pure fractions were evaporated to dryness to afford 4-bromo-5-methyl-1-(oxan-2-yl)-1H-benzotriazole (1.150 g, 54.9%) as a brown oil. 1H NMR (400 MHz, DMSO, 52° C.) 1.6-1.7 (2H, m), 1.75-1.88 (1H, m), 2-2.2 (2H, m), 2.39-2.46 (1H, m), 2.53 (3H, s), 3.74-3.93 (2H, m), 6.15 (1H, dd), 7.49-7.57 (1H, m), 7.81 (1H, d).

Tert-butyl (8aS)-4-fluoro-5-[5-methyl-1-(oxan-2-yl)-1H-benzotriazol-4-yl]-8a,9,11,12-tetrahydropyrazino[2',1':3,4][1,4]oxazepino[5,6,7-de]quinazoline-10(8H)-carboxylate

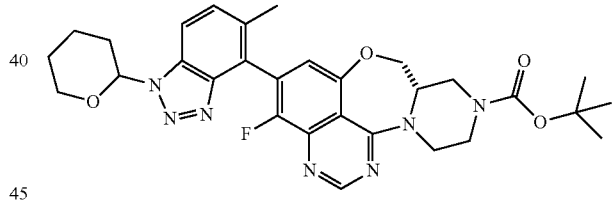

RuPhos-Pd-G3 (152 mg, 0.18 mmol), {2',6'-bis[(propan-2-yl)oxy][1,1'-biphenyl]-2-yl}(dicyclohexyl)phosphane (85 mg, 0.18 mmol), potassium carbonate (504 mg, 3.64 mmol), 4-bromo-5-methyl-1-(oxan-2-yl)-1H-benzotriazole (540 mg, 1.82 mmol) and [(8aS)-10-(tert-butoxycarbonyl)-4-fluoro-8,8a,9,10,11,12-hexahydropyrazino[2',1':3,4][1,4] oxazepino[5,6,7-de]quinazolin-5-yl]boronic acid (735 mg, 1.82 mmol) were combined under nitrogen and degassed 1,4-dioxane (40 ml) and degassed water (10 ml) were added. The resulting mixture was degassed with nitrogen for a further 1 minute then stirred under nitrogen at 80° C. for 90 minutes. The reaction mixture was allowed to cool then diluted with EtOAc (125 ml) and washed sequentially with water (50 ml) and saturated brine (25 ml). The aqueous portion was extracted with EtOAc (75 ml). The organic extracts were combined, dried with MgSO4, filtered and evaporated under reduced pressure to afford the crude product. The crude product was purified by flash silica chromatography, elution gradient 0 to 80% EtOAc in heptane. Pure fractions were evaporated to dryness to tert-butyl (8aS)-4-fluoro-5-[5-methyl-1-(oxan-2-yl)-1H-benzotriazol-4-yl]-8a, 9,11,12-tetrahydropyrazino[2',1':3,4][1,4]oxazepino[5,6,7-de]quinazoline-10(8H)-carboxylate (850 mg, 81%) as a brown gum. 1H NMR (400 MHz, CDCl₃, 30° C.) 1.51 (9H, d), 1.68-1.91 (3H, m), 2.12-2.3 (2H, m), 2.34-2.43 (3H, m), 2.58 (1H, dd), 3.16 (3H, dt), 3.87 (3H, ddt), 4.05-4.2 (2H, m), 4.32-4.57 (2H, m), 5.10 (1H, d), 6.06 (1H, dd), 7.08-7.18 (1H, m), 7.45 (1H, d), 7.68-7.77 (1H, m), 8.70 (1H, s). m/z: ES+ [M+H]+ 576.

Tert-butyl (8aS)-6-chloro-4-fluoro-5-(5-methyl-1H-benzotriazol-4-yl)-8a,9,11,12-tetrahydropyrazino[2',1':3,4][1,4]oxazepino[5,6,7-de]quinazoline-10(8H)-carboxylate

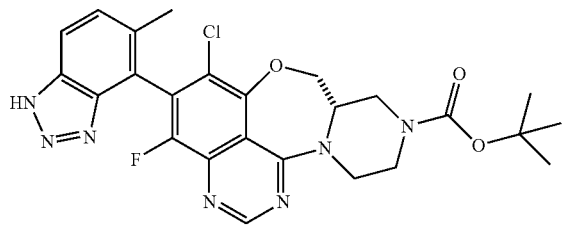 [SMILES: Cc1ccc2[nH]nnc2c1-c1c(Cl)c2c3c(ncnc3c1F)N1CCN(C(=O)OC(C)(C)C)C[C@H]1CO2]

N-Chlorosuccinimide (174 mg, 1.30 mmol) was added to a stirred solution of tert-butyl (8aS)-4-fluoro-5-[5-methyl-1-(oxan-2-yl)-1H-benzotriazol-4-yl]-8a,9,11,12-tetrahydropyrazino[2',1':3,4][1,4] oxazepino[5,6,7-de]quinazoline-10 (8H)-carboxylate (850 mg, 1.18 mmol) in DMF (5 ml) at room temperature. The resulting solution was stirred at 120° C. for 17 hours. The reaction mixture was allowed to cool, diluted with EtOAc (50 ml), and washed sequentially with water (25 ml) and saturated brine (25 ml). The combined organic portions were dried with MgSO₄, filtered and evaporated to afford a crude brown oil. The crude product was purified by flash silica chromatography, elution gradient 0 to 8% 1M methanolic ammonia in DCM to afford tert-butyl (8aS)-6-chloro-4-fluoro-5-(5-methyl-1H-benzotriazol-4-yl)-8a,9,11,12-tetrahydropyrazino[2',1':3,4][1,4]oxazepino [5,6,7-de] quinazoline-10(8H)-carboxylate (380 mg, 61.2%) as a gum which was used without further purification. m/z: ES+ [M+H]+ 526, 528.

(8aS)-6-Chloro-4-fluoro-5-(5-methyl-1H-benzotriazol-4-yl)-8,8a,9,10,11,12-hexahydropyrazino[2',1':3,4][1,4]oxazepino[5,6,7-de]quinazoline

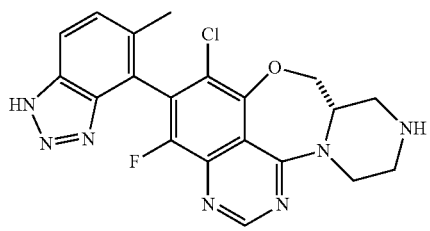 [SMILES: Cc1ccc2[nH]nnc2c1-c1c(Cl)c2c3c(ncnc3c1F)N1CCNC[C@H]1CO2]

To a solution of tert-butyl (8aS)-6-chloro-4-fluoro-5-(5-methyl-1H-benzotriazol-4-yl)-8a,9,11,12-tetrahydropyrazino[2',1':3,4][1,4]oxazepino[5,6,7-de]quinazoline-10 (8H)-carboxylate (380 mg, 0.72 mmol) as a mixture of Atropisomer 1 and Atropisomer 2 in dichloromethane (10 ml) at 0° C. under nitrogen was added 2,2,2-trifluoroacetic acid (3 ml, 39.18 mmol) and the reaction mixture stirred for 2 hours then the solvents were evaporated under reduced pressure. The residue was dissolved in methanol and applied to a SCX column, washing thoroughly with methanol then the product was eluted using 1M ammonia in methanol. The solvent was evaporated to afford (8aS)-6-chloro-4-fluoro-5-(5-methyl-1H-benzotriazol-4-yl)-8,8a,9,10,11,12-hexahydropyrazino[2',1':3,4][1,4]oxazepino[5,6,7-de]quinazoline as a mixture of Atropisomer 1 and Atropisomer 2 (240 mg, 79%) as an off-white solid which was used without further purification. m/z: ES+ [M+H]+ 426, 428.

1-[(8aS)-6-Chloro-4-fluoro-5-(5-methyl-1H-benzotriazol-4-yl)-8a,9,11,12-tetrahydropyrazino[2',1':3,4][1,4]oxazepino[5,6,7-de]quinazolin-10(8H)-yl]prop-2-en-1-one—Atropisomer 1 (Example 18) and atropisomer 2 (Example 19)

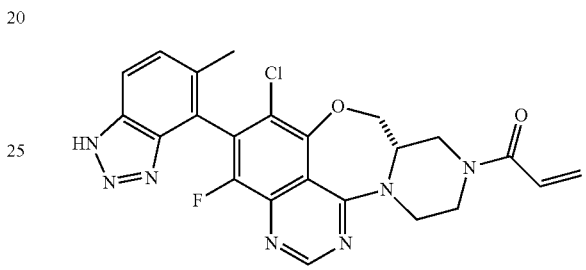

To a solution of (8aS)-6-chloro-4-fluoro-5-(5-methyl-1H-benzotriazol-4-yl)-8,8a,9,10,11,12-hexahydropyrazino[2',1':3,4][1,4]oxazepino[5,6,7-de]quinazoline in DCM (16.4 ml), IPA (4.1 ml) and pyridine (0.091 ml, 1.13 mmol) at −78° C. was added a solution of acryloyl chloride (0.048 ml, 0.59 mmol) in dichloromethane (3.4 ml) (drop-wise over 5 minutes) and the reaction mixture was stirred at −78° C. for ten minutes. Additional acryloyl chloride (7.774, 0.096 mmol) in dichloromethane (0.55 ml) was added and the reaction was allowed to stir at −78° C. for an additional 10 minutes. The reaction mixture was allowed to warm to room temperature and the volatiles were removed under reduced pressure. The resulting residue was dissolved in DMSO (4 ml) and the crude product was purified by preparative HPLC (2× injections) (Waters CSH C18 OBD column, 30×100 mm id, 5 micron particle size), using decreasingly polar mixtures of water (containing 1% by volume of NH₄OH (28-30% in H₂O)) and MeCN (5-30% gradient) as eluents. Pure fractions were evaporated to afford 1-[(8aS)-6-chloro-4-fluoro-5-(5-methyl-1H-benzotriazol-4-yl)-8a,9,11,12-tetrahydropyrazino[2',1':3,4][1,4]oxazepino [5,6,7-de]quinazolin-10 (8H)-yl]prop-2-en-1-one as a white solid. The solid was dissolved in MeOH (2 ml) and purified using chiral SFC (Phenomenex C1, 30×250 mm, 5 micron, Mobile phase: 40% MeOH+0.1% NH₃/60% scCO₂, Flow rate: 90 ml/min, BPR:120 bar, Column temperature: 40° C., UV @ 220 nm) to afford 1-[(8aS)-6-chloro-4-fluoro-5-(5-methyl-1H-benzotriazol-4-yl)-8a,9,11,12-tetrahydropyrazino[2',1':3,4][1,4] oxazepino[5,6,7-de]quinazolin-10(8H)-yl]prop-2-en-1-one—Atropisomer 1 (Example 18) (11 mg, 8%, d.e. 79%) as the first eluting peak. 1H NMR (400 MHz, CDCl₃, 30° C.) 2.25 (3H, s), 3.16-3.32 (1H, m), 3.44-3.66 (2H, m), 3.93-4.08 (2H, m), 4.5-4.57 (2H, m), 4.74 (2H, s), 5.84 (1H, dd), 6.42 (1H, dd), 6.59 (1H, dd), 7.34 (1H, d), 7.98 (1H, s), 8.36 (1H, s). 1 exchangeable NH signal not observed. m/z: ES+ [M+H]+ 480, 482.

1-[(8aS)-6-chloro-4-fluoro-5-(5-methyl-1H-benzotriazol-4-yl)-8a,9,11,12-tetrahydropyrazino[2',1':3,4] [1,4]oxazepino[5,6,7-de]quinazolin-10(8H)-yl]prop-2-en-1-one (Atropisomer 2, Example 19) was obtained as the second eluting peak (7 mg, 5.1%, d.e. 79%). 1H NMR (400 MHz, CDCl₃, 30° C.) 2.25 (3H, s), 3.13 (2H, s), 3.40 (1H, s), 3.89 (1H, s), 4.07 (1H, s), 4.50 (1H, s), 4.62 (1H, dd), 4.76 (1H, s), 5.19 (1H, d), 5.84 (1H, d), 6.40 (1H, d), 6.61 (1H, dd), 7.35 (1H, d), 7.98 (1H, s), 8.35 (1H, s). 1 exchangeable NH signal not observed. m/z: ES+ [M+H]+ 480, 482.

Tert-butyl (8aS)-4-fluoro-5-(5-fluoro-1H-benzimidazol-4-yl)-8a,9,11,12-tetrahydropyrazino[2',1':3,4][1,4]oxazepino[5,6,7-de]quinazoline-10(8H)-carboxylate

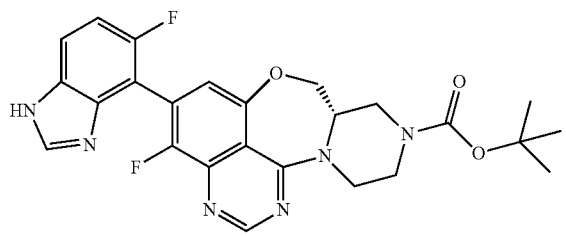 [SMILES: CC(C)(C)OC(=O)N1CCN2c3ncnc4c(F)c(-c5c(F)ccc6[nH]cnc56)cc(c34)OC[C@@H]2C1]

4-Bromo-5-fluoro-1-(tetrahydro-2H-pyran-2-yl)-1H-benzimidazole (0.257 g, 0.86 mmol), dicyclohexyl(2',6'-diisopropoxy-[1,1'-biphenyl]-2-yl)phosphane (0.040 g, 0.09 mmol), potassium carbonate (0.237 g, 1.72 mmol) and [(8aS)-10-(tert-butoxycarbonyl)-4-fluoro-8,8a,9,10,11,12-hexahydropyrazino[2',1':3,4][1,4]oxazepino[5,6,7-de]quinazolin-5-yl]boronic acid (0.347 g, 0.86 mmol) were combined in a degassed mixture of dioxane (5 ml) and water (1.5 ml). RuPhos Pd G3 (0.072 g, 0.09 mmol) was then added and the mixture degassed for a further 1 minute. The reaction was then heated at 80° C. for 16 hours. The cooled reaction mixture was diluted with EtOAc (50 ml), washed with 2M aqueous Na₂CO₃ (2×30 ml), brine (30 ml), dried (MgSO₄), filtered and the filtrate concentrated in vacuo. The crude product was purified by flash silica chromatography, elution gradient 0 to 80% EtOAc in heptane. Pure fractions were evaporated to dryness to afford tert-butyl (8aS)-4-fluoro-5-(5-fluoro-1-(tetrahydro-2H-pyran-2-yl)-1H-benzo[d]imidazol-4-yl)-8a,9,11,12-tetrahydropyrazino[2',1':3,4][1,4]oxazepino[5,6,7-de]quinazoline-10(8H)-carboxylate (0.497 g, 100%) as a brown gum. 1H NMR (400 MHz, CDCl₃, 30° C.) 1.51 (9H, s), 1.64-1.84 (4H, m), 2.06-2.3 (2H, m), 2.55 (1H, d), 2.89-3.29 (3H, m), 3.97-4.25 (3H, m), 4.29-4.57 (3H, m), 5.11 (1H, d), 5.75 (1H, dd), 7.12 (1H, d), 7.30 (1H, t), 7.66 (1H, dd), 7.87 (1H, s), 8.72 (1H, s). m/z (ES+), [M+H]+ 579.

(8aS)-6-Chloro-4-fluoro-5-(5-fluoro-1H-benzimidazol-4-yl)-8,8a,9,10,11,12-hexahydropyrazino[2',1':3,4][1,4]oxazepino[5,6,7-de]quinazoline

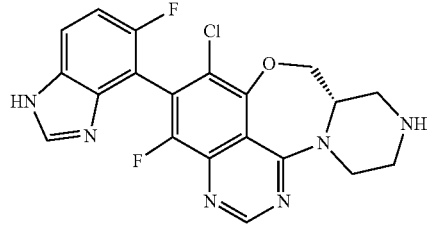 [SMILES: Fc1ccc2[nH]cnc2c1-c1c(Cl)c2c3c(ncnc3c1F)N1CCNC[C@H]1CO2]

N-Chlorosuccinimide (0.115 g, 0.86 mmol) was added in one portion to a stirred solution of tert-butyl (8aS)-4-fluoro-5-(5-fluoro-1H-benzimidazol-4-yl)-8a,9,11,12-tetrahydropyrazino[2',1':3,4][1,4] oxazepino[5,6,7-de]quinazoline-10(8H)-carboxylate (0.497 g, 0.86 mmol) in DMF (2.86 ml) and the reaction stirred at 110° C. for 1 hour. Additional N-chlorosuccinimide (0.115 g, 0.86 mmol) was then added and the reaction stirred at 110° C. for a further 1 hour and then cooled to ambient temperature. The solvents were removed in vacuo to give a brown gum. The gum was dissolved in DCM (10 ml) and TFA (10 ml) was then added at 20° C. and the reaction stirred for 1 hour. The crude product was purified by ion exchange chromatography, using an SCX column. The desired product was eluted from the column using 1M NH₃/MeOH and pure fractions were evaporated to dryness to afford (8aS)-6-chloro-4-fluoro-5-(5-fluoro-1H-benzo[d]imidazol-4-yl)-8,8a,9,10,11,12-hexahydropyrazino[2',1':3,4][1,4] oxazepino[5,6,7-de]quinazoline (0.328 g, 89%) as a yellow solid. 1H NMR (400 MHz, DMSO, 30° C.) 3.02-3.21 (4H, m), 4.06 (1H, s), 4.33-4.82 (2H, m), 5.01 (1H, s), 7.44 (1H, t), 7.65-7.87 (2H, m), 7.92 (1H, d), 8.62 (1H, s), 13.41 (1H, s). 1× exchangeable not seen. m/z (ES+), [M+H]+ 429.

1-((8aS)-6-chloro-4-fluoro-5-(5-fluoro-1H-benzo[d]imidazol-4-yl)-8a,9,11,12-tetrahydropyrazino[2',1':3,4][1,4]oxazepino[5,6,7-de]quinazolin-10(8H)-yl)prop-2-en-1-one—Atropisomer 1 (Example 20) and Atropisomer 2 (Example 21)

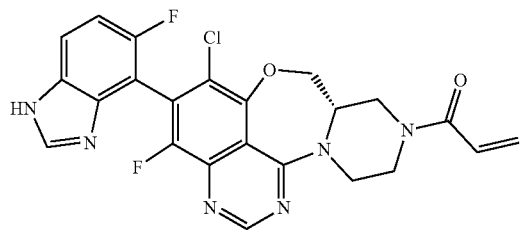 [SMILES: C=CC(=O)N1CCN2c3ncnc4c(F)c(-c5c(F)ccc6[nH]cnc56)c(Cl)c(c34)OC[C@@H]2C1]

To a solution of (8aS)-6-chloro-4-fluoro-5-(5-fluoro-1H-benzimidazol-4-yl)-8,8a,9,10,11,12-hexahydropyrazino[2',1':3,4][1,4]oxazepino[5,6,7-de]quinazoline (0.325 g, 0.76 mmol) in DCM (10 ml), 2-propanol (2.0 ml) and triethylamine (0.106 ml, 0.76 mmol) at −78° C. was added a solution of acryloyl chloride (0.072 g, 0.80 mmol) in DCM (1 ml) (added slowly dropwise over 5 min) and the reaction mixture stirred at −78° C. for 10 minutes. The reaction mixture was brought up to room temperature, diluted with DCM (20 ml), washed with water (20 ml), the organic layer passed through phase separating cartridge and concentrated in vacuo to give crude product. The crude product was purified by preparative HPLC (Waters XSelect CSH C18 column, 5μ silica, 30 mm diameter, 100 mm length), using decreasingly polar mixtures of water (containing 1% NH$_4$OH) and MeCN as eluents. Pure fractions were evaporated to dryness to afford a white solid. This was dissolved in MeOH and separated using SFC (Column: Phenomonex C4 30×250 mm, 5 micron, Mobile phase: 45% MeOH+0.1% NH$_3$/55% scCO$_2$, Flow rate: 100 ml/min, 120 bar, Column temp: 40° C.). The pure fractions were dried down to give the first eluting atropisomer 1-((8aS)-6-chloro-4-fluoro-5-(5-fluoro-1H-benzo[d]imidazol-4-yl)-8a,9,11,12-tetrahydropyrazino[2',1':3,4][1,4]oxazepino[5,6,7-de]quinazolin-10(8H)-yl)prop-2-en-1-one—Atropisomer 1 (12 mg, 36%). 1H NMR (400 MHz, MeOD, 30° C.) 3.14-3.25 (1H, m), 3.36-3.72 (2H, m), 3.99-4.41 (2H, m), 4.44-4.66 (3H, m), 5.09 (1H, d), 5.82 (1H, dd), 6.29 (1H, dd), 6.66-6.96 (1H, m), 7.37 (1H, t), 7.72 (2H, d), 8.60 (1H, s). 1 exchangeable proton not observed. m/z (ES+), [M+H]+ 483.

The 2nd eluting atropisomer 1-((8aS)-6-chloro-4-fluoro-5-(5-fluoro-1H-benzo[d]imidazol-4-yl)-8a,9,11,12-tetrahydropyrazino [2',1':3,4][1,4]oxazepino [5,6,7-de]quinazolin-10(8H)-yl)prop-2-en-1-one—Atropisomer 2 (14 mg, 42%) was also obtained. 1H NMR (400 MHz, MeOD, 30° C.) 3.33-3.72 (3H, m), 4.05-4.41 (2H, m), 4.46-4.69 (3H, m), 5.09 (1H, d), 5.82 (1H, dd), 6.29 (1H, dd), 6.79-6.96 (1H, m), 7.33-7.47 (1H, m), 7.62-7.83 (2H, m), 8.60 (1H, s). 1× exchangeable proton not observed. m/z (ES+), [M+H]+ 483.

Tert-butyl (8aS)-4-fluoro-5-(6-fluoro-2-methyl-3-nitrophenyl)-8a,9,11,12-tetrahydropyrazino [2',1':3,4][1,4]oxazepino[5,6,7-de]quinazoline-10(8H)-carboxylate

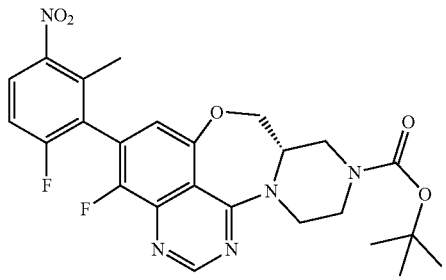 [SMILES: Cc1c([N+](=O)[O-])ccc(F)c1-c1cc2c3c(ncnc3c1F)N1CCN(C(=O)OC(C)(C)C)C[C@H]1CO2]

2-Bromo-1-fluoro-3-methyl-4-nitrobenzene (CAS 1427502-92-8; 0.440 g, 1.88 mmol), dicyclohexyl(2',6'-diisopropoxy-[1,1'-biphenyl]-2-yl)phosphane (0.070 g, 0.15 mmol), potassium carbonate (0.416 g, 3.01 mmol) and [(8aS)-10-(tert-butoxycarbonyl)-4-fluoro-8,8a,9,10,11,12-hexahydropyrazino[2',1':3,4][1,4]oxazepino[5,6,7-de]quinazolin-5-yl]boronic acid (0.608 g, 1.50 mmol) were combined in a degassed mixture of dioxane (10 ml) and water (3 ml). RuPhos Pd G3 (0.126 g, 0.15 mmol) was then added and the reaction was degassed for a further 1 minute then heated at 80° C. for 2 hours. The cooled reaction mixture was diluted with EtOAc (50 ml), washed with 2M aqueous Na$_2$CO$_3$ (2×30 ml), brine (30 ml), dried (MgSO$_4$), filtered and the filtrate concentrated in vacuo. The crude product was purified by flash silica chromatography, elution gradient 0 to 50% EtOAc in heptane. Pure fractions were evaporated to dryness to afford tert-butyl (8aS)-4-fluoro-5-(6-fluoro-2-methyl-3-nitrophenyl)-8a,9,11,12-tetrahydropyrazino[2',1':3,4][1,4]oxazepino[5,6,7-de]quinazoline-10(8H)-carboxylate (0.422 g, 54.6%) as a brown gum. 1H NMR (400 MHz, CDCl$_3$, 30° C.) 1.50 (9H, d), 2.96-3.27 (3H, m), 3.48 (3H, s), 3.75-3.97 (1H, m), 4.29-4.59 (3H, m), 5.11 (1H, d), 6.82 (1H, d), 7.12-7.23 (1H, m), 8.04 (1H, dd), 8.71 (1H, s). m/z (ES+), [M+H]+ 548.

Tert-butyl (8aS)-6-Chloro-4-fluoro-5-(6-fluoro-2-methyl-3-nitrophenyl)-8a,9,11,12-tetrahydropyrazino[2',1':3,4][1,4]oxazepino[5,6,7-de]quinazoline-10(8H)-carboxylate

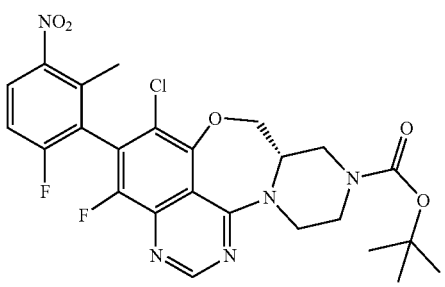 [SMILES: Cc1c([N+](=O)[O-])ccc(F)c1-c1c(Cl)c2c3c(ncnc3c1F)N1CCN(C(=O)OC(C)(C)C)C[C@H]1CO2]

N-Chlorosuccinimide (0.608 g, 4.55 mmol) was added in one portion to a stirred solution of tert-butyl (8aS)-4-fluoro-5-(6-fluoro-2-methyl-3-nitrophenyl)-8a,9,11,12-tetrahydropyrazino[2',1':3,4] [1,4]oxazepino[5,6,7-de]quinazoline-10(8H)-carboxylate (2.338 g, 4.55 mmol) in DMF (15.18 ml) and the reaction stirred at 110° C. for 1 hour. The reaction was then cooled to ambient temperature and the volatiles were removed in vacuo to give a brown gum. The crude product was purified by flash silica chromatography, elution gradient 0 to 50% EtOAc in heptane. Pure fractions were evaporated to dryness to afford tert-butyl (8aS)-6-chloro-4-fluoro-5-(6-fluoro-2-methyl-3-nitrophenyl)-8a,9,11,12-tetrahydropyrazino[2',1':3,4][1,4]oxazepino[5,6,7-de]quinazoline-10(8H)-carboxylate (1.339 g, 53.7%) as a yellow solid. 1H NMR (400 MHz, CDCl$_3$, 30° C.) 1.51 (9H, s), 2.34 (3H, d), 2.94-3.43 (3H, m), 3.78-4.01 (1H, m), 4.02-4.29 (2H, m), 4.36-4.65 (2H, m), 5.03 (1H, s), 7.12-7.23 (1H, m), 8.12 (1H, dd), 8.71 (1H, s). m/z (ES+), [M+H]+ 548.

Tert-butyl (8aS)-5-(3-amino-6-fluoro-2-methylphenyl)-6-chloro-4-fluoro-8a,9,11,12-tetrahydropyrazino[2',1':3,4][1,4]oxazepino[5,6,7-de]quinazoline-10(8H)-carboxylate

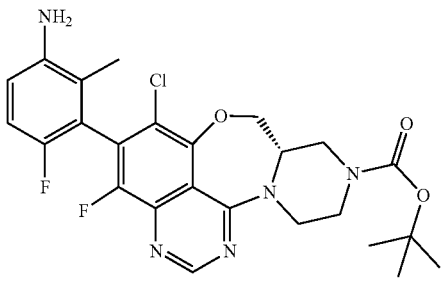 [SMILES: Cc1c(N)ccc(F)c1-c1c(Cl)c2c3c(ncnc3c1F)N1CCN(C(=O)OC(C)(C)C)C[C@H]1CO2]

Tert-butyl (8aS)-6-chloro-4-fluoro-5-(6-fluoro-2-methyl-3-nitrophenyl)-8a,9,11,12-tetrahydropyrazino[2',1':3,4][1,4]

oxazepino[5,6,7-de]quinazoline-10(8H)-carboxylate (1.337 g, 2.44 mmol) was dissolved in IPA (15 ml) and water (3 ml). Iron (0.681 g, 12.20 mmol) then ammonium chloride (0.653 g, 12.20 mmol) were added at ambient temperature. The reaction was then heated at 85° C. for 1 hour. The reaction was allowed to cool to ambient temperate and then filtered through celite. The celite was washed with ethyl acetate (50 ml) then methanol (50 ml). The combined filtrates were concentrated under reduced pressure, dissolved in DCM (50 ml) washed with sat NaHCO$_3$ (100 ml) and sat. aq. NaCl (100 ml). The organic was dried MgSO$_4$, filtered and evaporated to afford tert-butyl (8aS)-5-(3-amino-6-fluoro-2-methylphenyl)-6-chloro-4-fluoro-8a,9,11,12-tetrahydropyrazino [2',1':3,4][1,4]oxazepino[5,6,7-de]quinazoline-10(8H)-carboxylate (1.483 g, 117%) as a brown gum which was used without further purification. 1H NMR (400 MHz, CDCl3, 30° C.) 1.51 (9H, s), 1.91 (3H, d), 2.95-3.34 (3H, m), 3.58 (2H, s), 3.76-4 (1H, m), 4.01-4.28 (2H, m), 4.37-4.61 (2H, m), 4.87-5.08 (1H, m), 6.77 (1H, dd), 6.90 (1H, t), 8.69 (1H, s). m/z (ES+), [M+H]+ 571.

Tert-butyl (8aS)-5-(1-acetyl-5-fluoro-1H-indazol-4-yl)-6-chloro-4-fluoro-8a,9,11,12-tetrahydropyrazino [2',1':3,4][1,4]oxazepino[5,6,7-de]quinazoline-10(8H)-carboxylate

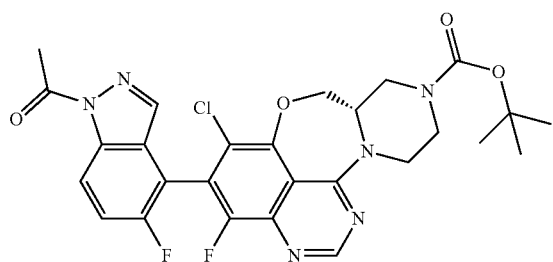 [SMILES: CC(=O)n1ncc2c(-c3c(Cl)c4c5c(ncnc5c3F)N3CCN(C(=O)OC(C)(C)C)C[C@H]3CO4)c(F)ccc21]

Acetic anhydride (0.047 ml, 0.50 mmol) was added to tert-butyl (8aS)-5-(3-amino-6-fluoro-2-methylphenyl)-6-chloro-4-fluoro-8a,9,11,12-tetrahydropyrazino[2',1':3,4][1, 4]oxazepino[5,6,7-de]quinazoline-10(8H)-carboxylate (0.103 g, 0.20 mmol) and potassium acetate (0.049 g, 0.50 mmol) in chloroform (20 ml). After heating to 70° C. for 30 min, 18-crown-6 (0.013 g, 0.05 mmol) and isopentyl nitrite (0.107 ml, 0.80 mmol) were added and the reaction was stirred for 16 hours at 70° C. After cooling, the reaction was washed with water, and the aqueous was extracted with DCM. The combined organics were concentrated, then the crude product was purified by flash silica chromatography, elution gradient 0 to 50% EtOAc in heptane. Pure fractions were evaporated to dryness to afford tert-butyl (8aS)-5-(1-acetyl-5-fluoro-1H-indazol-4-yl)-6-chloro-4-fluoro-8a,9,11, 12-tetrahydropyrazino[2',1':3,4][1,4]oxazepino[5,6,7-de] quinazoline-10(8H)-carboxylate (0.074 g, 65.2%) as an off-white solid. 1H NMR (400 MHz, CDCl$_3$, 30° C.) 1.52 (9H, s), 2.80 (3H, s), 2.97-3.38 (3H, m), 4.06-4.28 (3H, m), 4.32-4.69 (2H, m), 4.82-5.2 (1H, m), 7.4-7.53 (1H, m), 7.80 (1H, d), 8.57 (1H, dd), 8.73 (1H, s). m/z (ES+), [M+H]+ 571.

Tert-butyl (8aS)-6-chloro-4-fluoro-5-(5-fluoro-1H-indazol-4-yl)-8a,9,11,12-tetrahydropyrazino [2',1':3, 4][1,4]oxazepino[5,6,7-de]quinazoline-10(8H)-carboxylate—Atropisomer 1 and Atropisomer 2

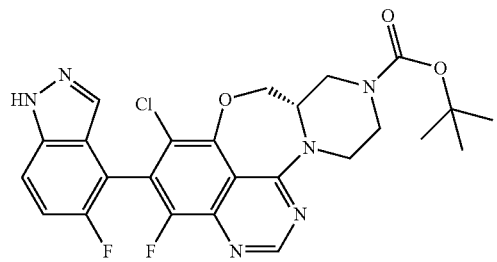 [SMILES: CC(C)(C)OC(=O)N1CCN2c3ncnc4c(F)c(-c5c(F)ccc6[nH]ncc56)c(Cl)c(c34)OC[C@@H]2C1]

Sodium hydroxide (9.94 ml, 19.88 mmol) was added to a stirred solution of tert-butyl (8aS)-5-(1-acetyl-5-fluoro-1H-indazol-4-yl)-6-chloro-4-fluoro-8a,9,11,12-tetrahydropyrazino[2',1':3,4][1,4]oxazepino [5,6,7-de]quinazoline-10 (8H)-carboxylate (1.135 g, 1.99 mmol) in a mixture of THF (15 ml) and MeOH (3 ml) and the reaction stirred for 1 hour. The crude product was purified by ion exchange chromatography, using an SCX column. The desired product was eluted from the column using 1M NH$_3$/MeOH and pure fractions were evaporated to dryness. The crude product was purified by flash silica chromatography, elution gradient 0 to 100% EtOAc in heptane. Pure fractions were evaporated to dryness to afford a pinkish solid. This was dissolved in MeOH and separated using the SFC (Column: Phenomonex C1 3×50 mm, 3 micron, Mobile phase: 45% MeOH+0.1% NH$_3$/55% scCO$_2$, Flow rate: 2 ml/min, 120 bar, Column temp: 40° C.). The fractions were evaporated to give, as first eluting atropisomer, tert-butyl (8aS)-6-chloro-4-fluoro-5-(5-fluoro-1H-indazol-4-yl)-8a,9,11,12-tetrahydropyrazino[2', 1':3,4][1,4]oxazepino[5,6,7-de]quinazoline-10(8H)-carboxylate—Atropisomer 1 (187 mg, 37%). 1H NMR (400 MHz, CDCl$_3$, 30° C.) 1.52 (9H, s), 2.95-3.34 (3H, m), 3.83-4.03 (1H, m), 4.03-4.34 (2H, m), 4.50 (1H, dd), 4.59 (1H, dd), 5.05 (1H, d), 7.33 (1H, t), 7.60 (1H, dd), 7.78 (1H, s), 8.73 (1H, s), 10.31 (1H, s). m/z (ES+), [M+H]+ 529.

A 2$^{nd}$ eluting atropisomer of tert-butyl (8aS)-6-chloro-4-fluoro-5-(5-fluoro-1H-indazol-4-yl)-8a,9,11,12-tetrahydropyrazino[2',1':3,4][1,4]oxazepino[5,6,7-de]quinazoline-10 (8H)-carboxylate, Atropisomer 2, was also obtained (180 mg, 36%). 1H NMR (400 MHz, CDCl$_3$, 30° C.) 1.52 (9H, s), 2.9-3.41 (3H, m), 3.82-3.98 (1H, m), 4-4.33 (2H, m), 4.44-4.63 (2H, m), 5.04 (1H, d), 7.33 (1H, t), 7.60 (1H, dd), 7.76 (1H, s), 8.73 (1H, s), 10.33 (1H, s). m/z (ES+), [M+H]+ 529.

(8aS)-6-Chloro-4-fluoro-5-(5-fluoro-1H-indazol-4-yl)-8,8a,9,10,11,12-hexahydropyrazino[2',1':3,4][1, 4]oxazepino[5,6,7-de]quinazoline—Atropisomer 1

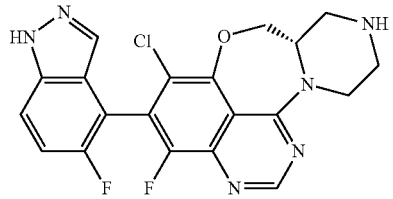 [SMILES: Fc1ccc2[nH]ncc2c1-c1c(Cl)c2c3c(ncnc3c1F)N1CCNC[C@H]1CO2]

TFA (1 ml) was added to a stirred solution of tert-butyl (8aS)-6-chloro-4-fluoro-5-(5-fluoro-1H-indazol-4-yl)-8a,9,11,12-tetrahydropyrazino[2',1':3,4][1,4]oxazepino[5,6,7-de]quinazoline-10(8H)-carboxylate—Atropisomer 1 (0.187 g, 0.35 mmol) in DCM (2 ml) at 20° C. and the reaction stirred for 1 hour. The crude product was purified by ion exchange chromatography, using an SCX column. The desired product was eluted from the column using 1M NH₃/MeOH and pure fractions were evaporated to dryness to afford (8aS)-6-chloro-4-fluoro-5-(5-fluoro-1H-indazol-4-yl)-8,8a,9,10,11,12-hexahydropyrazino[2',1':3,4][1,4]oxazepino[5,6,7-de]quinazoline—Atropisomer 1 (0.152 g, 100%) as a yellow solid. 1H NMR (400 MHz, DMSO, 30° C.) 2.71-2.89 (2H, m), 2.95-3.15 (2H, m), 3.87-4.21 (2H, m), 4.45-4.73 (2H, m), 4.98 (1H, d), 7.36-7.49 (1H, m), 7.69-7.86 (2H, m), 8.60 (1H, s), 13.41 (1H, s). 1× exchangeable proton not observed. m/z (ES+), [M+H]+ 429.

(8aS)-6-Chloro-4-fluoro-5-(5-fluoro-1H-indazol-4-yl)-8,8a,9,10,11,12-hexahydropyrazino[2',1':3,4][1,4]oxazepino[5,6,7-de]quinazoline—Atropisomer 2

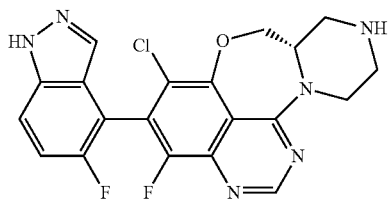 [SMILES: Fc1ccc2[nH]ncc2c1-c1c(Cl)c2c3c(ncnc3c1F)N1CCNC[C@H]1CO2]

(8aS)-6-Chloro-4-fluoro-5-(5-fluoro-1H-indazol-4-yl)-8,8a,9,10,11,12-hexahydropyrazino[2',1¹:3,4] [1,4]oxazepino[5,6,7-de]quinazoline—Atropisomer 2 was made in analogous manner to the foregoing Atropisomer 1, starting from tert-butyl (8aS)-6-chloro-4-fluoro-5-(5-fluoro-1H-indazol-4-yl)-8a,9,11,12-tetrahydropyrazino[2',1':3,4][1,4]oxazepino[5,6,7-de]quinazoline-10(8H)-carboxylate—Atropisomer 2. The desired atropisomer 2 exhibited: 1H NMR (400 MHz, DMSO, 30° C.) 2.63-2.88 (3H, m), 2.91-3.14 (2H, m), 3.8-4 (1H, m), 4.41-4.72 (2H, m), 4.95 (1H, d), 7.43 (1H, t), 7.65-7.89 (2H, m), 8.59 (1H, s), 13.40 (1H, s).1× exchangeable not seen. m/z: ES+ [M+H]+ 429.

1-[(8aS)-6-Chloro-4-fluoro-5-(5-fluoro-1H-indazol-4-yl)-8a,9,11,12-tetrahydropyrazino[2',1':3,4][1,4]oxazepino[5,6,7-de]quinazolin-10(8H)-yl]prop-2-en-1-one—Atropisomer 1 (Example 22)

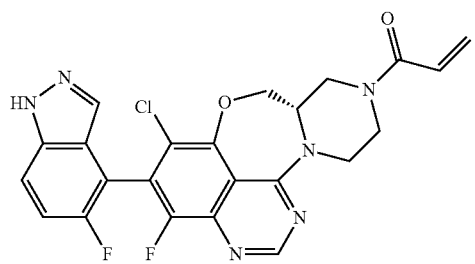 [SMILES: C=CC(=O)N1CCN2c3ncnc4c(F)c(-c5c(F)ccc6[nH]ncc56)c(Cl)c(c34)OC[C@@H]2C1]

To a solution of (8aS)-6-chloro-4-fluoro-5-(5-fluoro-1H-indazol-4-yl)-8,8a,9,10,11,12-hexahydropyrazino[2',1':3,4][1,4]oxazepino[5,6,7-de]quinazoline—Atropisomer 1 (0.152 g, 0.35 mmol) in dichloromethane (5 ml), 2-propanol (1 ml) and triethylamine (0.049 ml, 0.35 mmol) at −78° C. was added a solution of acryloyl chloride (0.034 g, 0.37 mmol) in dichloromethane (1 ml) (added slowly dropwise over 5 min) and the reaction mixture stirred at −78° C. for ten minutes. The reaction mixture was brought up to room temperature, diluted with DCM (20 ml), washed with water (20 ml), organic layer passed through phase separating cartridge and concentrated in vacuo to give crude product. The crude product was purified by preparative HPLC (Waters XSelect CSH C18 column, 5μ silica, 30 mm diameter, 100 mm length), using decreasingly polar mixtures of water (containing 1% NH₄OH) and MeCN as eluents. Fractions containing the desired compound were evaporated to dryness to afford Example 22, 1-((13aS)-11-chloro-9-fluoro-10-(5-fluoro-1H-indazol-4-yl)-3,4,13,13a-tetrahydropyrazino[2',1':3,4][1,4]oxazepino[5,6,7-de]quinazolin-2(1H)-yl)prop-2-en-1-one—Atropsiomer 1, (0.065 g, 38%) as an off-white solid. 1H NMR (400 MHz, DMSO, 30° C.) 3.17 (2H, s), 3.35-3.56 (1H, m), 3.95-4.24 (2H, m), 4.26-4.56 (1H, m), 4.57-4.78 (2H, m), 4.77-5 (1H, m), 5.76 (1H, dd), 6.19 (1H, dd), 6.86 (1H, s), 7.44 (1H, t), 7.67-8.01 (2H, m), 8.65 (1H, s), 13.42 (1H, s). m/z (ES+), [M+H]+ 483.

1-[(8aS)-6-Chloro-4-fluoro-5-(5-fluoro-1H-indazol-4-yl)-8a,9,11,12-tetrahydropyrazino[2',1':3,4][1,4]oxazepino[5,6,7-de]quinazolin-10(8H)-yl]prop-2-en-1-one—Atropisomer 2 (Example 23)

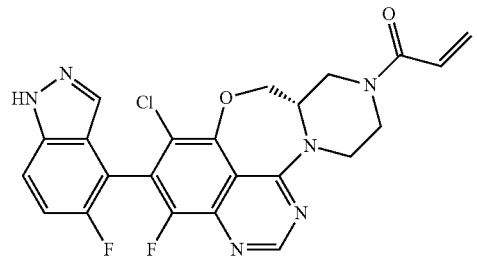 [SMILES: C=CC(=O)N1CCN2c3ncnc4c(F)c(-c5c(F)ccc6[nH]ncc56)c(Cl)c(c34)OC[C@@H]2C1]

1-[(8aS)-6-Chloro-4-fluoro-5-(5-fluoro-1H-indazol-4-yl)-8a,9,11,12-tetrahydropyrazino[2',1':3,4] [1,4]oxazepino[5,6,7-de]quinazolin-10(8H)-yl]prop-2-en-1-one—Atropisomer 2 (Example 23) was prepared in an analogous fashion to Example 22, starting from (8aS)-6-Chloro-4-fluoro-5-(5-fluoro-1H-indazol-4-yl)-8,8a,9,10,11,12-hexahydropyrazino[2',1':3,4][1,4]oxazepino[5,6,7-de]quinazoline—Atropisomer 2. Example 23 showed: 1H NMR (400 MHz, DMSO, 30° C.) 3.36-3.55 (2H, m), 3.97-4.24 (2H, m), 4.27-4.57 (2H, m), 4.59-4.77 (2H, m), 4.78-5.01 (1H, m), 5.76 (1H, dd), 6.19 (1H, dd), 6.7-7.07 (1H, m), 7.44 (1H, t), 7.68-7.83 (2H, m), 8.65 (1H, s), 13.41 (1H, s). m/z: ES+ [M+H]+ 483.

4-Bromo-5-fluoro-1-methyl-1H-benzo[d]imidazole

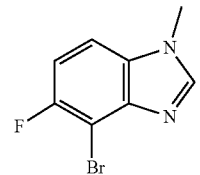

Iodomethane (2 ml, 32.13 mmol) was added to a stirred mixture of 4-bromo-5-fluoro-1H-benzo[d]imidazole (CAS 1360962-58-8; 1.834 g, 8.53 mmol), potassium carbonate (2.4 g, 17.06 mmol) and IPA (50 ml). The mixture was stirred at 80° C. for 24 hours and then cooled to ambient temperature. The mixture was diluted with EtOAc and the resulting solid was filtered off. The filtrate was concentrated in vacuo and the crude product was purified by flash silica chromatography, elution gradient 0 to 7% MeOH in DCM. Pure fractions were evaporated to dryness to afford a mixture of regioisomers. This mixture was purified further by preparative HPLC (Waters CSH C18 OBD column, 30×100 mm id, 5 micron particle size), using decreasingly polar mixtures of water (containing 1% by volume of NH$_4$OH (28-30% in H2O)) and MeCN as eluents. Fractions were evaporated to dryness to afford 7-bromo-6-fluoro-1-methyl-1H-benzo[d]imidazole (0.180 g, 9%) as a white solid and the desired 4-bromo-5-fluoro-1-methyl-1H-benzo[d]imidazole (0.195 g, 10%) as a white solid. 1H NMR (400 MHz, CDCl$_3$, 27° C.) 4.14 (3H, s), 7.05-7.12 (1H, m), 7.65 (1H, dd), 7.79 (1H, s). m/z (ES+), [M+H]+ 229.

Tert-butyl (8aS)-4-fluoro-5-(5-fluoro-1-methyl-1H-benzimidazol-4-yl)-8a,9,11,12-tetrahydropyrazino [2',1':3,4][1,4]oxazepino[5,6,7-de]quinazoline-10(8H)-carboxylate

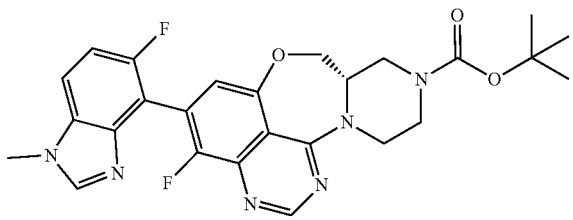 [SMILES: Cn1cnc2c(-c3cc4c5c(ncnc5c3F)N3CCN(C(=O)OC(C)(C)C)C[C@H]3CO4)c(F)ccc21]

4-Bromo-5-fluoro-1-methyl-1H-benzo[d]imidazole (0.190 g, 0.83 mmol), dicyclohexyl(2',6'-diisopropoxy-[1,1'-biphenyl]-2-yl)phosphane (0.039 g, 0.08 mmol), potassium carbonate (0.229 g, 1.66 mmol) and [(8aS)-10-(tert-butoxycarbonyl)-4-fluoro-8,8a,9,10,11,12-hexahydropyrazino[2',1':3,4] [1,4]oxazepino[5,6,7-de]quinazolin-5-yl]boronic acid (0.335 g, 0.83 mmol) were combined in a degassed mixture of dioxane (5 ml) and water (1.5 ml). RuPhos Pd G3 (0.069 g, 0.08 mmol) was added and the reaction was degassed for a further 1 minute then heated at 80° C. for 16 hours. The cooled reaction mixture was diluted with EtOAc (50 ml), washed with 2M aqueous Na$_2$CO$_3$ (2×30 ml), brine (30 ml), dried (MgSO$_4$), filtered and the filtrate concentrated in vacuo. The crude product was purified by flash silica chromatography, elution gradient 0 to 100% EtOAc in heptane followed by 10% MeOH in EtOAc. Pure fractions were evaporated to dryness to afford tert-butyl (8aS)-4-fluoro-5-(5-fluoro-1-methyl-1H-benzo[d]imidazol-4-yl)-8a,9,11,12-tetrahydropyrazino[2',1':3,4][1,4]oxazepino[5,6,7-de]quinazoline-10(8H)-carboxylate (0.329 g, 78%) as a brown solid. 1H NMR (400 MHz, CDCl$_3$, 30° C.) 1.51 (9H, s), 2.87-3.33 (3H, m), 3.75-3.87 (1H, m), 3.89 (3H, s), 3.99-4.25 (2H, m), 4.3-4.55 (2H, m), 5.08 (1H, d), 7.15-7.3 (2H, m), 7.41 (1H, dd), 7.90 (1H, s), 8.70 (1H, s). m/z (ES+), [M+H]+ 509.

Tert-butyl (8aS)-6-chloro-4-fluoro-5-(5-fluoro-1-methyl-1H-benzimidazol-4-yl)-8a,9,11,12-tetrahydropyrazino[2',1':3,4][1,4]oxazepino[5,6,7-de]quinazoline-10(8H)-carboxylate—Atropisomer 1 and Atropisomer 2

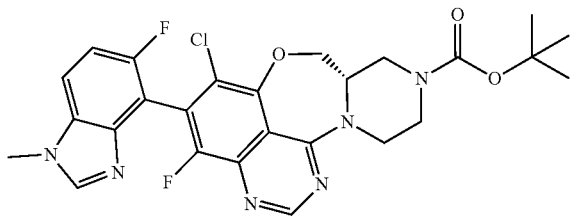 [SMILES: Cn1cnc2c(-c3c(Cl)c4c5c(ncnc5c3F)N3CCN(C(=O)OC(C)(C)C)C[C@H]3CO4)c(F)ccc21]

N-Chlorosuccinimide (0.086 g, 0.65 mmol) was added in one portion to a stirred solution of tert-butyl (8aS)-4-fluoro-5-(5-fluoro-1-methyl-1H-benzimidazol-4-yl)-8a,9,11,12-tetrahydropyrazino[2',1':3,4] [1,4]oxazepino[5,6,7-de]quinazoline-10(8H)-carboxylate (0.329 g, 0.65 mmol) in DMF (2.2 ml), the reaction stirred at 110° C. for 1 hour then cooled to ambient temperature. The solvents were removed in vacuo to give a brown gum. The crude product was purified by flash silica chromatography, elution gradient 0 to 100% EtOAc in heptane followed by 10% MeOH in EtOAc. Pure fractions were evaporated to dryness to afford a yellow solid. This was dissolved in MeOH and separated using SFC (Column: Phenomonex A1, 30×250 mm, 5 micron, Mobile phase: 45% IPA+0.1% DEA/55% scCO$_2$, Flow rate: 80 ml/min, 120 bar, Column temp: 40° C.). The fractions were dried down to give the 1$^{st}$ eluting atropisomer tert-butyl (8aS)-6-chloro-4-fluoro-5-(5-fluoro-1-methyl-1H-benzimidazol-4-yl)-8a,9,11,12-tetrahydropyrazino[2',1':3,4][1,4] oxazepino[5,6,7-de]quinazoline-10(8H)-carboxylate—Atropisomer 1 (61 mg, 37%). 1H NMR (400 MHz, CDCl3, 30° C.) 1.51 (9H, s), 2.89-3.27 (3H, m), 3.76-3.95 (4H, m), 3.99-4.31 (2H, m), 4.36-4.68 (2H, m), 5.00 (1H, d), 7.15-7.3 (1H, m), 7.38-7.57 (1H, m), 7.86 (1H, s), 8.68 (1H, d). m/z (ES+), [M+H]+ 543.

A 2$^{nd}$ eluting atropisomer of the same compound, Atropisomer 2, was also isolated (58 mg, 35%). 1H NMR (400 MHz, CDCl3, 30° C.) 1.51 (9H, s), 2.85-3.4 (3H, m), 3.75-3.94 (4H, m), 4.01-4.28 (2H, m), 4.4-4.66 (2H, m), 5.00 (1H, d), 7.23 (1H, d), 7.46 (1H, dd), 7.88 (1H, s), 8.69 (1H, s). m/z (ES+), [M+H]+ 543.

(8aS)-6-Chloro-4-fluoro-5-(5-fluoro-1-methyl-1H-benzimidazol-4-yl)-8,8a,9,10,11,12-hexahydropyrazino[2',1':3,4][1,4]oxazepino[5,6,7-de]quinazoline—Atropisomer 2

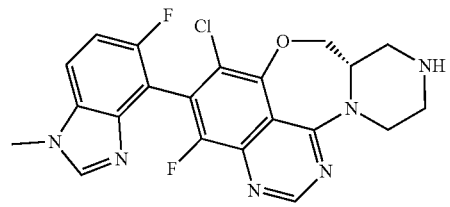 [SMILES: Cn1cnc2c(-c3c(Cl)c4c5c(ncnc5c3F)N3CCNC[C@H]3CO4)c(F)ccc21]

TFA (0.5 ml) was added to a stirred solution of tert-butyl (8aS)-6-chloro-4-fluoro-5-(5-fluoro-1-methyl-1H-benzimidazol-4-yl)-8a,9,11,12-tetrahydropyrazino[2',1':3,4][1,4]
oxazepino[5,6,7-de]quinazoline-10(8H)-carboxylate Atropsiomer 2 (0.058 g, 0.11 mmol) in DCM (1 ml) at 20° C. The reaction was allowed to stir for 1 hour. The crude product was purified by ion exchange chromatography, using an SCX column. The desired product was eluted from the column using 1M NH$_3$/MeOH and pure fractions were evaporated to dryness to afford (8aS)-6-chloro-4-fluoro-5-(5-fluoro-1-methyl-1H-benzimidazol-4-yl)-8,8a,9,10,11,12-hexahydropyrazino[2',1':3,4][1,4]oxazepino[5,6,7-de]quinazoline (0.043 g, 91%) as a yellow solid. m/z (ES+), [M+H]+ 443.

(8aS)-6-Chloro-4-fluoro-5-(5-fluoro-1-methyl-1H-benzimidazol-4-yl)-8,8a,9,10,11,12-hexahydropyrazino[2',1':3,4][1,4]oxazepino[5,6,7-de]quinazoline—Atropisomer 1

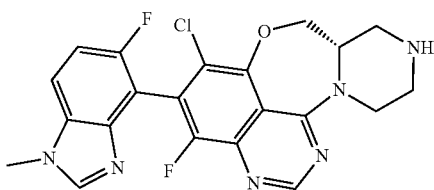 [SMILES: Cn1cnc2c(-c3c(Cl)c4c5c(ncnc5c3F)N3CCNC[C@H]3CO4)c(F)ccc21]

(8aS)-6-Chloro-4-fluoro-5-(5-fluoro-1-methyl-1H-benzimidazol-4-yl)-8,8a,9,10,11,12-hexahydropyrazino[2',1':3,4][1,4]oxazepino[5,6,7-de]quinazoline—Atropisomer 1 was prepared in an analogous fashion to (8aS)-6-Chloro-4-fluoro-5-(5-fluoro-1-methyl-1H-benzimidazol-4-yl)-8,8a,9,10,11,12-hexahydropyrazino[2',1':3,4][1,4]oxazepino[5,6,7-de]quinazoline—Atropisomer 2, starting from tert-butyl (8aS)-6-chloro-4-fluoro-5-(5-fluoro-1-methyl-1H-benzimidazol-4-yl)-8a,9,11,12-tetrahydropyrazino[2',1':3,4][1,4]oxazepino[5,6,7-de]quinazoline-10(8H)-carboxylate—Atropsiomer 1 that exhibited: 1H NMR (400 MHz, DMSO, 30° C.) 2.63-2.88 (3H, m), 2.91-3.14 (2H, m), 3.8-4 (1H, m), 4.41-4.72 (2H, m), 4.95 (1H, d), 7.43 (1H, t), 7.65-7.89 (2H, m), 8.59 (1H, s), 13.40 (1H, s). 1× exchangeable not seen. m/z: ES+ [M+H]+ 429.

1-((8aS)-6-Chloro-4-fluoro-5-(5-fluoro-1-methyl-1H-benzo[d]imidazol-4-yl)-8a,9,11,12-tetrahydropyrazino[2',1':3,4][1,4]oxazepino[5,6,7-de]quinazolin-10(8H)-yl)prop-2-en-1-one—Atropisomer 2
(Example 24)

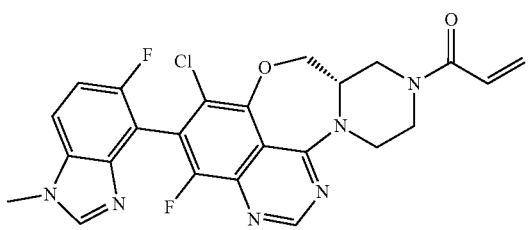 [SMILES: C=CC(=O)N1CCN2c3ncnc4c(F)c(-c5c(F)ccc6c5ncn6C)c(Cl)c(c34)OC[C@@H]2C1]

To a solution of (8aS)-6-chloro-4-fluoro-5-(5-fluoro-1-methyl-1H-benzo[d]imidazol-4-yl)-8,8a,9,10,11,12-hexahydropyrazino[2',1':3,4][1,4]oxazepino[5,6,7-de]quinazoline—Atropisomer 2 (0.043 g, 0.10 mmol) in dichloromethane (1 ml), 2-propanol (0.2 ml) and triethylamine (0.014 ml, 0.10 mmol) at −78° C. was added a solution of acryloyl chloride (9.23 mg, 0.10 mmol) in dichloromethane (1 ml) (added slowly dropwise over 5 min) and the reaction mixture stirred at −78° C. for 10 minutes. The reaction mixture was brought up to room temperature, diluted with DCM (20 ml), washed with water (20 ml), the organic layer passed through phase separating cartridge and concentrated in vacuo to give crude product. The crude product was purified by preparative HPLC (Waters XSelect CSH C18 column, 5µ silica, 30 mm diameter, 100 mm length), using decreasingly polar mixtures of water (containing 1% NH$_4$OH) and MeCN as eluents. Fractions containing the desired compound were evaporated to dryness to afford 1-((8aS)-6-chloro-4-fluoro-5-(5-fluoro-1-methyl-1H-benzo[d]imidazol-4-yl)-8a,9,11,12-tetrahydropyrazino[2',1':3,4][1,4]oxazepino[5,6,7-de]quinazolin-10(8H)-yl)prop-2-en-1-one—Atropisomer 2, Example 24, (0.026 g, 53.9%) as an off-white solid. 1H NMR (400 MHz, DMSO, 30° C.) 3.34-3.57 (2H, m), 3.90 (3H, s), 4.03-4.23 (2H, m), 4.26-4.55 (2H, m), 4.59-4.75 (2H, m), 4.78-4.99 (1H, m), 5.76 (1H, dd), 6.19 (1H, dd), 6.61-6.99 (1H, m), 7.24-7.43 (1H, m), 7.76 (1H, dd), 8.23 (1H, s), 8.63 (1H, s). m/z (ES+), [M+H]+ 497.

1-((8aS)-6-Chloro-4-fluoro-5-(5-fluoro-1-methyl-1H-benzo[d]imidazol-4-yl)-8a,9,11,12-tetrahydropyrazino[2',1':3,4][1,4]oxazepino[5,6,7-de]quinazolin-10(8H)-yl)prop-2-en-1-one—Atropisomer 1
(Example 25)

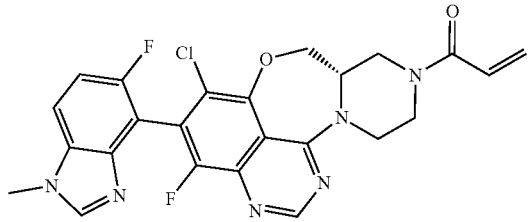 [SMILES: C=CC(=O)N1CCN2c3ncnc4c(F)c(-c5c(F)ccc6c5ncn6C)c(Cl)c(c34)OC[C@@H]2C1]

1-((8aS)-6-Chloro-4-fluoro-5-(5-fluoro-1-methyl-1H-benzo[d]imidazol-4-yl)-8a,9,11,12-tetrahydropyrazino[2',1':3,4][1,4]oxazepino[5,6,7-de]quinazolin-10(8H)-yl)prop-2-en-1-one—Atropisomer 1 (Example 25) was prepared in an analogous fashion to Example 24, starting from (8aS)-6-chloro-4-fluoro-5-(5-fluoro-1-methyl-1H-benzo[d]imidazol-4-yl)-8,8a,9,10,11,12-hexahydropyrazino[2',1':3,4][1,4]oxazepino [5,6,7-de]quinazoline—Atropisomer 1. Example 25 showed: 1H NMR (400 MHz, DMSO, 30° C.) 3.35-3.55 (2H, m), 3.90 (3H, s), 4.01-4.24 (2H, m), 4.25-4.56 (2H, m), 4.56-4.77 (2H, m), 4.78-5.01 (1H, m), 5.76 (1H, dd), 6.19 (1H, dd), 6.69-7.04 (1H, m), 7.22-7.52 (1H, m), 7.76 (1H, dd), 8.22 (1H, s), 8.63 (1H, s). m/z: ES+ [M+H]+ 497.

2-Bromo-3-fluoro-6-nitroaniline

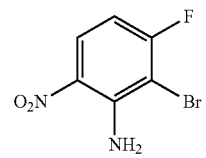 [SMILES: Nc1c([N+](=O)[O-])ccc(F)c1Br]

Triethylamine (8.87 ml, 63.63 mmol) was added to a stirred suspension of 2-bromo-1,3-difluoro-4-nitrobenzene (CAS 103977-78-2; 5.05 g, 21.21 mmol) and ammonium carbonate (2.04 g, 21.21 mmol) in DMF (35 ml) at ambient temperature and the reaction stirred for 18 hours. Water (100 ml) was then added and the mixture extracted with DCM (3×50 ml). The combined organics were washed with water (3×100 ml), brine (100 ml), passed through a phase separating cartridge and concentrated in vacuo to give 2-bromo-3-fluoro-6-nitroaniline (5.35 g, 107%) as a yellow solid which was used without further purification. 1H NMR (400 MHz, CDCl$_3$, 30° C.) 6.55 (1H, dd), 6.90 (2H, s), 8.21 (1H, dd). m/z: ES+[M+H]+ 233.

Tert-butyl (8aS)-5-(2-amino-6-fluoro-3-nitrophenyl)-4-fluoro-8a,9,11,12-tetrahydropyrazino[2',1':3,4][1,4]oxazepino[5,6,7-de]quinazoline-10(8H)-carboxylate

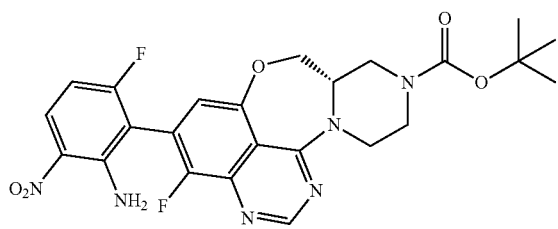 [SMILES: CC(C)(C)OC(=O)N1CCN2c3ncnc4c(F)c(-c5c(F)ccc([N+](=O)[O-])c5N)cc(c34)OC[C@@H]2C1]

2-Bromo-3-fluoro-6-nitroaniline (0.538 g, 2.29 mmol), dicyclohexyl(2',6'-diisopropoxy-[1,1'-biphenyl]-2-yl)phosphane (0.107 g, 0.23 mmol), potassium carbonate (0.633 g, 4.58 mmol) and [(8aS)-10-(tert-butoxycarbonyl)-4-fluoro-8,8a,9,10,11,12-hexahydropyrazino[2',1':3,4][1,4]oxazepino[5,6,7-de]quinazolin-5-yl]boronic acid (0.926 g, 2.29 mmol) were combined in a degassed mixture of dioxane (10 ml) and water (3.0 ml). RuPhos Pd G3 (0.192 g, 0.23 mmol) was added and the reaction was degassed for a further 1 minute then heated at 80° C. for 16 hours. The cooled reaction mixture was diluted with EtOAc (50 ml), washed with 2M aqueous Na$_2$CO$_3$ (2×30 ml), brine (30 ml), dried (MgSO$_4$), filtered and the filtrate concentrated in vacuo. The crude product was purified by flash silica chromatography, elution gradient 0 to 60% EtOAc in heptane. Pure fractions were evaporated to dryness to afford tert-butyl (8aS)-5-(2-amino-6-fluoro-3-nitrophenyl)-4-fluoro-8a,9,11,12-tetrahydropyrazino[2',1':3,4][1,4]oxazepino[5,6,7-de]quinazoline-10(8H)-carboxylate (0.850 g, 72.1%) as a brown solid. 1H NMR (400 MHz, CDCl$_3$, 30° C.) 1.50 (9H, d), 2.86-3.32 (3H, m), 3.76-3.98 (1H, m), 4-4.26 (2H, m), 4.27-4.55 (2H, m), 4.92-5.23 (1H, m), 6.31 (2H, d), 6.52-6.67 (1H, m), 6.85-6.97 (1H, m), 8.31 (1H, dd), 8.70 (1H, d). m/z (ES+), [M+H]+ 515.

Tert-butyl (8aS)-5-(2-amino-6-fluoro-3-nitrophenyl)-6-chloro-4-fluoro-8a,9,11,12-tetrahydropyrazino[2',1':3,4][1,4]oxazepino[5,6,7-de]quinazoline-10(8H)-carboxylate

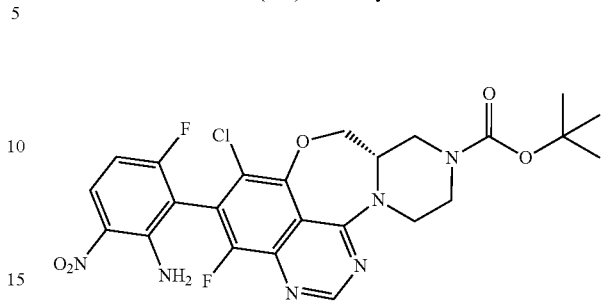

N-Chlorosuccinimide (0.108 g, 0.81 mmol) was added in one portion to a stirred solution of tert-butyl (8aS)-5-(2-amino-6-fluoro-3-nitrophenyl)-4-fluoro-8a,9,11,12-tetrahydropyrazino[2',1':3,4] [1,4]oxazepino[5,6,7-de]quinazoline-10(8H)-carboxylate (0.415 g, 0.81 mmol) in DMF (2.69 ml) and the reaction stirred at 110° C. for 1 hour and then cooled to ambient temperature. The solvents were removed in vacuo to give a brown gum. The crude product was purified by preparative HPLC (Waters XSelect CSH C18 column, 5μ silica, 30 mm diameter, 100 mm length), using decreasingly polar mixtures of water (containing 1% NH$_3$) and MeCN as eluents. Fractions containing the desired compound were evaporated to dryness to afford tert-butyl (8aS)-5-(2-amino-6-fluoro-3-nitrophenyl)-6-chloro-4-fluoro-8a,9,11,12-tetrahydropyrazino[2',1':3,4][1,4]oxazepino[5,6,7-de]quinazoline-10(8H)-carboxylate (0.105 g, 23.71%) as a yellow solid. 1H NMR (400 MHz, CDCl3, 30° C.) 1.51 (9H, s), 2.77-3.41 (3H, m), 3.73-4.34 (3H, m), 4.37-4.62 (2H, m), 5.04 (1H, s), 6.17 (2H, d), 6.62 (1H, ddd), 8.36 (1H, dd), 8.71 (1H, d). m/z (ES+), [M+H]+ 549

Tert-butyl (8aS)-6-chloro-5-(2,3-diamino-6-fluorophenyl)-4-fluoro-8a,9,11,12-tetrahydropyrazino[2',1':3,4][1,4]oxazepino[5,6,7-de]quinazoline-10(8H)-carboxylate

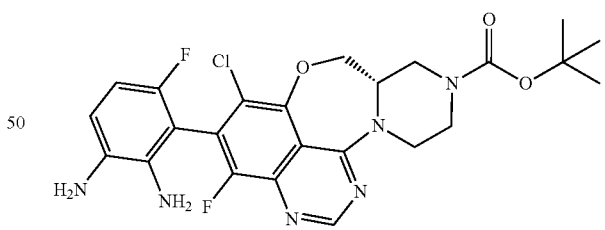

Tert-butyl (8aS)-5-(2-amino-6-fluoro-3-nitrophenyl)-6-chloro-4-fluoro-8a,9,11,12-tetrahydropyrazino [2',1':3,4][1,4]oxazepino[5,6,7-de]quinazoline-10(8H)-carboxylate (0.187 g, 0.34 mmol) was dissolved in IPA (3 ml) and water (0.5 ml). Iron (0.095 g, 1.70 mmol) then ammonium chloride (0.091 g, 1.70 mmol) were added at ambient temperature. The reaction was then heated at 85° C. for 1 hour. The reaction was cooled to ambient temperature then filtered through celite. The celite was washed with ethyl acetate (100 ml) and the combined filtrates were washed with sat. aq. NaHCO$_3$ (100 ml) then sat. NaCl (100 ml). The organic phase were dried over MgSO$_4$, filtered and evaporated to afford tert-butyl (8aS)-6-chloro-5-(2,3-diamino-6-fluorophenyl)-4-fluoro-8a,9,11,12-tetrahydropyrazino [2',1':3,4][1,4]oxazepino[5,6,7-de]quinazoline-10(8H)-carboxylate (0.177 g, 100%) as a yellow solid as a mixture of atropisomers. 1H NMR (400 MHz, CDCl3, 30° C.) 1.53 (9H, d), 2.91-3.36 (5H, m), 3.47 (2H, d), 3.73-4.03 (1H, m), 3.99-4.29 (2H, m), 4.35-4.68 (2H, m), 4.78-5.17 (1H, m), 6.55 (1H, t), 6.68-6.86 (1H, m), 8.70 (1H, s). m/z (ES+), [M+H]+ 519.

Tert-butyl (8aS)-6-chloro-4-fluoro-5-(5-fluoro-1H-benzotriazol-4-yl)-8a,9,11,12-tetrahydropyrazino[2',1':3,4][1,4]oxazepino[5,6,7-de]quinazoline-10(8H)-carboxylate—Atropsiomer 1 and Atropisomer 2

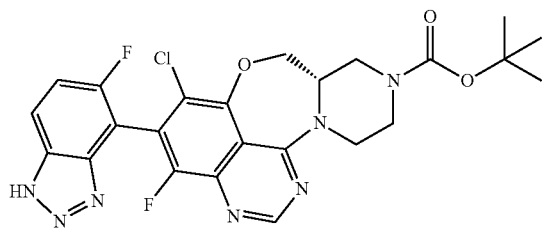 [SMILES: CC(C)(C)OC(=O)N1CCN2c3ncnc4c(F)c(-c5c(F)ccc6[nH]nnc56)c(Cl)c(c34)OC[C@@H]2C1]

Sodium nitrite (0.038 g, 0.55 mmol) in water (0.5 ml) was added dropwise to a stirred solution tert-butyl (8aS)-6-chloro-5-(2,3-diamino-6-fluorophenyl)-4-fluoro-8a,9,11,12-tetrahydropyrazino [2',1':3,4][1,4]oxazepino[5,6,7-de]quinazoline-10(8H)-carboxylate (0.177 g, 0.34 mmol) in acetic acid (2 ml) at 8° C. The reaction was allowed to warm to ambient temperature and stirred for a further 1 hour. The solvents were removed in vacuo, the residue dissolved in DCM (50 ml) and washed with saturated sodium bicarbonate solution (100 ml). The organic layer was passed through a phase separating cartridge and concentrated under reduced pressure to give a brown solid. The residue was dissolved in MeOH and separated using SFC (Column: Chiralpak ID, 30×250 mm, 5 micron, Mobile phase: 30% MeOH+0.1% NH3/70% scCO2, Flow rate: 90 ml/min, 120 bar, Column temp: 40° C.). Fractions containing product were evaporated to give the 1st eluting atropisomer tert-butyl (8aS)-6-chloro-4-fluoro-5-(5-fluoro-1H-benzotriazol-4-yl)-8a,9,11,12-tetrahydropyrazino[2',1':3,4] [1,4]oxazepino[5,6,7-de]quinazoline-10(8H)-carboxylate—Atropisomer 1 (43 mg, 27%). 1H NMR (400 MHz, CDCl3, 30° C.) 1.52 (9H, s), 2.82-3.19 (3H, m), 3.82-4.03 (1H, m), 4.04-4.44 (3H, m), 4.57 (1H, dd), 5.22 (1H, d), 7.23 (1H, d), 8.14 (1H, dd), 8.24 (1H, s). 1 exchangeable proton not observed. m/z (ES+), [M+H]+ 530.

Also isolated from the SFC purification was the 2$^{nd}$ eluting atropisomer tert-butyl (8aS)-6-chloro-4-fluoro-5-(5-fluoro-1H-benzotriazol-4-yl)-8a,9,11,12-tetrahydropyrazino [2',1':3,4][1,4]oxazepino [5,6,7-de]quinazoline-10(8H)-carboxylate—Atropisomer 2 (38 mg, 24%). 1H NMR (400 MHz, CDCl3, 30° C.) 1.52 (9H, s), 2.93-3.44 (3H, m), 3.66 (1H, s), 3.8-4.24 (3H, m), 4.47 (2H, s), 7.22 (1H, d), 8.13 (1H, dd), 8.28 (1H, s). 1× exchangeable proton not observed. m/z (ES+), [M+H]+ 530.

(8aS)-6-Chloro-4-fluoro-5-(5-fluoro-1H-benzotriazol-4-yl)-8,8a,9,10,11,12-hexahydropyrazino[2',1':3,4][1,4]oxazepino[5,6,7-de]quinazoline—Atropisomer 1

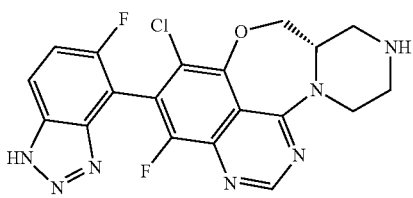 [SMILES: Fc1ccc2[nH]nnc2c1-c1c(Cl)c2c3c(ncnc3c1F)N1CCNC[C@H]1CO2]

TFA (0.5 ml) was added to a stirred solution of tert-butyl (8aS)-6-chloro-4-fluoro-5-(5-fluoro-1H-benzotriazol-4-yl)-8a,9,11,12-tetrahydropyrazino[2',1':3,4][1,4]oxazepino[5,6,7-de]quinazoline-10(8H)-carboxylate—Atropisomer 1 (0.043 g, 0.08 mmol) in DCM (1 ml) at 20° C. The reaction was allowed to stir for 1 hour. The crude product was purified by ion exchange chromatography, using an SCX column. The desired product was eluted from the column using 1M NH3/MeOH and pure fractions were evaporated to dryness to afford (8aS)-6-chloro-4-fluoro-5-(5-fluoro-1H-benzotriazol-4-yl)-8,8a,9,10,11,12-hexahydropyrazino[2',1':3,4][1,4]oxazepino[5,6,7-de]quinazoline—Atropisomer 1 (0.033 g, 95%) as a yellow solid. m/z (ES+), [M+H]+ 430.

(8aS)-6-Chloro-4-fluoro-5-(5-fluoro-1H-benzotriazol-4-yl)-8,8a,9,10,11,12-hexahydropyrazino[2',1':3,4][1,4]oxazepino[5,6,7-de]quinazoline—Atropisomer 2

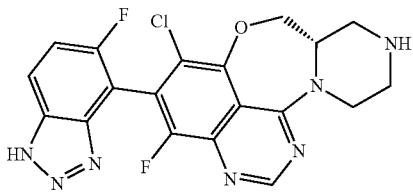 [SMILES: Fc1ccc2[nH]nnc2c1-c1c(Cl)c2c3c(ncnc3c1F)N1CCNC[C@H]1CO2]

(8aS)-6-Chloro-4-fluoro-5-(5-fluoro-1H-benzotriazol-4-yl)-8,8a,9,10,11,12-hexahydropyrazino [2',1':3,4][1,4]oxazepino[5,6,7-de]quinazoline—Atropisomer 2 was prepared in an analogous fashion to the foregoing Atropisomer 1, starting from tert-butyl (8aS)-6-chloro-4-fluoro-5-(5-fluoro-1H-benzotriazol-4-yl)-8a,9,11,12-tetrahydropyrazino [2',1':3,4][1,4] oxazepino [5,6,7-de]quinazoline-10(8H)-carboxylate—Atropisomer 2. The desired product exhibited: m/z: ES+ [M+H]+ 430.

1-[(8aS)-6-Chloro-4-fluoro-5-(5-fluoro-1H-benzotriazol-4-yl)-8a,9,11,12-tetrahydropyrazino[2',1':3,4][1,4]oxazepino[5,6,7-de]quinazolin-10(8H)-yl]prop-2-en-1-one—Atropisomer 1 (Example 26)

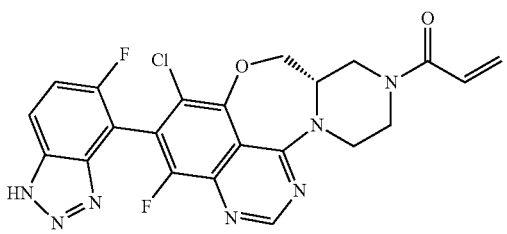 [SMILES: C=CC(=O)N1CCN2c3ncnc4c(F)c(-c5c(F)ccc6[nH]nnc56)c(Cl)c(c34)OC[C@@H]2C1]

To a solution of (8aS)-6-chloro-4-fluoro-5-(5-fluoro-1H-benzotriazol-4-yl)-8,8a,9,10,11,12-hexahydropyrazino[2',1':3,4][1,4]oxazepino[5,6,7-de]quinazoline—Atropisomer 1 (0.033 g, 0.08 mmol) in DCM (1 ml), 2-propanol (0.2 ml) and TEA (10.70 µl, 0.08 mmol) at −78° C. was added a solution of acryloyl chloride (7.30 mg, 0.08 mmol) in DCM (1 ml) (added slowly dropwise over 5 min) and the reaction mixture stirred at −78° C. for 10 minutes. The reaction mixture was brought up to room temperature, diluted with DCM (20 ml), washed with water (20 ml) and the organic layer passed through phase separating cartridge and concentrated in vacuo to give crude product. The crude product was purified by preparative HPLC (Waters XSelect CSH C18 column, 5µ silica, 30 mm diameter, 100 mm length), using decreasingly polar mixtures of water (containing 1% NH$_4$OH) and MeCN as eluents. Fractions containing the desired compound were evaporated to dryness to afford 88 mg of a white solid (formate salt). This solid was dissolved in DCM (25 ml) stirred with saturated sodium hydrogen carbonate solution (25 ml) for 2 hours. The organic layer was passed through a phase separating cartridge and concentrated in vacuo to give Example 26, 1-[(8aS)-6-chloro-4-fluoro-5-(5-fluoro-1H-benzotriazol-4-yl)-8a,9,11,12-tetrahydropyrazino [2',1':3,4][1,4] oxazepino [5,6,7-de] quinazolin-10(8H)-yl]prop-2-en-1-one, (7.5 mg, 20.19%) as an off-white solid. 1H NMR (400 MHz, CDCl3, 30° C.) 2.72-3.26 (3H, m), 3.26-3.47 (1H, m), 3.69-4.2 (2H, m), 4.22-4.86 (3H, m), 5.03-5.42 (1H, m), 5.82 (1H, d), 6.38 (1H, d), 6.58 (1H, t), 8.12 (1H, s), 8.31 (1H, s). m/z (ES+), [M+H]+ 484.

1-[(8aS)-6-Chloro-4-fluoro-5-(5-fluoro-1H-benzotriazol-4-yl)-8a,9,11,12-tetrahydropyrazino[2',1':3,4][1,4]oxazepino[5,6,7-de]quinazolin-10(8H)-yl]prop-2-en-1-one—Atropisomer 2 (Example 27)

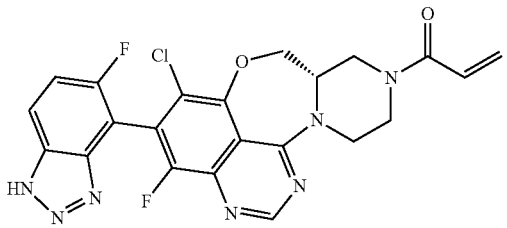 [SMILES: C=CC(=O)N1CCN2c3ncnc4c(F)c(-c5c(F)ccc6[nH]nnc56)c(Cl)c(c34)OC[C@@H]2C1]

1-[(8aS)-6-Chloro-4-fluoro-5-(5-fluoro-1H-benzotriazol-4-yl)-8a,9,11,12-tetrahydropyrazino[2',1':3,4] [1,4]oxazepino[5,6,7-de]quinazolin-10(8H)-yl]prop-2-en-1-one—Atropisomer 2 (Example 27) was prepared in an analogous fashion to Example 26, starting from (8aS)-6-chloro-4-fluoro-5-(5-fluoro-1H-benzotriazol-4-yl)-8,8a,9,10,11,12-hexahydropyrazino[2',1':3,4][1,4]oxazepino[5,6,7-de] quinazoline—Atropisomer 2. Example 27 exhibited: 1H NMR (400 MHz, CDCl$_3$, 30° C.) 3.08-3.75 (4H, m), 3.82-4.08 (2H, m), 4.28-4.6 (3H, m), 4.6-4.94 (1H, m), 5.85 (1H, d), 6.43 (1H, d), 6.49-6.67 (1H, m), 8.13 (1H, dd), 8.38 (1H, s). 1× exchangeable not seen. m/z: ES+ [M+H]+ 484

8-Bromo-7-fluoroisoquinoline

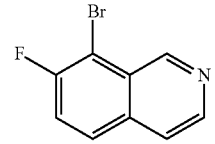 [SMILES: Fc1ccc2ccncc2c1Br]

2,2-Diethoxyethan-1-amine (6.07 ml, 41.77 mmol) was added to a stirred solution of 2-bromo-3-fluorobenzaldehyde (CAS 891180-59-9; 8.479 g, 41.77 mmol) in anhydrous toluene (20 ml) and the mixture was stirred at 100° C. for 18 hours. The reaction mixture was allowed to cool to ambient temperature and concentrated in vacuo. The crude residue was dissolved in DCM (30 ml) and cooled to 0° C. Aluminum trichloride (18.38 g, 137.83 mmol) was added portionwise and the resultant dark red suspension was left to stir at 0° C. for 30 mins and then allowed to slowly warm to ambient temperature over 1 hour and stirred for 16 hours. The reaction mixture was poured into ice water and was diluted with DCM. The reaction mixture was basified with 2M aqueous NaOH solution and the phases separated. The aqueous phase was extracted with DCM, the combined organic extracts were passed through a phase separator cartridge and the filtrate was concentrated in vacuo. The crude product was purified by flash silica chromatography, elution gradient 0 to 40% EtOAc. Fractions containing the desired product were concentrated in vacuo to give 8-bromo-7-fluoroisoquinoline (2.23 g, 23.6%) as a brown solid. 1H NMR (400 MHz, CDCl$_3$, 30° C.) 7.52 (1H, t), 7.64 (1H, d), 7.81 (1H, dd), 8.62 (1H, d), 9.63 (1H, s). m/z: ES+ [M+H]+ 228.

8-Bromo-7-fluoroisoquinoline 2-oxide

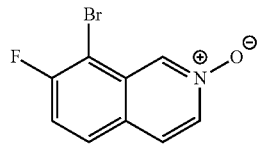 [SMILES: [O-][n+]1ccc2ccc(F)c(Br)c2c1]

mCPBA (0.523 g, 2.34 mmol) was added to a stirred solution of 8-bromo-7-fluoroisoquinoline (0.44 g, 1.95 mmol) in DCM (10 ml) at ambient temperature and the reaction stirred for 2 hours. The mixture was diluted with DCM (100 ml) and washed with saturated sodium bicarbonate solution (2×100 ml). The organic layer was passed through a phase separating cartridge and concentrated in vacuo to give 8-bromo-7-fluoroisoquinoline 2-oxide (0.466 g, 99%) as a pale yellow solid. 1H NMR (400 MHz, CDCl$_3$, 30° C.) 7.38 (1H, dd), 7.66 (1H, d), 7.76 (1H, dd), 8.16 (1H, dd), 9.09-9.2 (1H, m). m/z: ES+ [M+H]+ 242.

8-Bromo-7-fluoro-1-methoxyisoquinoline

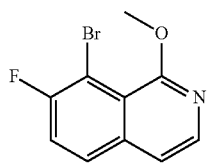

Triethylamine (0.924 ml, 6.63 mmol) was added to a stirred suspension of 8-bromo-7-fluoroisoquinoline 2-oxide (0.802 g, 3.31 mmol) and methyl chloroformate (0.333 ml, 4.31 mmol) at 0° C. The reaction was allowed to stir overnight at ambient temperature. Further methyl chloroformate (0.333 ml, 4.31 mmol) and triethylamine (0.924 ml, 6.63 mmol) were added and the reaction stirred for a further 2 h. Volatiles were removed under reduced pressure and the residue was dissolved in DCM (50 ml) and washed with water (50 ml) then brine (50 ml). The organic layer was passed through a phase separating cartridge and concentrated in vacuo. The crude product was purified by flash silica chromatography, elution gradient 0 to 25% EtOAc in heptane. Pure fractions were evaporated to dryness to afford 8-bromo-7-fluoro-1-methoxyisoquinoline (0.386 g, 45.5%) as a white solid. 1H NMR (400 MHz, CDCl3, 30° C.) 4.11 (3H, s), 7.21 (1H, d), 7.42 (1H, dd), 7.67 (1H, dd), 7.99 (1H, d). m/z: ES+ [M+H]+ 258.

Tert-butyl (8aS)-6-chloro-4-fluoro-5-(7-fluoro-1-methoxyisoquinolin-8-yl)-8a,9,11,12-tetrahydropyrazino[2',1':3,4][1,4]oxazepino[5,6,7-de]quinazoline-10(8H)-carboxylate

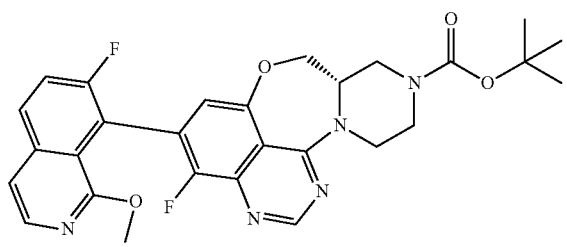 [SMILES: COc1nccc2ccc(F)c(-c3cc4c5c(ncnc5c3F)N3CCN(C(=O)OC(C)(C)C)C[C@H]3CO4)c12]

8-Bromo-7-fluoro-1-methoxyisoquinoline (0.251 g, 0.98 mmol), dicyclohexyl(2',6'-diisopropoxy-[1,1'-biphenyl]-2-yl)phosphane (0.046 g, 0.10 mmol), potassium carbonate (0.271 g, 1.96 mmol) and [(8aS)-10-(tert-butoxycarbonyl)-4-fluoro-8,8a,9,10,11,12-hexahydropyrazino[2',1':3,4][1,4]oxazepino[5,6,7-de]quinazolin-5-yl]boronic acid (0.396 g, 0.98 mmol) were combined in a degassed mixture of dioxane (5 ml) and water (1.5 ml). RuPhos Pd G3 (0.082 g, 0.10 mmol), was added and the reaction was degassed for a further 1 minute then heated at 80° C. for 2 hours. The cooled reaction mixture was diluted with EtOAc (50 ml), washed with 2M aqueous Na2CO3 (2×30 ml), brine (30 ml), dried (MgSO4), filtered and the filtrate concentrated in vacuo. The crude product was purified by flash silica chromatography, elution gradient 0 to 60% EtOAc in heptane. Pure fractions were evaporated to dryness to afford tert-butyl (8aS)-6-chloro-4-fluoro-5-(7-fluoro-1-methoxyisoquinolin-8-yl)-8a,9,11,12-tetrahydropyrazino[2',1':3,4][1,4]oxazepino[5,6,7-de]quinazoline-10(8H)-carboxylate (0.525 g, 100%) as a brown gum. 1H NMR (400 MHz, CDCl3, 30° C.) 1.51 (9H, s), 2.89-3.32 (3H, m), 3.64 (3H, d), 3.76-3.98 (1H, m), 3.99-4.25 (2H, m), 4.31-4.57 (2H, m), 5.13 (1H, s), 6.94 (1H, d), 7.28 (1H, d), 7.52 (1H, t), 7.85 (1H, dd), 8.01 (1H, d), 8.70 (1H, s). m/z: ES+ [M+H]+ 536.

Tert-butyl (8aS)-6-chloro-4-fluoro-5-(7-fluoro-1-methoxyisoquinolin-8-yl)-8a,9,11,12-tetrahydropyrazino[2',1':3,4][1,4]oxazepino[5,6,7-de]quinazoline-10(8H)-carboxylate—Atropisomer 1 and Atropisomer 2

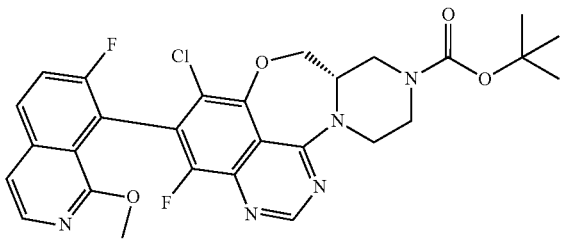 [SMILES: COc1nccc2ccc(F)c(-c3c(Cl)c4c5c(ncnc5c3F)N3CCN(C(=O)OC(C)(C)C)C[C@H]3CO4)c12]

N-Chlorosuccinimide (0.137 g, 1.03 mmol) was added in one portion to a stirred solution of tert-butyl (8aS)-6-chloro-4-fluoro-5-(7-fluoro-1-methoxyisoquinolin-8-yl)-8a,9,11,12-tetrahydropyrazino [2',1':3,4][1,4]oxazepino[5,6,7-de] quinazoline-10(8H)-carboxylate (0.525 g, 0.98 mmol) in DMF (4 ml) and the reaction stirred at 120° C. for 30 minutes. The reaction was cooled to ambient temperature and the solvents were removed in vacuo to give a brown gum. The crude product was purified by flash silica chromatography, elution gradient 0 to 70% EtOAc in heptane. Pure fractions were evaporated to dryness to afford a yellow solid. This was dissolved in MeOH and separated using SFC (Column: Chiralpak IG, 30×250 mm, 5 micron, Mobile phase: 45% MeOH+0.1% NH3/65% scCO2, Flow rate: 100 ml/min, 120 bar, Column temp: 40° C.). Product containing fractions were evaporated to the first eluting atropisomer give tert-butyl (8aS)-6-chloro-4-fluoro-5-(7-fluoro-1-methoxyisoquinolin-8-yl)-8a,9,11,12-tetrahydropyrazino[2',1':3,4][1,4]oxazepino[5,6,7-de]quinazoline-10(8H)-carboxylate—Atropisomer 1 (132 mg, 23%). 1H NMR (400 MHz, CDCl3, 30° C.) 1.52 (9H, s), 3-3.3 (3H, m), 3.63 (3H, s), 3.97 (1H, s), 4.16 (2H, s), 4.37-4.63 (2H, m), 5.08 (1H, d), 7.31 (1H, s), 7.56 (1H, t), 7.90 (1H, dd), 8.02 (1H, d), 8.71 (1H, s). m/z: ES+ [M+H]+ 570. Also isolated from the SFC purification was the 2nd eluting atropisomer tert-butyl (8aS)-6-chloro-4-fluoro-5-(7-fluoro-1-methoxyisoquinolin-8-yl)-8a,9,11,12-tetrahydropyrazino[2',1':3,4][1,4]oxazepino[5,6,7-de]quinazoline-10(8H)-carboxylate—Atropisomer 2 (245 mg, 42%). 1H NMR (400 MHz, CDCl3, 30° C.) 1.51 (9H, s), 3.05-3.42 (3H, m), 3.63 (3H, s), 3.83-4.04 (1H, m), 4.05-4.32 (2H, m), 4.38-4.69 (2H, m), 5.03 (1H, s), 7.30 (1H, d), 7.56 (1H, t), 7.90 (2H, dd), 8.02 (1H, d), 8.71 (1H, s). ES+ [M+H]+ 570.

8-[(8aS)-6-Chloro-4-fluoro-8,8a,9,10,11,12-hexahydropyrazino[2',1':3,4][1,4]oxazepino[5,6,7-de]quinazolin-5-yl]-7-fluoroisoquinolin-1(2H)-one—Atropisomer 1

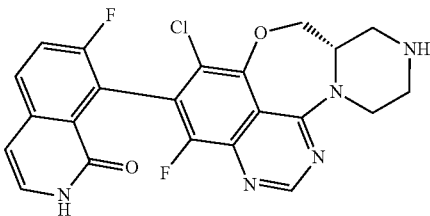 [SMILES: O=c1[nH]ccc2ccc(F)c(-c3c(Cl)c4c5c(ncnc5c3F)N3CCNC[C@H]3CO4)c12]

A microwave vial was charged with tert-butyl (8aS)-6-chloro-4-fluoro-5-(7-fluoro-1-methoxyisoquinolin-8-yl)-8a,9,11,12-tetrahydropyrazino[2',1':3,4][1,4]oxazepino[5,6,7-de] quinazoline-10(8H)-carboxylate—Atropisomer 1 (132 mg, 0.23 mmol), lithium chloride (49.1 mg, 1.16 mmol), 4-methylbenzenesulfonic acid hydrate (220 mg, 1.16 mmol) and anhydrous DMF (4 ml). The microwave vial was sealed and irradiated in the microwave at 120° C. for 30 mins. The crude product was purified by ion exchange chromatography, using an SCX column (10 g), loading in MeOH. The column was washed with MeOH, then the desired product was eluted from the column using 1M NH$_3$/MeOH and the pure fractions were evaporated to dryness to afford 8-((13aS)-11-chloro-9-fluoro-1,2,3,4,13,13a-hexahydropyrazino[2',1':3,4][1,4]oxazepino[5,6,7-de]quinazolin-10-yl)-7-fluoroisoquinolin-1(2H)-one—Atropisomer 1 (106 mg, 100%) as an off white solid. 1H NMR (400 MHz, CDCl3, 30° C.) 2.84-3.21 (5H, m), 3.47 (1H, s), 3.78-4.01 (1H, m), 4.36 (1H, dd), 4.51 (1H, dd), 5.06 (1H, d), 6.50 (1H, d), 6.91 (1H, d), 7.51 (1H, t), 7.66 (1H, dd), 8.65 (1H, s). 1 exchangeable proton not observed. m/z: ES+ [M+H]+ 456.

8-[(8aS)-6-Chloro-4-fluoro-8,8a,9,10,11,12-hexahydropyrazino[2',1':3,4][1,4]oxazepino[5,6,7-de]quinazolin-5-yl]-7-fluoroisoquinolin-1(2H)-one—Atropisomer 2

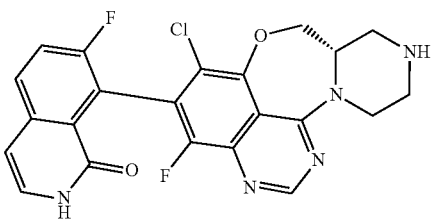 [SMILES: O=c1[nH]ccc2ccc(F)c(-c3c(Cl)c4c5c(ncnc5c3F)N3CCNC[C@H]3CO4)c12]

8-[(8aS)-6-Chloro-4-fluoro-8,8a,9,10,11,12-hexahydropyrazino[2',1':3,4][1,4]oxazepino[5,6,7-de] quinazolin-5-yl]-7-fluoroisoquinolin-1(2H)-one—Atropisomer 2 (151 mg, 77%), an off white solid, was prepared in an analogous fashion to the foregoing, corresponding, Atropisomer 1 described, starting from tert-butyl (8aS)-6-chloro-4-fluoro-5-(7-fluoro-1-methoxyisoquinolin-8-yl)-8a,9,11,12-tetrahydropyrazino[2',1':3,4][1,4]oxazepino [5,6,7-de]quinazoline-10(8H)-carboxylate—Atropisomer 2. The desired Atropisomer 2 showed: 1H NMR (400 MHz, CDCl$_3$, 30° C.) 2.89-3.21 (5H, m), 3.78-4.01 (1H, m), 4.32-4.57 (2H, m), 5.06 (1H, d), 6.51 (1H, d), 6.95 (1H, d), 7.52 (1H, t), 7.67 (1H, dd), 8.65 (1H, s). 2× exchangeable H's not seen. m/z: ES+ [M+H]+ 456.

8-[(8aS)-6-Chloro-4-fluoro-10-(prop-2-enoyl)-8,8a,9,10,11,12-hexahydropyrazino[2',1':3,4][1,4]oxazepino[5,6,7-de]quinazolin-5-yl]-7-fluoroisoquinolin-1(2H)-one—Atropisomer 1 (Example 28)

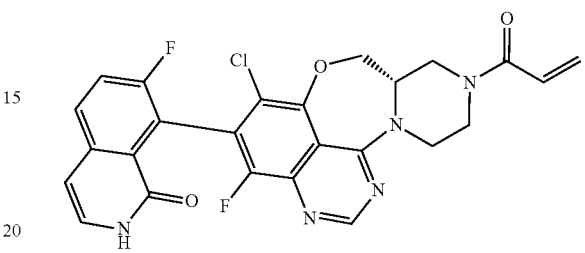

To a solution of 8-[(8aS)-6-chloro-4-fluoro-8,8a,9,10,11,12-hexahydropyrazino[2',1':3,4] [1,4]oxazepino[5,6,7-de]quinazolin-5-yl]-7-fluoroisoquinolin-1(2H)-one—Atropisomer 1 (0.106 g, 0.23 mmol) in dichloromethane (3 ml), 2-propanol (1 ml) and triethylamine (0.032 ml, 0.23 mmol) at −78° C. was added a solution of acryloyl chloride (0.022 g, 0.24 mmol) in dichloromethane (1 ml) (added slowly dropwise over 5 min) and the reaction mixture stirred at −78° C. for 10 minutes. The reaction mixture was brought up to ambient temperature, diluted with DCM (20 ml), washed with water (20 ml), the organic layer passed through a phase separating cartridge and concentrated in vacuo to give crude product. The crude product was purified by preparative HPLC (Waters XSelect CSH C18 column, 5µ silica, 30 mm diameter, 100 mm length), using decreasingly polar mixtures of water (containing 1% NH$_3$) and MeCN as eluents. Fractions containing the desired compound, Example 28, were evaporated to dryness to afford 8-[(8aS)-6-chloro-4-fluoro-10-(prop-2-enoyl)-8,8a,9,10,11,12-hexahydropyrazino [2',1':3,4] [1,4]oxazepino[5,6,7-de]quinazolin-5-yl]-7-fluoroisoquinolin-1(2H)-one—Atropisomer 1 (0.066 g, 55.7%) as a white solid. 1H NMR (400 MHz, DMSO, 30° C.) 2.94-3.14 (2H, m), 3.99-4.22 (3H, m), 4.23-4.52 (1H, m), 4.52-4.75 (2H, m), 4.74-5 (1H, m), 5.75 (1H, dd), 6.18 (1H, dd), 6.68 (1H, d), 6.86 (1H, s), 7.19 (1H, d), 7.78 (1H, t), 7.93 (1H, dd), 8.60 (1H, s). m/z: ES+ [M+H]+ 510.

8-[(8aS)-6-Chloro-4-fluoro-10-(prop-2-enoyl)-8,8a,9,10,11,12-hexahydropyrazino[2',1':3,4][1,4]oxazepino[5,6,7-de]quinazolin-5-yl]-7-fluoroisoquinolin-1(2H)-one—Atropisomer 2 (Example 29)

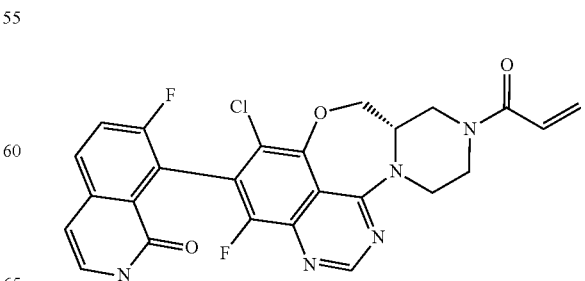

Example 29, 8-[(8aS)-6-Chloro-4-fluoro-10-(prop-2-enoyl)-8,8a,9,10,11,12-hexahydropyrazino [2',1':3,4][1,4]oxazepino[5,6,7-de]quinazolin-5-yl]-7-fluoroisoquinolin-1(2H)-one—Atropisomer 2, (0.083 g, 49%) a white solid, was prepared in an analogous fashion to Example 28, starting from 8-[(8aS)-6-chloro-4-fluoro-8,8a,9,10,11,12-hexahydropyrazino[2',1':3,4][1,4]oxazepino[5,6,7-de] quinazolin-5-yl]-7-fluoroisoquinolin-1(2H)-one—Atropisomer 2. Example 29 showed: 1H NMR (400 MHz, DMSO, 30° C.) 2.93-3.2 (1H, m), 3.35-3.58 (2H, m), 4.02 (1H, d), 4.09-4.75 (4H, m), 4.86 (1H, dd), 5.75 (1H, dd), 6.19 (1H, dd), 6.68 (1H, d), 6.76-7.02 (1H, m), 7.19 (1H, d), 7.79 (1H, t), 7.94 (1H, dd), 8.61 (1H, s), 11.01 (1H, s). m/z: ES+ [M+H]+ 510.

Tert-butyl (8aS)-6-chloro-4-fluoro-5-(5-methyl-1H-indazol-4-yl)-8a,9,11,12-tetrahydropyrazino[2',1':3,4][1,4]oxazepino[5,6,7-de]quinazoline-10(8H)-carboxylate—Atropisomer 1 and Atropisomer 2

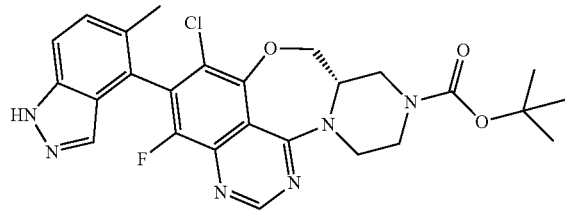 [SMILES: Cc1ccc2[nH]ncc2c1-c1c(Cl)c2c3c(ncnc3c1F)N1CCN(C(=O)OC(C)(C)C)C[C@H]1CO2]

Pd118 (0.086 g, 0.13 mmol) was added to a degassed suspension of (5-methyl-1H-indazol-4-yl)boronic acid (CAS 1245816-10-7; 0.418 g, 2.37 mmol) and tert-butyl (S)-10-bromo-11-chloro-9-fluoro-3,4,13,13a-tetrahydropyrazino[2',1':3,4][1,4]oxazepino[5,6,7-de]quinazoline-2(1H)-carboxylate (0.5 g, 1.06 mmol) in a mixture of dioxane (15 ml) and 2M aqueous sodium carbonate (2.90 ml, 5.81 mmol). The reaction mixture was stirred at 100° C. for 2 hours. The cooled reaction mixture was diluted with EtOAc (50 ml), washed with 2M aqueous Na$_2$CO$_3$ (2×30 ml), brine (30 ml), dried (MgSO$_4$), filtered and the filtrate concentrated in vacuo. The crude material was purified by flash silica chromatography, elution gradient 0-100% EtOAc in heptane. Pure fractions were evaporated to dryness to afford a yellow solid. This was dissolved in MeOH and separated using SFC (Column: Phenomenex C1, 30×250 mm, 5 micron, Mobile phase: 40% MeOH+0.1% NH$_3$/60% scCO$_2$, Flow rate: 100 ml/min, 120 bar, Column temp: 40° C.). Product containing fractions were evaporated to give the 1$^{st}$ eluting atropisomer tert-butyl (8aS)-6-chloro-4-fluoro-5-(5-methyl-1H-indazol-4-yl)-8a,9,11,12-tetrahydropyrazino [2',1':3,4][1,4]oxazepino[5,6,7-de]quinazoline-10(8H)-carboxylate—Atropisomer 1 (58 mg, 49%) as an off-white solid. 1H NMR (400 MHz, CDCl$_3$, 30° C.) 1.51 (9H, s), 2.23 (3H, s), 2.95-3.37 (3H, m), 3.74-4.01 (1H, m), 4.16 (2H, s), 4.36-4.69 (2H, m), 5.04 (1H, d), 7.36 (1H, d), 7.50 (1H, d), 7.58 (1H, s), 8.71 (1H, s), 10.83 (1H, s). m/z: ES+ [M+H]+ 525.

A 2$^{nd}$ eluting atropisomer, Atropisomer 2, of the same compound (34 mg, 29%) was also isolated as an off white solid. 1H NMR (400 MHz, CDCl$_3$, 30° C.) 1.51 (9H, s), 2.23 (3H, s), 2.98-3.4 (3H, m), 3.95 (1H, d), 4.17 (2H, s), 4.42-4.68 (2H, m), 5.05 (1H, d), 7.38 (1H, d), 7.51 (1H, d), 7.60 (1H, s), 8.72 (1H, s), 10.34 (1H, s). m/z: ES+ [M+H]+ 525.

(8aS)-6-Chloro-4-fluoro-5-(5-methyl-1H-indazol-4-yl)-8,8a,9,10,11,12-hexahydropyrazino[2',1':3,4][1,4]oxazepino[5,6,7-de]quinazoline—Atropisomer 2

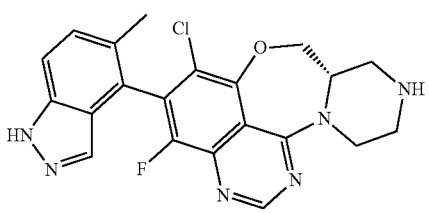 [SMILES: Cc1ccc2[nH]ncc2c1-c1c(Cl)c2c3c(ncnc3c1F)N1CCNC[C@H]1CO2]

To a solution of tert-butyl (8aS)-6-chloro-4-fluoro-5-(5-methyl-1H-indazol-4-yl)-8a,9,11,12-tetrahydropyrazino[2',1':3,4][1,4]oxazepino[5,6,7-de]quinazoline-10(8H)-carboxylate—Atropisomer 2 (0.151 g, 0.29 mmol) in dichloromethane (2 ml) at 0° C. under nitrogen was added 2,2,2-trifluoroacetic acid (1 ml, 13.06 mmol) and the reaction mixture stirred for two hours then the solvents evaporated. The residue was dissolved in methanol and applied to a 5 g SCX column washing thoroughly with methanol then the product was eluted using 1M ammonia in methanol. The solvent was evaporated and to afford (13aS)-11-chloro-9-fluoro-10-(5-methyl-1H-indazol-4-yl)-1,2,3,4,13,13a-hexahydropyrazino[2',1':3,4][1,4]oxazepino[5,6,7-de]quinazoline—Atropisomer 2 (0.122 g, 100%) as an off-white solid. m/z: ES+ [M+H]+ 425.

(8aS)-6-Chloro-4-fluoro-5-(5-methyl-1H-indazol-4-yl)-8,8a,9,10,11,12-hexahydropyrazino[2',1':3,4][1,4]oxazepino[5,6,7-de]quinazoline—Atropisomer 1

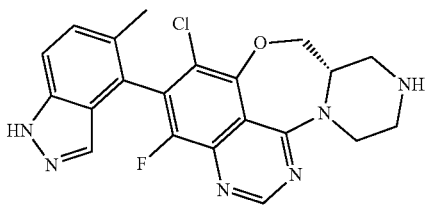 [SMILES: Cc1ccc2[nH]ncc2c1-c1c(Cl)c2c3c(ncnc3c1F)N1CCNC[C@H]1CO2]

(8aS)-6-Chloro-4-fluoro-5-(5-methyl-1H-indazol-4-yl)-8,8a,9,10,11,12-hexahydropyrazino[2',1':3,4] [1,4]oxazepino[5,6,7-de]quinazoline—Atropisomer 1 (0.116 g, 100%), an off-white solid, was made in an analogous fashion to the foregoing, corresponding, Atropisomer 2, starting from tert-butyl (8aS)-6-chloro-4-fluoro-5-(5-methyl-1H-indazol-4-yl)-8a,9,11,12-tetrahydropyrazino[2',1':3,4][1,4] oxazepino[5,6,7-de]quinazoline-10(8H)-carboxylate—Atropisomer 1. The product exhibited: m/z: ES+[M+H]+ 425.

(2E)-1-[(8aS)-6-chloro-4-fluoro-5-(5-methyl-1H-indazol-4-yl)-8a,9,11,12-tetrahydropyrazino[2',1':3,4][1,4]oxazepino[5,6,7-de]quinazolin-10(8H)-yl]-4-(dimethylamino)but-2-en-1-one—Atropisomer 2 (Example 30)

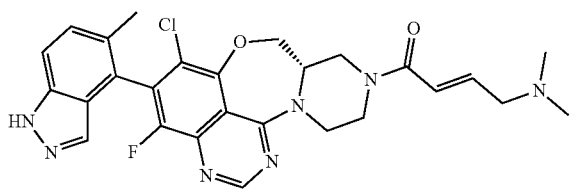 [SMILES: Cc1ccc2[nH]ncc2c1-c1c(Cl)c2c3c(ncnc3c1F)N1CCN(C(=O)/C=C/CN(C)C)C[C@H]1CO2]

DIPEA (150 μL, 0.86 mmol) was added in one portion to (8aS)-6-chloro-4-fluoro-5-(5-methyl-1H-indazol-4-yl)-8,8a,9,10,11,12-hexahydropyrazino[2',1':3,4][1,4]oxazepino[5,6,7-de]quinazoline—Atropisomer 2 (122 mg, 0.29 mmol), O-(7-Azabenzotriazol-1-yl)-N,N,N',N'-tetramethyluronium hexafluorophosphate (131 mg, 0.34 mmol) and (E)-4-(dimethylamino)but-2-enoic acid. HCl salt (52.3 mg, 0.32 mmol) in DMA (1.2 ml) at ambient temperature. The resulting solution was stirred for 1 hour.

The reaction mixture was poured into water (10 ml), extracted into EtOAc (2×25 ml), washed with brine (20 ml), the organic layer dried over MgSO$_4$, filtered and evaporated to afford crude product. The crude product was purified by preparative HPLC (Waters XSelect CSH C18 column, 5μ silica, 50 mm diameter, 100 mm length), using decreasingly polar mixtures of water (containing 0.1% NH$_3$) and MeCN as eluents. Fractions containing the desired compound were evaporated to dryness to afford Example 30, (79 mg, 51%), (2E)-1-[(8aS)-6-chloro-4-fluoro-5-(5-methyl-1H-indazol-4-yl)-8a,9,11,12-tetrahydropyrazino[2',1':3,4][1,4]oxazepino[5,6,7-de]quinazolin-10(8H)-yl]-4-(dimethylamino)but-2-en-1-one—Atropisomer 2, as a white solid. 1H NMR (400 MHz, DMSO, 30° C.) 2.14 (3H, s), 2.17 (6H, s), 3.03-3.09 (3H, m), 3.38-3.53 (2H, m), 3.92-4.21 (2H, m), 4.22-4.42 (1H, m), 4.43-4.56 (1H, m), 4.56-4.76 (2H, m), 4.75-4.97 (1H, m), 6.42-6.78 (2H, m), 7.37 (1H, d), 7.5-7.65 (2H, m), 8.63 (1H, s). m/z: ES+ [M+H]+ 536.

(2E)-1-[(8aS)-6-chloro-4-fluoro-5-(5-methyl-1H-indazol-4-yl)-8a,9,11,12-tetrahydropyrazino[2',1':3,4][1,4]oxazepino[5,6,7-de]quinazolin-10(8H)-yl]-4-(dimethylamino)but-2-en-1-one—Atropisomer 1 (Example 31)

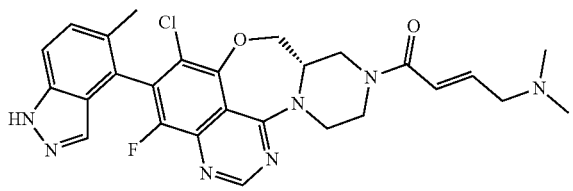 [SMILES: Cc1ccc2[nH]ncc2c1-c1c(Cl)c2c3c(ncnc3c1F)N1CCN(C(=O)/C=C/CN(C)C)C[C@H]1CO2]

(2E)-1-[(8aS)-6-chloro-4-fluoro-5-(5-methyl-1H-indazol-4-yl)-8a,9,11,12-tetrahydropyrazino [2',1':3,4] [1,4]oxazepino[5,6,7-de]quinazolin-10(8H)-yl]-4-(dimethylamino)but-2-en-1-one—Atropisomer 1 (Example 31) (68 mg, 47%), a white solid, was prepared in an analogous fashion to Example 30, starting from (8aS)-6-chloro-4-fluoro-5-(5-methyl-1H-indazol-4-yl)-8,8a,9,10,11,12-hexahydropyrazino [2',1':3,4][1,4]oxazepino[5,6,7-de]quinazoline—Atropisomer 1. Example 31 showed: 1H NMR (400 MHz, DMSO, 100° C.) 2.17 (3H, s), 2.21 (6H, s), 3.27-3.61 (5H, m), 4.03-4.28 (3H, m), 4.34 (1H, d), 4.60 (1H, dd), 4.69 (1H, dd), 4.78-4.94 (1H, m), 6.5-6.78 (2H, m), 7.36 (1H, d), 7.50 (1H, s), 7.57 (1H, d), 8.62 (1H, s). m/z: ES+ [M+H]+ 536.

Methyl N-benzyl-D-alaninate

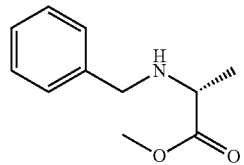

Sodium borohydride (27.1 g, 716.44 mmol) was added portionwise to a solution of methyl D-alaninate hydrochloride (25 g, 179.11 mmol), benzaldehyde (18.15 ml, 179.11 mmol) and triethylamine (49.9 ml, 358.22 mmol) in MeOH (250 ml) at 0° C. The resulting solution was stirred at 25° C. overnight. The reaction mixture was quenched with saturated NH$_4$Cl (200 ml), extracted with DCM (3×100 ml) and dried over Na$_2$SO$_4$, and filtrate evaporated to dryness. The crude product was purified by flash silica chromatography, elution gradient 10 to 30% EtOAc in petroleum ether. Pure fractions were evaporated to dryness to afford methyl N-benzyl-D-alaninate (15 g, 43%) as a colourless oil. 1H NMR (300 MHz, CDCl$_3$, 30° C.) 1.35 (3H, d), 2.07 (1H, s), 3.32-3.47 (1H, m), 3.69 (1H, d), 3.75 (3H, s), 3.82 (1H, d), 7.29-7.43 (5H, m). m/z: ES+ [M+H]+=194.

Methyl (3R)-4-{benzyl[(2S)-1-methoxy-1-oxopropan-2-yl]amino}-3-[(tert-butoxycarbonyl)amino]-4-oxobutanoate

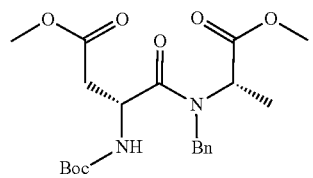

2-Methylpropyl carbonochloridate (0.848 g, 6.21 mmol) was added slowly to (2R)-2-[(tert-butoxycarbonyl)amino]-4-methoxy-4-oxobutanoic acid (1.407 g, 5.69 mmol) and N-methylmorpholine (0.628 g, 6.21 mmol) in THF (4 ml) at 0° C. The resulting solution was stirred at 0° C. for 1 hour. A solution of methyl N-benzyl-D-alaninate (1 g, 5.17 mmol) in THF (4 ml) was added and the reaction was stirred overnight. The reaction mixture was quenched with water (50 ml), extracted with EtOAc (3×20 ml), the organic layer was dried over Na$_2$SO$_4$, filtered and evaporated to dryness. The crude product was purified by flash silica chromatography, elution gradient 0 to 40% EtOAc in petroleum ether. Pure fractions were evaporated to dryness to afford methyl (3R)-4-{benzyl[(2S)-1-methoxy-1-oxopropan-2-yl]amino}-3-[(tert-butoxycarbonyl)amino]-4-oxobutanoate (0.52 g, 24%) as a colourless liquid. 1H NMR (400 MHz, CDCl$_3$, 30° C.) 11.39 (9H, s), 1.47 (3H, s), 2.62 (1H, dd), 2.72 (1H, dd), 3.54 (1H, s), 3.67 (3H, s), 3.68 (3H, s), 4.25 (1H, d), 4.75 (2H, s), 4.98 (1H, s), 7.37 (5H, d). m/z: ES+ [M+H]+= 423.

Methyl [(2R,5S)-4-benzyl-5-methyl-3,6-dioxopiperazin-2-yl]acetate

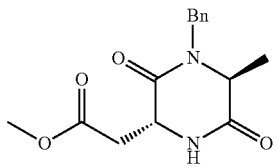 [SMILES: COC(=O)C[C@H]1NC(=O)[C@H](C)N(Cc2ccccc2)C1=O]

TFA (1 ml) was added to a solution of methyl (3R)-4-{benzyl[(2S)-1-methoxy-1-oxopropan-2-yl]amino}-3-[(tert-butoxycarbonyl)amino]-4-oxobutanoate (500 mg, 1.18 mmol) in DCM (5 ml) at room temperature. The resulting solution was stirred at 25° C. for 2 hours. The reaction mixture was evaporated and the residue suspended in saturated sodium carbonate and stirred for 4 hours, then extracted with DCM and evaporated. The crude product was purified by flash C18-flash chromatography, elution gradient 0 to 40% MeCN in water (0.1% TFA). Pure fractions were evaporated to dryness to afford methyl [(2R,5S)-4-benzyl-5-methyl-3,6-dioxopiperazin-2-yl]acetate (330 mg, 96%) as a yellow oil. 1H NMR (400 MHz, CDCl$_3$, 30° C.) 1.51 (3H, d), 2.87 (1H, dd), 3.27 (1H, dd), 3.77 (3H, s), 3.97 (1H, m), 4.11 (1H, d), 4.50 (1H, dd), 5.26 (1H, d), 7.28-7.46 (5H, m), 7.65 (1H, s). m/z: ES+ [M+H]+=291.

2-[(2R,5S)-4-Benzyl-5-methylpiperazin-2-yl]ethan-1-ol

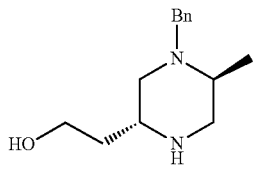 [SMILES: C[C@H]1CN[C@H](CCO)CN1Cc1ccccc1]

Lithium aluminium hydride hydride (2.56 g, 67.51 mmol) was added portionwise to methyl [(2R,5S)-4-benzyl-5-methyl-3,6-dioxopiperazin-2-yl]acetate (2.45 g, 8.44 mmol) in THF (50 ml) at 0° C. The resulting suspension was stirred at 60° C. for 3 hours. The reaction mixture was diluted with DCM at room temperature and quenched with water (2.56 ml) and 15% NaOH (7.68 ml), then filtered and evaporated to afford 2-[(2R,5S)-4-benzyl-5-methylpiperazin-2-yl]ethan-1-ol (1.8 g, 91%) as a colourless oil which solidified on standing. 1H NMR (400 MHz, CDCl$_3$, 30° C.) 1.08 (1H, d), 1.15 (3H, d), 1.45-1.53 (2H, m), 1.68-1.81 (1H, m), 2.17-2.27 (1H, m), 2.54-2.65 (1H, m), 2.65-2.73 (1H, m), 2.87-2.98 (2H, m), 3.10 (1H, d), 3.72-3.79 (2H, m), 4.12 (1H, d), 7.29-7.36 (5H, m). One exchangeable proton not seen. m/z: ES+ [M+H]+=235.

5-{2-[(2R,5S)-4-Benzyl-5-methylpiperazin-2-yl]ethoxy}-7-bromo-8-fluoroquinazolin-4-ol

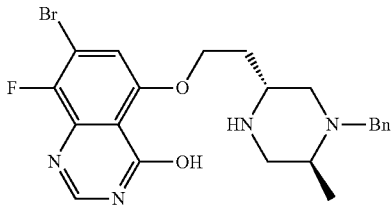 [SMILES: C[C@H]1CN[C@H](CCOc2cc(Br)c(F)c3ncnc(O)c23)CN1Cc1ccccc1]

Sodium hydride (0.888 g, 22.19 mmol) was added portionwise to 2-[(2R,5S)-4-benzyl-5-methylpiperazin-2-yl]ethan-1-ol (1.3 g, 5.55 mmol) in THF (40 ml) at 25° C. The resulting suspension was stirred at room temperature for 30 minutes. 7-Bromo-5,8-difluoroquinazolin-4(3H)-one (2.172 g, 8.32 mmol) was then added and the resulting mixture stirred at 60° C. for 4 hours. The reaction mixture was quenched with water (1 ml) and evaporated to dryness. The crude product was purified by flash C18-flash chromatography, elution gradient 0 to 30% MeOH in water (0.1% TFA). Pure fractions were evaporated to dryness to afford 5-{2-[(2R,5S)-4-benzyl-5-methylpiperazin-2-yl]ethoxy}-7-bromo-8-fluoroquinazolin-4-ol (1.8 g, 68%) as a yellow solid. 1H NMR (400 MHz, CDCl$_3$, 30° C.) 1.28 (3H, d), 1.35 (1H, q), 1.92 (1H, d), 2.56 (2H, dq), 2.73-3.04 (2H, m), 3.18 (2H, dd), 3.51 (2H, s), 3.75-4.00 (1H, m), 4.18-4.45 (2H, m), 6.84 (1H, d), 7.27-7.38 (5H, m), 8.51 (1H, s). One exchangeable proton not seen. m/z: ES+ [M+H]+=475.

(6aR,9S)-8-Benzyl-2-bromo-1-fluoro-9-methyl-6,6a,7,8,9,10-hexahydro-5H-pyrazino[1',2':5,6][1,5]oxazocino[4,3,2-de]quinazoline

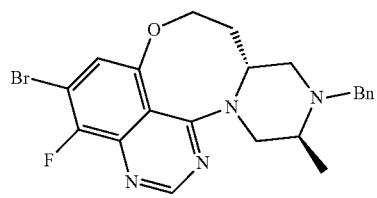 [SMILES: C[C@H]1CN2c3ncnc4c(F)c(Br)cc(c34)OCC[C@@H]2CN1Cc1ccccc1]

Tetrachloromethane (1.827 ml, 18.93 mmol) was added to 5-{2-[(2R,5S)-4-benzyl-5-methylpiperazin-2-yl]ethoxy}-7-bromo-8-fluoroquinazolin-4-ol (1.8 g, 3.79 mmol) and triphenylphosphine (2.98 g, 11.36 mmol) in DCE (0.5 ml) at 25° C. The resulting mixture was stirred at 80° C. for 4 hours then evaporated to dryness. The crude product was purified by flash C18-flash chromatography, elution gradient 0 to 20% MeOH in water (0.1% TFA). Pure fractions were evaporated to dryness to afford (6aR,9S)-8-benzyl-2-bromo-1-fluoro-9-methyl-6,6a,7,8,9,10-hexahydro-5H-pyrazino[1',2':5,6][1,5] oxazocino[4,3,2-de]quinazoline (1.6 g, 92%) as a brown solid. 1H NMR (400 MHz, DMSO, 30° C.) 0.93-1.36 (3H, m), 1.55-2.37 (2H, m), 2.65-3.26 (3H, m), 3.34-3.69 (2H, m), 3.73-4.82 (5H, m), 7.17 (3H, s), 7.30 (3H, s), 7.43 (1H, s). m/z: ES+ [M+H]+=457.

(6aR,9S)-8-Benzyl-2-bromo-3-chloro-1-fluoro-9-methyl-6,6a,7,8,9,10-hexahydro-5H-pyrazino[1',2':5,6][1,5]oxazocino[4,3,2-de]quinazoline

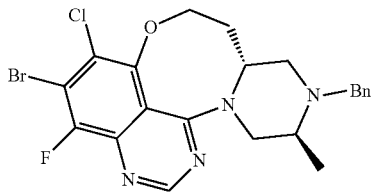 [SMILES: C[C@H]1CN2c3ncnc4c(F)c(Br)c(Cl)c(c34)OCC[C@@H]2CN1Cc1ccccc1]

N-Chlorosuccinimide (657 mg, 4.92 mmol) was added to (6aR,9S)-8-benzyl-2-bromo-1-fluoro-9-methyl-6,6a,7,8,9,10-hexahydro-5H-pyrazino[1',2':5,6][1,5]oxazocino[4,3,2-de]quinazoline (750 mg, 1.64 mmol) in MeCN (10 ml) at 25° C. The resulting mixture was stirred at 60° C. for 1 hour. The crude product was purified by flash C18-flash chromatography, elution gradient 0 to 40% MeOH in water. Pure fractions were evaporated to dryness to afford (6a R,9S)-8-benzyl-2-bromo-3-chloro-1-fluoro-9-methyl-6,6a,7,8,9,10-hexahydro-5H-pyrazino[1',2':5,6][1,5]oxazocino[4,3,2-de]quinazoline (550 mg, 68%) as a pale yellow solid. 1H NMR (400 MHz, DMSO, 30° C.) 1.56 (3H, td), 1.85-1.94 (2H, m), 2.92-3.33 (2H, m), 3.47-4.47 (7H, m), 4.73 (1H, s), 7.26-7.73 (5H, m), 8.80 (1H, s). m/z: ES+ [M+H]+=491.

2-[(6aR,9S)-8-Benzyl-3-chloro-1-fluoro-9-methyl-6,6a,7,8,9,10-hexahydro-5H-pyrazino[1',2':5,6][1,5]oxazocino[4,3,2-de]quinazolin-2-yl]-3-fluorophenol Atropisomer 1 and 2

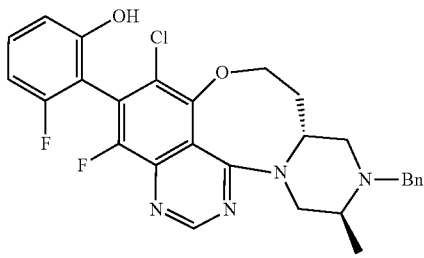 [SMILES: C[C@H]1CN2c3ncnc4c(F)c(-c5c(O)cccc5F)c(Cl)c(c34)OCC[C@@H]2CN1Cc1ccccc1]

RuPhos-Pd-G3 (85 mg, 0.10 mmol) was added to a solution of (6aR,9S)-8-benzyl-2-bromo-3-chloro-1-fluoro-9-methyl-6,6a,7,8,9,10-hexahydro-5H-pyrazino[1',2':5,6][1,5]oxazocino [4,3,2-de]quinazoline (500 mg, 1.02 mmol), (2-fluoro-6-hydroxyphenyl)boronic acid (396 mg, 2.54 mmol), potassium carbonate (422 mg, 3.05 mmol) and dicyclohexyl(2',6'-diisopropoxy-[1,1'-biphenyl]-2-yl)phosphane (47.4 mg, 0.10 mmol) in 1,4-dioxane/water (10 ml) (4:1 ratio) under nitrogen. The resulting mixture was stirred at 100° C. for 30 minutes then evaporated to dryness. Crude product was purified by flash silica chromatography, elution gradient 0 to 60% EtOAc in petroleum ether. Pure fractions were evaporated to dryness to afford atropisomer 1 of 2-[(6aR,9S)-8-benzyl-3-chloro-1-fluoro-9-methyl-6,6a,7,8,9,10-hexahydro-5H-pyrazino[1',2':5,6][1,5]oxazocino [4,3,2-de]quinazolin-2-yl]-3-fluorophenol (65.0 mg, 12.22%) as a pale yellow solid. 1H NMR (400 MHz, CD3OD, 30° C.) 0.97-1.07 (3H, m), 1.16-1.22 (3H, m), 1.64-1.76 (1H, m), 2.77-2.87 (1H, m), 3.06-3.19 (1H, m), 3.36-3.53 (2H, m), 3.84-3.93 (1H, m), 4.03-4.62 (3H, m), 6.68-6.82 (2H, m), 7.17-7.50 (7H, m), 8.38 (1H, s). One exchangeable proton not seen. m/z: ES+ [M+H]+=523. This was followed by atropisomer 2 of 2-[(6aR,9S)-8-benzyl-3-chloro-1-fluoro-9-methyl-6,6a,7,8,9,10-hexahydro-5H-pyrazino[1',2':5,6][1,5]oxazocino[4,3,2-de]quinazolin-2-yl]-3-fluorophenol (55 mg, 10%) as a pale yellow product. 1H NMR (400 MHz, CD3OD, 30° C.) 1.19 (3H, d), 1.75-1.92 (1H, m), 2.30-2.46 (3H, m), 2.78-2.86 (1H, m), 3.09-3.13 (1H, m), 3.44-3.57 (1H, m), 3.79-3.98 (4H, m), 4.23-4.57 (1H, m), 6.68-6.81 (2H, m), 7.21-7.42 (7H, m), 8.48 (1H, s). One exchangeable proton not seen. m/z: ES+ [M+H]+=523.

2-[(6aR,9S)-3-Chloro-1-fluoro-9-methyl-6,6a,7,8,9,10-hexahydro-5H-pyrazino[1',2':5,6][1,5]oxazocino[4,3,2-de]quinazolin-2-yl]-3-fluorophenol Atropisomer 2

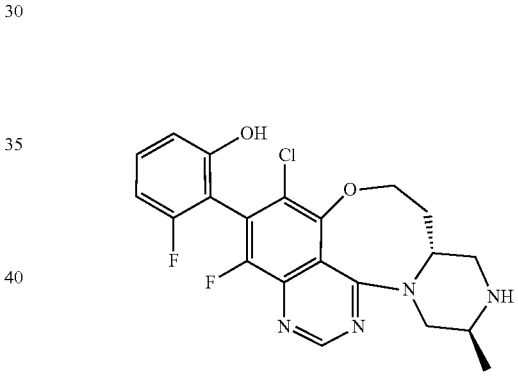

2-[(6aR,9S)-8-benzyl-3-chloro-1-fluoro-9-methyl-6,6a,7,8,9,10-hexahydro-5H-pyrazino[1',2':5,6][1,5] oxazocino [4,3,2-de]quinazolin-2-yl]-3-fluorophenol atropisomer 2 (50 mg, 0.10 mmol), di-tert-butyl dicarbonate (0.111 ml, 0.48 mmol) and 10% palladium on carbon (20.35 mg, 0.02 mmol) in THF (5 ml) were stirred under one atmosphere of hydrogen at room temperature for 1 hour. The reaction mixture was filtered through celite and the filtrate removed under reduced pressure. The reaction mixture was diluted with MeOH (5 ml) and 4M HCl in 1,4-dioxane (2 ml, 8 mmol) added. The resulting solution was stirred at room temperature for 1 hour. The solvent was removed under reduced pressure. The crude product was purified by ion exchange chromatography, using an SCX column. The desired product was eluted from the column using 7M NH3/MeOH and pure fractions were evaporated to dryness to afford 2-[(6aR,9S)-3-chloro-1-fluoro-9-methyl-6,6a,7,8,9,10-hexahydro-5H-pyrazino[1',2':5,6][1,5] oxazocino[4,3,2-de]quinazolin-2-yl]-3-fluorophenol atropisomer 2 (40 mg, 97%) as a pale yellow solid. The product was used in the next step directly without further purification. m/z: ES+ [M+H]+=433.

1-[(6aR,9S)-3-Chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl]prop-2-en-1-one—Atropisomer 2, Example 32

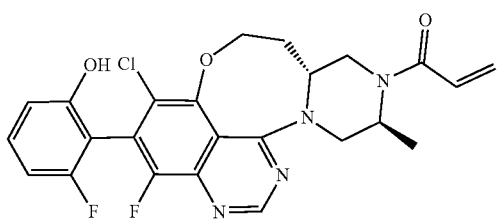 [SMILES: C=CC(=O)N1C[C@H]2CCOc3c(Cl)c(-c4c(O)cccc4F)c(F)c4ncnc(c34)N2C[C@@H]1C]

A solution of acryloyl chloride (8.36 mg, 0.09 mmol) in DMF (1 ml) was added to a stirred solution of 2-[(6aR,9S)-3-chloro-1-fluoro-9-methyl-6,6a,7,8,9,10-hexahydro-5H-pyrazino[1',2':5,6][1,5]oxazocino [4,3,2-de]quinazolin-2-yl]-3-fluorophenol Atropisomer 2 (40 mg, 0.09 mmol) and DIPEA (0.032 ml, 0.18 mmol) in DMF (2.000 ml) at 0° C. The resulting solution was stirred at 0° C. for 1 hour. The crude product was purified by flash C18-flash chromatography, elution gradient 0 to 40% MeCN in water (0.1% TFA). Pure fractions were evaporated to dryness to afford 1-[(6aR,9S)-3-chloro-1-fluoro-2-(2-fluoro-6-hydroxyphenyl)-9-methyl-5,6,6a,7,9,10-hexahydro-8H-pyrazino[1',2':5, 6][1,5]oxazocino[4,3,2-de] quinazolin-8-yl]prop-2-en-1-one, atropisomer 2, (Example 32) (17 mg, 37%) as a white solid. 1H NMR (400 MHz, DMSO, 30° C.) 1.13-1.22 (3H, m), 1.98 (1H, dd), 2.20-2.38 (1H, m), 3.41-3.69 (2H, m), 3.88-4.33 (3H, m), 4.45-4.52 (1H, m), 4.53-5.07 (2H, m), 5.74 (1H, d), 6.18 (1H, d), 6.75-6.87 (3H, m), 7.34 (1H, q), 8.45 (1H, s), 10.19 (1H, s). m/z: ES+ [M+H]+=487.

2-(3S,14aR)-11-Chloro-9-fluoro-3-methyl-1,3,4,13,14,14a-hexahydro-2H-pyrazino[1',2':5,6][1,5]oxazocino[4,3,2-de]quinazolin-10-yl)-3-fluorophenol Atropisomer 1

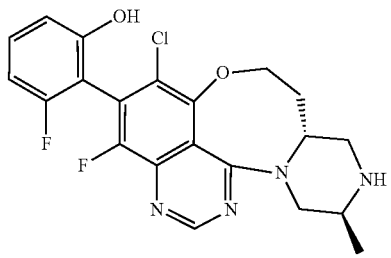 [SMILES: C[C@H]1CN2c3ncnc4c(F)c(-c5c(O)cccc5F)c(Cl)c(c34)OCC[C@@H]2CN1]

2-[(6aR,9S)-8-benzyl-3-chloro-1-fluoro-9-methyl-6,6a,7,8,9,10-hexahydro-5H-pyrazino[1',2':5,6][1,5] oxazocino[4,3,2-de]quinazolin-2-yl]-3-fluorophenol (55 mg, 0.11 mmol), Di-tert-butyl dicarbonate (0.122 ml, 0.53 mmol) and 10% palladium on carbon (22.38 mg, 0.02 mmol) in THF (5 ml) were stirred under one atmosphere of hydrogen at room temperature for 1 hour. The reaction mixture was filtered through celite and the filtrate removed under reduced pressure. The reaction mixture was diluted with MeOH (5 ml) and 4 M HCl in 1,4-dioxane (2 ml, 8 mmol) added. The resulting solution was stirred at room temperature for 1 hour. The solvent was removed under reduced pressure. The crude product was purified by ion exchange chromatography, using an SCX column. The desired product was eluted from the column using 7M NH$_3$/MeOH and pure fractions were evaporated to dryness to afford 2-[(6aR,9S)-3-chloro-1-fluoro-9-methyl-6,6a,7,8,9,10-hexahydro-5H-pyrazino[1',2':5,6][1,5]oxazocino [4,3,2-de]quinazolin-2-yl]-3-fluorophenol atropisomer 1 (40 mg, 88%) as a pale yellow solid. The product was used in the next step directly without further purification. m/z: ES+ [M+H]+=433.

1-[(6aR,9S)-3-Chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl]prop-2-en-1-one—Atropisomer 1, Example 33

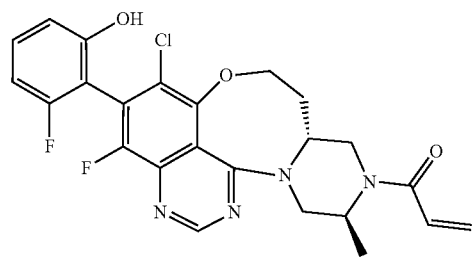 [SMILES: C=CC(=O)N1C[C@H]2CCOc3c(Cl)c(-c4c(O)cccc4F)c(F)c4ncnc(c34)N2C[C@@H]1C]

A solution of acryloyl chloride (8.36 mg, 0.09 mmol) in DMF (1 ml) was added to a stirred solution of 2-[(6aR,9S)-3-chloro-1-fluoro-9-methyl-6,6a,7,8,9,10-hexahydro-5H-pyrazino[1',2':5,6][1,5]oxazocino [4,3,2-de]quinazolin-2-yl]-3-fluorophenol atropisomer 1 (40 mg, 0.09 mmol) and DIPEA (0.032 ml, 0.18 mmol) in DMF (2.000 ml) at 0° C. The resulting solution was stirred at 0° C. for 1 hour. The crude product was purified by flash C18-flash chromatography, elution gradient 0 to 30% MeCN in water (0.1% TFA). Pure fractions were evaporated to dryness to afford 1-[(6aR,9S)-3-chloro-1-fluoro-2-(2-fluoro-6-hydroxyphenyl)-9-methyl-5,6,6a,7,9,10-hexahydro-8H-pyrazino[1',2':5, 6][1,5]oxazocino[4,3,2-de] quinazolin-8-yl]prop-2-en-1-one (25 mg, 56%) atropisomer 1 (Example 33) as a white solid. 1H NMR (400 MHz, DMSO, 30° C.) 1.17 (3H, d), 1.98-2.05 (1H, m), 2.24-2.34 (1H, m), 3.52-3.77 (2H, m), 3.93-4.38 (3H, m), 4.48-5.09 (3H, m), 5.76 (1H, d), 6.18 (1H, d), 6.77-6.89 (3H, m), 7.37 (1H, q), 8.55 (1H, s). One exchangeable not seen. m/z: ES+ [M+H]+=487.

7-Bromo-4-chloro-5,8-difluoroquinazoline

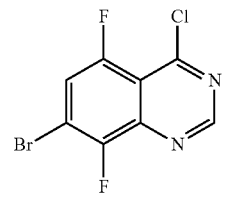 [SMILES: Fc1c(Br)cc(F)c2c(Cl)ncnc12]

Oxalyl dichloride (2.74 ml, 31.26 mmol) was added to a stirred suspension of 7-bromo-5,8-difluoroquinazolin-4(3H)-one (2.04 g, 7.82 mmol) and DMF (0.030 ml, 0.39 mmol) in DCM (150 ml) at room temperature. The resulting mixture was stirred at room temperature for 2 days. Further oxalyl dichloride (1.0 ml) was added and the suspension was stirred at room temperature for a further 24 hours. The reaction mixture was evaporated to afford crude product, still contained ~30% SM by LCMS so the mixture was suspended in DCM (150 ml) and oxalyl dichloride (2.74 ml, 31.26 mmol) was added and the resulting mixture was stirred at room temperature for a further 24 hours. The resulting solution was evaporated to afford crude product as a yellow solid, 2.1 g, which was used without further purification.

Tert-butyl 4-(7-bromo-5,8-difluoroquinazolin-4-yl)-3-(2-hydroxyethyl)piperazine-1-carboxylate

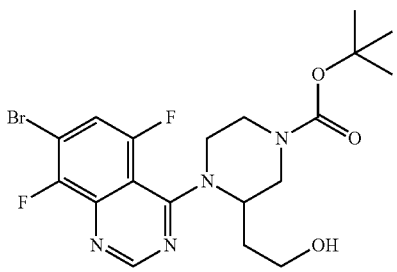 [SMILES: CC(C)(C)OC(=O)N1CCN(c2ncnc3c(F)c(Br)cc(F)c23)C(CCO)C1]

DIPEA (5.24 ml, 30.06 mmol) was added to a stirred mixture of tert-butyl 3-(2-hydroxyethyl)piperazine-1-carboxylate (1.73 g, 7.51 mmol) and 7-bromo-4-chloro-5,8-difluoroquinazoline (2.1 g, 7.51 mmol) in MeCN (100 ml) at room temperature. The resulting solution was stirred at room temperature for 3 hours, a suspension developed after ~30 minutes. The precipitate was collected by filtration, washed with MeCN (3×20 ml) and dried under vacuum to afford desired product, 2.64 g. On standing overnight a second crop of desired product, 300 mgs was isolated to afford tert-butyl 4-(7-bromo-5,8-difluoroquinazolin-4-yl)-3-(2-hydroxyethyl)piperazine-1-carboxylate (2.94 g, 83%), as a white solid, which was used without further purification. ¹H NMR (400 MHz, DMSO, 30° C.) 1.43 (9H, s), 1.71-1.82 (2H, m), 2.86 (1H, s), 3.18 (1H, s), 3.37-3.51 (2H, m), 3.72 (1H, d), 3.97 (2H, d), 4.36 (1H, s), 4.70 (1H, s), 7.75 (1H, dd), 8.62 (1H, s) OH not observed, m/z (ES+), [M+H]+ 473, 475.

Tert-butyl 2-bromo-1-fluoro-5,6,6a,7,9,10-hexahydro-8H-pyrazino[1',2':5,6][1,5]oxazocino[4,3,2-de]quinazoline-8-carboxylate

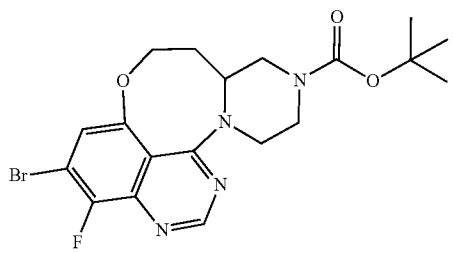 [SMILES: CC(C)(C)OC(=O)N1CCN2c3ncnc4c(F)c(Br)cc(c34)OCCC2C1]

Lithium bis(trimethylsilyl)amide (6.2 ml, 6.21 mmol, 1M solution in THF) was added to a stirred suspension of tert-butyl 4-(7-bromo-5,8-difluoroquinazolin-4-yl)-3-(2-hydroxyethyl)piperazine-1-carboxylate (2.94 g, 6.21 mmol) in NMP (100 ml) at room temperature, under nitrogen. The resulting solution was stirred at 100° C. for 45 minutes. The reaction mixture was allowed to cool, diluted with water (100 ml), and extracted with ether (3×200 ml), the organic layers were combined, washed with saturated brine (2×150 ml), dried with MgSO₄, filtered and evaporated to afford crude product. This was suspended in DCM (3 ml) and MeOH (0.5 ml) the solid collected by filtration, washed with DCM (2 ml) and dried under vacuum to afford tert-butyl 2-bromo-1-fluoro-5,6,6a,7,9,10-hexahydro-8H-pyrazino[1',2':5,6][1,5]oxazocino[4,3,2-de]quinazoline-8-carboxylate (0.854 g, 30%) as a cream solid. ¹H NMR (400 MHz, DMSO, 30° C.) 1.57 (9H, s), 2.01-2.16 (1H, m), 2.23-2.35 (1H, m), 3.34-3.53 (2H, m), 3.68-3.86 (2H, m), 3.91-4.11 (2H, m), 4.32 (1H, t), 4.54 (1H, dd), 4.81 (1H, s), 7.40 (1H, d), 8.59 (1H, s), m/z (ES+), [M+H]+ 453, 455.

Tert-butyl 1-fluoro-2-(4,4,5,5-tetramethyl-1,3,2-dioxaborolan-2-yl)-5,6,6a,7,9,10-hexahydro-8H-pyrazino[1',2':5,6][1,5]oxazocino[4,3,2-de]quinazoline-8-carboxylate

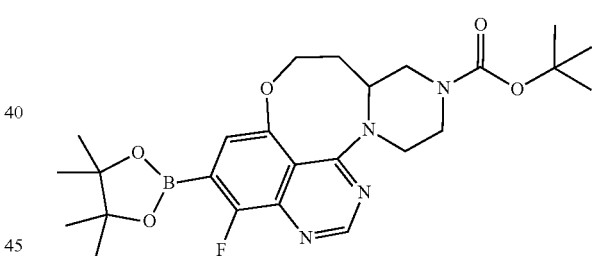

[1,1'-Bis(diphenylphosphino)ferrocene]dichloropalladium(II) complex with dichloromethane (155 mg, 0.189 mmol), 4,4,4',4',5,5,5',5'-octamethyl-2,2'-bi(1,3,2-dioxaborolane) (1.45 g, 5.69 mmol) and potassium acetate (373 mg, 3.8 mmol) were added to a stirred and degassed solution of tert-butyl 2-bromo-1-fluoro-5,6,6a,7,9,10-hexahydro-8H-pyrazino[1',2':5,6][1,5]oxazocino[4,3,2-de]quinazoline-8-carboxylate (861 mg, 1.9 mmol) in dioxane (45 ml) under nitrogen. The resulting mixture was stirred at 90° C. for 17 hours. The reaction mixture was allowed to cool, evaporated and partitioned between EtOAc (150 ml), and water (75 ml)/saturated brine (50 ml), the mixture was filtered through celite, the organic layer separated, dried with MgSO₄, filtered and evaporated to afford crude product, tert-butyl 1-fluoro-2-(4,4,5,5-tetra methyl-1,3,2-dioxaborolan-2-yl)-5,6,6a,7,9,10-hexahydro-8H-pyrazino[1',2':5,6][1,5]oxazocino[4,3,2-de]quinazoline-8-carboxylate (2.3 g) which was used without further purification, m/z (ES+), [M+H]+ 501.

Tert-butyl 1-fluoro-2-(1-methoxy-7-methylisoquinolin-8-yl)-5,6,6a,7,9,10-hexahydro-8H-pyrazino[1',2':5,6][1,5]oxazocino[4,3,2-de]quinazoline-8-carboxylate

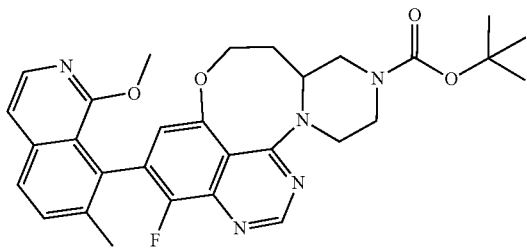 [SMILES: COc1nccc2ccc(C)c(-c3cc4c5c(ncnc5c3F)N3CCN(C(=O)OC(C)(C)C)CC3CCO4)c12]

RuPhos Pd G3 (159 mg, 0.19 mmol), dicyclohexyl(2',6'-diisopropoxy-[1,1'-biphenyl]-2-yl)phosphane (89 mg, 0.19 mmol) and potassium carbonate (525 mg, 3.80 mmol) were added to a stirred and degassed solution of 8-bromo-1-methoxy-7-methylisoquinoline (479 mg, 1.90 mmol) tert-butyl 1-fluoro-2-(4,4,5,5-tetramethyl-1,3,2-dioxaborolan-2-yl)-5,6,6a,7,9,10-hexahydro-8H-pyrazino [1',2':5,6][1,5] oxazocino[4,3,2-de]quinazoline-8-carboxylate (1.9 mmol) in dioxane (20 ml) and water (5 ml), the mixture was evacuated with nitrogen (5 cycles), and stirred at 80° C. for 90 minutes. The reaction mixture was allowed to cool diluted with EtOAc (75 ml), and washed with water (50 ml)/saturated brine (50 ml), the aqueous layer was re extracted with EtOAc (75 ml). The organic extracts were combined, dried with MgSO$_4$, filtered and evaporated to afford crude product. The crude product was purified by flash silica chromatography, elution gradient 0 to 70% EtOAc in heptane. Pure fractions were evaporated to dryness to afford tert-butyl 1-fluoro-2-(1-methoxy-7-methylisoquinolin-8-yl)-5,6,6a,7,9,10-hexahydro-8H-pyrazino[1',2':5,6][1,5]oxazocino[4,3,2-de]quinazoline-8-carboxylate (619 mg, 60%) as a beige foam. $^1$H NMR (400 MHz, CDCl$_3$, 30° C.) 1.50 (9H, s), 1.65-1.77 (1H, m), 1.95-2.1 (3H, m), 2.22 (3H, d), 3.4-3.57 (5H, m), 3.64-3.78 (2H, m), 3.95-4.07 (1H, m), 4.22 (1H, t), 4.38 (1H, dt), 6.81-6.86 (1H, m), 7.24 (1H, d), 7.59 (1H, dd), 7.73 (1H, d), 7.95 (1H, dd), 8.63 (1H, s). m/z (ES+), [M+H]+ 546.

Tert-butyl 3-chloro-1-fluoro-2-(1-methoxy-7-methylisoquinolin-8-yl)-5,6,6a,7,9,10-hexahydro-8H-pyrazino[1',2':5,6][1,5]oxazocino[4,3,2-de]quinazoline-8-carboxylate

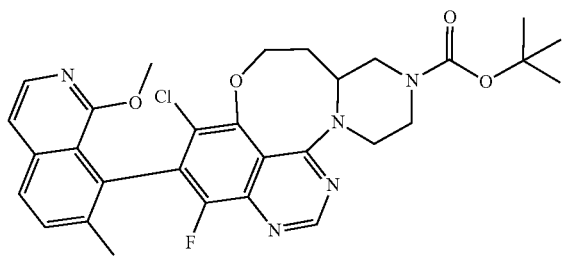 [SMILES: COc1nccc2ccc(C)c(-c3c(Cl)c4c5c(ncnc5c3F)N3CCN(C(=O)OC(C)(C)C)CC3CCO4)c12]

1-Chloropyrrolidine-2,5-dione (167 mg, 1.25 mmol) was added to a stirred solution of tert-butyl 1-fluoro-2-(1-methoxy-7-methylisoquinolin-8-yl)-5,6,6a,7,9,10-hexahydro-8H-pyrazino[1',2':5,6][1,5] oxazocino[4,3,2-de]quinazoline-8-carboxylate (619 mg, 1.13 mmol) in DMF (6 ml) at room temperature. The resulting solution was stirred at 120° C. for 1 hour. The reaction mixture was allowed to cool, diluted with water (25 ml), extracted into EtOAc (75 ml), and washed with saturated brine (50 ml). The organic layer was dried with a phase separating cartridge, filtered and evaporated to afford crude product. The crude product was purified by flash silica chromatography, elution gradient 0 to 80% EtOAc in heptane. Pure fractions were evaporated to dryness to afford tert-butyl 3-chloro-1-fluoro-2-(1-methoxy-7-methylisoquinolin-8-yl)-5,6,6a,7,9,10-hexahydro-8H-pyrazino[1',2':5,6][1,5] oxazocino[4,3,2-de]quinazoline-8-carboxylate (485 mg, 74%) as a pale yellow gum. A further purification by chiral SFC using Chiralpak IC, 30×250 mm, 5 micron column, Mobile phase 45% MeOH+0.1% NH$_3$/55% scCO$_2$, Flow rate 90 ml/min, BPR 120 bar, Column temperature 40° C., UV detection at 220 nm isolated the first eluting isomer (designated enantiomer 2, atropisomer 1) of tert-butyl 3-chloro-1-fluoro-2-(1-methoxy-7-methylisoquinolin-8-yl)-5,6,6a,7,9,10-hexahydro-8H-pyrazino[1',2':5,6][1,5]oxazocino[4,3,2-de]quinazoline-8-carboxylate, (63.7 mg, 13%). $^1$H NMR (400 MHz, CDCl$_3$, 30° C.) 1.49 (9H, s), 1.98 (1H, s), 2.19 (3H, s), 2.25 (1H, s), 3.54 (3H, s), 3.57-3.95 (6H, m), 4.45 (3H, s), 7.27 (1H, d), 7.63 (1H, d), 7.78 (1H, d), 7.96 (1H, d), 8.67 (1H, s), $^{19}$F NMR (376 MHz, CDCl$_3$, 30° C.) −128.46, −128.02, m/z (ES+), [M+H]+ 580; 582. Chiral Analysis Chiralpak IC, 3.0×150 mm, 3 micron column, mobile phase: 45% MeOH+0.1% NH$_3$/55% scCO$_2$, Flow rate 2.0 ml/min, BPR 120 bar, temperature 40° C., rT 1.49 min. This was followed by the second eluting isomer (designated enantiomer 1, atropisomer 1) of tert-butyl 3-chloro-1-fluoro-2-(1-methoxy-7-methylisoquinolin-8-yl)-5,6,6a,7,9,10-hexahydro-8H-pyrazino[1',2':5,6][1,5]oxazocino[4,3,2-de] quinazoline-8-carboxylate (32.6 mg, 7%). $^1$H NMR (400 MHz, CDCl$_3$, 30° C.) 1.49 (9H, s), 1.99-2.11 (1H, m), 2.19 (3H, s), 2.22-2.3 (1H, m), 3.56 (3H, s), 3.59-3.91 (6H, m), 4.24-4.59 (3H, m), 7.27 (1H, d), 7.64 (1H, d), 7.78 (1H, d), 7.96 (1H, d), 8.68 (1H, s), $^{19}$F NMR (376 MHz, CDCl$_3$, 30° C.) −129.30, −128.54, m/z (ES+), [M+H]+ 580; 582. Chiral Analysis Chiralpak IC, 3.0×150 mm, 3 micron column, mobile phase: 45% MeOH+0.1% NH$_3$/55% scCO$_2$, Flow rate 2.0 ml/min, BPR 120 bar, temperature 40° C., rT 1.66 min. This was followed by the third eluting (designated enantiomer 2, atropisomer 2) of tert-butyl 3-chloro-1-fluoro-2-(1-methoxy-7-methylisoquinolin-8-yl)-5,6,6a,7,9,10-hexahydro-8H-pyrazino[1',2':5,6][1,5]oxazocino[4,3,2-de] quinazoline-8-carboxylate (42.6 mg, 9%). $^1$H NMR (400 MHz, CDCl$_3$, 30° C.) 1.49 (9H, s), 2-2.11 (1H, m), 2.19 (3H, s), 2.25 (1H, s), 3.56 (3H, s), 3.61-3.87 (6H, m), 4.27-4.53 (3H, m), 7.25-7.29 (1H, m), 7.64 (1H, d), 7.78 (1H, d), 7.96 (1H, d), 8.68 (1H, s), $^{19}$F NMR (376 MHz, CDCl$_3$, 30° C.) −129.34, −128.54, m/z (ES+), [M+H]+ 580, 582. Chiral Analysis Chiralpak IC, 3.0×150 mm, 3 micron column, mobile phase: 45% MeOH+0.1% NH$_3$/55% scCO$_2$, Flow rate 2.0 ml/min, BPR 120 bar, temperature 40° C., rT 2.79 min. This was followed by the fourth eluting (designated enantiomer 1, atropisomer 2) of tert-butyl 3-chloro-1-fluoro-2-(1-methoxy-7-methylisoquinolin-8-yl)-5,6,6a,7,9,10-hexahydro-8H-pyrazino[1',2':5,6][1,5]oxazocino[4,3,2-de] quinazoline-8-carboxylate (68.5 mg, 14%). $^1$H NMR (400 MHz, CDCl$_3$, 30° C.) 1.49 (9H, s), 1.92-2.03 (1H, m), 2.19 (3H, s), 2.21-2.32 (1H, m), 3.54 (3H, s), 3.4-3.95 (6H, m), 4.21-4.54 (3H, m), 7.27 (1H, d), 7.63 (1H, d), 7.78 (1H, d), 7.96 (1H, d), 8.67 (1H, s), $^{19}$F NMR (376 MHz, CDCl$_3$, 30° C.) −128.02, −128.46, m/z (ES+), [M+H]+ 580; 582. Chiral Analysis Chiralpak IC, 3.0×150 mm, 3 micron column, mobile phase: 45% MeOH+0.1% NH₃/55% scCO₂, Flow rate 2.0 ml/min, BPR 120 bar, temperature 40° C., rT 4.11 min.

8-(3-Chloro-1-fluoro-6,6a,7,8,9,10-hexahydro-5H-pyrazino[1',2':5,6][1,5]oxazocino[4,3,2-de]quinazolin-2-yl)-7-methylisoquinolin-1(2H)-one enantiomer 1, atropisomer 1

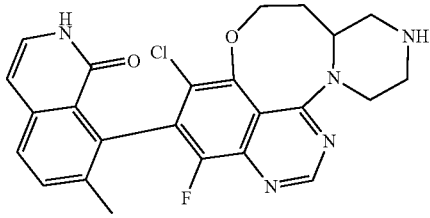 [SMILES: Cc1ccc2cc[nH]c(=O)c2c1-c1c(Cl)c2c3c(ncnc3c1F)N1CCNCC1CCO2]

A solution of enantiomer 1, atropisomer 1 of tert-butyl 3-chloro-1-fluoro-2-(1-methoxy-7-methylisoquinolin-8-yl)-5,6,6a,7,9,10-hexahydro-8H-pyrazino[1',2':5,6][1,5]oxazocino[4,3,2-de] quinazoline-8-carboxylate (39 mg, 0.07 mmol) in DMF (1.0 ml) was added to 4-methyl benzenesulfonic acid hydrate (63.9 mg, 0.34 mmol) and lithium chloride (14 mg, 0.34 mmol) and sealed into a microwave tube. The reaction was heated at 120° C. for 30 minutes in the microwave reactor and cooled to room temperature. The crude reaction mixture was purified by ion exchange chromatography, using an SCX column. The desired product was eluted from the column using 1M NH₃/MeOH and pure fractions were evaporated to dryness to afford enantiomer 1, atropisomer 1 of 8-(3-chloro-1-fluoro-6,6a,7,8,9,10-hexahydro-5H-pyrazino[1',2':5,6][1,5]oxazocino [4,3,2-de] quinazolin-2-yl)-7-methylisoquinolin-1(2H)-one (30 mg, 96%) as a cream solid. ¹H NMR (400 MHz, CDCl₃, 30° C.) 1.91-2.04 (1H, m), 2.16 (3H, s), 2.44-2.58 (1H, m), 2.94-3.02 (3H, m), 3.12-3.21 (1H, m), 3.4-3.47 (1H, m), 3.84 (1H, s), 4.32-4.5 (2H, m), 4.85 (1H, s), 6.52 (1H, d), 6.93 (1H, d), 7.58 (1H, d), 7.65 (1H, d), 8.44 (1H, s), 8.56 (1H, s), NH not seen, m/z (ES+), [M+H]+ 466,468.

8-(3-Chloro-1-fluoro-6,6a,7,8,9,10-hexahydro-5H-pyrazino[1',2':5,6][1,5]oxazocino[4,3,2-de]quinazolin-2-yl)-7-methylisoquinolin-1(2H)-one Enantiomer 1, Atropisomer 2

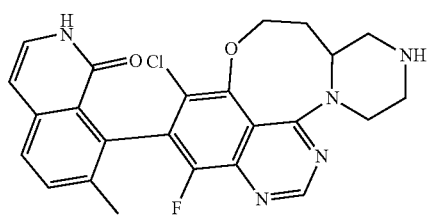 [SMILES: Cc1ccc2cc[nH]c(=O)c2c1-c1c(Cl)c2c3c(ncnc3c1F)N1CCNCC1CCO2]

A solution of enantiomer 1, atropisomer 2 of tert-butyl 3-chloro-1-fluoro-2-(1-methoxy-7-methylisoquinolin-8-yl)-5,6,6a,7,9,10-hexahydro-8H-pyrazino[1',2':5,6][1,5]oxazocino[4,3,2-de] quinazoline-8-carboxylate (81 mg, 0.14 mmol) in DMF (2 ml) was added to 4-methyl benzenesulfonic acid hydrate (133 mg, 0.70 mmol) and lithium chloride (29 mg, 0.70 mmol) and sealed into a microwave tube. The reaction was heated at 120° C. for 30 minutes in the microwave reactor and cooled to room temperature. The crude reaction mixture was purified by ion exchange chromatography, using an SCX column. The desired product was eluted from the column using 1M NH₃/MeOH and pure fractions were evaporated to dryness to afford enantiomer 1, atropisomer 2 of 8-(3-chloro-1-fluoro-6,6a,7,8,9,10-hexahydro-5H-pyrazino[1',2':5,6][1,5]oxazocino [4,3,2-de] quinazolin-2-yl)-7-methylisoquinolin-1(2H)-one (56 mg, 86%) as a pale yellow solid. ¹H NMR (400 MHz, DMSO, 30° C.) 1.8-1.93 (1H, m), 2.04 (3H, s), 2.66-2.75 (2H, m), 2.81 (2H, d), 3.04 (1H, d), 3.33-3.45 (1H, m), 3.72 (1H, d), 4.23-4.36 (1H, m), 4.36-4.47 (1H, m), 4.74 (1H, s), 6.58 (1H, d), 7.05-7.18 (1H, m), 7.70 (2H, s), 8.42 (1H, s), 10.87 (1H, d), NH not seen, ¹⁹F NMR (376 MHz, DMSO, 30° C.) −131.44, m/z (ES+), [M+H]+ 466,468.

8-(3-Chloro-1-fluoro-6,6a,7,8,9,10-hexahydro-5H-pyrazino[1',2':5,6][1,5]oxazocino[4,3,2-de]quinazolin-2-yl)-7-methylisoquinolin-1(2H)-one enantiomer 2, atropisomer 1

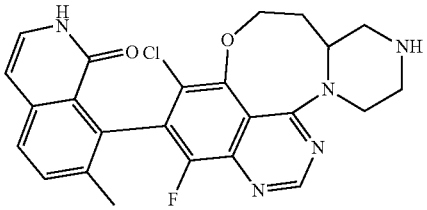 [SMILES: Cc1ccc2cc[nH]c(=O)c2c1-c1c(Cl)c2c3c(ncnc3c1F)N1CCNCC1CCO2]

A solution of enantiomer 2, atropisomer 1 of tert-butyl 3-chloro-1-fluoro-2-(1-methoxy-7-methylisoquinolin-8-yl)-5,6,6a,7,9,10-hexahydro-8H-pyrazino[1',2':5,6][1,5]oxazocino [4,3,2-de] quinazoline-8-carboxylate (74 mg, 0.13 mmol) in DMF (1.2 ml) was added to 4-methyl benzenesulfonic acid hydrate (121 mg, 0.64 mmol) and lithium chloride (27 mg, 0.64 mmol) and sealed into a microwave tube. The reaction was heated at 120° C. for 30 minutes in the microwave reactor and cooled to room temperature. The crude reaction mixture was purified by ion exchange chromatography, using an SCX column. The desired product was eluted from the column using 1M NH₃/MeOH and pure fractions were evaporated to dryness to afford enantiomer 2, atropisomer 1 of 8-(3-chloro-1-fluoro-6,6a,7,8,9,10-hexahydro-5H-pyrazino[1',2':5,6][1,5]oxazocino[4,3,2-de] quinazolin-2-yl)-7-methylisoquinolin-1(2H)-one (46 mg, 77%) as a cream solid. ¹H NMR (400 MHz, DMSO, 30° C.) 1.8-1.93 (1H, m), 2.04 (3H, s), 2.66-2.75 (2H, m), 2.81 (2H, d), 3.04 (1H, d), 3.33-3.45 (1H, m), 3.72 (1H, d), 4.23-4.36 (1H, m), 4.36-4.47 (1H, m), 4.74 (1H, s), 6.58 (1H, d), 7.05-7.18 (1H, m), 7.70 (2H, s), 8.42 (1H, s), 10.87 (1H, d), piperazine NH not seen, ¹⁹F NMR (376 MHz, DMSO, 30° C.) −131.44, m/z (ES+), [M+H]+ 466,468.

8-(3-Chloro-1-fluoro-6,6a,7,8,9,10-hexahydro-5H-pyrazino[1',2':5,6][1,5]oxazocino[4,3,2-de]quinazolin-2-yl)-7-methylisoquinolin-1(2H)-one enantiomer 2, atropisomer 2

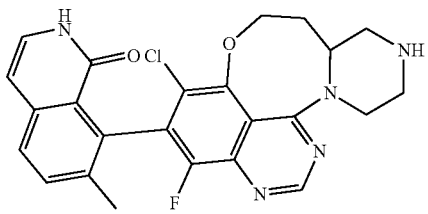 [SMILES: Cc1ccc2cc[nH]c(=O)c2c1-c1c(Cl)c2c3c(ncnc3c1F)N1CCNCC1CCO2]

A solution of enantiomer 2, atropisomer 2 of tert-butyl 3-chloro-1-fluoro-2-(1-methoxy-7-methylisoquinolin-8-yl)-5,6,6a,7,9,10-hexahydro-8H-pyrazino[1',2':5,6][1,5]oxazocino[4,3,2-de]quinazoline-8-carboxylate (44 mg, 0.08 mmol) in DMF (1.1 ml) was added to 4-methylbenzenesulfonic acid hydrate (72.1 mg, 0.38 mmol) and lithium chloride (16 mg, 0.38 mmol) and sealed into a microwave tube. The reaction was heated at 120° C. for 30 minutes in the microwave reactor and cooled to room temperature. The crude reaction mixture was purified by ion exchange chromatography, using an SCX column. The desired product was eluted from the column using 1M $NH_3$/MeOH and pure fractions were evaporated to dryness to afford enantiomer 2, atropisomer 2 of 8-(3-chloro-1-fluoro-6,6a,7,8,9,10-hexahydro-5H-pyrazino[1',2':5,6][1,5]oxazocino [4,3,2-de] quinazolin-2-yl)-7-methylisoquinolin-1(2H)-one (35 mg, 99%) as a pale yellow solid. $^1$H NMR (400 MHz, DMSO, 30° C.) 1.82-1.94 (1H, m), 2.04 (3H, s), 2.66-2.74 (2H, m), 2.79-2.89 (2H, m), 3.05 (1H, d), 3.35-3.45 (1H, m), 3.69 (1H, d), 4.29 (1H, t), 4.42 (1H, d), 4.75 (1H, s), 6.58 (1H, d), 7.08-7.18 (1H, m), 7.66-7.76 (2H, m), 8.42 (1H, s), 10.86 (1H, d), NH piperazine not seen, $^{19}$F NMR (376 MHz, DMSO, 30° C.) −132.19, m/z (ES+), [M+H]+ 466,468.

8-[3-Chloro-1-fluoro-8-(prop-2-enoyl)-6,6a,7,8,9,10-hexahydro-5H-pyrazino[1',2':5,6][1,5]oxazocino[4,3,2-de]quinazolin-2-yl]-7-methylisoquinolin-1(2H)-one, enantiomer 1, atropisomer 1 Example 34

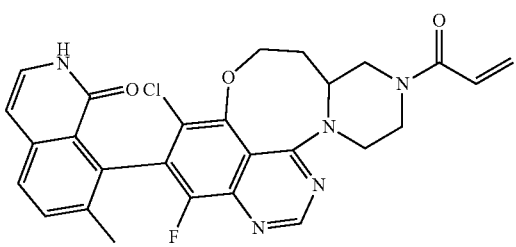 [SMILES: C=CC(=O)N1CCN2c3ncnc4c(F)c(-c5c(C)ccc6cc[nH]c(=O)c56)c(Cl)c(c34)OCCC2C1]

Acryloyl chloride (5.41 µl, 0.07 mmol) was added slowly to a stirred solution of enantiomer 1, atropisomer 1 of 8-(3-chloro-1-fluoro-6,6a,7,8,9,10-hexahydro-5H-pyrazino [1',2':5,6][1,5] oxazocino[4,3,2-de]quinazolin-2-yl)-7-methylisoquinolin-1(2H)-one (31 mg, 0.07 mmol) and triethylamine (9.27 µl, 0.07 mmol) in DCM (2 ml) cooled to −70° C. The resulting solution was stirred at −70° C. for 20 min. The reaction mixture was evaporated and the crude product was purified by preparative HPLC (Waters CSH C18 OBD column, 30×100 mm id, 5 micron particle size), using decreasingly polar mixtures of water (containing 1% by volume of $NH_4OH$ (28-30% in $H_2O$)) and MeCN as eluents. Shallow gradient: 30 to 60% MeCN. Detection UV @ 254 nm. Fractions containing the desired compound were evaporated to dryness to afford enantiomer 1, atropisomer 1 of 8-[3-chloro-1-fluoro-8-(prop-2-enoyl)-6,6a,7,8,9,10-hexahydro-5H-pyrazino[1',2':5,6][1,5]oxazocino[4,3,2-de] quinazolin-2-yl]-7-methylisoquinolin-1(2H)-one (19.3 mg, 56%) as a white solid. $^1$H NMR (400 MHz, DMSO, 30° C.) 1.89-2.01 (1H, m), 2.05 (3H, s), 2.14-2.27 (1H, m), 3.64-3.95 (6H, m), 4.29-4.57 (3H, m), 5.73 (1H, s), 6.17 (1H, d), 6.59 (1H, d), 6.80 (1H, s), 7.14 (1H, d), 7.72 (2H, d), 8.52 (1H, s), 10.87 (1H, s), $^{19}$F NMR (376 MHz, DMSO, 30° C.) −131.09, −130.89, m/z (ES+), [M+H]+ 520,522. Analytical chiral SFC analysis was carried out on a Phenomenex C3, 3.0×150 mm, 3 micron column, eluent 20% MeOH+0.1% $NH_3$/80% $scCO_2$, flow rate: 2.0 ml/min, BPR 120 bar, Column temperature 40° C., rT 0.84 min.

8-[3-Chloro-1-fluoro-8-(prop-2-enoyl)-6,6a,7,8,9,10-hexahydro-5H-pyrazino[1',2':5,6][1,5]oxazocino[4,3,2-de]quinazolin-2-yl]-7-methylisoquinolin-1(2H)-one, Enantiomer 1, Atropisomer 2 Example 35

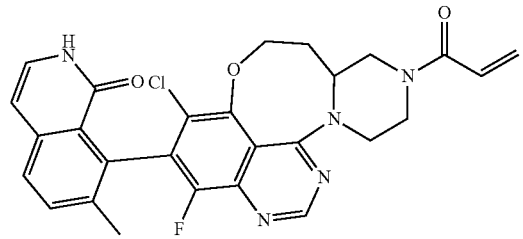 [SMILES: C=CC(=O)N1CCN2c3ncnc4c(F)c(-c5c(C)ccc6cc[nH]c(=O)c56)c(Cl)c(c34)OCCC2C1]

Acryloyl chloride (5.41 µl, 0.07 mmol) was added slowly to a stirred solution of enantiomer 1, atropisomer 2 of 8-(3-chloro-1-fluoro-6,6a,7,8,9,10-hexahydro-5H-pyrazino [1',2':5,6][1,5] oxazocino[4,3,2-de]quinazolin-2-yl)-7-methylisoquinolin-1(2H)-one (31 mg, 0.07 mmol) and triethylamine (9.27 µl, 0.07 mmol) in DCM (2 ml) cooled to −70° C. The resulting solution was stirred at −70° C. for 20 minutes. The reaction mixture was evaporated and the crude product was purified by preparative HPLC (Waters CSH C18 OBD column, 30×100 mm id, 5 micron particle size), using decreasingly polar mixtures of water (containing 1% by volume of $NH_4OH$ (28-30% in H2O)) and MeCN as eluents. Shallow gradient: 30 to 60% MeCN. Detection UV @ 254 nm. Fractions containing the desired compound were evaporated to dryness to afford enantiomer 1, atropisomer 2 of 8-[3-chloro-1-fluoro-8-(prop-2-enoyl)-6,6a,7,8,9,10-hexahydro-5H-pyrazino[1',2':5,6][1,5]oxazocino[4,3,2-de] quinazolin-2-yl]-7-methylisoquinolin-1(2H)-one (22.8 mg, 66%) as a white solid. $^1$H NMR (400 MHz, DMSO, 30° C.) 1.82-2 (1H, m), 2.06 (3H, s), 2.15-2.29 (1H, m), 3.64-3.98 (6H, m), 4.31-4.58 (3H, m), 5.66-5.8 (1H, m), 6.16 (1H, dd), 6.59 (1H, d), 6.79 (1H, dd), 7.08-7.17 (1H, m), 7.71 (2H, s), 8.51 (1H, s), 10.89 (1H, d), $^{19}$F NMR (376 MHz, DMSO, 30° C.) −130.46, −130.25, m/z (ES+), [M+H]+ 520,522. Analytical chiral SFC analysis was carried out on a Phenomonex C3, 3.0×150 mm, 3 micron column, eluent 30% MeOH+0.1% $NH_3$/70% $scCO_2$, flow rate: 2.0 ml/min, BPR 120 bar, Column temperature 40° C., rT 1.29 min.

8-[3-Chloro-1-fluoro-8-(prop-2-enoyl)-6,6a,7,8,9,10-hexahydro-5H-pyrazino[1',2':5,6][1,5]oxazocino[4,3,2-de]quinazolin-2-yl]-7-methylisoquinolin-1(2H)-one, enantiomer 2, atropisomer 1 Example 36

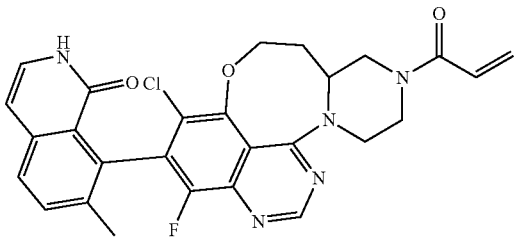 [SMILES: C=CC(=O)N1CCN2c3ncnc4c(F)c(-c5c(C)ccc6cc[nH]c(=O)c56)c(Cl)c(c34)OCCC2C1]

Acryloyl chloride (8.02 μL, 0.10 mmol) was added slowly to a stirred solution of enantiomer 2, atropisomer 1 of 8-(3-chloro-1-fluoro-6,6a,7,8,9,10-hexahydro-5H-pyrazino[1',2':5,6][1,5]oxazocino [4,3,2-de]quinazolin-2-yl)-7-methylisoquinolin-1(2H)-one (46 mg, 0.10 mmol) and triethylamine (14 μL, 0.10 mmol) in DCM (2 ml) cooled to −70° C. The resulting solution was stirred at −70° C. for 15 minutes. The reaction mixture was evaporated and the crude product was purified by preparative HPLC (Waters CSH C18 OBD column, 30×100 mm id, 5 micron particle size), using decreasingly polar mixtures of water (containing 1% by volume of $NH_4OH$ (28-30% in H2O)) and MeCN as eluents. Shallow gradient: 30 to 60% MeCN. Detection UV @ 254 nm. Fractions containing the desired compound were evaporated to dryness to afford enantiomer 2, atropisomer 1 of 8-[3-chloro-1-fluoro-8-(prop-2-enoyl)-6,6a,7,8,9,10-hexahydro-5H-pyrazino[1',2':5,6][1,5]oxazocino[4,3,2-de]quinazolin-2-yl]-7-methylisoquinolin-1(2H)-one (23.5 mg, 46%) as a white solid. $^1$H NMR (400 MHz, DMSO, 30° C.) 1.90 (1H, s), 2.06 (3H, s), 2.23 (1H, d), 3.61-3.99 (6H, m), 4.28-4.59 (3H, m), 5.66-5.79 (1H, m), 6.16 (1H, dd), 6.59 (1H, d), 6.79 (1H, dd), 7.09-7.16 (1H, m), 7.71 (2H, s), 8.51 (1H, s), 10.89 (1H, d), $^{19}$F NMR (376 MHz, DMSO, 30° C.) −130.46, −130.25, m/z (ES+), [M+H]+ 520,522. Analytical chiral SFC analysis was carried out on a Phenomonex C3, 3.0×150 mm, 3 micron column, eluent 25% MeOH+0.1% $NH_3$/75% $scCO_2$, flow rate: 2.0 ml/min, BPR 120 bar, Column temperature 40° C., rT 1.30 min.

8-[3-Chloro-1-fluoro-8-(prop-2-enoyl)-6,6a,7,8,9,10-hexahydro-5H-pyrazino[1',2':5,6][1,5]oxazocino[4,3,2-de]quinazolin-2-yl]-7-methylisoquinolin-1(2H)-one Enantiomer 2, Atropisomer 2 Example 37

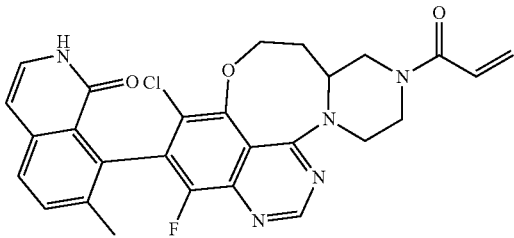 [SMILES: C=CC(=O)N1CCN2c3ncnc4c(F)c(-c5c(C)ccc6cc[nH]c(=O)c56)c(Cl)c(c34)OCCC2C1]

Acryloyl chloride (6.10 μl, 0.08 mmol) was added slowly to a stirred solution of enantiomer 2, atropisomer 2 of 8-(3-chloro-1-fluoro-6,6a,7,8,9,10-hexahydro-5H-pyrazino[1',2':5,6][1,5]oxazocino [4,3,2-de]quinazolin-2-yl)-7-methylisoquinolin-1(2H)-one (35 mg, 0.08 mmol) and triethylamine (10.47 μl, 0.08 mmol) in DCM (2 ml) cooled to −70° C. The resulting solution was stirred at −70° C. for 15 minutes. The reaction mixture was evaporated and the crude product was purified by preparative HPLC (Waters CSH C18 OBD column, 30×100 mm id, 5 micron particle size), using decreasingly polar mixtures of water (containing 1% by volume of $NH_4OH$ (28-30% in H2O)) and MeCN as eluents. Shallow gradient: 30 to 60% MeCN. Detection UV @ 254 nm. Fractions containing the desired compound were evaporated to dryness to afford enantiomer 2, atropisomer 2 of 8-[3-chloro-1-fluoro-8-(prop-2-enoyl)-6,6a,7,8,9,10-hexahydro-5H-pyrazino[1',2':5,6][1,5]oxazocino[4,3,2-de]quinazolin-2-yl]-7-methylisoquinolin-1(2H)-one (13.3 mg, 34%) as a white solid. $^1$H NMR (400 MHz, DMSO, 30° C.) 1.85-2.02 (1H, m), 2.05 (3H, s), 2.16-2.27 (1H, m), 3.62-3.99 (6H, m), 4.29-4.57 (3H, m), 5.68-5.77 (1H, m), 6.17 (1H, d), 6.59 (1H, d), 6.71-6.86 (1H, m), 7.08-7.19 (1H, m), 7.65-7.78 (2H, m), 8.52 (1H, s), 10.87 (1H, s), $^{19}$F NMR (376 MHz, DMSO, 30° C.) −131.09, −130.89, m/z (ES+), [M+H]+ 520,522. Analytical chiral SFC analysis was carried out on a Phenomonex C3, 3.0×150 mm, 3 micron column, eluent 25% MeOH+0.1% $NH_3$/75% $scCO_2$, flow rate: 2.0 ml/min, BPR 120 bar, Column temperature 40° C., rT 0.89 min.

2-Amino-4-bromo-5-chloro-3,6-difluorobenzoic acid

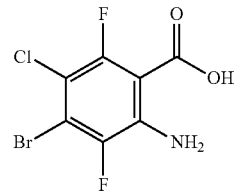 [SMILES: Nc1c(F)c(Br)c(Cl)c(F)c1C(=O)O]

N-Chlorosuccinimide (5.30 g, 39.68 mmol) was added to 2-amino-4-bromo-3,6-difluorobenzoic acid (5 g, 19.84 mmol) in conc. $H_2SO_4$ (80 mL) at rt and then the reaction mixture was stirred at 80° C. for 16 h. The resulting solution was cooled to room temperature and poured into ice. The precipitate was collected by filtration and dried under vacuum to afford 2-amino-4-bromo-5-chloro-3,6-difluorobenzoic acid (4.50 g, 79%) as a yellow solid. $^1$H NMR (400 MHz, DMSO) 7.78 (2H, br s). m/z: $ES^+[M+H]^+$=286.

7-Bromo-6-chloro-5,8-difluoroquinazolin-4-ol

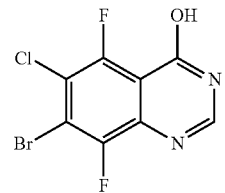 [SMILES: Oc1ncnc2c(F)c(Br)c(Cl)c(F)c12]

2-Amino-4-bromo-5-chloro-3,6-difluorobenzoic acid (4.5 g, 15.71 mmol) was added to a solution of formamidine acetate (19.63 g, 188.51 mmol) in iPrOH (40 mL) and ethanol (40 mL) at rt. The resulting solution was stirred at 100° C. overnight then cooled to rt and poured into water and the precipitate collected by filtration, washed with water (400 ml), and dried under vacuum to afford 7-bromo-6-chloro-5,8-difluoroquinazolin-4-ol (3.70 g, 80%) as a brown solid. ¹H NMR (400 MHz, DMSO) 8.20 (1H, s), 12.67 (1H, s). m/z: ES⁺[M+H]⁺=295.

Methyl N-benzyl-D-alaninate

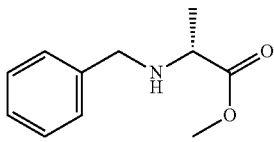

Sodium borohydride (11.0 g, 291 mmol) was added portionwise to methyl D-alaninate (30 g, 290 mmol), triethylamine (162 ml, 1160 mmol) and benzaldehyde (61.7 g, 581.8 mmol) in MeOH (1 l) at 0° C. The resulting mixture was stirred at rt for 4 h. The reaction mixture was quenched with sat. NH₄Cl (200 ml), extracted with DCM (3×100 ml), the organic layer was dried over Na₂SO₄, filtered and evaporated to dryness. The crude product was purified by flash silica chromatography (20 to 30% EtOAc in petroleum ether) to give methyl N-benzyl-D-alaninate (42.1 g, 75%) as a colourless oil. ¹H NMR (400 MHz, DMSO) 1.31 (3H, d), 3.54 (3H, s), 4.02-4.07 (1H, m), 4.53 (2H, s), 7.22-7.26 (5H, m). m/z: ES+ [M+H]+=194.

Methyl (3S)-4-{benzyl[(2R)-1-methoxy-1-oxopropan-2-yl]amino}-3-[(tert-butoxycarbonyl)amino]-4-oxobutanoate

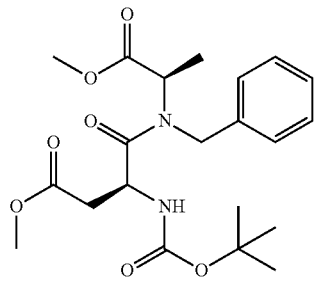 [SMILES: COC(=O)C[C@H](NC(=O)OC(C)(C)C)C(=O)N(Cc1ccccc1)[C@H](C)C(=O)OC]

4-Methylmorpholine (12.6 g, 124 mmol) was added to (2S)-2-[(tert-butoxycarbonyl)amino]-4-methoxy-4-oxobutanoic acid (30.7 g, 124 mmol) and isobutyl chloroformate (15.55 g, 113.8 mmol) in THF (250 ml) at 0° C. The resulting solution was stirred at 0° C. for 1 h and then a solution of methyl N-benzyl-D-alaninate (20 g, 100 mmol) in THF (250 ml) was added at 0° C. The resulting solution was stirred at rt for 16 h. The solvent was removed in vacuo. The crude product was purified by flash silica chromatography (0 to 50% EtOAc in petroleum ether) to give methyl (3S)-4-{benzyl[(2R)-1-methoxy-1-oxopropan-2-yl]amino}-3-[(tert-butoxycarbonyl)amino]-4-oxobutanoate (4.9 g, 11%) as a yellow oil. ¹H NMR (400 MHz, DMSO) 1.47 (9H, s), 1.47-1.52 (3H, s), 2.39-2.54 (1H, m), 2.64-2.89 (1H, m), 3.44-3.64 (7H, m), 3.93-4.29 (1H, m), 4.57-4.90 (2H, m), 7.01-7.76 (6H, m). m/z: ES+ [M+H]+=423.

Methyl [(2S,5R)-4-benzyl-5-methyl-3,6-dioxopiperazin-2-yl]acetate

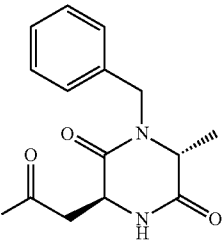

TFA (8.94 ml, 116 mmol) was added to methyl (3S)-4-{benzyl[(2R)-1-methoxy-1-oxopropan-2-yl]amino}-3-[(tert-butoxycarbonyl)amino]-4-oxobutanoate (4.9 g, 12 mmol) in DCM (50 ml) at 0° C. The resulting solution was stirred at rt for 1 h and evaporated. The crude was dissolved in sat. aq. Na₂CO₃ (100 ml) and stirred at rt for 2 h then purified by C18-flash chromatography (0 to 70% MeOH in water), to give methyl [(2S,5R)-4-benzyl-5-methyl-3,6-dioxopiperazin-2-yl]acetate (2.8 g, 83%) as a yellow oil. ¹H NMR (400 MHz, DMSO) 1.43 (3H, d), 2.73-2.98 (2H, m), 3.64 (3H, s), 3.65-3.72 (1H, m), 4.07-4.21 (1H, m), 4.51 (1H, t), 4.84-5.07 (1H, m), 7.22-7.41 (5H, m), 8.30 (1H, s). m/z: ES⁺[M+H]⁺=291.

2-[(2S,5R)-4-Benzyl-5-methylpiperazin-2-yl]ethan-1-ol

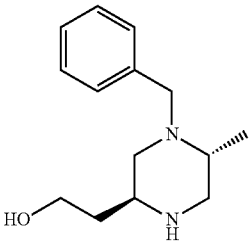 [SMILES: C[C@@H]1CN[C@@H](CCO)CN1Cc1ccccc1]

Lithium aluminium hydride (2.93 g, 77.2 mmol) was added portionwise to a solution of methyl [(2S,5R)-4-benzyl-5-methyl-3,6-dioxopiperazin-2-yl]acetate (2.8 g, 9.6 mmol) in THF (50 ml) at 0° C. The resulting solution was stirred at 0° C. for 0.5 h then at rt for another 2 h. The reaction mixture was quenched with water (7.8 ml) and 15% NaOH (23.5 ml) and filtered through CELITE. The organic layer was dried (Na₂SO₄), filtered and evaporated to afford a yellow oil. The crude product was purified by C18-flash chromatography (0 to 55% MeOH in water), to give 2-[(2S,5R)-4-benzyl-5-methylpiperazin-2-yl]ethan-1-ol (2.02 g, 89%) as a colourless oil. ¹H NMR (400 MHz, DMSO) 1.09 (3H, d), 1.16-1.43 (2H, m), 1.48-1.69 (1H, m), 2.01-2.24 (1H, m), 2.29-2.40 (1H, m), 2.47-2.63 (2H, m), 2.70-2.85 (1H, m), 2.93-3.11 (1H, m), 3.25-3.58 (4H, m), 4.00 (1H, d), 7.24-7.38 (5H, m). m/z: ES⁺[M+H]⁺=235.

5-{2-[(2S,5R)-4-Benzyl-5-methylpiperazin-2-yl]ethoxy}-7-bromo-6-chloro-8-fluoroquinazolin-4-ol

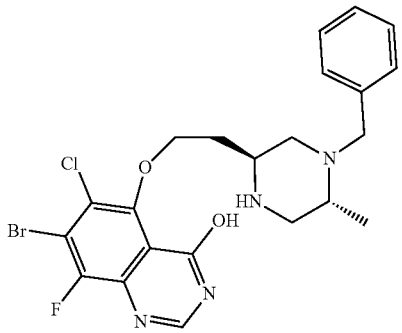 [SMILES: C[C@@H]1CN[C@@H](CCOc2c(Cl)c(Br)c(F)c3ncnc(O)c23)CN1Cc1ccccc1]

Sodium hydride (0.725 g, 18.1 mmol) was added to 2-[(2S,5R)-4-benzyl-5-methylpiperazin-2-yl]ethan-1-ol (2.142 g, 7.25 mmol) in THF (200 ml) at 0° C. The resulting mixture was stirred at 0° C. for 15 min. 7-Bromo-6-chloro-5,8-difluoroquinazolin-4-ol (2.14 g, 7.25 mmol) was then added and the mixture stirred at 60° C. for 4 h. The reaction mixture was quenched with water (5 ml) and acidified with 2M HCl to pH=7, extracted with EtOAc (3×200 ml) and the organic layer dried (Na$_2$SO$_4$), filtered and evaporated to afford crude product. The crude product was purified by flash C18-flash chromatography (0 to 60% MeCN in water (0.1% NH$_4$HCO$_3$)) to give 5-{2-[(2S,5R)-4-benzyl-5-methylpiperazin-2-yl]ethoxy}-7-bromo-6-chloro-8-fluoroquinazolin-4-ol (1.75 g, 47%) as a white solid. $^1$H NMR (400 MHz, CD$_3$OD) 1.30 (3H, d), 1.83-2.02 (2H, m), 2.88-2.96 (1H, m), 2.97-3.07 (1H, m), 3.17-3.25 (1H, m), 3.66-3.97 (4H, m), 3.97-4.04 (1H, m), 4.04-4.11 (1H, m), 4.15-4.27 (1H, m), 7.26-7.36 (5H, m), 8.22 (1H, s). m/z: ES$^+$[M+H]$^+$= 509.

(6aS,9R)-8-Benzyl-2-bromo-3-chloro-1-fluoro-9-methyl-6,6a,7,8,9,10-hexahydro-5H-pyrazino [1',2':5,6][1,5]oxazocino[4,3,2-de]quinazoline

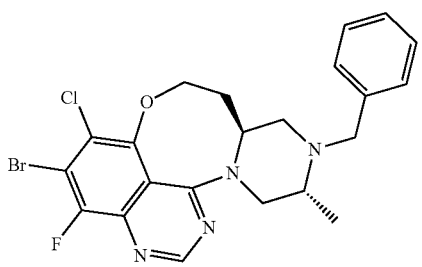 [SMILES: C[C@@H]1CN2c3ncnc4c(F)c(Br)c(Cl)c(c34)OCC[C@H]2CN1Cc1ccccc1]

Tetrachloromethane (1.609 ml, 16.67 mmol) was added to 5-{2-[(2S,5R)-4-benzyl-5-methylpiperazin-2-yl]ethoxy}-7-bromo-6-chloro-8-fluoroquinazolin-4-ol (1.7 g, 3.33 mmol) and triphenylphosphine (2.62 g, 10 mmol) in 1,2-dichloroethane (50 ml) at rt. The resulting mixture was stirred at 80° C. for 2 h. The solvent was removed in vacuo. The crude product was purified by flash C18-flash chromatography (0 to 80% MeCN in water (0.1% NH$_4$HCO$_3$)), to give (6aS,9R)-8-benzyl-2-bromo-3-chloro-1-fluoro-9-methyl-6,6a,7,8,9,10-hexahydro-5H-pyrazino[1',2':5,6][1,5]oxazocino[4,3,2-de]quinazoline (0.68 g, 42%) as a yellow solid. $^1$H NMR (400 MHz, CD$_3$OD) 1.15 (3H, d), 1.75-1.90 (1H, m), 2.29-2.56 (3H, m), 2.80-2.85 (1H, m), 3.05-3.21 (2H, m), 3.46-3.56 (1H, m), 3.71-3.92 (2H, m), 4.25-4.50 (2H, m), 7.25-7.37 (5H, m), 8.44 (1H, s). m/z: ES$^+$[M+H]$^+$=491.

2-[(6aS,9R)-8-Benzyl-3-chloro-1-fluoro-9-methyl-6,6a,7,8,9,10-hexahydro-5H-pyrazino[1',2':5,6] [1,5]oxazocino[4,3,2-de]quinazolin-2-yl]-3-fluorophenol

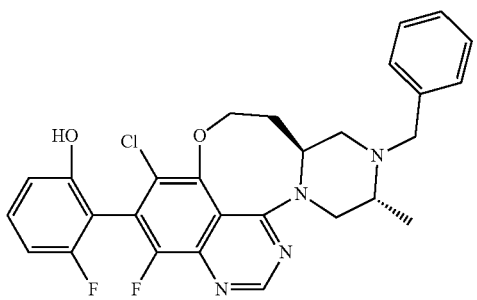 [SMILES: C[C@@H]1CN2c3ncnc4c(F)c(-c5c(O)cccc5F)c(Cl)c(c34)OCC[C@H]2CN1Cc1ccccc1]

RuPhos-Pd-G3 (187 mg, 0.22 mmol) was added to a solution of (6aS,9R)-8-benzyl-2-bromo-3-chloro-1-fluoro-9-methyl-6,6a,7,8,9,10-hexahydro-5H-pyrazino[1',2':5,6][1,5]oxazocino[4,3,2-de] quinazoline (550 mg, 1.12 mmol), (2-fluoro-6-hydroxyphenyl)boronic acid (436 mg, 2.80 mmol), Na$_2$CO$_3$ (474 mg, 4.47 mmol) and dicyclohexyl(2',6'-diisopropoxy-[1,1'-biphenyl]-2-yl)phosphane (104 mg, 0.22 mmol) in 1,4-dioxane/H$_2$O (30 ml, 4:1 ratio). The resulting mixture was stirred at 80° C. for 1 h. The solvent was removed in vacuo. The crude product was purified by flash silica chromatography (80 to 100% EtOAc in petroleum ether) to give 2-[(6aS,9R)-8-benzyl-3-chloro-1-fluoro-9-methyl-6,6a,7,8,9,10-hexahydro-5H-pyrazino[1',2':5,6][1,5]oxazocino[4,3,2-de]quinazolin-2-yl]-3-fluorophenol (480 mg, 82%) as a yellow solid. $^1$H NMR (400 MHz, CD$_3$OD) 0.95-1.03 (3H, m), 1.85-1.90 (2H, m), 2.30-2.54 (1H, m), 2.74-2.92 (1H, m), 3.05-3.19 (1H, m), 3.48-3.51 (1H, m), 3.77-4.19 (3H, m), 4.31-4.52 (3H, m), 7.05-7.13 (1H, m), 7.22-7.42 (5H, m), 7.46-7.54 (2H, m), 8.48 (1H, s). m/z: ES+ [M+H]+=523.

2-(((3R,14aS)-11-Chloro-9-fluoro-3-methyl-1,3,4,13,14,14a-hexahydro-2H-pyrazino[1',2':5,6][1,5]oxazocino[4,3,2-de]quinazolin-10-yl)-3-fluorophenol

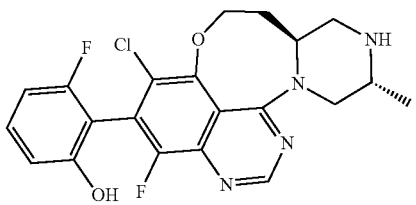 [SMILES: C[C@@H]1CN2c3ncnc4c(F)c(-c5c(O)cccc5F)c(Cl)c(c34)OCC[C@H]2CN1]

10% Palladium on charcoal (1.02 g, 0.96 mmol), di-tert-butyl dicarbonate (0.222 ml, 0.96 mmol) and 2-[(6aS,9R)-8-benzyl-3-chloro-1-fluoro-9-methyl-6,6a,7,8,9,10-hexahydro-5H-pyrazino[1',2':5,6] oxazocino[4,3,2-de]quinazolin-2-yl]-3-fluorophenol (500 mg, 0.96 mmol) in THF (10 ml) was stirred under an atmosphere of hydrogen at 1 atm and rt for 1 h. The reaction mixture was filtered through silica gel and the solvent removed in vacuo. The residue was dissolved in DCM (10 ml) and 4M HCl in 1,4-dioxane (1.2 ml, 4.78 mmol) added. The resulting solution was stirred at rt for 1 h. The solvent was removed in vacuo. The crude product was purified by flash C18-flash chromatography (0 to 40% MeCN in water (0.1% NH₄HCO₃)) to give 2-((3R,14aS)-11-chloro-9-fluoro-3-methyl-1,3,4,13,14,14a-hexahydro-2H-pyrazino[1',2':5,6][1,5]oxazocino[4,3,2-de]quinazolin-10-yl)-3-fluorophenol (350 mg, 85%) as a white solid. $^1$H NMR (400 MHz, DMSO) 0.98-1.16 (3H, m), 1.74-1.90 (1H, m), 1.95-2.05 (1H, m), 2.56-2.81 (1H, m), 2.89-3.01 (1H, m), 3.01-3.45 (2H, m), 3.61-3.70 (1H, m), 3.86-4.06 (1H, m), 4.20-4.31 (2H, m), 6.73-6.88 (2H, m), 7.34-7.35 (1H, m), 8.64 (1H, s), 10.20 (1H, s). m/z: ES+ [M+H]+=433.

1-[(6aS,9R)-3-Chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl]prop-2-en-1-one (Atropisomer 1, Example 38; Atropisomer 2, Example 39)

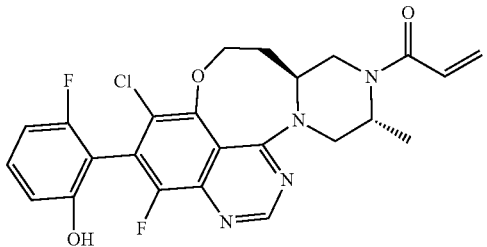 [SMILES: C=CC(=O)N1C[C@@H]2CCOc3c(Cl)c(-c4c(O)cccc4F)c(F)c4ncnc(c34)N2C[C@H]1C]

A solution of acryloyl chloride (32.2 mg, 0.36 mmol) in DMF (0.5 ml) was added dropwise to a stirred solution of 2-((3R,14aS)-11-chloro-9-fluoro-3-methyl-1,3,4,13,14,14a-hexahydro-2H-pyrazino [1',2':5,6][1,5]oxazocino[4,3,2-de]quinazolin-10-yl)-3-fluorophenol (220 mg, 0.51 mmol) and DIPEA (0.133 ml, 0.76 mmol) in DMF (3.0 ml) at 0° C. The resulting solution was stirred at 0° C. for 0.5 h. The reaction mixture was quenched with water (1 ml) and the resulting mixture purified by flash C18-flash chromatography (0 to 40% MeCN in water (1% NH₄HCO₃)), to give a mixture of two atropisomers which were then separated by preparative chiral-HPLC (Column: CHIRALPAK IE, 2×25 cm, 5 µm; Mobile Phase A: Hex (8 mmol/L NH₃.MeOH)-HPLC, Mobile Phase B: EtOH-HPLC; Flow rate: 20 ml/min; Gradient: 30 B to 30 B in 16 min; 220/254 nm; RT1: 9.899; RT2:13.349). The fractions containing desired compounds were evaporated to dryness to afford firstly atropisomer 1, 1-[(6aS,9R)-3-chloro-1-fluoro-2-(2-fluoro-6-hydroxyphenyl)-9-methyl-5,6,6a,7,9,10-hexahydro-8H-pyrazino[1',2':5,6][1,5]oxazocino [4,3,2-de]quinazolin-8-yl] prop-2-en-1-one (Example 38, 33 mg, 13%) as a white solid. $^1$H NMR (400 MHz, DMSO) 1.12-1.23 (3H, m), 1.82-2.06 (1H, m), 3.15-3.27 (0.5H, m), 3.43-3.72 (1.5H, m), 3.86-4.04 (2H, m), 4.19-4.52 (3H, m), 4.54-5.08 (2H, m), 5.74 (1H, d), 6.18 (1H, d), 6.73-6.93 (3H, m), 7.34-7.35 (1H, m), 8.45 (1H, s), 10.15 (1H, s). m/z: ES' [M+H]+=487. This was followed by atropisomer 2, 1-[(6aS,9R)-3-chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl]prop-2-en-1-on (Example 39, 33 mg, 13%) as a white solid. $^1$H NMR (400 MHz, DMSO) 1.18-1.28 (3H, m), 1.83-2.15 (1H, m), 3.13-3.27 (0.5H, m), 3.43-3.69 (1.5H, m), 3.88-4.04 (2H, m), 4.19-4.52 (3H, m), 4.55-5.05 (2H, m), 5.74 (1H, d), 6.18 (1H, d), 6.74-6.97 (3H, m), 7.34-7.35 (1H, m), 8.45 (1H, s), 10.19 (H, d). m/z: ES+[M+H]+=487.

Methyl (3S)-4-{benzyl[(2S)-1-methoxy-1-oxopropan-2-yl]amino}-3-[(tert-butoxycarbonyl)amino]-4-oxobutanoate

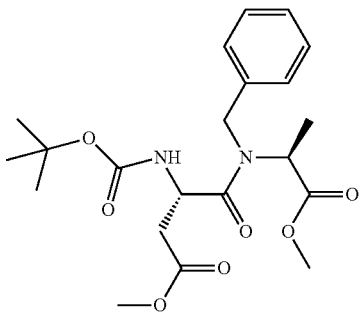 [SMILES: COC(=O)C[C@H](NC(=O)OC(C)(C)C)C(=O)N(Cc1ccccc1)[C@@H](C)C(=O)OC]

Isobutyl chloroformate (15.55 g, 113.84 mmol) was added to a solution of (2R)-2-[(tert-butoxycarbonyl)amino]-4-methoxy-4-oxobutanoic acid (30.7 g, 124 mmol) and 4-methylmorpholine (12.56 g, 124.19 mmol) in THF (100 ml) at 0° C. The resulting solution was stirred at 0° C. for 1 h and then a solution of methyl N-benzyl-D-alaninate (20 g, 100 mmol) in THF (10 ml) was added at 0° C. The resulting mixture was stirred at rt overnight. The reaction mixture was quenched with water (200 ml), extracted with EtOAc (3×100 ml), the organic layer was dried (Na₂SO₄), filtered and evaporated to give the crude product. The crude product was purified by flash silica chromatography (10 to 25% EtOAc in petroleum ether) to give methyl (3R)-4-{benzyl[(2R)-1-methoxy-1-oxopropan-2-yl]amino}-3-[(tert-butoxycarbonyl)amino]-4-oxobutanoate (5.6 g, 13%) as a yellow liquid. $^1$H NMR (400 MHz, CD₃OD) 1.34 (9H, s), 1.45 (3H, d), 2.53-2.66 (1H, m), 2.77-2.94 (1H, m), 3.65 (3H, s), 3.67 (3H, s), 3.97-4.09 (1H, m), 4.65-4.76 (1H, m), 4.80-4.95 (1H, m), 5.01-5.07 (1H, m), 7.17-7.52 (5H, m). m/z: ES+ [M+H]+=423.

Methyl [(2R,5R)-4-benzyl-5-methyl-3,6-dioxopiperazin-2-yl]acetate

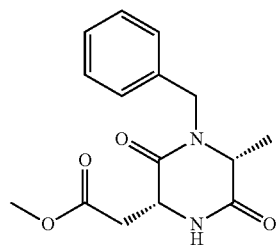

4M HCl in 1,4-dioxane (4.97 ml, 19.9 mmol) was added to methyl (3R)-4-{benzyl[(2R)-1-methoxy-1-oxopropan-2-yl]amino}-3-[(tert-butoxycarbonyl)amino]-4-oxobutanoate (5.6 g, 13 mmol) in MeOH (20 ml) at rt. The resulting solution was stirred at rt for 1 h. The solvent was removed in vacuo. The reaction mixture was diluted with sat. aq.

Na₂CO₃ (50 ml). The resulting mixture was stirred at rt for 2 h then purified by flash C18-flash chromatography (0 to 70% MeOH in water) to give methyl [(2R,5R)-4-benzyl-5-methyl-3,6-dioxopiperazin-2-yl]acetate (2.5 g, 65%) as a colourless liquid. ¹H NMR (400 MHz, CD₃OD) 1.53 (3H, d), 2.82-3.05 (2H, m), 3.74 (3H, s), 3.87-4.01 (1H, m), 4.37 (1H, d), 4.41-4.47 (1H, m), 5.06 (1H, d), 7.18-7.41 (5H, m). m/z: ES⁺[M+H]⁺=291.

2-[(2R,5R)-4-Benzyl-5-methylpiperazin-2-yl]ethan-1-ol

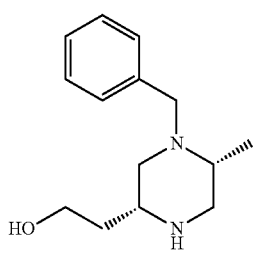 [SMILES: C[C@@H]1CN[C@H](CCO)CN1Cc1ccccc1]

Lithium aluminium hydride (2.61 g, 68.89 mmol) was added portionwise to a solution of methyl [(2R,5R)-4-benzyl-5-methyl-3,6-dioxopiperazin-2-yl]acetate (2.5 g, 8.6 mmol) in THF (50 ml) at 0° C. The resulting solution was stirred at 0° C. for 0.5 h then at 60° C. for another 4 h. The reaction mixture was quenched with water (2.6 ml) and 15% aq. NaOH (7.8 ml), diluted with DCM (200 ml) and filtered through CELITE. The organic layer were evaporated to dryness to afford 2-[(2R,5R)-4-benzyl-5-methylpiperazin-2-yl]ethan-1-ol (1.8 g, 89%) as a yellow liquid. ¹H NMR (400 MHz, CD₃OD) 1.11 (3H, d), 1.57-1.83 (2H, m), 2.35-2.44 (2H, m), 2.69-2.80 (2H, m), 2.85-2.98 (2H, m), 3.44 (1H, d), 3.52-3.64 (2H, m), 3.73 (1H, d), 7.19-7.39 (5H, m). m/z: ES⁺[M+H]⁺=235.

5-{2-[(2R,5R)-4-Benzyl-5-methylpiperazin-2-yl]ethoxy}-7-bromo-6-chloro-8-fluoroquinazolin-4-ol

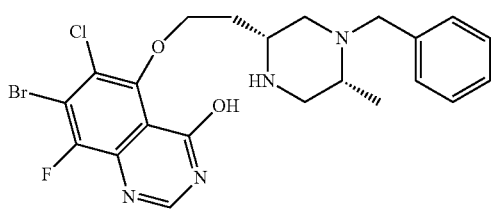 [SMILES: C[C@@H]1CN[C@H](CCOc2c(Cl)c(Br)c(F)c3ncnc(O)c23)CN1Cc1ccccc1]

Sodium hydride (0.447 g, 18.6 mmol) was added to 2-[(2R,5R)-4-benzyl-5-methylpiperazin-2-yl]ethan-1-ol (1.745 g, 7.45 mmol) in THF (50 ml) at 0° C. The resulting mixture was stirred at 0° C. for 15 min. 7-Bromo-6-chloro-5,8-difluoroquinazolin-4-ol (2.2 g, 7.5 mmol) was added and the mixture stirred at 60° C. for 4 h. The reaction mixture was quenched with water (5 ml), acidified with 2M HCl to pH=7, extracted with EtOAc (3×200 ml) and the organic layer dried (Na₂SO₄), filtered and evaporated to afford crude product. This was purified by C18-flash chromatography (0 to 70% MeCN in water (0.1% NH₄HCO₃)) to give 5-{2-[(2R,5R)-4-benzyl-5-methylpiperazin-2-yl]ethoxy}-7-bromo-6-chloro-8-fluoroquinazolin-4-ol (1.8 g, 47%) as a brown solid. ¹H NMR (400 MHz, DMSO) 1.00-1.11 (3H, m), 1.68-1.87 (1H, m), 1.87-2.11 (1H, m), 2.28-2.42 (2H, m), 2.66-2.86 (3H, m), 2.85-3.17 (2H, m), 3.86-4.09 (2H, m), 4.10-4.20 (1H, m), 7.25-7.34 (5H, m), 8.16 (1H, s). m/z: ES⁺[M+H]⁺=509.

(6aR,9R)-8-Benzyl-2-bromo-3-chloro-1-fluoro-9-methyl-6,6a,7,8,9,10-hexahydro-5H-pyrazino [1',2':5,6][1,5]oxazocino[4,3,2-de]quinazoline

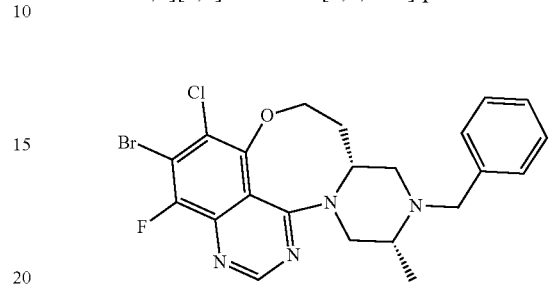

Tetrachloromethane (1.703 ml, 17.65 mmol) was added to 5-{2-[(2R,5R)-4-benzyl-5-methylpiperazin-2-yl]ethoxy}-7-bromo-6-chloro-8-fluoroquinazolin-4-ol (1.8 g, 3.53 mmol) and triphenylphosphine (2.78 g, 10.6 mmol) in 1,2-dichloroethane (20 ml) at rt. The resulting mixture was stirred at 80° C. for 2 h. The solvent was removed in vacuo. The crude product was purified by flash C18-flash chromatography (0 to 90% MeOH in water (0.1% NH₄HCO₃)) to give (6aR,9R)-8-benzyl-2-bromo-3-chloro-1-fluoro-9-methyl-6,6a,7,8,9,10-hexahydro-5H-pyrazino[1',2':5,6][1,5]oxazocino[4,3,2-de] quinazoline (0.42 g, 24%) as a yellow solid. ¹H NMR (400 MHz, DMSO) 1.14-1.25 (3H, m), 2.11-2.21 (1H, m), 2.35-2.41 (1H, m), 2.56-2.67 (2H, m), 2.96-3.12 (2H, m), 3.54-3.62 (2H, m), 3.68-3.77 (1H, m), 3.95-4.06 (1H, m), 4.23-4.44 (1H, m), 4.93-5.04 (1H, m), 7.07-7.36 (5H, m), 8.38 (1H, s). m/z: ES⁺[M+H]⁺=491.

2-[(6aR,9R)-8-Benzyl-3-chloro-1-fluoro-9-methyl-6,6a,7,8,9,10-hexahydro-5H-pyrazino [1',2':5,6][1,5] oxazocino[4,3,2-de]quinazolin-2-yl]-3-fluorophenol

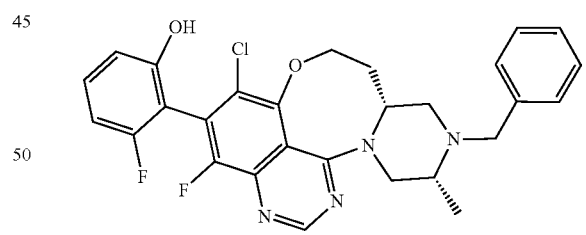

RuPhos-Pd-G3 (119 mg, 0.14 mmol) was added to a solution of (6aR,9R)-8-benzyl-2-bromo-3-chloro-1-fluoro-9-methyl-6,6a,7,8,9,10-hexahydro-5H-pyrazino[1',2':5,6][1,5]oxazocino[4,3,2-de] quinazoline (350 mg, 0.71 mmol), (2-fluoro-6-hydroxyphenyl)boronic acid (277 mg, 1.78 mmol), Na₂CO₃ (302 mg, 2.85 mmol) and dicyclohexyl(2',6'-diisopropoxy-[1,1'-biphenyl]-2-yl)phosphane (66.4 mg, 0.14 mmol) in 1,4-dioxane/H₂O (15 ml; 4:1 ratio). The resulting mixture was stirred at 80° C. for 1 h. The solvent was removed in vacuo. The crude product was purified by flash silica chromatography (60 to 80% EtOAc in petroleum ether) to give 2-[(6aR,9R)-8-benzyl-3-chloro-1-fluoro-9-methyl-6,6a,7,8,9,10-hexahydro-5H-pyrazino[1',2':5,6][1,5]

oxazocino[4,3,2-de]quinazolin-2-yl]-3-fluorophenol (365 mg, 98%) as a pale yellow solid. ¹H NMR (400 MHz, CD₃OD) 1.02 (3H, d), 1.81-1.94 (1H, m), 2.23-2.32 (1H, m), 2.49-2.79 (3H, m), 3.03-3.18 (2H, m), 3.79-3.92 (1H, m), 4.12-4.20 (1H, m), 4.40-4.52 (2H, m), 5.13-5.21 (1H, m), 6.65-6.81 (3H, m), 7.27-7.37 (5H, m), 8.36 (1H, s). m/z: ES⁺[M+H]⁺=523.

2-[(6aR,9R)-3-Chloro-1-fluoro-9-methyl-6,6a,7,8,9, 10-hexahydro-5H-pyrazino[1',2':5,6][1,5] oxazocino [4,3,2-de]quinazolin-2-yl]-3-fluorophenol

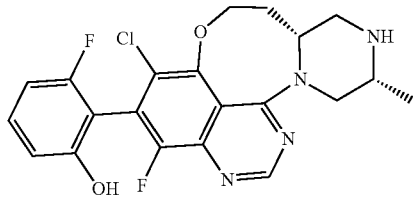 [SMILES: C[C@@H]1CN2c3ncnc4c(F)c(-c5c(O)cccc5F)c(Cl)c(c34)OCC[C@@H]2CN1]

10% Palladium on charcoal (712 mg, 0.67 mmol), di-tert-butyl dicarbonate (0.311 ml, 1.34 mmol) and 2-[(6aR,9R)-8-benzyl-3-chloro-1-fluoro-9-methyl-6,6a,7,8,9,10-hexahydro-5H-pyrazino[1',2':5,6][1,5] oxazocino[4,3,2-de]quinazolin-2-yl]-3-fluorophenol (350 mg, 0.67 mmol) in THF (20 ml) was stirred under an atmosphere of hydrogen at 1 atm and rt for 1 h. The reaction mixture was filtered through silica gel and the solvent removed in vacuo. The reaction mixture was diluted with DCM (20 ml). 4M HCl in 1,4-dioxane (0.84 ml, 3.35 mmol) was added. The resulting solution was stirred at rt for 1 h. The solvent was removed in vacuo and the crude product purified by ion exchange chromatography, using an SCX column. The column was eluted with 7M NH₃/MeOH to give 2-[(6aR,9R)-3-chloro-1-fluoro-9-methyl-6,6a,7,8,9,10-hexahydro-5H-pyrazino[1', 2':5,6][1,5]oxazocino[4,3,2-de]quinazolin-2-yl]-3-fluorophenol (310 mg, >100%) as a yellow solid. ¹H NMR (400 MHz, DMSO). 1.08 (3H, d), 1.35-1.71 (5H, m), 1.74-2.29 (1H, m), 3.10-3.31 (2H, m), 3.95-4.20 (1H, m), 4.30-4.56 (1H, m) 6.63 (1H, d), 6.71-6.82 (1H, m), 6.85-7.01 (1H, m), 8.48 (1H, s). m/z: ES⁺[M+H]⁺=433.

1-[(6aR,9R)-3-Chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl]prop-2-en-1-one (Atropisomer 1, Example 40; Atropisomer 2, Example 41)

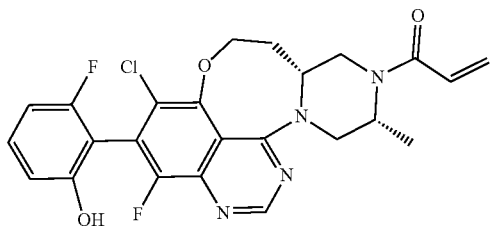 [SMILES: C=CC(=O)N1C[C@H]2CCOc3c(Cl)c(-c4c(O)cccc4F)c(F)c4ncnc(c34)N2C[C@H]1C]

A solution of acryloyl chloride (43.1 mg, 0.48 mmol) in DMF (0.5 ml) was added portionwise to a stirred solution 2-[(6aR,9R)-3-chloro-1-fluoro-9-methyl-6,6a,7,8,9,10-hexahydro-5H-pyrazino[1',2':5,6][1,5] oxazocino[4,3,2-de] quinazolin-2-yl]-3-fluorophenol (300 mg, 0.69 mmol) and DIPEA (0.12 ml, 0.69 mmol) in DMF (2.5 ml) at 0° C. The resulting solution was stirred at 0° C. for 0.5 h. The reaction mixture was quenched with water (0.5 ml) and the resulting mixture purified by C18-flash chromatography (0 to 40% MeCN in water (0.1% NH₄HCO₃)) to give a mixture of two atropisomers which were then separated by preparative chiral-HPLC (Column: CHIRALPAK IA, 2×25 cm, 5 μm; Mobile Phase A:Hex-HPLC, Mobile Phase B: IPA-HPLC; Flow rate: 20 ml/min; Gradient: 30 B to 30 B in 18 min; 254/220 nm; RT1:9.284; RT2:13.389). This gave atropisomer 1, 1-[(6aR,9R)-3-chloro-1-fluoro-2-(2-fluoro-6-hydroxyphenyl)-9-methyl-5,6,6a,7,9,10-hexahydro-8H-pyrazino[1',2':5,6][1,5] oxazocino[4,3,2-de] quinazolin-8-yl]prop-2-en-1-one (Example 40, 5 mg, 1%) as a white solid. ¹H NMR (400 MHz, CD₃CN) 1.18-1.33 (3H, m), 1.67-1.81 (1H, m), 2.26-2.33 (1H, m), 2.93-3.48 (2H, m), 3.48-4.47 (3H, m), 4.53-4.83 (3H, m), 5.49-5.74 (1H, m), 6.05 (1H, d), 6.42-6.62 (1H, m), 6.74-6.96 (2H, m), 7.30-7.44 (1H, m), 8.47 (1H, s). m/z: ES' [M+H]⁺=487. This was followed by atropisomer 2, 1-[(6aR,9R)-3-chloro-1-fluoro-2-(2-fluoro-6-hydroxyphenyl)-9-methyl-5,6,6a,7,9,10-hexahydro-8H-pyrazino[1',2':5,6][1,5]oxazocino [4,3,2-de]quinazolin-8-yl] prop-2-en-1-one (Example 41, 30 mg, 9%) as a white solid. ¹H NMR (400 MHz, CD₃CN) 1.16-1.38 (3H, m), 1.70-1.80 (1H, m), 2.25-2.40 (1H, m), 2.92-3.44 (2H, m), 3.56-4.46 (3H, m), 4.57-4.76 (3H, m), 5.48-5.70 (1H, m), 6.05 (1H, d), 6.48-6.59 (1H, m), 6.78-6.91 (2H, m), 7.34-7.44 (1H, m), 8.40-8.51 (1H, m). m/z: ES' [M+H]⁺=487.

Methyl N-benzyl-L-alaninate

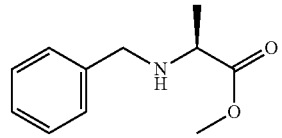

Sodium borohydride (11.01 g, 290.92 mmol) was added portionwise to methyl L-alaninate (30 g, 290 mmol), triethylamine (162 ml, 1160 mmol) and benzaldehyde (61.7 g, 582 mmol) in MeOH (1 l) at 0° C. The resulting mixture was stirred at rt for 4 h. The reaction mixture was quenched with sat. NH₄Cl (200 ml), extracted with DCM (3×100 ml), the organic layer was dried (Na₂SO₄), filtered and evaporated to dryness. The crude product was purified by flash silica chromatography (20 to 30% EtOAc in petroleum ether) to give methyl N-benzyl-L-alaninate (45 g, 80%) as a colourless oil. ¹H NMR (300 MHz, CDCl₃) 1.33 (3H, d), 3.32-3.46 (1H, m), 3.74 (3H, s), 4.66 (2H, s), 7.34-7.45 (5H, m). m/z: ES' [M+H]⁺=194.

Methyl (3S)-4-{benzyl[(2S)-1-methoxy-1-oxopropan-2-yl]amino}-3-[(tert-butoxycarbonyl)amino]-4-oxobutanoate

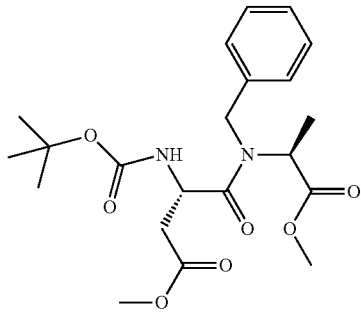 [SMILES: COC(=O)C[C@H](NC(=O)OC(C)(C)C)C(=O)N(Cc1ccccc1)[C@@H](C)C(=O)OC]

Isobutyl chloroformate (19.44 g, 142.3 mmol) was added to a solution of (2S)-2-[(tert-butoxycarbonyl)amino]-4-methoxy-4-oxobutanoic acid (32 g, 130 mmol) and 4-methylmorpholine (15.7 g, 155.24 mmol) in THF (50 ml) at 0° C. The resulting solution was stirred at 0° C. for 1 h and then a solution of methyl N-benzyl-L-alaninate (25 g, 130 mmol) in THF (20 ml) was added at 0° C. The resulting mixture was stirred at rt overnight. The reaction mixture was quenched with water (50 ml), extracted with EtOAc (3×200 ml), the organic layer was dried (Na$_2$SO$_4$), filtered and evaporated to afford a yellow liquid. The crude product was purified by flash silica chromatography (0 to 30% EtOAc in petroleum ether) to give methyl (3S)-4-{benzyl[(2S)-1-methoxy-1-oxopropan-2-yl]amino}-3-[(tert-butoxycarbonyl)amino]-4-oxobutanoate (20 g, 37%) as a yellow oil. $^1$H NMR (300 MHz, CDCl$_3$) 1.31-1.38 (3H, m), 1.45 (9H, s), 2.77-3.09 (2H, m), 3.46 (2H, s), 3.59-3.72 (6H, m), 4.49-4.72 (1H, m), 5.16-5.21 (1H, m), 7.29-7.43 (5H, m). m/z: ES$^+$[M+H]$^+$=423.

Methyl [(2S,5S)-4-benzyl-5-methyl-3,6-dioxopiperazin-2-yl]acetate

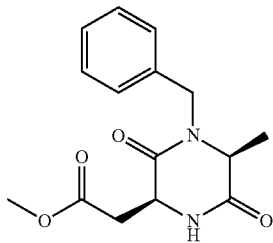

TFA (54 g, 470 mmol) was added to a solution of methyl (3S)-4-{benzyl[(2S)-1-methoxy-1-oxopropan-2-yl]amino}-3-[(tert-butoxycarbonyl)amino]-4-oxobutanoate (20 g, 47 mmol) in DCM (100 ml) at rt.

The resulting solution was stirred at rt for 2 h and evaporated. The crude was redissolved in sat. aq. NaHCO$_3$ (200 ml). The solution was stirred at rt for 2 h then purified by C18-flash chromatography (0 to 60% MeCN in water) to give methyl [(2S,5S)-4-benzyl-5-methyl-3,6-dioxopiperazin-2-yl]acetate (6.5 g, 47%) as a yellow oil. $^1$H NMR (300 MHz, CDCl$_3$) 1.50 (3H, d), 2.68-2.81 (2H, m), 3.70-3.71 (1H, m), 3.74 (3H, s), 3.97-4.06 (1H, m), 4.41-4.54 (1H, m), 5.25-5.31 (1H, m), 7.22-7.37 (6H, m). m/z: ES+ [M+H]+= 291.

2-[(2S,5S)-4-Benzyl-5-methylpiperazin-2-yl]ethan-1-ol

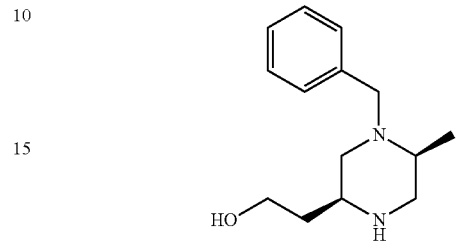

Lithium aluminium hydride (6.80 g, 179 mmol) was added portionwise to a solution of methyl [(2S,5S)-4-benzyl-5-methyl-3,6-dioxopiperazin-2-yl]acetate (6.5 g, 22 mmol) in THF (20 ml) at 0° C. The resulting solution was stirred at 0° C. for 0.5 h then at rt for another 4 h. The reaction mixture was quenched with water (6.5 ml) and 15% aq. NaOH (19.5 ml), filtered through a CELITE pad and washed with DCM (3×100 ml) to afford after evaporation 2-[(2S,5S)-4-benzyl-5-methylpiperazin-2-yl]ethan-1-ol (4.6 g, 88%) as a pale yellow liquid. $^1$H NMR (300 MHz, CDCl$_3$) 1.07 (3H, d), 1.42-1.50 (1H, m), 2.25-2.32 (1H, m), 2.34-2.44 (2H, m), 2.65-2.87 (3H, m), 2.92-3.05 (2H, m), 3.35-3.48 (1H, m), 3.69-3.82 (3H, m), 4.71 (1H, s), 7.32-7.35 (3H, m), 7.37-7.40 (2H, m). m/z: ES$^+$[M+H]$^+$=235.

5-{2-[(2S,5S)-4-Benzyl-5-methylpiperazin-2-yl]ethoxy}-7-bromo-6-chloro-8-fluoroquinazolin-4-ol

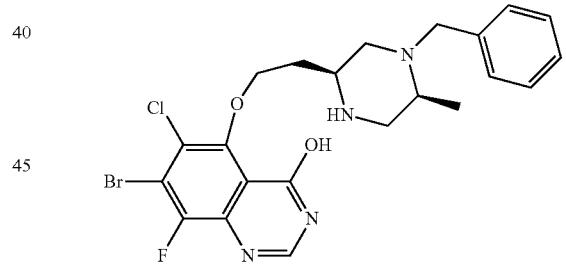

Sodium hydride (0.85 g, 21 mmol) was added to 2-[(2S,5S)-4-benzyl-5-methylpiperazin-2-yl]ethan-1-ol (2 g, 8.5 mmol) in THF (20 ml) at 0° C. The resulting mixture was stirred at 0° C. for 15 min. 7-bromo-6-chloro-5,8-difluoroquinazolin-4-ol (2.52 g, 8.53 mmol) was then added and the mixture stirred at 60° C. for 3 h. The reaction mixture was quenched with water (20 ml) and acidified with 2H HCl to pH=7. The mixture was extracted with EtOAc (3×100 ml). The organic layer was combined and concentrated. The crude product was purified by flash silica chromatography (0 to 10% MeOH in DCM) to give 5-{12-[(2S,5S)-4-benzyl-5-methylpiperazin-2-yl]ethoxy}-7-bromo-6-chloro-8-fluoroquinazolin-4-(1.4 g, 32%) as a brown solid. $^1$H NMR (400 MHz, DMSO) 1.17 (3H, d), 2.14-2.25 (1H, m), 2.46-2.51 (2H, m), 2.71-2.94 (3H, m), 3.11-3.25 (1H, m), 3.45 (1H, d), 3.69 (1H, d), 3.89-4.24 (3H, m), 7.31-7.45 (5H, m, 8.19 (1H, s). m/z: ES$^+$[M+H]$^+$=509.

(6aS,9S)-8-Benzyl-2-bromo-3-chloro-1-fluoro-9-methyl-6,6a,7,8,9,10-hexahydro-5H-pyrazino [1',2':5,6][1,5]oxazocino[4,3,2-de]quinazoline

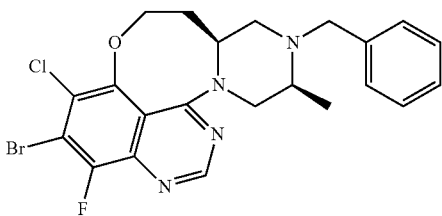 [SMILES: C[C@H]1CN2c3ncnc4c(F)c(Br)c(Cl)c(c34)OCC[C@H]2CN1Cc1ccccc1]

Tetrachloromethane (1.33 ml, 13.7 mmol) was added to 5-{12-[(2S,5S)-4-benzyl-5-methylpiperazin-2-yl]ethoxy}-7-bromo-6-chloro-8-fluoroquinazolin-4-ol (1.4 g, 2.8 mmol) and triphenylphosphine (2.16 g, 8.24 mmol) in 1,2-dichloroethane (20 ml) at rt. The resulting mixture was stirred at 80° C. for 2 h. The solvent was removed in vacuo. The crude product was purified by C18-flash chromatography (0 to 80% MeCN in water (0.1% NH$_4$HCO$_3$)) to give (6aS,9S)-8-benzyl-2-bromo-3-chloro-1-fluoro-9-methyl-6,6a,7,8,9,10-hexahydro-5H-pyrazino[1',2':5,6][1,5]oxazocino[4,3,2-de]quinazoline (0.45 g, 33%) as a yellow solid. $^1$H NMR (400 MHz, DMSO) 1.20 (3H, d), 1.58-1.81 (1H, m), 2.14-2.24 (1H, m), 2.40-2.45 (1H, m), 2.63-2.71 (2H, m), 3.06-3.21 (3H, m), 3.61-3.86 (1H, m), 4.03-4.10 (1H, m), 4.19-4.49 (1H, m), 5.01-5.12 (1H, m), 7.31-7.45 (5H, m), 8.40 (1H, s). m/z: ES+ [M+H]+=491.

2-[(6aS,9S)-8-Benzyl-3-chloro-1-fluoro-9-methyl-6,6a,7,8,9,10-hexahydro-5H-pyrazino[1',2':5,6] [1,5]oxazocino[4,3,2-de]quinazolin-2-yl]-3-fluorophenol

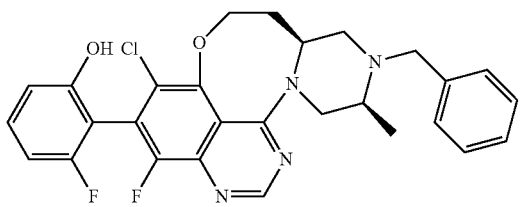 [SMILES: C[C@H]1CN2c3ncnc4c(F)c(-c5c(O)cccc5F)c(Cl)c(c34)OCC[C@H]2CN1Cc1ccccc1]

RuPhos-Pd-G3 (153 mg, 0.18 mmol) was added to a solution of (6aS,9S)-8-benzyl-2-bromo-3-chloro-1-fluoro-9-methyl-6,6a,7,8,9,10-hexahydro-5H-pyrazino[1',2':5,6][1,5]oxazocino[4,3,2-de] quinazoline (450 mg, 0.92 mmol), (2-fluoro-6-hydroxyphenyl)boronic acid (357 mg, 2.29 mmol), Na$_2$CO$_3$ (388 mg, 3.66 mmol) and dicyclohexyl(2',6'-diisopropoxy-[1,1'-biphenyl]-2-yl)phosphane (85 mg, 0.18 mmol) in 1,4-dioxane/H$_2$O (8 ml)(4:1 ratio). The resulting mixture was stirred at 80° C. for 1 h. The solvent was removed in vacuo. The crude product was purified by flash silica chromatography (40 to 60% EtOAc in petroleum ether) to give 2-[(6aS,9S)-8-benzyl-3-chloro-1-fluoro-9-methyl-6,6a,7,8,9,10-hexahydro-5H-pyrazino[1',2':5,6][1,5]oxazocino[4,3,2-de]quinazolin-2-yl]-3-fluorophenol (260 mg, 54%) as a yellow solid. $^1$H NMR (400 MHz, DMSO) 1.20 (3H, d), 0.94 (3H, d), 1.54-1.79 (3H, m), 2.26-2.31 (1H, m), 2.67-2.71 (1H, m), 3.03-3.19 (2H, m), 3.36-3.62 (1H, m), 3.81-3.85 (1H, m), 4.03-4.05 (1H, m), 4.28-4.45 (2H, m), 6.64 (1H, d), 6.73-6.87 (1H, m), 7.18-7.28 (1H, m), 7.29-7.38 (5H, m), 8.42 (1H, s), 10.16 (1H, d). m/z: ES+ [M+H]+=523.

2-[(6aS,9S)-3-Chloro-1-fluoro-9-methyl-6,6a,7,8,9,10-hexahydro-5H-pyrazino[1',2':5,6][1,5]oxazocino [4,3,2-de]quinazolin-2-yl]-3-fluorophenol

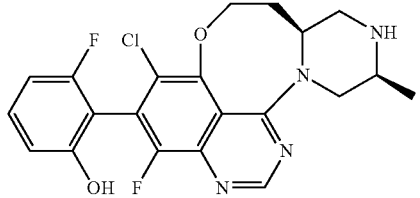 [SMILES: C[C@H]1CN2c3ncnc4c(F)c(-c5c(O)cccc5F)c(Cl)c(c34)OCC[C@H]2CN1]

10% Palladium on charcoal (509 mg, 0.48 mmol), di-tert-butyl dicarbonate (0.111 ml, 0.48 mmol) and 2-[(6aS,9S)-8-benzyl-3-chloro-1-fluoro-9-methyl-6,6a,7,8,9,10-hexahydro-5H-pyrazino[1',2':5,6][1,5] oxazocino[4,3,2-de] quinazolin-2-yl]-3-fluorophenol (250 mg, 0.48 mmol) in THF (10 ml) was stirred under an atmosphere of hydrogen at 1 atm and rt for 1 h. The reaction mixture was filtered through silica gel and the solvent removed in vacuo. The reaction mixture was diluted with DCM (10.00 ml) and TFA (0.37 ml, 4.8 mmol) added. The resulting solution was stirred at rt for 1 h. The solvent was removed in vacuo. The crude product was purified by ion exchange chromatography, using an SCX column. Elution with 7M NH$_3$/MeOH gave 2-[(6aS,9S)-3-chloro-1-fluoro-9-methyl-6,6a,7,8,9,10-hexahydro-5H-pyrazino[1',2':5,6][1,5]oxazocino[4,3,2-de]quinazolin-2-yl]-3-fluorophenol (200 mg, 97%) as a pale yellow solid. $^1$H NMR (400 MHz, DMSO) 1.40 (3H, d), 1.88-1.99 (1H, m), 2.63-2.78 (1H, m), 3.17-3.30 (4H, m), 4.02-4.09 (1H, m), 4.37-4.50 (2H, m), 5.07-5.15 (1H, m), 6.78 (1H, t), 6.89 (1H, d), 7.34-7.45 (1H, m), 8.51 (1H, s), 10.30 (1H, s). m/z: ES+[M+H]+=433.

1-[(6aS,9S)-3-Chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl]prop-2-en-1-one (Atropisomer 1, Example 42; Atropisomer 2, Example 43)

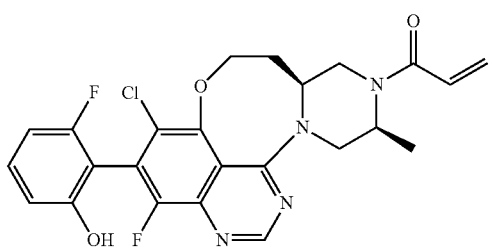 [SMILES: C=CC(=O)N1C[C@@H]2CCOc3c(Cl)c(-c4c(O)cccc4F)c(F)c4ncnc(c34)N2C[C@@H]1C]

A solution of acryloyl chloride (37.6 mg, 0.42 mmol) in DMF (0.5 ml) was added dropwise to a stirred solution of 2-[(6aS,9S)-3-chloro-1-fluoro-9-methyl-6,6a,7,8,9,10-hexahydro-5H-pyrazino[1',2':5,6] [1,5]oxazocino[4,3,2-de]quinazolin-2-yl]-3-fluorophenol (200 mg, 0.46 mmol) and DIPEA (0.12 ml, 0.69 mmol) in DMF (3.0 ml) at 0° C. The resulting solution was stirred at 0° C. for 30 min. The reaction mixture was quenched with water (1 ml) and the resulting mixture purified by C18-flash chromatography (0 to 40% MeCN in water (1% $NH_4HCO_3$)) to give a mixture of two atropisomers which were then separated by preparative chiral-HPLC on a Column: (R,R)Whelk-01, 21.1×250 mm, 5 μm; Mobile Phase A:Hex (8 mmol/L $NH_3$.MeOH)-HPLC, Mobile Phase B: EtOH-HPLC; Flow rate: 20 ml/min; Gradient: 50 B to 50 B in 20 min; 220/254 nm; RT1:12.723; RT2:15.375. This gave atropisomer 1 of 1-[(6aS,9S)-3-chloro-1-fluoro-2-(2-fluoro-6-hydroxyphenyl)-9-methyl-5,6,6a,7,9,10-hexahydro-8H-pyrazino[1',2':5,6][1,5] oxazocino[4,3,2-de]quinazolin-8-yl]prop-2-en-1-one (Example 42, 25 mg, 25%) as a white solid. $^1$H NMR (400 MHz, $CD_3CN$) 1.13-1.35 (3H, m), 1.63-1.87 (1H, m), 2.24-2.46 (1H, m), 2.87-3.46 (2H, m), 3.50-4.09 (2H, m), 4.15-4.81 (4H, m), 5.46-5.66 (1H, m), 6.04 (1H, d), 6.53 (1H, dd), 6.76-6.94 (2H, m), 7.29-7.48 (1H, m), 8.35 (1H, d). m/z: ES+ [M+H]+=487. This was followed by atropisomer 2 of 1-[(6aS,9S)-3-chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl] prop-2-en-1-one (Example 43, 8 mg, 8%) as a white solid. 1H NMR (400 MHz, $CD_3CN$) 1.13-1.35 (3H, m), 1.52-1.86 (2H, m), 2.90-4.09 (4H, m), 4.13-4.89 (4H, m), 5.48-5.70 (1H, m), 6.06 (1H, d), 6.55 (1H, dd), 6.75-6.98 (2H, m), 7.26-7.47 (1H, m), 8.49 (1H, s). m/z: $ES^+[M+H]^+$=487.

3-Bromo-2-chloro-4,5-difluoroaniline

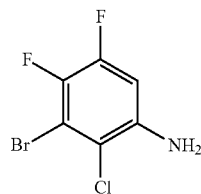 [SMILES: Nc1cc(F)c(F)c(Br)c1Cl]

N-Chlorosuccinimide (2.76 g, 20.67 mmol) was added to 3-bromo-4,5-difluoroaniline (4.3 g, 21 mmol) in MeCN (20 ml) at rt. The resulting solution was stirred at 60° C. overnight. The crude product was purified by C18-flash chromatography (0 to 20% MeOH in MeCN (1% $NH_4HCO_3$)) to give 3-bromo-2-chloro-4,5-difluoroaniline (3.5 g, 70%) as a brown solid. $^1$H NMR (400 MHz, DMSO) 5.80 (2H, s), 6.82 (1H, dd). m/z: $ES^+[M+H]^+$=242.

2-N-(3-Bromo-2-chloro-4,5-difluorophenyl)-2-(hydroxyimino)acetamide

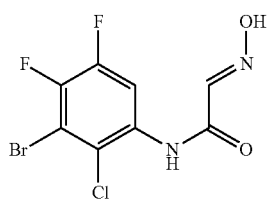

A solution of 3-bromo-2-chloro-4,5-difluoroaniline (3.5 g, 14.44 mmol), chloral hydrate (1.27 g, 18.4 mmol) and hydroxylamine hydrochloride (3.01 g, 43.3 mmol) in water (40 ml), EtOH (70 ml) and 11.65 M HCl (30 ml) was added to a stirred solution of sodium sulfate (13.94 g, 98.17 mmol) in water (400 ml) at rt. The resulting mixture was stirred at 60° C. overnight. The reaction was cooled to rt and a precipitate collected by filtration, washed with water and dried under vacuum to afford 2-N-(3-bromo-2-chloro-4,5-difluorophenyl)-2-(hydroxyimino)acetamide (4 g, 88%) as a beige solid. $^1$H NMR (300 MHz, $CDCl_3$) 7.61 (1H, s), 8.05 (1H, s), 8.51 (1H, dd), 8.95 (1H, s).

6-Bromo-7-chloro-4,5-difluoro-1H-indole-2,3-dione

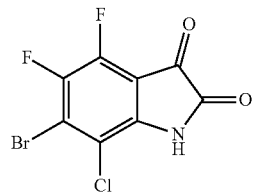

2-N-(3-Bromo-2-chloro-4,5-difluorophenyl)-2-(hydroxyimino)acetamide (4 g, 13 mmol) was added to conc. $H_2SO_4$ (30 ml, 560 mmol) at rt. The resulting mixture was stirred at 80° C. for 3 h. After cooling to rt the mixture was poured onto ice, and the precipitate formed was filtered off and washed with water. The solid was dried under vacuum to afford 6-bromo-7-chloro-4,5-difluoro-1H-indole-2,3-dione (3.7 g, 98%) as a dark red solid. $^1$H NMR (400 MHz, DMSO) 11.81 (1H, s). m/z: ES− [M+H]−=294.

2-Amino-4-bromo-3-chloro-5,6-difluorobenzoic acid

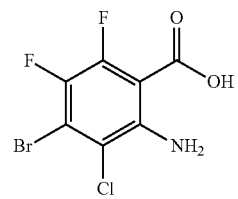 [SMILES: Nc1c(Cl)c(Br)c(F)c(F)c1C(=O)O]

Hydrogen peroxide (6.37 ml, 62.4 mmol) was added to a solution of 6-bromo-7-chloro-4,5-difluoro-1H-indole-2,3-dione (3.7 g, 12 mmol) in 2M NaOH (56.2 ml, 112 mmol) at rt. The resulting mixture was stirred at rt overnight. The reaction mixture was quenched with excess $Na_2SO_3$. The aqueous was adjusted to pH 7 with 2M HCl and purified by C18-flash chromatography (0 to 50% MeOH in water) to give 2-amino-4-bromo-3-chloro-5,6-difluorobenzoic acid (2.85 g, 80%) as a pale yellow solid. $^1$H NMR (400 MHz, DMSO) 5.83 (2H, s). m/z: $ES^+[M+H]^+$=286.

7-Bromo-8-chloro-5,6-difluoroquinazolin-4-ol

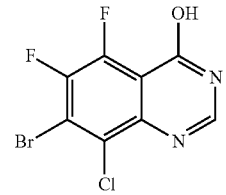 [SMILES: Oc1ncnc2c(Cl)c(Br)c(F)c(F)c12]

Formimidamide acetate (12.43 g, 119.4 mmol) was added to a solution of 2-amino-4-bromo-3-chloro-5,6-difluorobenzoic acid (2.85 g, 9.95 mmol) in ethanol (20 ml) and isopropanol (20 ml) at rt. The resulting suspension was stirred at 90° C. overnight. The reaction mixture was evaporated, and the residue suspended in water (100 ml). A precipitate was collected by filtration, washed with water (3×10 ml) and dried under vacuum to afford 7-bromo-8-chloro-5,6-difluoroquinazolin-4-ol (1.9 g, 65%) as a tan solid. $^1$H NMR (400 MHz, DMSO) 8.23 (1H, s). m/z: ES$^+$[M+H]$^+$=295.

tert-Butyl (3S)-3-{[(7-bromo-8-chloro-6-fluoro-4-hydroxyquinazolin-5-yl)oxy]methyl}piperazine-1-carboxylate

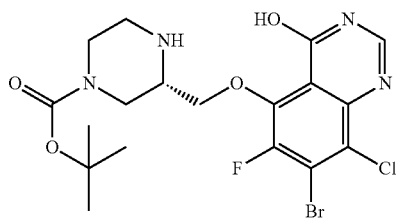 [SMILES: CC(C)(C)OC(=O)N1CCN[C@H](COc2c(F)c(Br)c(Cl)c3ncnc(O)c23)C1]

Sodium hydride (0.86 g, 21 mmol) was added to tert-butyl (3S)-3-(hydroxymethyl)piperazine-1-carboxylate (1.244 g, 5.75 mmol) in THF (40 ml) at rt. The resulting mixture was stirred at rt for 10 min. 7-Bromo-8-chloro-5,6-difluoroquinazolin-4-ol (1.7 g, 5.75 mmol) was added slowly and the resulting solution was stirred at 40° C. for 1 h. The reaction mixture was quenched with water (2 ml). The reaction mixture was adjusted to pH=7 with 2M HCl. The crude product was purified by C18-flash chromatography (0 to 65% MeOH in water (0.1% TFA)) to afford tert-butyl (3S)-3-{[(7-bromo-8-chloro-6-fluoro-4-hydroxyquinazolin-5-yl)oxy]methyl}piperazine-1-carboxylate (1.65 g, 58%) as a brown solid. $^1$H NMR (400 MHz, DMSO) 1.35 (9H, s), 2.62-3.07 (2H, m), 3.11-3.19 (2H, m), 3.20-3.76 (1H, m), 3.80-3.88 (1H, m), 3.98-4.29 (3H, m), 8.23 (1H, s). m/z: ES$^+$[M+H]$^+$=491. tert-Butyl (8aS)-5-bromo-4-chloro-6-fluoro-8a,9,11,12-tetrahydropyrazino[2',1':3,4][1,4]oxazepino [5,6,7-de]quinazoline-10(8l-1)-carboxylate

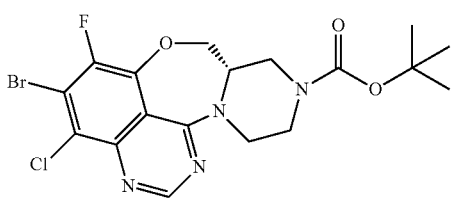 [SMILES: CC(C)(C)OC(=O)N1CCN2c3ncnc4c(Cl)c(Br)c(F)c(c34)OC[C@@H]2C1]

(Benzotriazol-1-yloxy)tripyrrolidinophosphonium hexafluorophosphate (3.49 g, 6.71 mmol) was added to tert-butyl (3S)-3-{[(7-bromo-8-chloro-6-fluoro-4-hydroxyquinazolin-5-yl)oxy]methyl}piperazine-1-carboxylate (1.65 g, 3.36 mmol) and 1,8-diazabicyclo[5.4.0]undec-7-ene (1.01 ml, 6.71 mmol) in acetonitrile (20 ml) at rt. The resulting solution was stirred at 40° C. for 1 h. Following standard work up, the crude product was purified by C18-flash chromatography (0 to 40% MeCN in water (0.1% formic acid)) to give tert-butyl (8aS)-5-bromo-4-chloro-6-fluoro-8a,9,11,12-tetrahydropyrazino[2',1':3,4][1,4] oxazepino[5,6,7-de]quinazoline-10(8H)-carboxylate (0.82 g, 52%) as a brown solid. $^1$H NMR (300 MHz, CDCl$_3$) 1.52 (9H, s), 1.82-2.04 (3H, m), 3.03-3.56 (3H, m), 3.96-5.27 (3H, m), 8.82 (1H, s). m/z: ES$^+$[M+H]$^+$=473.

tert-Butyl (8aS)-4-chloro-6-fluoro-5-(2-fluoro-6-hydroxyphenyl)-8a,9,11,12-tetrahydropyrazino [2',1':3,4][1,4]oxazepino[5,6,7-de]quinazoline-10(8H)-carboxylate

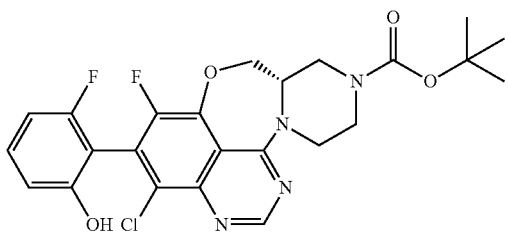 [SMILES: CC(C)(C)OC(=O)N1CCN2c3ncnc4c(Cl)c(-c5c(O)cccc5F)c(F)c(c34)OC[C@@H]2C1]

RuPhos-Pd-G3 (70.6 mg, 0.08 mmol) was added to a solution of tert-butyl (8aS)-5-bromo-4-chloro-6-fluoro-8a,9,11,12-tetrahydropyrazino[2',1':3,4][1,4]oxazepino[5,6,7-de]quinazoline-10(8H)-carboxylate (400 mg, 0.84 mmol), (2-fluoro-6-hydroxyphenyl)boronic acid (329 mg, 2.11 mmol), potassium carbonate (350 mg, 2.53 mmol) and dicyclohexyl(2',6'-diisopropoxy-[1,1'-biphenyl]-2-yl)phosphane (39.4 mg, 0.08 mmol) in 1,4-dioxane/H$_2$O (5 ml; 4:1 ratio). The resulting mixture was stirred at 100° C. for 30 min. The solvent was removed in vacuo. The crude product was purified by flash silica chromatography (20 to 60% EtOAc in petroleum ether) and then by C18-flash chromatography (0 to 35% MeOH in water (0.1% TFA)) to give tert-butyl (8aS)-4-chloro-6-fluoro-5-(2-fluoro-6-hydroxyphenyl)-8a,9,11,12-tetrahydropyrazino[2',1':3,4][1,4]oxazepino[5,6,7-de]quinazoline-10(8H)-carboxylate (150 mg, 35%) as a pale yellow solid. $^1$H NMR (300 MHz, CDCl$_3$) 1.53 (9H, s), 3.22-3.35 (2H, m), 3.88-4.00 (1H, m), 4.04-4.22 (3H, m), 4.45-4.64 (2H, m), 4.92-5.06 (1H, m), 6.57 (1H, d), 6.77 (1H, t), 6.88 (1H, d), 8.71 (1H, d). m/z: ES$^+$[M+H]$^+$=505.

2-[(8aS)-4-Chloro-6-fluoro-8,8a,9,10,11,12-hexahydropyrazino[2',1':3,4][1,4]oxazepino[5,6,7-de]quinazolin-5-yl]-3-fluorophenol

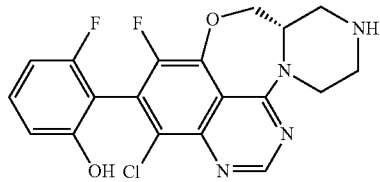 [SMILES: Oc1cccc(F)c1-c1c(F)c2c3c(ncnc3c1Cl)N1CCNC[C@H]1CO2]

4M HCl in 1,4-dioxane (2 ml, 66 mmol) was added to a solution of tert-butyl (8aS)-4-chloro-6-fluoro-5-(2-fluoro-6-hydroxyphenyl)-8a,9,11,12-tetrahydropyrazino[2',1':3,4][1,4]oxazepino[5,6,7-de] quinazoline-10(8H)-carboxylate (150 mg, 0.3 mmol) in MeOH (0.5 ml). The resulting mixture was stirred at rt for 2 h. The mixture was purified by C18-flash chromatography (0 to 38% MeOH in water (0.1% TFA)) to give crude product. This was purified by ion exchange chromatography, using an SCX column. The desired product was eluted from the column using 7M NH₃/MeOH to give 2-[(8aS)-4-chloro-6-fluoro-8,8a,9,10,11,12-hexahydropyrazino[2',1':3,4][1,4]oxazepino[5,6,7-de]quinazolin-5-yl]-3-fluorophenol (120 mg, 99%) as a pale yellow solid. ¹H NMR (400 MHz, DMSO) 3.05-3.20 (1H, m), 3.27-3.46 (3H, m), 3.49-3.63 (1H, m), 4.22-4.36 (1H, m), 4.60-4.81 (2H, m), 5.04-5.19 (1H, m), 6.74-6.92 (2H, m), 7.29-7.44 (1H, m), 8.69 (1H, s), 10.36 (1H, s). m/z: ES⁺[M+H]⁺=405.

1-[(8a5)-4-Chloro-6-fluoro-5-(2-fluoro-6-hydroxyphenyl)-8a,9,11,12-tetrahydropyrazino[2',1':3,4][1,4]oxazepino[5,6,7-de]quinazolin-10(8H)-yl]prop-2-en-1-one (Atropisomer 1, Example 44; Atropisomer 2, Example 45)

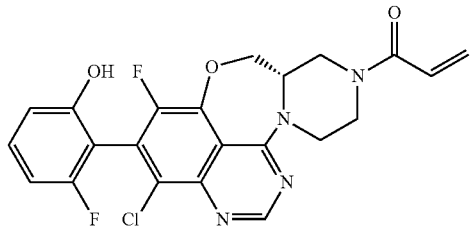 [SMILES: C=CC(=O)N1CCN2c3ncnc4c(Cl)c(-c5c(O)cccc5F)c(F)c(c34)OC[C@@H]2C1]

A solution of acryloyl chloride (26.82 mg, 0.29 mmol) in DMF (0.5 ml) was added dropwise to a stirred solution of 2-[(8aS)-4-chloro-6-fluoro-8,8a,9,10,11,12-hexahydropyrazino[2',1':3,4] [1,4]oxazepino [5,6,7-de]quinazolin-5-yl]-3-fluorophenol (120 mg, 0.29 mmol) and DIPEA (0.1 ml, 0.58 mmol) in DMF (2.00 ml) at 0° C. The resulting solution was stirred at 0° C. for 1 h and purified by C18-flash chromatography (0 to 40% MeOH in water (0.1% NH₄OH)) to give a mixture of two atropisomers which were then separated by preparative chiral-HPLC on Column: CHIRAL ART Cellulose-SB S-5 µm, 2×25 cm, 5 µm; Mobile Phase A:MTBE (10 mM NH₃-MeOH)-HPLC, Mobile Phase B: IPA-HPLC; Flow rate: 20 ml/min; Gradient: 30 B to 30 B in 22 min; 254/220 nm; RT1:13.164; RT2:18.688). This gave atropisomer 1 of 1-[(8aS)-4-chloro-6-fluoro-5-(2-fluoro-6-hydroxyphenyl)-8a,9,11,12-tetrahydropyrazino[2',1':3,4][1,4]oxazepino[5,6,7-de]quinazolin-10(8H)-yl]prop-2-en-1-one (Example 44, 32 mg, 24%) as a white solid. ¹H NMR (400 MHz, DMSO) 2.98-3.20 (1H, m), 3.39-3.55 (1H, m), 4.03-4.19 (2H, m), 4.26-4.53 (2H, m), 4.58-4.74 (2H, m), 4.76-4.93 (1H, m), 5.76 (1H, dd), 6.19 (1H, dd), 6.76-6.94 (3H, m), 7.30-7.41 (1H, m), 8.63 (1H, s), 10.16-10.30 (1H, m). m/z: ES⁺[M+H]⁺=459. This was followed by atropisomer 2 of 1-[(8aS)-4-chloro-6-fluoro-5-(2-fluoro-6-hydroxyphenyl)-8a,9,11,12-tetrahydropyrazino[2',1':3,4][1,4]oxazepino[5,6,7-de]quinazolin-10(8H)-yl]prop-2-en-1-one (Example 45, 22 mg, 16%) as a white solid. ¹H NMR (400 MHz, DMSO) 2.96-3.18 (1H, m), 3.37-3.57 (2H, m), 4.02-4.54 (3H, m), 4.61-4.74 (1H, m), 4.74-4.91 (1H, m), 5.76 (1H, dd), 6.19 (1H, dd), 6.69-6.94 (3H, m), 7.28-7.40 (1H, m), 8.63 (1H, s), 10.36 (1H, s). m/z: ES⁺[M+H]⁺=459.

Methyl N-[(benzyloxy)carbonyl]-D-seryl-D-alaninate

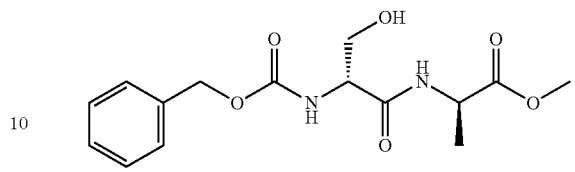

A suspension of methyl D-alaninate hydrochloride (18.21 g, 130.5 mmol) and ((benzyloxy)carbonyl)-D-serine (31.2 g, 130.5 mmol) in DCM (573 ml) was cooled in an ice-bath and 3-(((ethylimino)methylene)amino)-N,N-dimethylpropan-1-amine hydrochloride (30 g, 160 mmol) was added. DIPEA (80 ml, 460 mmol) was added dropwise over 20 min and then the solution was stirred at rt overnight. The mixture was concentrated in vacuo to give a colourless residue. The residue was dissolved in EtOAc (375 ml) and washed with 1:1 water/aq. sat. Na HCO₃ (470 ml). The organic portion was collected and the aqueous portion was washed with further EtOAc (375 ml). The combined organics were washed with aq. 2 M HCl (250 ml), brine (250 ml), dried (MgSO₄), filtered and concentrated to give methyl N-[(benzyloxy)carbonyl]-D-seryl-D-alaninate (38.8 g, 92%) as a colourless solid. ¹H NMR (400 MHz, MeOD, 30° C.) 1.38 (3H, d), 3.70 (3H, d), 3.77 (2H, q), 4.24 (1H, t), 4.45 (1H, q), 5.11 (2H, s), 7.23-7.44 (5H, m). m/z: ES⁺[M+H]⁺ 325.

(3R,6R)-3-(Hydroxymethyl)-6-methylpiperazine-2,5-dione

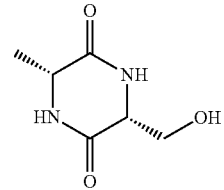

To methyl N-[(benzyloxy)carbonyl]-D-seryl-D-alaninate (38.76 g, 119.5 mmol) was added 10% palladium on carbon (1.925 g, 9.32 mmol), MeOH (130 ml) and cyclohexene (78 ml, 770 mmol). The resultant mixture was heated at reflux overnight. Methanol (450 ml) was added and the mixture was stirred at reflux for 1 h. The reaction mixture was filtered (whilst hot) through CELITE, washing with hot methanol (2×150 ml). The filtrate was concentrated to give a white solid. The solid was triturated with acetonitrile (170 ml), filtered, washed with acetonitrile (86 ml) and dried under vacuum at 40° C. for 1 h to give (3R,6R)-3-(hydroxymethyl)-6-methylpiperazine-2,5-dione (16.09 g, 85%) as a white solid. ¹H NMR (400 MHz, DMSO, 30° C.) 1.32 (3H, d), 3.51 (1H, ddd), 3.67-3.78 (2H, m), 3.81 (1H, dddd), 5.05 (1H, t), 7.83 (1H, s), 8.08 (1H, s).

[(2S,5R)-5-Methylpiperazin-2-yl]methanol dihydrochloride

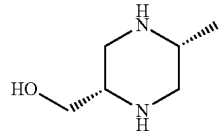

To (3R,6R)-3-(hydroxymethyl)-6-methylpiperazine-2,5-dione (14.77 g, 93.39 mmol) was added borane-THF Complex (1M in THF) (700 ml, 700 mmol) slowly with cooling. On addition, the mixture was brought to rt and then heated at reflux for 18 h. The reaction mixture was brought to rt and then cooled in an ice-bath. MeOH (185 ml) was added dropwise, followed by aq. 5 M HCl (49 ml, 250 mmol) dropwise. On addition, the mixture was heated at 70° C. for 2 h. The reaction was allowed to cool to rt then cooled in an ice-bath. A gum formed on the walls of the flask. The solvent was decanted, leaving a gum which was scratched with THF (100 ml). The THF was decanted and the resulting gum was azeotroped with toluene (3×100 ml) to afford [(2S,5R)-5-methylpiperazin-2-yl]methanol dihydrochloride (9.88 g, 52%) as a colourless semi-solid. $^1$H NMR (400 MHz, DMSO, 30° C.) 1.40 (3H, d), 3.14 (1H, dd), 3.26 (1H, dd), 3.32-3.39 (2H, m), 3.55-3.61 (1H, m), 3.69-3.76 (2H, m), 3.92 (1H, dd), 5.59 (1H, s), 9.97 (4H, d).

tert-Butyl (2R,5S)-5-(hydroxymethyl)-2-methylpiperazine-1-carboxylate

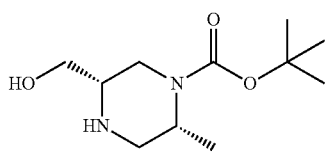 [SMILES: C[C@@H]1CN[C@H](CO)CN1C(=O)OC(C)(C)C]

[(2S,5R)-5-Methylpiperazin-2-yl]methanol dihydrochloride (9.88 g, 48.64 mmol) was suspended in methanol (50 ml) and cooled in an ice-bath. Triethylamine (21.02 ml, 150.8 mmol) was added and then a solution of di-tert-butyl dicarbonate (25.5 g, 117 mmol) in methanol (75 ml) was added dropwise over 30 min. The solution was stirred in the ice-bath for 30 min before being brought to rt and then heated at 50° C. for 18 h. The reaction mixture was concentrated in vacuo. The resultant residue was dissolved in ethanol (200 ml) and aq. 1.5 M KOH (162 ml, 243 mmol) was added. The solution was heated at 100° C. overnight. The mixture was cooled to rt and brought to pH 10 using aq. 1 M HCl (~150 ml). The solution was extracted with chloroform (3×200 ml) and the combined organics were dried (MgSO$_4$), filtered and concentrated in vacuo to give tert-butyl (2R,5S)-5-(hydroxymethyl)-2-methylpiperazine-1-carboxylate (9.5 g, 85%) as a colourless oil. $^1$H NMR (400 MHz, CDCl$_3$, 30° C.) 1.20 (3H, d), 1.46 (9H, s), 2.00 (2H, d), 2.75 (2H, dd), 2.83 (1H, dd), 2.96 (1H, dd), 3.45-3.54 (1H, m), 3.62-3.7 (1H, m), 3.77 (1H, s), 4.18 (1H, s). m/z: ES$^+$[M+H]$^+$ 321.

tert-Butyl (2R,5S)-5-{[(7-bromo-8-fluoro-4-oxo-3,4-dihydroquinazolin-5-yl)oxy]methyl}-2-methylpiperazine-1-carboxylate

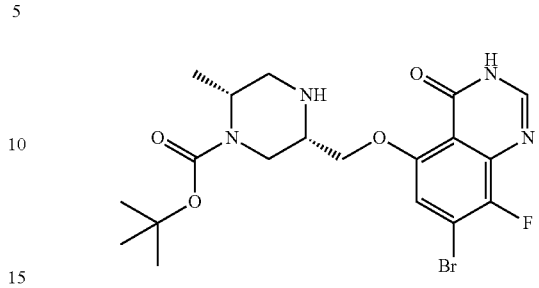

Sodium hydride (60% dispersion in mineral oil, 3.3 g, 82.55 mmol) was added portion-wise to a stirred suspension of tert-butyl (2R,5S)-5-(hydroxymethyl)-2-methylpiperazine-1-carboxylate (8.45 g, 36.7 mmol) and 7-bromo-5,8-difluoroquinazolin-4(3H)-one (9.58 g, 36.7 mmol) in THF (340 ml) with molecular sieves (10 g) at rt. The resulting suspension was stirred for 15 min and then at 65° C. for 4 h. The reaction was allowed to cool to rt then quenched with water (50 ml). The molecular sieves were removed by filtration through CELITE and the filter cake was washed with diethyl ether (100 ml). The combined filtrates were concentrated in vacuo. The resulting residue was diluted with water and the pH was adjusted to pH 8 with aq. 2M HCl. The aqueous was extracted with EtOAc (2×200 ml). The combined extracts were dried (MgSO$_4$) and concentrated to afford tert-butyl (2R,5S)-5-{[(7-bromo-8-fluoro-4-oxo-3,4-dihydroquinazolin-5-yl)oxy]methyl}-2-methylpiperazine-1-carboxylate (20.88 g, >100%) as pale brown foam. m/z: ES$^+$[M+H]$^+$ 471.

tert-Butyl (8aS,11R)-5-bromo-4-fluoro-11-methyl-8a,9,11,12-tetrahydropyrazino[2',1':3,4][1,4]oxazepino[5,6,7-de]quinazoline-10(8H)-carboxylate

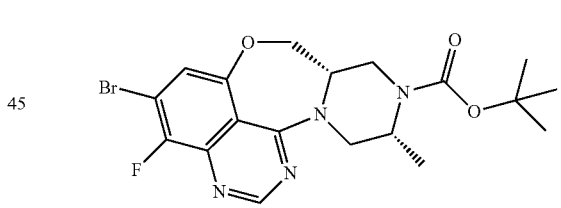

2,3,4,6,7,8,9,10-Octahydropyrimido[1,2-a]azepine (15.33 ml, 102.5 mmol) was added slowly to a stirred solution of tert-butyl (2R,5S)-5-{[(7-bromo-8-fluoro-4-oxo-3,4-dihydroquinazolin-5-yl)oxy]methyl}-2-methylpiperazine-1-carboxylate (19.32 g, 40.99 mmol) and ((1H-benzo[d][1,2,3]triazol-1-yl)oxy)tri(pyrrolidin-1-yl)phosphonium hexafluorophosphate(V) (27.7 g, 53.3 mmol) in acetonitrile (400 ml) at 0° C. The resulting solution was stirred at 0° C. for 15 min and then at rt for 16 h. The reaction mixture was concentrated and diluted with EtOAc (500 ml) and washed sequentially with 2M aq. Na$_2$CO$_3$ (300 ml) and brine (150 ml). The organic layer was dried (MgSO$_4$), filtered and evaporated to afford crude product. This was purified by flash silica chromatography (0 to 80% EtOAc in heptane) to give tert-butyl (8aS,11R)-5-bromo-4-fluoro-11-methyl-8a,9,11,12-tetrahydropyrazino[2',1':3,4][1,4]oxazepino[5,6,7-de]quinazoline-10(8H)-carboxylate (6.59 g, 36%) as a white solid. ¹H NMR (400 MHz, CDCl₃, 30° C.) 1.11 (3H, d), 1.49 (9H, s), 3.18-3.4 (2H, m), 3.75 (1H, d), 4.11 (1H, s), 4.34 (3H, d), 5.03 (1H, d), 7.16 (1H, d), 8.63 (1H, s). m/z: ES⁻ [M−H]⁻ 453.

tert-Butyl (8aS,11R)-5-bromo-6-chloro-4-fluoro-11-methyl-8a,9,11,12-tetrahydropyrazino[2',1':3,4] [1,4]oxazepino[5,6,7-de]quinazoline-10(8H)-carboxylate

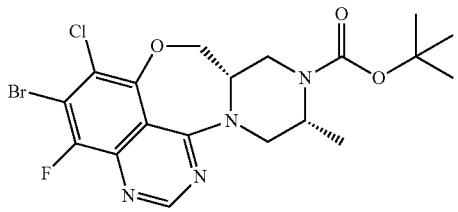 [SMILES: C[C@@H]1CN2c3ncnc4c(F)c(Br)c(Cl)c(c34)OC[C@@H]2CN1C(=O)OC(C)(C)C]

N-Chlorosuccinimide (0.551 g, 4.13 mmol) was added to a stirred suspension of tert-butyl (8aS,11R)-5-bromo-4-fluoro-11-methyl-8a,9,11,12-tetrahydropyrazino[2',1':3,4] [1,4]oxazepino[5,6,7-de] quinazoline-10(8H)-carboxylate (1.7 g, 3.75 mmol) in DMF (15 ml) at rt. The resulting suspension was stirred at 70° C. for 3 h. The reaction mixture was allowed to cool to rt and the suspension was diluted with water (57 ml), collected by filtration, washed with water (19 ml) and dried under vacuum at 50° C. for 16 h to afford tert-butyl (8aS,11R)-5-bromo-6-chloro-4-fluoro-11-methyl-8a,9,11,12-tetrahydropyrazino[2',1':3,4][1,4]oxazepino[5,6,7-de]quinazoline-10(8H)-carboxylate (1.67 g, 91%) as a yellow solid. ¹H NMR (400 MHz, CDCl₃, 30° C.) 1.13 (3H, s), 1.50 (9H, s), 3.35 (2H, d), 3.81 (1H, s), 4.04 (1H, d), 4.44 (3H, dd), 4.95 (1H, s), 8.64 (1H, s). m/z: ES⁺[M+H]⁺ 487.

[(8aS,11R)-10-(tert-Butoxycarbonyl)-4-fluoro-11-methyl-8,8a,9,10,11,12-hexahydropyrazino[2',1':3,4] [1,4]oxazepino[5,6,7-de]quinazolin-5-yl]boronic acid

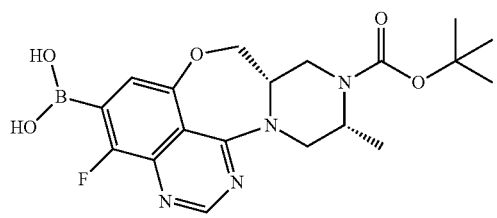 [SMILES: C[C@@H]1CN2c3ncnc4c(F)c(B(O)O)cc(c34)OC[C@@H]2CN1C(=O)OC(C)(C)C]

[1,1'-Bis(diphenylphosphino)ferrocene]dichloropalladium(II) complex with dichloromethane (252 mg, 0.31 mmol), bis(pinacolato)diboron (2353 mg, 9.27 mmol) and potassium acetate (606 mg, 6.18 mmol) were added to a stirred and degassed solution of tert-butyl (8aS,11R)-5-bromo-4-fluoro-11-methyl-8a,9,11,12-tetrahydropyrazino [2',1':3,4][1,4]oxazepino[5,6,7-de]quinazoline-10(8H)-carboxylate (1.4 g, 3.09 mmol) in dioxane (45 ml). The resulting mixture was stirred at 90° C. for 17 h. The reaction mixture was allowed to cool, evaporated and partitioned between EtOAc (125 ml), and water (75 ml), the organic layer was separated, washed with brine (50 ml), dried (MgSO₄), filtered and evaporated to afford the crude [(8aS, 11R)-10-(tert-butoxycarbonyl)-4-fluoro-11-methyl-8,8a,9,10,11,12-hexahydropyrazino[2',1':3,4][1,4]oxazepino[5,6,7-de]quinazolin-5-yl]boronic acid (assumed 3.09 mmol) as a brown oil which solidified on standing. m/z ES⁺[M+H]⁺ 419.

tert-Butyl (8aS,11R)-4-fluoro-11-methyl-5-[5-methyl-1-(oxan-2-yl)-1H-benzimidazol-4-yl]-8a,9,11,12-tetrahydropyrazino[2',1':3,4][1,4]oxazepino[5,6,7-de]quinazoline-10(8H)-carboxylate

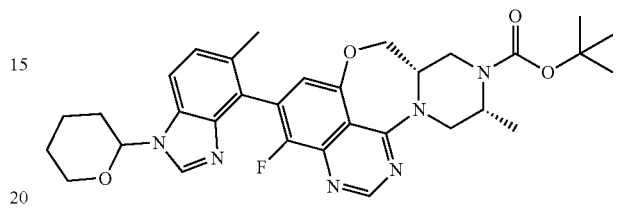

[(8aS,11R)-10-(tert-Butoxycarbonyl)-4-fluoro-11-methyl-8,8a,9,10,11,12-hexahydropyrazino [2',1':3,4][1,4]oxazepino[5,6,7-de]quinazolin-5-yl]boronic acid (0.862 g, 2.06 mmol), dicyclohexyl(2',6'-diisopropoxy-[1,1'-biphenyl]-2-yl)phosphane (0.096 g, 0.21 mmol), RuPhos Pd-G3 (0.172 g, 0.21 mmol), potassium carbonate (0.569 g, 4.12 mmol) and 4-bromo-5-methyl-1-(oxan-2-yl)-1H-benzimidazole (0.608 g, 2.06 mmol) were combined. A degassed mixture of 1,4-dioxane (15 ml) and water (4.5 ml) was added and the reaction was degassed for a further 1 minute then heated at 80° C. for 2 h. The cooled reaction mixture was diluted with EtOAc (90 ml), washed with 2M aq. Na₂CO₃ (2×45 ml), brine (45 ml), dried (MgSO₄), filtered and the filtrate concentrated in vacuo. The crude product was purified by flash silica chromatography (0 to 100% EtOAc in heptane, then 0 to 8% 1M methanolic ammonia in DCM) to give tert-butyl (8aS,11R)-4-fluoro-11-methyl-5-[5-methyl-1-(oxan-2-yl)-1H-benzimidazol-4-yl]-8a,9,11,12-tetrahydropyrazino[2',1':3,4][1,4]oxazepino[5,6,7-de] quinazoline-10(8H)-carboxylate (1.08 g, 89%) as a brown foam. ¹H NMR (400 MHz, CDCl₃, 30° C.) 1.14 (3H, d), 1.50 (9H, d), 1.74 (3H, d), 2.09-2.24 (3H, m), 2.34 (3H, d), 3.34 (2H, d), 3.71-3.84 (2H, m), 4.02-4.24 (2H, m), 4.26-4.52 (3H, m), 4.99-5.23 (1H, m), 5.44-5.58 (1H, m), 7.05 (1H, dt), 7.27-7.29 (1H, m), 7.50 (1H, dd), 7.99 (1H, t), 8.66 (1H, d). m/z (ES+), [M+H]⁺ 589.

tert-Butyl (8aS,11R)-6-chloro-4-fluoro-11-methyl-5-[5-methyl-1-(oxan-2-yl)-1H-benzimidazol-4-yl]-8a,9,11,12-tetrahydropyrazino[2',1':3,4][1,4]oxazepino [5,6,7-de]quinazoline-10(8H)-carboxylate and tert-butyl (8aS,11R)-6-chloro-4-fluoro-11-methyl-5-(5-methyl-1H-benzimidazol-4-yl)-8a,9,11,12-tetrahydropyrazino[2',1':3,4][1,4]oxazepino[5,6,7-de]quinazoline-10(8H)-carboxylate

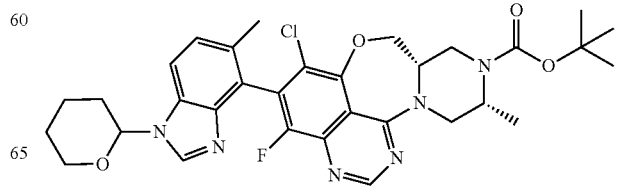

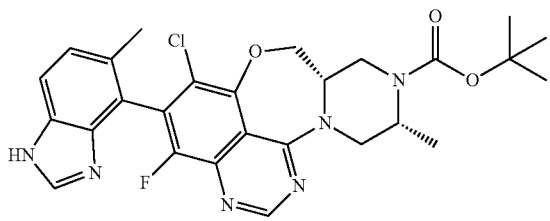

tert-Butyl (8aS,11R)-4-fluoro-11-methyl-5-[5-methyl-1-(oxan-2-yl)-1H-benzimidazol-4-yl]-8a,9,11,12-tetrahydropyrazino[2',1':3,4][1,4]oxazepino[5,6,7-de]quinazoline-10(8H)-carboxylate (1.08 g, 1.83 mmol) was dissolved in DMF (6 ml) then N-chlorosuccinimide (0.294 g, 2.20 mmol) was added with stirring. The reaction was then heated at 100° C. for 1 h then cooled to rt. The solvents were removed in vacuo to afford a mixture of tert-butyl (8aS,11R)-6-chloro-4-fluoro-11-methyl-5-[5-methyl-1-(oxan-2-yl)-1H-benzimidazol-4-yl]-8a,9,11,12-tetrahydropyrazino[2',1':3,4][1,4]oxazepino[5,6,7-de] quinazoline-10(8H)-carboxylate and tert-butyl (8aS,11R)-6-chloro-4-fluoro-11-methyl-5-(5-methyl-1H-benzimidazol-4-yl)-8a,9,11,12-tetrahydropyrazino[2',1':3,4][1,4]oxazepino[5,6,7-de]quinazoline-10(8H)-carboxylate (assumed 1.83 mmol) as a brown gum which was used directly in the next step. m/z ES+, [M+H]+ 539 (without THP group) and m/z (ES+), [M+H]+ 623 (with THP group).

(8aS,11R)-6-Chloro-4-fluoro-11-methyl-5-(5-methyl-1H-benzimidazol-4-yl)-8,8a,9,10,11,12-hexahydropyrazino[2',1':3,4][1,4]oxazepino[5,6,7-de]quinazoline

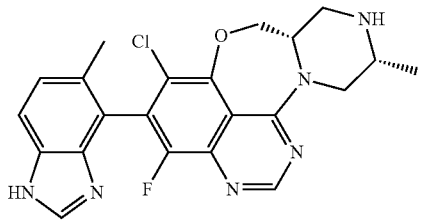 [SMILES: Cc1ccc2[nH]cnc2c1-c1c(Cl)c2c3c(ncnc3c1F)N1C[C@@H](C)NC[C@H]1CO2]

A mixture of tert-butyl (8aS,11R)-6-chloro-4-fluoro-11-methyl-5-[5-methyl-1-(oxan-2-yl)-1H-benzimidazol-4-yl]-8a,9,11,12-tetrahydropyrazino[2',1':3,4][1,4]oxazepino[5,6,7-de]quinazoline-10(8H)-carboxylate and tert-butyl (8aS,11R)-6-chloro-4-fluoro-11-methyl-5-(5-methyl-1H-benzimidazol-4-yl)-8a,9,11,12-tetrahydropyrazino[2',1':3,4][1,4]oxazepino[5,6,7-de]quinazoline-10(8H)-carboxylate (assumed 1.83 mmol) was stirred in 6M HCl in IPA (35 ml, 1.8 mmol). The resulting suspension was stirred at 70° C. for 2 h then the volatiles were removed in vacuo. The resulting residue was purified by ion exchange chromatography, using an SCX column. The desired product was eluted from the column using 1M NH₃/MeOH to give (8aS,11R)-6-chloro-4-fluoro-11-methyl-5-(5-methyl-1H-benzimidazol-4-yl)-8,8a,9,10,11,12-hexahydropyrazino[2',1':3,4][1,4]oxazepino[5,6,7-de]quinazoline (801 mg, 100%) as a brown foam. m/z ES⁻ [M−H]⁻ 437.

1-[(8aS,11R)-6-Chloro-4-fluoro-11-methyl-5-(5-methyl-1H-benzimidazol-4-yl)-8a,9,11,12-tetrahydropyrazino[2',1':3,4][1,4]oxazepino[5,6,7-de]quinazolin-10(8H)-yl]prop-2-en-1-one (Atropisomer 1, Example 46; Atropisomer 2, Example 47)

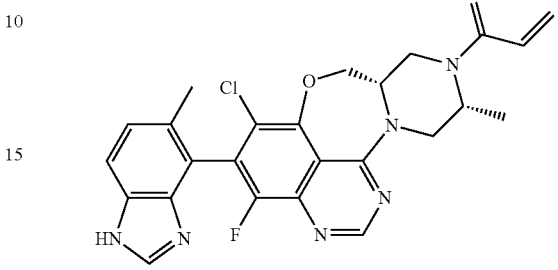

(8aS,11R)-6-Chloro-4-fluoro-11-methyl-5-(5-methyl-1H-benzimidazol-4-yl)-8,8a,9,10,11,12-hexahydropyrazino[2',1':3,4][1,4]oxazepino[5,6,7-de]quinazoline (400 mg, 0.91 mmol) was dissolved in DCM (12 ml) and IPA (2.5 ml) at rt with stirring, then triethylamine (0.127 ml, 0.91 mmol) was added. The solution was cooled at −78° C. then acryloyl chloride (0.078 ml, 0.96 mmol) was added dropwise over 5 min. The reaction was stirred at rt for 5 min then DCM was removed in vacuo and the resulting mixture purified by preparative HPLC (Waters XSelect CSH C18 ODB column, 5μ silica, 30 mm diameter, 100 mm length), using mixtures of water (containing 0.1% formic acid) and MeCN (gradient of 10% to 30%). Fractions containing the desired compound were evaporated to near dryness. The resulting solution ~5 ml was treated with 2M aq. K₂CO₃ (20 ml) and extracted with DCM (3×20 ml). The combined extracts were washed with water (10 ml) and brine (10 ml), passed through a phase separatory cartridge and evaporated to dryness to afford an off white glassy solid. This was separated using SFC (Column: Chiralpak OD, 20×250 mm, 5 μm, Mobile phase: 45% MeOH+0.1% NH₃/55% scCO₂, Flow rate: 60 ml/min, 120 bar, Column temp: 40° C.) to give atropisomer 1 of 1-[(8aS,11R)-6-chloro-4-fluoro-11-methyl-5-(5-methyl-1H-benzimidazol-4-yl)-8a,9,11,12-tetrahydropyrazino [2',1':3,4][1,4]oxazepino[5,6,7-de]quinazolin-10(8H)-yl]prop-2-en-1-one (Example 46, 26 mg, 12%, d.e. 99%) as a white solid. ¹H NMR (400 MHz, DMSO, 100° C.) 1.21 (3H, d), 2.20 (3H, s), 3.25-3.6 (2H, m), 3.99-4.13 (1H, m), 4.22-4.46 (1H, m), 4.59-4.78 (3H, m), 4.99 (1H, d), 5.72 (1H, dd), 6.16 (1H, dd), 6.74-6.9 (1H, m), 7.22 (1H, d), 7.49-7.7 (1H, m), 8.02 (1H, s), 8.61 (1H, s), 11.47-12.41 (1H, m). m/z (ES+), [M+H]⁺ 493, 495. This was followed by atropisomer 2 of 1-[(8aS,11R)-6-chloro-4-fluoro-11-methyl-5-(5-methyl-1H-benzimidazol-4-yl)-8a,9,11,12-tetrahydropyrazino[2',1':3,4][1,4]oxazepino[5,6,7-de]quinazolin-10(8H)-yl]prop-2-en-1-one (Example 47, 11 mg, 4%, d.e. 99%). ¹H NMR (400 MHz, DMSO, 100° C.) 1.21 (3H, d), 2.20 (3H, s), 3.25-3.6 (2H, m), 3.99-4.13 (1H, m), 4.22-4.46 (1H, m), 4.59-4.78 (3H, m), 4.99 (1H, d), 5.72 (1H, dd), 6.16 (1H, dd), 6.74-6.9 (1H, m), 7.22 (1H, d), 7.49-7.7 (1H, m), 8.02 (1H, s), 8.61 (1H, s), 11.47-12.41 (1H, m). m/z (ES+), [M+H]⁺ 493, 495.

tert-Butyl (8aS,11R)-4-fluoro-5-(1-methoxy-7-methylisoquinolin-8-yl)-11-methyl-8a,9,11,12-tetrahydropyrazino[2',1':3,4][1,4]oxazepino[5,6,7-de]quinazoline-10(8H)-carboxylate

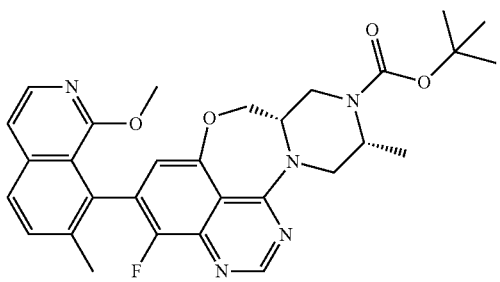 [SMILES: COc1nccc2ccc(C)c(-c3cc4c5c(ncnc5c3F)N3C[C@@H](C)N(C(=O)OC(C)(C)C)C[C@H]3CO4)c12]

RuPhos Pd G3 (110 mg, 0.13 mmol), dicyclohexyl(2',6'-diisopropoxy-[1,1'-biphenyl]-2-yl)phosphane (61.6 mg, 0.13 mmol), potassium carbonate (365 mg, 2.64 mmol), 8-bromo-1-methoxy-7-methylisoquinoline (333 mg, 1.32 mmol) and [(8aS,11R)-10-(tert-butoxycarbonyl)-4-fluoro-11-methyl-8,8a,9,10,11,12-hexahydropyrazino[2',1':3,4][1,4]oxazepino[5,6,7-de]quinazolin-5-yl]boronic acid (552 mg, 1.32 mmol) were combined and degassed dioxane (15 ml) and degassed water (4.5 ml) were then added. The resulting mixture was stirred at 80° C. for 2 h. The reaction mixture was allowed to cool then diluted with EtOAc (125 ml), washed with water (50 ml) and brine (25 ml), then the aqueous layer was re-extracted with EtOAc (75 ml). The organic extracts were combined, dried (MgSO$_4$), filtered and evaporated to afford crude product. The crude product was purified by flash silica chromatography (0 to 70% EtOAc in heptane) to give tert-butyl (8aS,11R)-4-fluoro-5-(1-methoxy-7-methylisoquinolin-8-yl)-11-methyl-8a,9,11,12-tetrahydropyrazino[2',1':3,4][1,4]oxazepino[5,6,7-de] quinazoline-10(8H)-carboxylate (890 mg, >100%) as a brown foam. $^1$H NMR (400 MHz, CDCl$_3$, 30° C.) 1.18 (3H, s), 1.57 (9H, s), 2.22 (3H, s), 3.21-3.46 (2H, m), 3.55 (3H, d), 3.83 (1H, s), 4-4.19 (1H, m), 4.24-4.62 (3H, m), 4.92-5.32 (1H, m), 6.81 (1H, d), 7.24 (1H, dd), 7.59 (1H, d), 7.74 (1H, d), 7.95 (1H, d), 8.68 (1H, s).

tert-Butyl (8aS,11R)-chloro-4-fluoro-5-(1-methoxy-7-methylisoquinolin-8-yl)-11-methyl-8a,9,11,12-tetrahydropyrazino[2',1':3,4][1,4]oxazepino[5,6,7-de]quinazoline-10(8H)-carboxylate

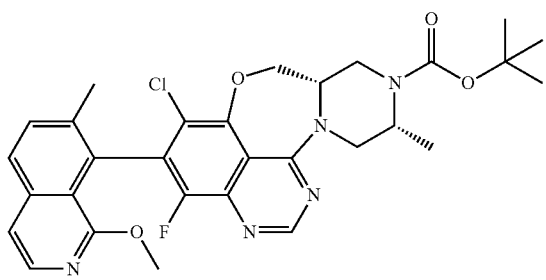 [SMILES: COc1nccc2ccc(C)c(-c3c(Cl)c4c5c(ncnc5c3F)N3C[C@@H](C)N(C(=O)OC(C)(C)C)C[C@H]3CO4)c12]

tert-Butyl (8aS,11R)-4-fluoro-5-(1-methoxy-7-methylisoquinolin-8-yl)-11-methyl-8a,9,11,12-tetrahydropyrazino[2',1':3,4][1,4]oxazepino[5,6,7-de]quinazoline-10(8H)-carboxylate (720 mg, 1.32 mmol) was dissolved in DMF (4.5 ml) then N-chlorosuccinimide (176 mg, 1.32 mmol) was added with stirring. The reaction was then heated at 110° C. for 30 min. Additional N-chlorosuccinimide (70 mg, 0.52 mmol) was added and the reaction was stirred at 110° C. for 0.5 h. The reaction mixture was allowed to cool then purified by reverse phase chromatography (150 g C18 RF GOLD), eluting with a gradient of 40-80% MeCN in water with formic acid 0.1% as a modifier, to give a beige foam. This was dissolved in MeOH and separated using SFC (Column: Chiralpak IC, 20×250 mm, 5 μm, Mobile phase: 45% MeOH+0.1% NH$_3$/65% scCO$_2$, Flow rate: 60 ml/min, 120 bar, Column temp: 40° C.). This gave tert-butyl (8aS,11R)-6-chloro-4-fluoro-5-(1-methoxy-7-methylisoquinolin-8-yl)-11-methyl-8a,9,11,12-tetrahydropyrazino[2',1':3,4][1,4]oxazepino[5,6,7-de]quinazoline-10(8H)-carboxylate atropisomer 1 (82 mg, 21%, d.e. 98.4%) as a beige foam. $^1$H NMR (400 MHz, CDCl$_3$, 30° C.) 1.21 (3H, d), 1.51 (9H, s), 2.19 (3H, s), 3.35 (2H, d), 3.56 (3H, s), 3.81-4.42 (3H, m), 4.45-4.71 (2H, m), 4.97-5.26 (1H, m), 7.26-7.28 (1H, m), 7.63 (1H, d), 7.78 (1H, d), 7.96 (1H, d), 8.65-8.71 (1H, m). m/z (ES+), [M+H]$^+$ 580, 582. This was followed by tert-butyl (8aS,11R)-6-chloro-4-fluoro-5-(1-methoxy-7-methylisoquinolin-8-yl)-11-methyl-8a,9,11,12-tetrahydropyrazino[2',1':3,4][1,4]oxazepino[5,6,7-de]quinazoline-10(8H)-carboxylate atropisomer 2 (100 mg, 26%, d.e. 99%) as a beige foam. $^1$H NMR (400 MHz, CDCl$_3$, 30° C.) 1.14-1.28 (3H, m), 1.51 (9H, s), 2.20 (3H, s), 3.33 (2H, s), 3.55 (3H, s), 3.82-4.41 (3H, m), 4.45-4.61 (2H, m), 4.94 (1H, d), 7.27 (1H, s), 7.63 (1H, d), 7.78 (1H, d), 7.96 (1H, d), 8.68 (1H, s). m/z (ES+), [M+H]$^+$ 580, 582.

8-[(8aS,11R)-6-Chloro-4-fluoro-11-methyl-8,8a,9,10,11,12-hexahydropyrazino[2',1':3,4][1,4]oxazepino[5,6,7-de]quinazolin-5-yl]-7-methylisoquinolin-1(2H)-one (Atropisomer 1)

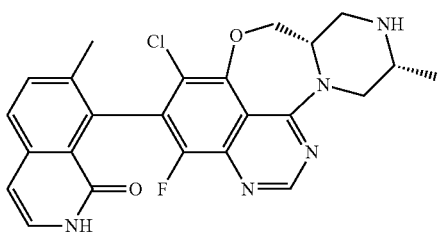 [SMILES: Cc1ccc2cc[nH]c(=O)c2c1-c1c(Cl)c2c3c(ncnc3c1F)N1C[C@@H](C)NC[C@H]1CO2]

A mixture of tert-butyl (8aS,11R)-6-chloro-4-fluoro-5-(1-methoxy-7-methylisoquinolin-8-yl)-11-methyl-8a,9,11,12-tetrahydropyrazino[2',1':3,4][1,4]oxazepino[5,6,7-de]quinazoline-10(8H)-carboxylate atropisomer 1 (82 mg, 0.14 mmol), lithium chloride (30 mg, 0.71 mmol), 4-methylbenzenesulfonic acid hydrate (134 mg, 0.71 mmol) and anhydrous DMF (2.6 ml) was stirred in a microwave reactor at 120° C. for 30 mins. The crude product was purified by ion exchange chromatography, using an SCX cartridge loading in MeOH. The column was eluted using 1M NH$_3$/MeOH to afford 8-[(8aS,11R)-6-chloro-4-fluoro-11-methyl-8,8a,9,10,11,12-hexahydropyrazino [2',1':3,4][1,4]oxazepino[5,6,7-de]quinazolin-5-yl]-7-methylisoquinolin-1(2H)-one atropisomer 1 (72 mg, >100%) as an off white solid. $^1$H NMR (400 MHz, MeOD, 30° C.) 1.21 (3H, d), 2.11 (3H, s), 2.94-2.99 (1H, m), 3.48-3.59 (1H, m), 4.03 (1H, dq), 4.55 (2H, dd), 4.87 (2H, dd), 6.68 (1H, d), 7.11 (1H, d), 7.64-7.75 (2H, m), 8.46 (1H, s). m/z (ES+), [M+1-1]+466, 468.

8-[(8aS,11R)-6-Chloro-4-fluoro-11-methyl-8,8a,9, 10,11,12-hexahydropyrazino[2',1':3,4][1,4] oxazepino[5,6,7-de]quinazolin-5-yl]-7-methylisoquinolin-1(2H)-one (Atropisomer 2)

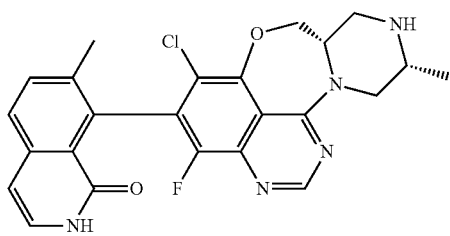 [SMILES: Cc1ccc2cc[nH]c(=O)c2c1-c1c(Cl)c2c3c(ncnc3c1F)N1C[C@@H](C)NC[C@H]1CO2]

The title compound was prepared in an analogous fashion to the corresponding atropisomer, starting from tert-butyl (8aS,11R)-6-chloro-4-fluoro-5-(1-methoxy-7-methylisoquinolin-8-yl)-11-methyl-8a,9,11,12-tetrahydropyrazino[2',1':3,4][1,4]oxazepino[5,6,7-de]quinazoline-10(8H)-carboxylate atropisomer 2. The title compound was isolated as an off white solid (84 mg, >100%). ¹H NMR (400 MHz, MeOD, 30° C.) 1.22 (3H, d), 2.12 (3H, s), 2.95 (1H, dd), 3.38-3.49 (1H, m), 4.02 (1H, dq), 4.38-4.63 (2H, m), 4.99 (1H, dd), 6.67 (1H, d), 7.10 (1H, d), 7.65-7.76 (2H, m), 8.46 (1H, s). m/z ES⁺, [M+H]⁺ 466.

8-[(8aS,11R)-6-Chloro-4-fluoro-11-methyl-10-(prop-2-enoyl)-8,8a,9,10,11,12-hexahydropyrazino [2',1':3, 4][1,4]oxazepino[5,6,7-de]quinazolin-5-yl]-7-methylisoquinolin-1(2H)-one (Atropisomer 1, Example 48)

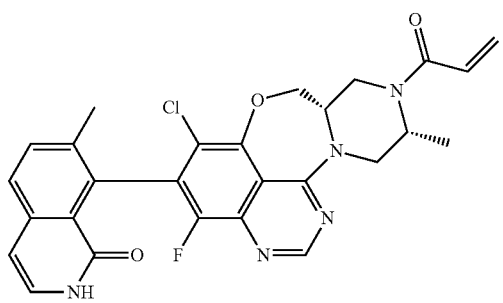 [SMILES: C=CC(=O)N1C[C@H]2COc3c(Cl)c(-c4c(C)ccc5cc[nH]c(=O)c45)c(F)c4ncnc(c34)N2C[C@H]1C]

8-[(8aS,11R)-6-Chloro-4-fluoro-11-methyl-8,8a,9,10,11, 12-hexahydropyrazino[2',1':3,4][1,4] oxazepino[5,6,7-de] quinazolin-5-yl]-7-methylisoquinolin-1(2H)-one atropisomer 1 (65.2 mg, 0.14 mmol) was dissolved in DCM (5 ml) and IPA (1 ml) at rt with stirring, then triethylamine (0.02 ml, 0.14 mmol) was added. The solution was cooled at −78° C., then acryloyl chloride (0.012 ml, 0.15 mmol) was added dropwise over 5 min. The reaction mixture was allowed to warm to rt, diluted with DCM (20 ml) and washed with water (20 ml). The organic layer was dried (phase separator) and concentrated in vacuo. The crude product was purified by preparative HPLC (WatersXSelect CSH C18 column, 5µ silica, 30×100 mm), using water (containing 1% NH₃) and MeCN (gradient of 25 to 50%) as eluents. This gave 8-[(8aS,11R)-6-chloro-4-fluoro-11-methyl-10-(prop-2-enoyl)-8,8a,9,10,11,12-hexahydropyrazino[2',1':3,4][1,4] oxazepino[5,6,7-de]quinazolin-5-yl]-7-methylisoquinolin-1 (2H)-one atropisomer 1 (Example 48, 37 mg, 51%, d.e. 99%) as an off white solid. ¹H NMR (400 MHz, DMSO, 100° C.) 1.21 (3H, d), 2.07 (3H, s), 3.33 (1H, s), 3.50 (1H, dd), 4.03 (1H, dd), 4.32 (1H, s), 4.62 (3H, d), 5.00 (1H, dd), 5.72 (1H, dd), 6.15 (1H, dd), 6.55 (1H, d), 6.81 (1H, dd), 7.09 (1H, d), 7.66-7.78 (2H, m), 8.56 (1H, s), 10.55 (1H, s). m/z ES⁺, [M+H]⁺ 520, 522.

8-[(8aS,11R)-6-Chloro-4-fluoro-11-methyl-10-(prop-2-enoyl)-8,8a,9,10,11,12-hexahydropyrazino[2',1':3, 4][1,4]oxazepino[5,6,7-de]quinazolin-5-yl]-7-methylisoquinolin-1(2H)-one (Atropisomer 2, Example 49)

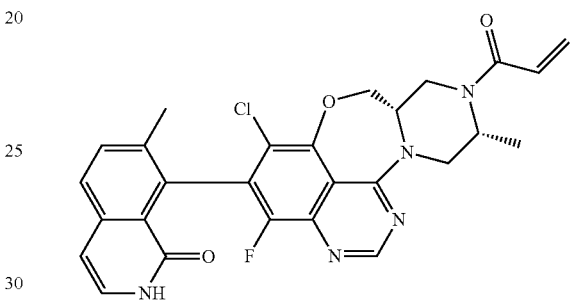

The title compound was prepared in an analogous fashion to the corresponding atropisomer, starting from 8-[(8aS, 11R)-6-chloro-4-fluoro-11-methyl-8,8a,9,10,11,12-hexahydropyrazino[2',1':3,4][1,4] oxazepino[5,6,7-de]quinazolin-5-yl]-7-methylisoquinolin-1(2H)-one atropisomer 2. The title compound (Example 49, 46 mg, 53%, d.e. 99%) was isolated as an off white solid. ¹H NMR (400 MHz, DMSO, 100° C.) 1.21 (3H, d), 2.08 (3H, s), 3.27 (1H, s), 3.51 (1H, dd), 3.95-4.08 (1H, m), 4.33 (1H, s), 4.63 (3H, d), 4.97 (1H, dd), 5.72 (1H, dd), 6.15 (1H, dd), 6.55 (1H, d), 6.81 (1H, dd), 7.09 (1H, d), 7.64-7.77 (2H, m), 8.56 (1H, s), 10.55 (1H, s). m/z ES⁺, [M+H]⁺ 520, 522.

tert-Butyl (8aS,11R)-6-chloro-4-fluoro-11-methyl-5-(5-methyl-1H-benzimidazol-4-yl)-8a,9,11,12-tetrahydropyrazino[2',1':3,4][1,4]oxazepino[5,6,7-de] quinazoline-10(8H)-carboxylate (Atropisomer 1 and Atropisomer 2)

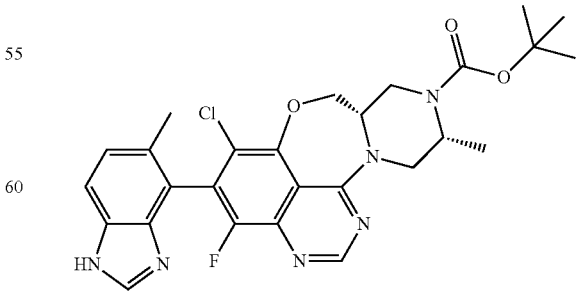

(8aS,11R)-6-Chloro-4-fluoro-11-methyl-5-(5-methyl-1H-benzimidazol-4-yl)-8,8a,9,10,11,12-hexahydropyrazino[2', 1':3,4][1,4]oxazepino[5,6,7-de]quinazoline (1088 mg, 2.48 mmol) was dissolved in MeOH (20 ml) and cooled to 0° C. then a solution of di-tert-butyl dicarbonate (541 mg, 2.48 mmol) in MeOH (20 ml) was added dropwise over 0.5 h. The solution was stirred at 0° C. for 30 min then allowed to reach rt over 18 h. Cesium carbonate (808 mg, 2.48 mmol) was added and the reaction was stirred at rt for 30 min. The solvents were removed in vacuo and the resulting residue was partitioned between EtOAc (50 ml) and water (20 ml). The layers were separated and the aqueous phase extracted with EtOAc (2×50 ml). The combined organic phases were dried (phase separator) and concentrated in vacuo. The crude material was purified with a REDISEP GOLD 150 g C18 cartridge, using water (containing 0.1% formic acid) and MeCN (gradient 15-55%). Fractions containing the desired compound were evaporated to remove acetonitrile. The resulting emulsion (150 ml) was treated with 2M aq. solution of $K_2CO_3$ (50 ml) then the mixture was extracted with EtOAc (130 ml×3). The combined organic extracts were dried (phase separator) and evaporated in vacuo to afford tert-butyl (8aS,11R)-6-chloro-4-fluoro-11-methyl-5-(5-methyl-1H-benzimidazol-4-yl)-8a,9,11,12-tetrahydropyrazino[TX:3,4][1,4]oxazepino[5,6,7-de]quinazoline-10(8H)-carboxylate as a yellow gum. This was dissolved in MeOH and separated using SFC (Column: Phenomenex C2, 20×250 mm, 5 µm, Mobile phase: 45% MeOH+0.1% $NH_3$/55% $scCO_2$, Flow rate: 60 ml/min, 120 bar, Column temp: 40° C.), to give tert-butyl (8aS,11R)-6-chloro-4-fluoro-11-methyl-5-(5-methyl-1H-benzimidazol-4-yl)-8a,9,11,12-tetrahydropyrazino[2',1':3,4][1,4]oxazepino[5,6,7-de]quinazoline-10(8H)-carboxylate atropisomer 1 (145 mg, 21%, d.e. 99%) as an off white solid. $^1$H NMR (400 MHz, DMSO, 100° C.) 1.15 (3H, d), 1.48 (9H, s), 2.19 (3H, s), 3.28 (1H, t), 3.51 (1H, dd), 3.96-4.08 (2H, m), 4.28-4.4 (1H, m), 4.54-4.72 (2H, m), 4.88-4.99 (1H, m), 7.22 (1H, d), 7.60 (1H, d), 8.02 (1H, s), 8.59 (1H, s). m/z ES+, [M+H]+ 539, 541. This was followed by tert-butyl (8aS,11R)-6-chloro-4-fluoro-11-methyl-5-(5-methyl-1H-benzimidazol-4-yl)-8a,9,11,12-tetrahydropyrazino[2',1':3,4][1,4]oxazepino[5,6,7-de]quinazoline-10(8H)-carboxylate atropisomer 2 (267 mg, 40%, d.e. 99%) as an off white solid. $^1$H NMR (400 MHz, DMSO, 100° C.) 1.14 (3H, d), 1.48 (9H, s), 2.21 (3H, s), 3.21-3.38 (1H, m), 3.43-3.57 (1H, m), 3.91-4.13 (2H, m), 4.27-4.38 (1H, m), 4.64 (2H, d), 4.93 (1H, dd), 7.22 (1H, d), 7.59 (1H, s), 8.01 (1H, s), 8.59 (1H, s). m/z (ES+), [M+H]$^+$ 539, 541.

(8aS,11R)-6-Chloro-4-fluoro-11-methyl-5-(5-methyl-1H-benzimidazol-4-yl)-8,8a,9,10,11,12-hexahydropyrazino[2',1':3,4][1,4]oxazepino[5,6,7-de]quinazoline (Atropisomer 1)

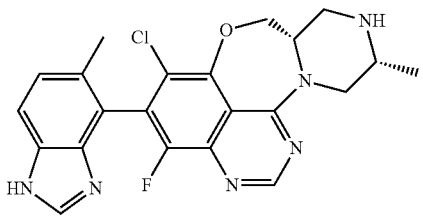

To a solution of tert-butyl (8aS,11R)-6-chloro-4-fluoro-11-methyl-5-(5-methyl-1H-benzimidazol-4-yl)-8a,9,11,12-tetrahydropyrazino[2',1':3,4][1,4]oxazepino[5,6,7-de]quinazoline-10(8H)-carboxylate atropisomer 1 (145 mg, 0.27 mmol) in DCM (5 ml) was added TFA (1.13 ml, 14.8 mmol) and the reaction mixture stirred for 2 h then the solvents evaporated. The residue was dissolved in methanol and applied to a SCX column washing thoroughly with methanol. The product was eluted using 1M solution of ammonia in methanol. The solvent was evaporated to afford (8aS,11R)-6-chloro-4-fluoro-11-methyl-5-(5-methyl-1H-benzimidazol-4-yl)-8,8a,9,10,11,12-hexahydropyrazino[2',1':3,4][1,4] oxazepino[5,6,7-de]quinazoline atropisomer 1 (108 mg, 91%) as an off-white solid. $^1$H NMR (400 MHz, MeOD, 30° C.) 1.21 (3H, d), 2.22 (3H, s), 2.98 (1H, dd), 3.32-3.34 (1H, m), 3.51 (1H, dd), 4.04 (1H, dq), 4.49-4.62 (2H, m), 4.93 (2H, dd), 7.29 (1H, d), 7.62 (1H, d), 8.06 (1H, s), 8.50 (1H, s). m/z (ES+), [M+H]+ 439, 441.

(8aS,11R)-6-Chloro-4-fluoro-11-methyl-5-(5-methyl-1H-benzimidazol-4-yl)-8,8a,9,10,11,12-hexahydropyrazino[2',1':3,4][1,4]oxazepino[5,6,7-de]quinazoline (Atropisomer 2)

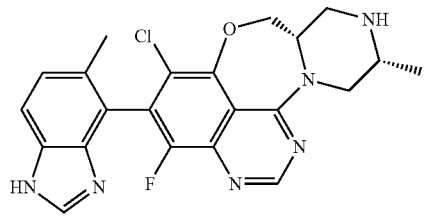 [SMILES: Cc1ccc2[nH]cnc2c1-c1c(Cl)c2c3c(ncnc3c1F)N1C[C@@H](C)NC[C@H]1CO2]

The title compound was prepared in an analogous fashion to the corresponding atropisomer starting from tert-butyl (8aS,11R)-6-chloro-4-fluoro-11-methyl-5-(5-methyl-1H-benzimidazol-4-yl)-8a,9,11,12-tetrahydropyrazino[2',1':3,4][1,4]oxazepino[5,6,7-de]quinazoline-10(8H)-carboxylate atropisomer 2. The title compound was isolated as an off white solid (187 mg, 86%). $^1$H NMR (400 MHz, MeOD, 30° C.) 1.19 (3H, d), 2.24 (3H, s), 2.86-3.04 (1H, m), 3.22-3.29 (1H, m), 3.46-3.54 (1H, m), 3.96-4.1 (1H, m), 4.54 (2H, d), 4.95 (2H, dd), 7.28 (1H, d), 7.62 (1H, d), 8.03 (1H, s), 8.50 (1H, s). m/z (ES+), [M+H]+ 439, 441.

(2E)-1-[(8aS,11R)-6-Chloro-4-fluoro-11-methyl-5-(5-methyl-1H-benzimidazol-4-yl)-8a,9,11,12-tetrahydropyrazino[2',1':3,4][1,4]oxazepino[5,6,7-de]quinazolin-10(8H)-yl]-4-(dimethylamino)but-2-en-1-one (Atropisomer 1, Example 50)

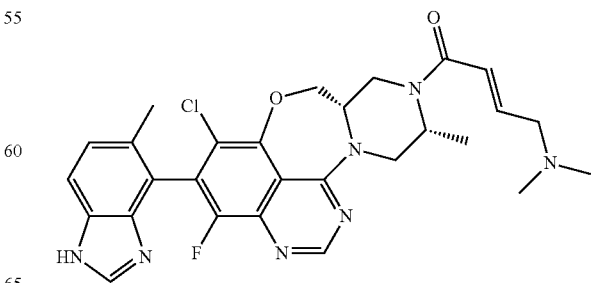

DIPEA (129 μl, 0.74 mmol) was added to a mixture of (8aS,11R)-6-chloro-4-fluoro-11-methyl-5-(5-methyl-1H-benzimidazol-4-yl)-8,8a,9,10,11,12-hexahydropyrazino[2',1':3,4][1,4]oxazepino[5,6,7-de]quinazoline atropisomer 1 (108 mg, 0.25 mmol), O-(7-azabenzotriazol-1-yl)-N,N,N',N'-tetramethyluronium hexafluorophosphate (112 mg, 0.30 mmol) and (E)-4-(dimethylamino)but-2-enoic acid. HCl salt (44.8 mg, 0.27 mmol) in DMA (1.1 ml) at rt. The resulting solution was stirred at rt for 1 h. The reaction mixture was poured into water (10 ml), extracted into EtOAc (3×20 ml), the organic extracts dried (phase separator) and concentrated in vacuo to give the crude product. This was purified by preparative HPLC (Waters XSelect CSH C18 column, 5μ silica, 50 mm diameter, 100 mm length), using water (containing 0.1% NH₃) and MeCN (25-55% gradient) as eluents. This gave (2E)-1-[(8aS,11R)-6-chloro-4-fluoro-11-methyl-5-(5-methyl-1H-benzimidazol-4-yl)-8a,9,11,12-tetrahydropyrazino[2', V:3,4] [1,4]oxazepino[5,6,7-de]quinazolin-10 (8H)-yl]-4-(dimethylamino)but-2-en-1-one atropisomer 1 (Example 50, 42 mg, 31%, d.e. 99%) as an off white solid. ¹H NMR (400 MHz, DMSO, 100° C.) 1.20 (3H, d), 2.20 (3H, s), 2.22 (6H, s), 3.09 (2H, d), 3.33-3.48 (1H, m), 3.54 (1H, d), 4.03 (1H, s), 4.23-4.45 (1H, m), 4.56-4.8 (3H, m), 4.98 (1H, dd), 6.54-6.81 (2H, m), 7.22 (1H, d), 7.60 (1H, d), 8.02 (1H, s), 8.60 (1H, s), 12.02 (1H, s). m/z ES⁺, [M+H]⁺ 550, 552.

(2E)-1-[(8aS,11R)-6-Chloro-4-fluoro-11-methyl-5-(5-methyl-1H-benzimidazol-4-yl)-8a,9,11,12-tetrahydropyrazino[2',1':3,4][1,4]oxazepino[5,6,7-de]quinazolin-10(8H)-yl]-4-(dimethylamino)but-2-en-1-one (Atropisomer 2, Example 51)

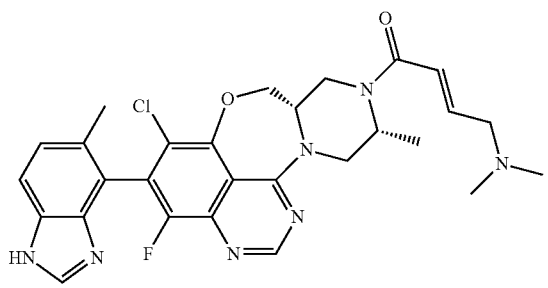 [SMILES: Cc1ccc2[nH]cnc2c1-c1c(Cl)c2c3c(ncnc3c1F)N1C[C@@H](C)N(C(=O)/C=C/CN(C)C)C[C@H]1CO2]

The title compound was prepared in an analogous fashion to the corresponding atropisomer, starting from (8aS,11R)-6-chloro-4-fluoro-11-methyl-5-(5-methyl-1H-benzimidazol-4-yl)-8,8a,9,10,11,12-hexahydropyrazino[2',1':3,4][1,4]oxazepino[5,6,7-de]quinazoline atropisomer 2. The title compound was isolated as an off white solid (Example 51, 63 mg, 27%). ¹H NMR (400 MHz, DMSO, 100° C.) 1.19 (3H, d), 2.21 (3H, s), 2.22 (6H, s), 3.09 (2H, d), 3.29-3.59 (2H, m), 3.89-4.11 (1H, m), 4.37 (1H, s), 4.52-4.77 (3H, m), 4.96 (1H, d), 6.48-6.78 (2H, m), 7.23 (1H, d), 7.60 (1H, s), 8.01 (1H, s), 8.60 (1H, s), 12.15 (1H, s). m/z ES+, [M+H]+ 550, 552.

tert-Butyl (8aS,11R)-6-chloro-4-fluoro-11-methyl-5-(5-methyl-1H-indazol-4-yl)-8a,9,11,12-tetrahydropyrazino[2',1':3,4][1,4]oxazepino[5,6,7-de]quinazoline-10(8H)-carboxylate (atropisomer 1 and atropisomer 2)

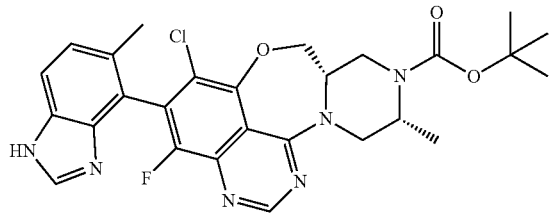 [SMILES: Cc1ccc2[nH]cnc2c1-c1c(Cl)c2c3c(ncnc3c1F)N1C[C@@H](C)N(C(=O)OC(C)(C)C)C[C@H]1CO2]

tert-Butyl (8aS,11R)-5-bromo-6-chloro-4-fluoro-11-methyl-8a,9,11,12-tetrahydropyrazino[2',1':3,4] [1,4]oxazepino[5,6,7-de]quinazoline-10(8H)-carboxylate (0.4 g, 0.82 mmol), dicyclohexyl(2',6'-diisopropoxy-[1,1'-biphenyl]-2-yl)phosphane (0.038 g, 0.08 mmol), RuPhos Pd G3 (0.069 g, 0.08 mmol), potassium carbonate (0.340 g, 2.46 mmol), (5-methyl-1H-indazol-4-yl)boronic acid (173 mg, 0.98 mmol) and dicyclohexyl(2',6'-diisopropoxy-[1,1'-biphenyl]-2-yl)phosphane (0.038 g, 0.08 mmol) were combined in a reaction tube. A degassed mixture of dioxane (9.14 ml) and water (3.04 ml) was added and the reaction was degassed for a further 1 minute then heated at 80° C. for 0.5 h. The reaction was allowed to cool to rt, degassed for 10 min then additional dicyclohexyl(2',6'-diisopropoxy-[1,1'-biphenyl]-2-yl)phosphane (38 mg, 0.08 mmol), RuPhos Pd-G3 (0.069 g, 0.08 mmol) and (5-methyl-1H-indazol-4-yl)boronic acid (144 mg, 0.82 mmol) were added. The reaction was stirred at 80° C. for 20 min. The reaction mixture was allowed to cool to rt. EtOAc (30 ml) was added and the whole was washed with water (2×20 ml). The combined aqueous was extracted with EtOAc (30 ml). The combined organic portions were washed with brine (30 ml), dried (MgSO₄) and concentrated in vacuo to afford an orange residue. This was purified by flash silica chromatography (0-100% EtOAc in heptane). This gave a residue which was separated using SFC (Column: Chiralpak OD, 20×250 mm, 5 μm, Mobile phase: 30% MeOH+0.1% NH₃/70% scCO₂, Flow rate: 60 ml/min, 120 bar, Column temp: 40° C.). This gave tert-butyl (8aS,11R)-6-chloro-4-fluoro-11-methyl-5-(5-methyl-1H-indazol-4-yl)-8a,9,11,12-tetrahydropyrazino[2',1':3,4][1,4] oxazepino[5,6,7-de]quinazoline-10(8H)-carboxylate atropisomer 1 (104 mg, 46%, d.e. 99%) as an off white solid. ¹H NMR (400 MHz, MeOD, 30° C.) 1.14-1.26 (3H, m), 1.51 (9H, s), 2.22 (3H, s), 3.38-3.57 (2H, m), 3.96-4.06 (1H, m), 4.06-4.15 (1H, m), 4.43 (1H, s), 4.59-4.68 (2H, m), 5.08-5.33 (1H, m), 7.42 (1H, d), 7.52 (1H, s), 7.58 (1H, d), 8.55 (1H, s). m/z (ES+), [M+H]+ 539, 541. This was followed by tert-butyl (8aS,11R)-6-chloro-4-fluoro-11-methyl-5-(5-methyl-1H-indazol-4-yl)-8a,9,11,12-tetrahydropyrazino[2',1':3,4][1,4]oxazepino[5,6,7-de]quinazoline-10(8H)-carboxylate atropisomer 2 (101 mg, 44%, d.e. 99%) as an off white solid. ¹H NMR (400 MHz, MeOD, 30° C.) 1.09-1.22 (3H, m), 1.51 (9H, s), 2.21 (3H, s), 3.36-3.57 (2H, m), 3.93-4.04 (1H, m), 4.04-4.17 (1H, m), 4.42 (1H, s), 4.64

(2H, d), 5.15 (1H, dd), 7.42 (1H, d), 7.54 (1H, s), 7.58 (1H, d), 8.55 (1H, s). m/z ES+, [M+H]+ 539, 541.

(8aS,11R)-6-Chloro-4-fluoro-11-methyl-5-(5-methyl-1H-indazol-4-yl)-8,8a,9,10,11,12-hexahydropyrazino[2',1':3,4][1,4]oxazepino[5,6,7-de]quinazoline (Atropisomer 1)

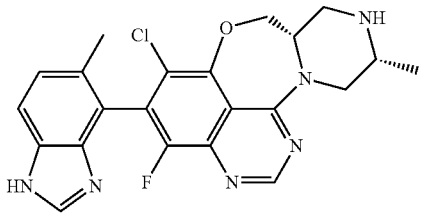 [SMILES: Cc1ccc2[nH]cnc2c1-c1c(Cl)c2c3c(ncnc3c1F)N1C[C@@H](C)NC[C@H]1CO2]

To a solution of tert-butyl (8aS,11R)-6-chloro-4-fluoro-11-methyl-5-(5-methyl-1H-indazol-4-yl)-8a,9,11,12-tetrahydropyrazino[2',1':3,4][1,4]oxazepino[5,6,7-de]quinazoline-10(8H)-carboxylate atropisomer 1 (104 mg, 0.19 mmol) in DCM (4 ml) was added TFA (0.813 ml, 10.6 mmol) and the reaction mixture stirred for 2 h then the solvents evaporated. The residue was purified using a SCX column, with the product eluted using 1M solution of ammonia in methanol. This gave (8aS,11R)-6-chloro-4-fluoro-11-methyl-5-(5-methyl-1H-indazol-4-yl)-8,8a,9,10,11,12-hexahydropyrazino[2',1':3,4] [1,4]oxazepino[5,6,7-de]quinazoline atropisomer 1 (83 mg, 98%) as an off-white solid. 1H NMR (400 MHz, MeOD, 30° C.) 1.23 (3H, d), 2.21 (3H, s), 2.99 (1H, dd), 3.35-3.41 (2H, m), 3.51 (1H, dd), 4.07 (1H, dq), 4.57 (2H, d), 4.96 (1H, dd), 7.41 (1H, d), 7.53 (1H, s), 7.58 (1H, d), 8.52 (1H, s). m/z (ES+), [M+H]+ 441.

(8aS,11R)-6-Chloro-4-fluoro-11-methyl-5-(5-methyl-1H-indazol-4-yl)-8,8a,9,10,11,12-hexahydropyrazino[2',1':3,4][1,4]oxazepino[5,6,7-de]quinazoline (Atropisomer 2)

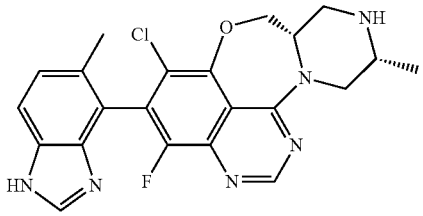 [SMILES: Cc1ccc2[nH]cnc2c1-c1c(Cl)c2c3c(ncnc3c1F)N1C[C@@H](C)NC[C@H]1CO2]

The title compound was prepared in an analogous fashion the corresponding atropisomer, starting from tert-butyl (8aS,11R)-6-chloro-4-fluoro-11-methyl-5-(5-methyl-1H-indazol-4-yl)-8a,9,11,12-tetrahydropyrazino[2',1':3,4][1,4]oxazepino[5,6,7-de]quinazoline-10(8H)-carboxylate atropisomer 2. The title compound was isolated as an off white solid (86 mg, >100%). 1H NMR (400 MHz, MeOD, 30° C.) 1.22 (3H, d), 2.21 (3H, s), 2.99 (1H, dd), 3.35-3.41 (2H, m), 3.49-3.57 (1H, m), 4.03-4.14 (1H, m), 4.58 (2H, d), 4.93 (1H, dd), 7.41 (1H, d), 7.53 (1H, s), 7.58 (1H, d), 8.52 (1H, s). m/z (ES+), [M+H]+ 441.

(2E)-1-[(8aS,11R)-6-Chloro-4-fluoro-11-methyl-5-(5-methyl-1H-indazol-4-yl)-8a,9,11,12-tetrahydropyrazino[2',1':3,4][1,4]oxazepino[5,6,7-de]quinazolin-10(8H)-yl]-4-(dimethylamino)but-2-en-1-one (Atropisomer 1, Example 52)

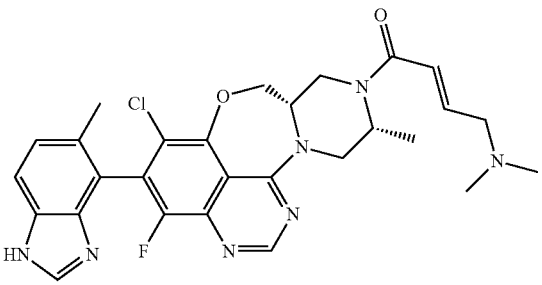 [SMILES: Cc1ccc2[nH]cnc2c1-c1c(Cl)c2c3c(ncnc3c1F)N1C[C@@H](C)N(C(=O)/C=C/CN(C)C)C[C@H]1CO2]

DIPEA (99 µl, 0.57 mmol) was added in one portion to (8aS,11R)-6-chloro-4-fluoro-11-methyl-5-(5-methyl-1H-indazol-4-yl)-8,8a,9,10,11,12-hexahydropyrazino[2',1':3,4][1,4]oxazepino[5,6,7-de] quinazoline atropisomer 1 (83 mg, 0.19 mmol), O-(7-Azabenzotriazol-1-yl)-N,N,N',N'-tetramethyluronium hexafluorophosphate (86 mg, 0.23 mmol) and (E)-4-(dimethylamino)but-2-enoic acid. HCl salt (34.5 mg, 0.21 mmol) in DMA (0.85 ml) at RT. The resulting solution was stirred at rt for 1 h. The reaction mixture was poured into water (10 ml), extracted into EtOAc (3×20 ml), dried (phase separator) and concentrated in vacuo. The crude product was purified by preparative HPLC (Waters XSelect CSH C18 column, 5µ silica, 50×100), using water (containing 0.1% NH3) and MeCN (25-55% gradient) as eluents. This gave (2E)-1-[(8aS,11R)-6-chloro-4-fluoro-11-methyl-5-(5-methyl-1H-indazol-4-yl)-8a,9,11,12-tetrahydropyrazino[2',1':3,4][1,4]oxazepino[5,6,7-de]quinazolin-10 (8H)-yl]-4-(dimethylamino)but-2-en-1-one atropisomer 1 (Example 52, 48 mg, 46%, d.e. 99%) as an off white solid. 1H NMR (400 MHz, DMSO, 100° C.) 1.21 (3H, d), 2.19 (3H, s), 2.22 (6H, s), 3.09 (2H, d), 3.55 (2H, dd), 4.05 (1H, dd), 4.36 (1H, s), 4.68 (3H, d), 4.98 (1H, dd), 6.47-6.79 (2H, m), 7.38 (1H, d), 7.45-7.71 (2H, m), 8.60 (1H, s), 12.86 (1H, s). m/z (ES+), [M+H]+ 550, 552.

(2E)-1-[(8aS,11R)-6-Chloro-4-fluoro-11-methyl-5-(5-methyl-1H-indazol-4-yl)-8a,9,11,12-tetrahydropyrazino[2',1':3,4][1,4]oxazepino[5,6,7-de]quinazolin-10(8H)-yl]-4-(dimethylamino)but-2-en-1-one (Atropisomer 2, Example 53)

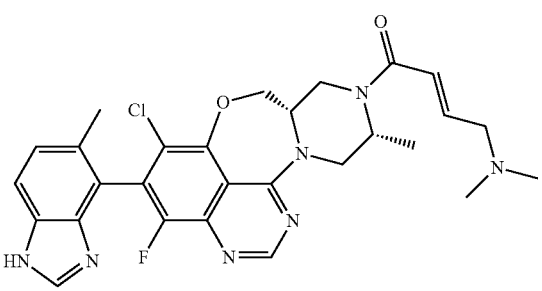 [SMILES: Cc1ccc2[nH]cnc2c1-c1c(Cl)c2c3c(ncnc3c1F)N1C[C@@H](C)N(C(=O)/C=C/CN(C)C)C[C@H]1CO2]

The title compound was prepared in an analogous fashion to the corresponding atropisomer, starting from (8aS,11R)-

6-Chloro-4-fluoro-11-methyl-5-(5-methyl-1H-indazol-4-yl)-8,8a,9,10,11,12-hexahydropyrazino[2',1':3,4][1,4]oxazepino[5,6,7-de]quinazoline atropisomer 2. The title compound was isolated as an off white solid (Example 53, 45 mg, 42%, d.e. 99%). $^1$H NMR (400 MHz, DMSO, 100° C.) 1.20 (3H, d), 2.18 (3H, s), 2.22 (6H, s), 3.09 (2H, d), 3.37 (1H, s), 3.57 (1H, dd), 4-4.12 (1H, m), 4.35 (1H, s), 4.59-4.76 (3H, m), 4.95 (1H, dd), 6.56-6.75 (2H, m), 7.38 (1H, d), 7.47-7.65 (2H, m), 8.60 (1H, s), 12.87 (1H, s). m/z ES$^+$, [M+H]$^+$ 550, 552.

The invention claimed is:

1. A compound, or a pharmaceutically acceptable salt thereof, wherein the compound is 1-[6aS,9R)-3-chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl]prop-2-en-1-one.

2. The compound of claim 1.

3. The pharmaceutically acceptable salt of claim 1.

4. An atropisomer of the compound 1-[6aS,9R)-3-chloro-1-fluoro-2-(2-fluoro-6-hydroxyphenyl)-9-methyl-5,6,6a,7,9,10-hexahydro-8H-pyrazino [1',2':5,6]-[1,5]oxazocino-[4,3,2-de]quinazolin-8-yl]prop-2-en-1-one, or a pharmaceutically acceptable salt thereof.

5. The atropisomer of claim 4, or pharmaceutically acceptable salt thereof, wherein:
the compound can have the stereochemical orientation of a first atropisomer or a second atropisomer;
the first atropisomer is the first eluting atropisomer and the second atropisomer is the second eluting atropisomer if a sample of the compound comprising both the first atropisomer and the second atropisomer is separated by preparative chiral-HPLC; and
the atropisomer of claim 4 is the first atropisomer.

6. The atropisomer, or pharmaceutically acceptable salt thereof, of claim 4, wherein:
the compound can have the stereochemical orientation of a first atropisomer or a second atropisomer;
the first atropisomer is the first eluting atropisomer and the second atropisomer is the second eluting atropisomer if a sample of the compound comprising both the first atropisomer and the second atropisomer is separated by preparative chiral-HPLC; and
the atropisomer of claim 4 is the second atropisomer.

7. The atropisomer, or pharmaceutically acceptable salt thereof, of claim 5, wherein the preparative chiral-HPLC conditions are:
Column: CHIRALPAK IE, 2×25 cm, 5 μm;
Mobile Phase A: Hex (8 mmol/L NH3.MeOH)-HPLC;
Mobile Phase B: EtOH-HPLC;
Flow rate: 20 ml/min;
Gradient: 30 B to 30 B in 16 min;
220/254 nm; and
RT1:9.899; RT2:13.349.

8. The atropisomer, or pharmaceutically acceptable salt thereof, of claim 6, wherein the preparative chiral-HPLC conditions are:
Column: CHIRALPAK IE, 2×25 cm, 5 μm;
Mobile Phase A: Hex (8 mmol/L NH3.MeOH)-HPLC;
Mobile Phase B: EtOH-HPLC;
Flow rate: 20 ml/min;
Gradient: 30 B to 30 B in 16 min;
220/254 nm; and
RT1:9.899; RT2:13.349.

9. A pharmaceutical composition comprising the compound 1-[(6aS,9R)-3-chloro-1-fluoro-2-(2-fluoro-6-hydroxyphenyl)-9-methyl-5,6,6a,7,9,10-hexahydro-8H-pyrazino[1',2':5,6][1,5]-oxazocino[4,3,2-de]quinazolin-8-yl]prop-2-en-1-one, or a pharmaceutically acceptable salt thereof.

10. The pharmaceutical composition of claim 9, wherein the composition comprises 1-[(6aS,9R)-3-chloro-1-fluoro-2-(2-fluoro-6-hydroxyphenyl)-9-methyl-5,6,6a,7,9,10-hexahydro-8H-pyrazino[1',2':5,6][1,5]oxazocino[4,3,2-de]quinazolin-8-yl]prop-2-en-1-one.

11. The pharmaceutical composition of claim 9, wherein the composition comprises the pharmaceutically acceptable salt of 1-[(6aS,9R)-3-chloro-1-fluoro-2-(2-fluoro-6-hydroxyphenyl)-9-methyl-5,6,6a,7,9,10-hexahydro-8H-pyrazino[1',2':5,6][1,5]-oxazocino[4,3,2-de]quinazolin-8-yl]prop-2-en-1-one.

12. The pharmaceutical composition of claim 9, wherein the composition is atropisomerically enriched for an atropisomer of the compound, or a pharmaceutically acceptable salt thereof.

13. The pharmaceutical composition of claim 12, wherein the enriched atropisomer is present in an atropisomeric excess of at least 90%.

14. The pharmaceutical composition of claim 12, wherein:
the compound can have the stereochemical orientation of a first atropisomer or a second atropisomer;
the first atropisomer is the first eluting atropisomer and the second atropisomer is the second eluting atropisomer if a sample of the compound comprising both the first atropisomer and the second atropisomer is separated by preparative chiral-HPLC; and
the enriched atropisomer is the first atropisomer.

15. The pharmaceutical composition of claim 14, wherein the enriched atropisomer is present in an atropisomeric excess of at least 90%.

16. The pharmaceutical composition of claim 12, wherein:
the compound can have the stereochemical orientation of a first atropisomer or a second atropisomer;
the first atropisomer is the first eluting atropisomer and the second atropisomer is the second eluting atropisomer if a sample of the compound comprising both the first atropisomer and the second atropisomer is separated by preparative chiral-HPLC; and
the enriched atropisomer is the second atropisomer.

17. The pharmaceutical composition of claim 16, wherein the enriched atropisomeric form is present in an atropisomeric excess of at least 90%.

18. The pharmaceutical composition of claim 14, wherein the preparative chiral-HPLC conditions are:
Column: CHIRALPAK IE, 2×25 cm, 5 μm;
Mobile Phase A: Hex (8 mmol/L NH3.MeOH)-HPLC;
Mobile Phase B: EtOH-HPLC;
Flow rate: 20 ml/min;
Gradient: 30 B to 30 B in 16 min;
220/254 nm; and
RT1:9.899; RT2:13.349.

19. The pharmaceutical composition of claim 16, wherein the preparative chiral-HPLC conditions are:
Column: CHIRALPAK IE, 2×25 cm, 5 μm;
Mobile Phase A: Hex (8 mmol/L NH3.MeOH)-HPLC;
Mobile Phase B: EtOH-HPLC;
Flow rate: 20 ml/min;
Gradient: 30 B to 30 B in 16 min;
220/254 nm; and
RT1:9.899; RT2:13.349.

* * * * *